US011377444B2

(12) United States Patent
Chen et al.

(10) Patent No.: US 11,377,444 B2
(45) Date of Patent: Jul. 5, 2022

(54) PYRIDOPYRIMIDINE COMPOUNDS ACTING AS MTORC 1/2 DUAL INHIBITORS

(71) Applicant: MEDSHINE DISCOVERY INC., Jiangsu (CN)

(72) Inventors: Kevin X Chen, Shanghai (CN); Zhaoguo Chen, Shanghai (CN); Li Zhang, Shanghai (CN); Yanxin Yu, Shanghai (CN); Kai Zhou, Shanghai (CN); Boyu Hu, Shanghai (CN); Xiaofei Wang, Shanghai (CN); Guoping Hu, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 48 days.

(21) Appl. No.: 16/760,740

(22) PCT Filed: Nov. 2, 2018

(86) PCT No.: PCT/CN2018/113683

§ 371 (c)(1),
(2) Date: Apr. 30, 2020

(87) PCT Pub. No.: WO2019/085996

PCT Pub. Date: May 9, 2019

(65) Prior Publication Data

US 2020/0339568 A1 Oct. 29, 2020

(30) Foreign Application Priority Data

Nov. 6, 2017 (CN) ......................... 201711080753.8
Feb. 9, 2018 (CN) ......................... 201810136962.8
Jun. 25, 2018 (CN) ......................... 201810661825.6

(51) Int. Cl.
*C07D 471/04* (2006.01)
*A61P 35/00* (2006.01)
*C07D 519/00* (2006.01)

(52) U.S. Cl.
CPC ............ *C07D 471/04* (2013.01); *A61P 35/00* (2018.01); *C07D 519/00* (2013.01)

(58) Field of Classification Search
CPC ..... C07D 471/04; C07D 519/00; A61P 35/00; A61P 35/02; A61K 31/5377; A61K 31/5383; A61K 31/5386
See application file for complete search history.

(56) References Cited

U.S. PATENT DOCUMENTS

2017/0281637 A1 10/2017 Duggan et al.

FOREIGN PATENT DOCUMENTS

| | | | |
|---|---|---|---|
| CN | 101360746 A | 2/2009 | |
| CN | 101558067 A | 10/2009 | |
| CN | 103030653 A | 4/2013 | |
| CN | 201711080753.8 | 11/2017 | |
| CN | 201810136962.8 | 2/2018 | |
| CN | 201810661825.6 | 6/2018 | |
| RU | 2473549 C2 | 1/2013 | |
| WO | WO-2007060404 A1 | 5/2007 | |
| WO | WO-2008023161 A1 | 2/2008 | |
| WO | WO-2011114275 A1 * | 9/2011 | ................ A61P 1/16 |

OTHER PUBLICATIONS

Powles, T., "A randomised phase 2 study of AZD2014 versus everolimus in patients with VEGF-refractory metastatic clear cell renal cancer." European urology 69.3 (2016): 450-456.*

Extended European Search Report issued in European Patent Application No. EP18872475.1, dated Mar. 30, 2021.

Pike, Kurt. G. et al. "Optimization of potent and selective dual mTORC1 and mTORC2 inhibitors: the discovery of AZD8055 and AZD2014." Bioorganic & Medicinal Chemistry Letters 23.5 (2013): pp. 1212-1216.

Jan. 30, 2019 International Search Report issued in International Patent Application No. PCT/CN2018/113683.

Jan. 30, 2019 Written Opinion of the International Searching Authority issued in International Patent Application No. PCT/CN2018/113683.

(Continued)

*Primary Examiner* — John M Mauro

(74) *Attorney, Agent, or Firm* — Harness, Dickey & Pierce, P.L.C.

(57) ABSTRACT

Disclosed are a series of pyridopyrimidine compounds and a use of same in the preparation of drugs associated with mTORC 1/2 dual complex inhibitors, and specifically disclosed is a use of the compounds as shown in formula (IV), tautomers thereof or pharmaceutically acceptable salts thereof in the preparation of drugs associated with mTORC 1/2 dual complex inhibitors.

(IV)

R4, O, R5, R1, N, R2, N, N, N, D1, D3, T1, D5, D2, D7, D4, T2, D6, D8, A, (R3)n

20 Claims, No Drawings

(56) References Cited

OTHER PUBLICATIONS

Chinese Office Action regarding Application No. 201880071134.9, dated Mar. 17, 2022.
First Office Action issued in Russian Application No. 2020118222, dated Oct. 25, 2021.

* cited by examiner

PYRIDOPYRIMIDINE COMPOUNDS ACTING AS MTORC 1/2 DUAL INHIBITORS

CROSS-REFERENCE TO RELATED APPLICATIONS

This application is a 371 National Phase of International Application No. PCT/CN2018/113683, filed Nov. 2, 2018, which claims the benefit of Chinese Patent Application No. CN 201711080753.8, filed Nov. 6, 2017, Chinese Patent Application No. CN 201810136962.8, filed Feb. 9, 2018, and Chinese Patent Application No. CN 201810661825.6, filed Jun. 25, 2018. The entire disclosures of the above applications are incorporated herein by reference.

FIELD OF INVENTION

The present disclosure relates to a series of pyridopyrimidine compounds and a use of same in the manufacture of medicaments associated with mTORC ½ dual inhibitors, specifically relates to a use of the compounds as shown in formula (IV), tautomers thereof or pharmaceutically acceptable salts thereof in the manufacture of medicaments associated with mTORC ½ dual inhibitors.

PRIOR ARTS

Tumors, especially malignant tumors, are currently one of the most serious diseases that endanger human health. With the development of science and technology and the deepening of people's research on tumor treatment, rapid progress in tumor occurrence and development mechanism and tumor treatment has been made. Many new mechanisms and biological markers have been discovered. The invention relates to a signaling pathway that plays a key role in tumor proliferation, invasive metastasis and anti-apoptosis, i.e. phosphatidylinositol 3-kinase (PI3K)-AKT-mammalian target of rapamycin (mTOR) signaling pathway.

The activation of PI3K is largely involved in the substrate close to the inside of its plasma membrane. A variety of growth factors and signaling complexes, including fibroblast growth factor (FGF), vascular endothelial growth factor (VEGF), human growth factor (HGF), angiopoietin-1 (Ang1), and insulin can initiate the PI3K activation process. These factors activate the receptor tyrosine kinase (RTK), which causes auto-phosphorylation. The result of PI3K activation is to produce a second messenger PIP3 on the plasma membrane. PIP3 binds to the signaling proteins AKT and PDK1 (phosphoinositide dependent kinase-1) containing PH domain in the cell, causing PDK1 to phosphorylate Ser308 of AKT protein, which leads to AKT activation. Other PDK1 substrates include PKC (protein kinase C), S6K (p70S6) and SGK (serum/glucocorticoid regulated kinases). AKT, also known as protein kinase B (PKB), is the main downstream effector of PI3K. Activated AKT regulates cell function by phosphorifying downstream factors such as enzymes, kinases, and transcription factors. AKT exert anti-apoptotic effect by phosphorylating target proteins through multiple downstream pathways. PTEN (phosphatase and tensin homology deleted on chromosome 10), a tumor suppressor gene, is mutated or deleted in a wide range of human tumors. PTEN is a PIP3-phosphatase that, contrary to the function of PI3K, can convert PIP3 into PIP2 by dephosphation. PTEN can reduce the activation of AKT and prevent all downstream signaling events regulated by AKT. As a downstream substrate of AKT, mTOR is relatively conservative in evolution, can integrate multiple signals of nutrition, energy and growth factors, participate in biological processes such as gene transcription, protein translation, ribosome synthesis and apoptosis, and plays an extremely important role in cell growth. There are two kinds of highly homologous complexes, Tor and KOG01 combine to form mTORC1, mTOR and AVO1/AVO2/AVO3/and LST8 form mTORC2 which is insensitive to rapamycin. mTOR regulates downstream protein translation by phosphorylating downstream target protein S40S ribosomal S6 protein kinase, such as S6K1 and 4EBP1. mTOR binds to eIF3, phosphorylates S6K1, allows S6K1 to be released from eIF3 and activated, followed by phosphorylation of cell substrate such as p70S6 to promote protein translation and expression. 4EBP1 binds to eukaryotic transcription initiation factor 4E and inhibits its activity. mTOR phosphorylates 4E-BP1 to activate it and separate it from eif-4e to achieve eukaryotic cell transcription. mTORC2 can phosphorylate AKT, thereby up-regulating its kinase activity.

As can be seen from the above, any mutation or overexpression in the upstream of the PI3K/AKT/mTOR signaling pathway will lead to a series of downstream cascade reactions, eventually leading to occurrence, development and metastasis of tumor. While mTOR is at the hub of the signaling pathway, the inhibition of mTORC1 and mTORC2 can effectively block the transmission of signals, thereby achieving the control of tumor development.

Studies have found that this signaling pathway is found in a variety of solid tumors, such as breast cancer, prostate cancer, lung cancer, colon cancer, pancreatic cancer, liver cancer, gastric cancer, colorectal cancer, kidney cancer, thyroid cancer, meningitis cancer, and acute and chronic lymphocytic leukemia, Merkel cell tumor, etc. And it is closely related to treatment tolerance and poor prognosis. It can be seen that the development of fine molecular compounds to achieve inhibition of PI3K/AKT/mTOR signaling pathway has good development prospects.

The present invention aims to find mTOR½ dual inhibitor targeting drugs, such compounds have good activity, and show excellent effects and functions.

US20170281637 discloses compound AZD2014, which belongs to mTORC1 & mTORC2 kinase inhibitors, and its structural formula is as follows:

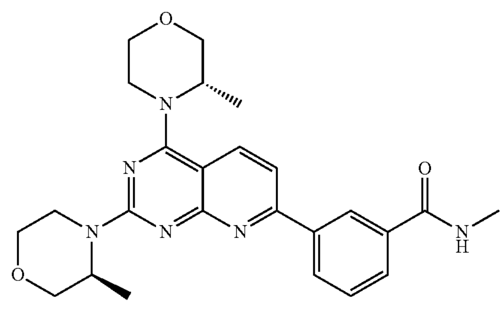

AZD2014

Content of the Present Disclosure

The present disclosure provides a compound represented by formula (IV), a pharmaceutical acceptable salt thereof or an isomer thereof, (IV)

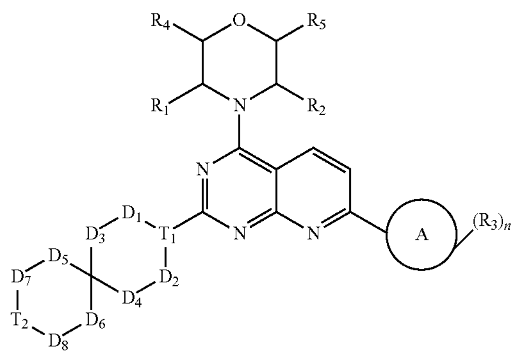

wherein, $R_1$ is H;

$R_2$ is Me;

alternatively, $R_1$, $R_2$ and the N atom on the morpholine ring form a 5-6 membered heterocycloalkyl;

$R_3$ is selected from $NH_2$,

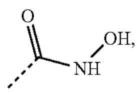

$C_{1-3}$ heteroalkyl, 5-6 membered heteroaryl and $C_{3-6}$ cycloalkyl-NH—C(=O)—, wherein the $C_{1-3}$ heteroalkyl, 5-6 membered heteroaryl and $C_{3-6}$ cycloalkyl-NH—C(=O)— are optionally substituted by R, and the number of R is 1, 2 or 3;

n is selected from 1 and 2;

ring A is selected from phenyl and 6-10 membered heteroaryl;

$R_4$ is H;

$R_5$ is H;

alternatively, $R_4$ and $R_5$ are linked together to form a 5-6 membered heterocycloalkyl;

$D_1$, $D_2$, $D_3$ and $D_4$ are respectively selected from single bond, —$CH_2$—, —$CH_2CH_2$— and —O—, and at least one of $D_1$, $D_2$, $D_3$ and $D_4$ is not a single bond, wherein the —$CH_2$— or —$CH_2CH_2$— is optionally substituted by R, and the number of R is 1 or 2;

$D_5$, $D_6$, $D_7$ and $D_8$ are respectively selected from single bond, —$CH_2$—, —O— and —NH—, and at least one of $D_5$, $D_6$, $D_7$ and $D_8$ is not a single bond, wherein —$CH_2$— is optionally substituted by R, and the number of R is 1 or 2, —NH— is optionally substituted by R;

$T_1$ is selected from CH and N;

$T_2$ is selected from —$CH_2$—, —NH—, —O—,

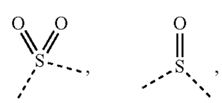

—S— and —C(=O)NH—, wherein the —$CH_2$— is optionally substituted by R, and the number of R is 1 or 2, —NH— is optionally substituted by R;

R is respectively selected from F, Cl, Br, I, OH, $NH_2$, $C_{1-3}$ alkyl, $C_{1-3}$ alkoxy and $C_{3-6}$ cycloalkyl, wherein the $C_{1-3}$ alkyl, $C_{1-3}$ alkoxy and $C_{3-6}$ cycloalkyl are optionally substituted by R', and the number of R' is 1 or 2;

R' is respectively selected from F, Cl, Br, I, OH and $NH_2$;

the $C_{1-3}$ heteroalkyl, 5-6 membered heteroaryl and 6-10 membered heteroaryl respectively contain 1, 2 or 3 heteroatoms or heteroatom groups indenpendently selected from —O—, —S—, —NH—, N, —C(=O)—, —C(=O)NH— and —C(=S) NH—.

The present disclosure provides the compound, the pharmaceutical acceptable salt thereof or the isomer thereof as described above, which is selected from (I)

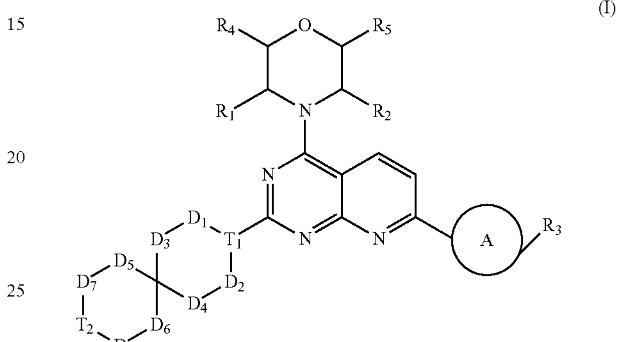

wherein, $R_1$ is H;

$R_2$ is Me;

alternatively, $R_1$, $R_2$ and the N atom on the morpholine ring form a 5-6 membered heterocycloalkyl;

$R_3$ is selected from $NH_2$,

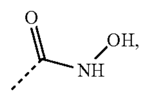

$C_{1-3}$ heteroalkyl, 5-6 membered heteroaryl and $C_{3-6}$ cycloalkyl-NH—C(=O)—, wherein the $C_{1-3}$ heteroalkyl, 5-6 membered heteroaryl and $C_{3-6}$ cycloalkyl-NH—C(=O)— are optionally substituted by R, and the number of R is 1, 2 or 3;

ring A is selected from phenyl and 6-10 membered heteroaryl;

$R_4$ is selected from H;

$R_5$ is selected from H;

alternatively, $R_4$ and $R_5$ are linked together to form a 5-6 membered heterocycloalkyl;

$D_1$, $D_2$, $D_3$ and $D_4$ are respectively selected from a single bond, —$CH_2$—, —$CH_2CH_2$— and —O—, and at least one of $D_1$, $D_2$, $D_3$ and $D_4$ is not a single bond, wherein the —$CH_2$— or —$CH_2CH_2$— is optionally substituted by R, and the number of R is 1 or 2;

$D_5$, $D_6$, $D_7$ and $D_8$ are respectively selected from single bond, —$CH_2$—, —O— and —NH—, and at least one of $D_5$, $D_6$, $D_7$ and $D_8$ is not single bond, wherein the —$CH_2$— is optionally substituted by R, and the number of R is 1 or 2, —NH— is optionally substituted by R;

$T_1$ is selected from CH and N;

$T_2$ is selected from —$CH_2$—, —NH—, —O—,

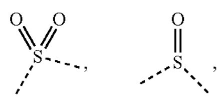

—S— and —C(═O) NH—, wherein —$CH_2$— is optionally substituted by R, and the number of R is 1 or 2, —NH— is optionally substituted by R;

R is respectively selected from F, Cl, Br, I, OH, $NH_2$, $C_{1-3}$ alkyl, $C_{1-3}$ alkoxy and $C_{3-6}$ cycloalkyl, wherein the $C_{1-3}$ alkyl, $C_{1-3}$ alkoxy and $C_{3-6}$ cycloalkyl are optionally substituted by R', and the number of R' is 1 or 2;

R' is respectively selected from F, Cl, Br, I, OH and $NH_2$;

the $C_{1-3}$ heteroalkyl, 5-6 membered heteroaryl and 6-10 membered heteroaryl respectively contain 1, 2 or 3 heteroatoms or heteroatom groups independently selected from —O—, —S—, —NH—, N, —C(═O)—, —C(═O)NH— and —C(═S)NH—.

The present disclosure provides a compound represented by formula (I), a pharmaceutical acceptable salt thereof or an isomer thereof,

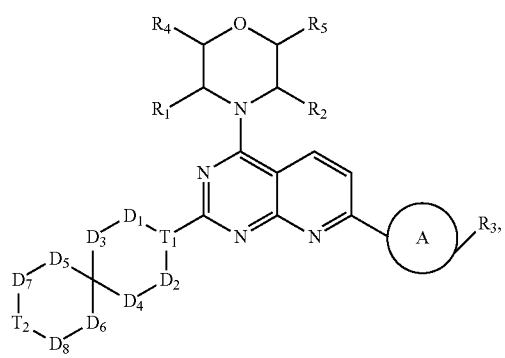

wherein, $R_1$ is selected from H;

$R_2$ is selected from Me;

alternatively, $R_1$ and $R_2$ are linked together to form a 5-6 membered heterocycloalkyl;

$R_3$ is selected from $NH_2$,

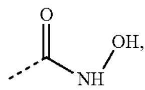

$C_{1-3}$ heteroalkyl, 5-6 membered heteroaryl and $C_{3-6}$ cycloalkyl-NH—C(═O)—, wherein the $C_{1-3}$ heteroalkyl, 5-6 membered heteroaryl and $C_{3-6}$ cycloalkyl-NH—C(═O)— are optionally substituted by R, and the number of R is 1, 2 or 3;

ring A is selected from phenyl and 6-10 membered heteroaryl;

$R_4$ is selected from H;

$R_5$ is selected from H;

$D_1$, $D_2$, $D_3$ and $D_4$ are respectively selected from a single bond, —$CH_2$—, —$CH_2CH_2$— and —O—, wherein the —$CH_2$— or —$CH_2CH_2$— are optionally substituted by R, and the number of R is 1 or 2;

$D_5$, $D_6$, $D_7$ and $D_8$ are respectively selected from a single bond, —$CH_2$—, —O— and —NH—, wherein the —$CH_2$— is optionally substituted by R, and the number of R is 1 or 2, and the —NH— is optionally substituted by R;

$T_1$ is selected from CH and N;

$T_2$ is selected from single bond, $CH_2$ and —O—;

R is respectively selected from F, Cl, Br, I, OH, $NH_2$, $C_{1-3}$ alkyl, $C_{1-3}$ alkoxy and $C_{3-6}$ cycloalkyl, wherein the $C_{1-3}$ alkyl, $C_{1-3}$ alkoxy and $C_{3-6}$ cycloalkyl are optionally substituted by R', the number of R' is 1 or 2;

R' is respectively selected from F, Cl, Br, I, OH and $NH_2$;

the $C_{1-3}$ heteroalkyl, 5-6 membered heteroaryl and 6-10 membered heteroaryl respectively contain 1, 2 or 3 heteroatoms or heteroatom groupsindenpendently selected from —O—, —S—, —NH—, N, —C(═O)—, —C(═O)NH— and —C(═S)NH—.

In some embodiments of the present disclosure, the R is respectively selected from F, Cl, Br, I, OH, $NH_2$, Me, Et,

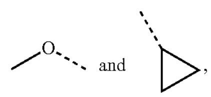

wherein the Me, Et,

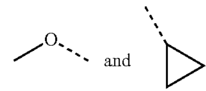

are optionally substituted by R', and the number of R' is 1 or 2, the other variables are as defined in the present disclosure.

In some embodiments of the present disclosure, the R is respectively selected from F, Cl, Br, I, OH, $NH_2$, Me, $CF_3$, Et,

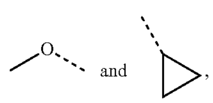

the other variables are as defined in the present disclosure.

In some embodiments of the present disclosure, the moiety

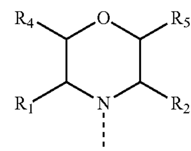

selected from

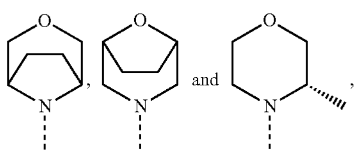

the other variables are as defined in the present disclosure.

In some embodiments of the present disclosure, the $R_1$ and $R_2$ are linked together, and the moiety

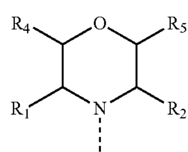

is selected from

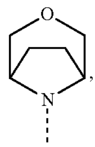

the other variables are as defined in the present disclosure.

In some embodiments of the present disclosure, the $R_3$ is selected from $NH_2$,

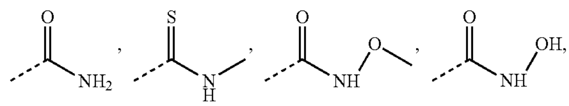

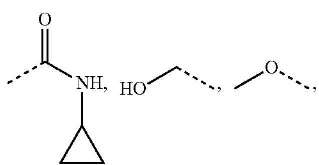

1H-pyrazolyl and 1H-1,2,4-triazolyl, wherein the $NH_2$,

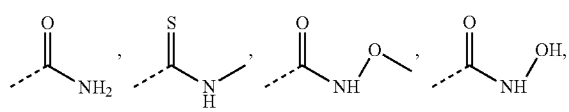

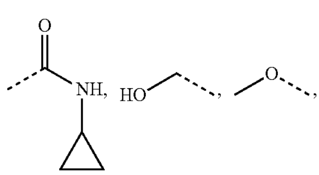

1H-pyrazolyl and 1H-1,2,4-triazolyl are optionally substituted by R, and the number of R is 1, 2 or 3, the other variables are as defined in the present disclosure.

In some embodiments of the present disclosure, the $R_3$ is selected from $NH_2$,

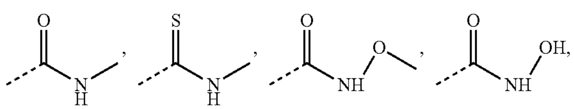

-continued

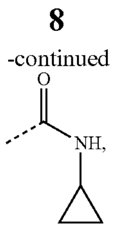

1H-pyrazolyl and 1H-1,2,4-triazolyl, wherein the $NH_2$,

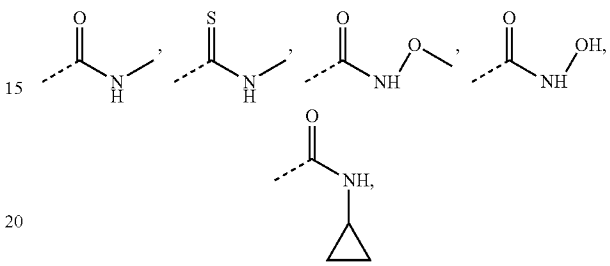

1H-pyrazolyl and 1H-1,2,4-triazolyl are optionally substituted by R, and the number of R is 1, 2 or 3, the other variables are as defined in the present disclosure.

In some embodiments of the present disclosure, the $R_3$ is selected from $NH_2$, wherein the $NH_2$, are optionally substituted by R, and the number of R is 1, 2 or 3, the other variables are as defined in the present disclosure.

In some embodiments of the present disclosure, the $R_3$ is selected from $NH_2$,

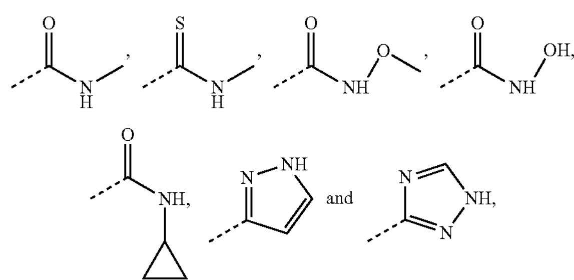

wherein the $NH_2$,

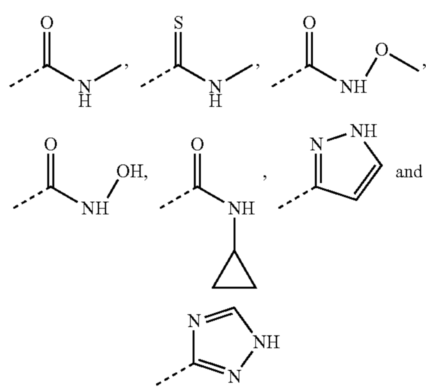

are optionally substituted by R, and the number of R is 1, 2 or 3, the other variables are as defined in the present disclosure.

In some embodiments of the present disclosure, the $R_3$ is selected from $NH_2$,

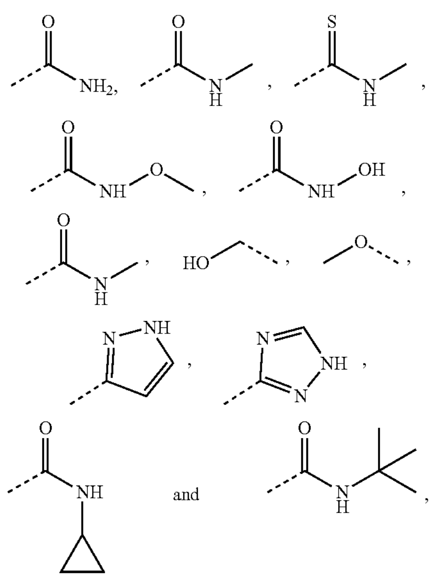

the other variables are as defined in the present disclosure.

In some embodiments of the present disclosure, the $R_3$ is selected from $NH_2$,

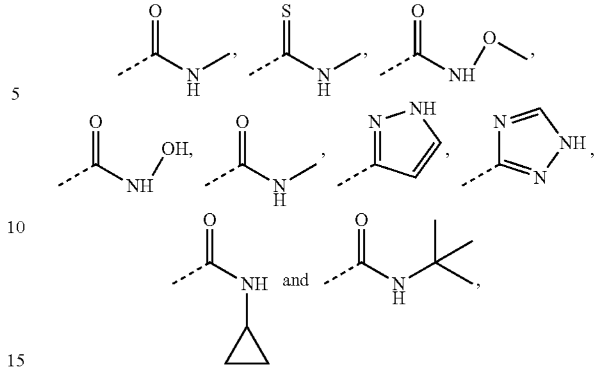

the other variables are as defined in the present disclosure.

In some embodiments of the present disclosure, the ring A is selected from phenyl, benzo[d]oxazole, quinolinyl and quinazolinyl, the other variables are as defined in the present disclosure.

In some embodiments of the present disclosure, the ring A is selected from

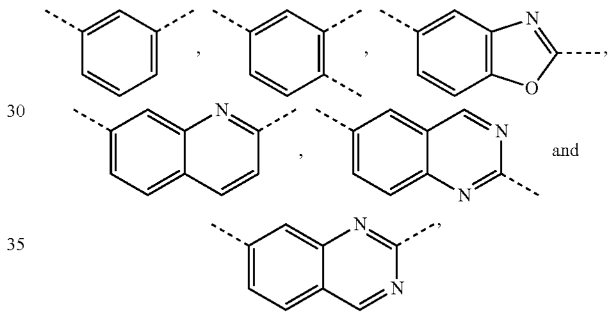

the other variables are as defined in the present disclosure.

In some embodiments of the present disclosure, the ring A is selected from

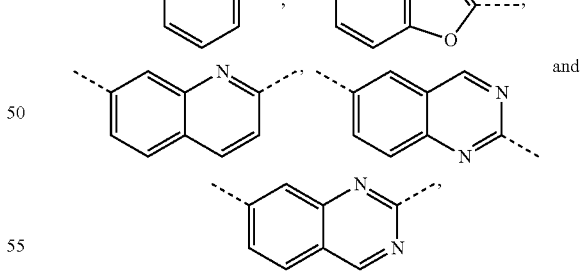

the other variables are as defined in the present disclosure.

In some embodiments of the present disclosure, the moiety

A $(R_3)_n$ is selected from

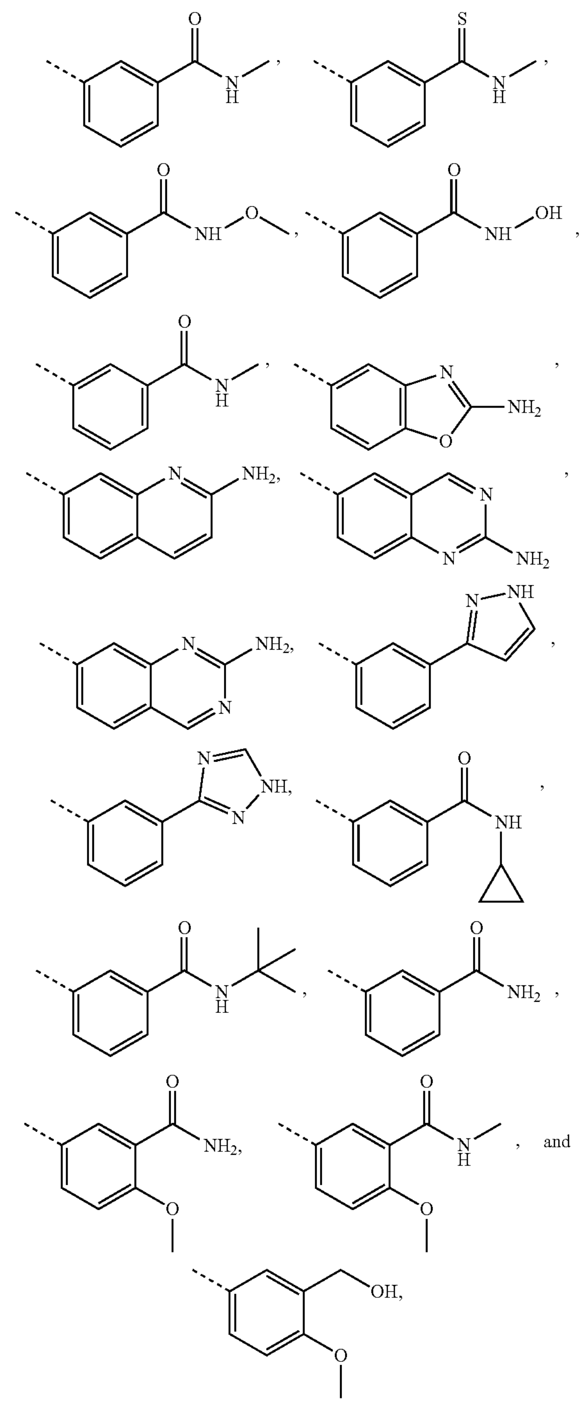

the other variables are as defined in the present disclosure.

In some embodiments of the resent disclosure, the moiety selected from the other variables are as defined in the present disclosure.

In some embodiments of the present disclosure, $D_1$, $D_2$, $D_3$ and $D_4$ described above are respectively selected from a single bond, —$CH_2$—, —$CH_2CH_2$—, —O— and and at least one of $D_1$, $D_2$, $D_3$ and $D_4$ is not a single bond, the other variables are as defined in the present disclosure.

In some embodiments of the present disclosure, $D_5$, $D_6$, $D_7$ and $D_8$ described above are respectively selected from a single bond, —$CH_2$—, —O—, —NH—, and and at least one of $D_5$, $D_6$, $D_7$ and $D_8$ is not a single bond, the other variables are as defined in the present disclosure.

In some embodiments of the present disclosure, the moiety
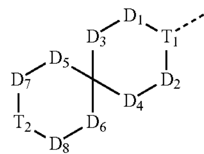
is selected from
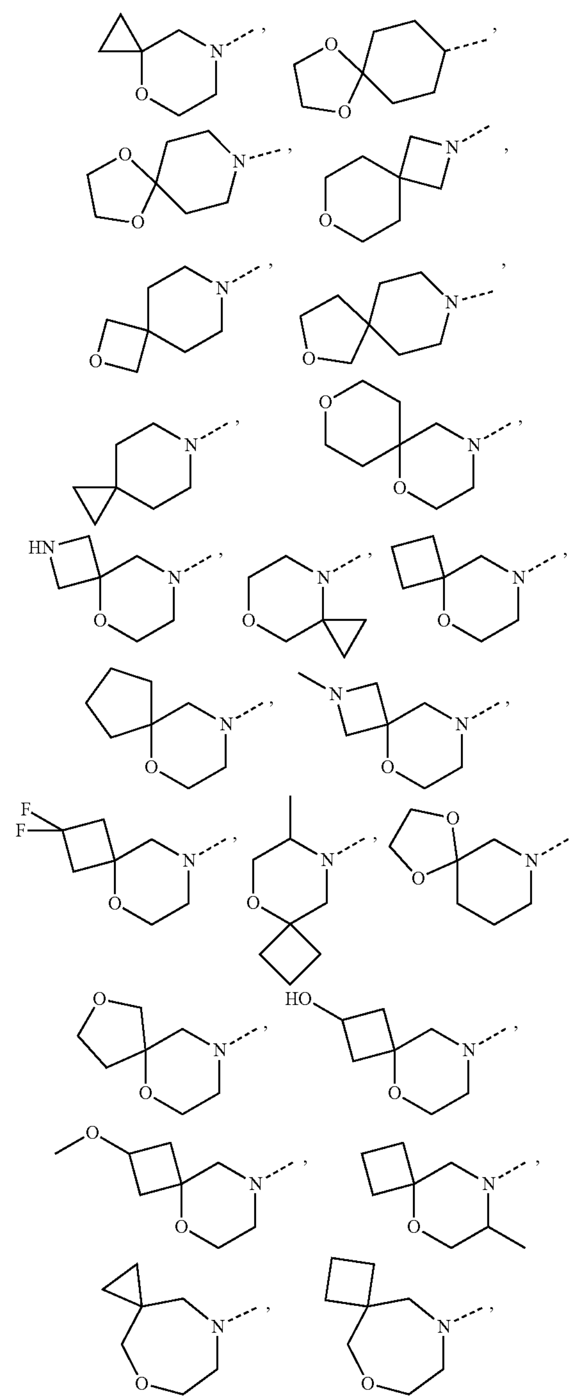
-continued
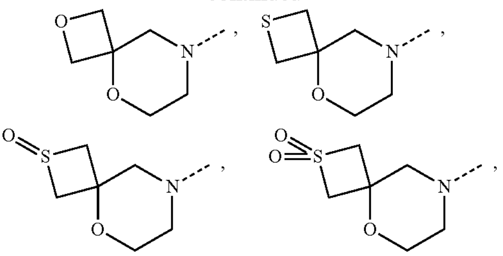
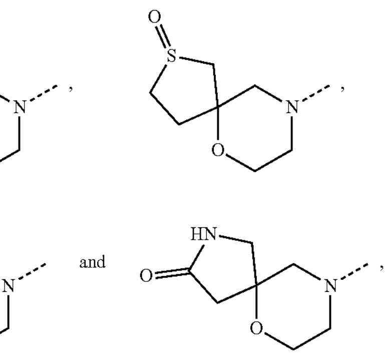
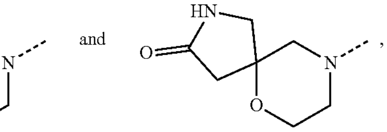
the other variables are as defined in the present disclosure.
In some embodiments of the present disclosure, the moiety
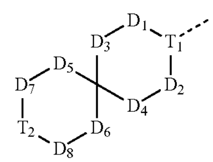
is selected from
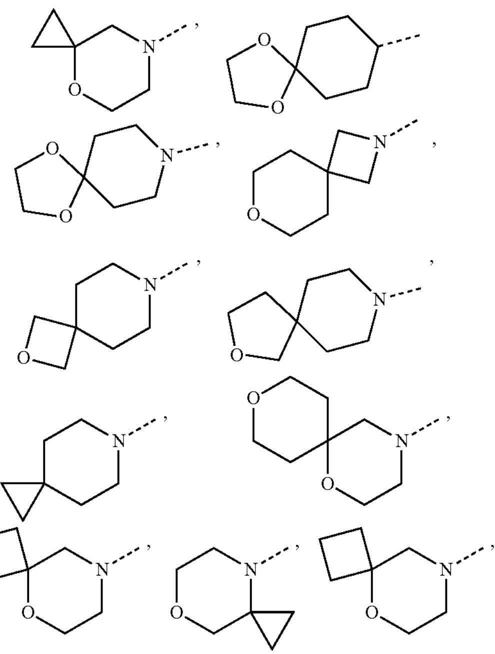

-continued
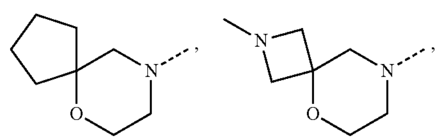
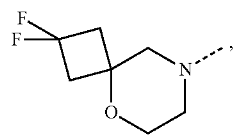
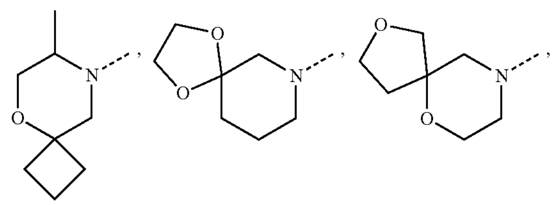
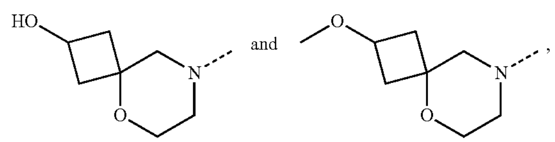
the other variables are as defined in the present disclosure.
In some embodiments of the present disclosure, the compound, the pharmaceutical acceptable salt thereof or the isomer thereof are selected from:
(I-1)
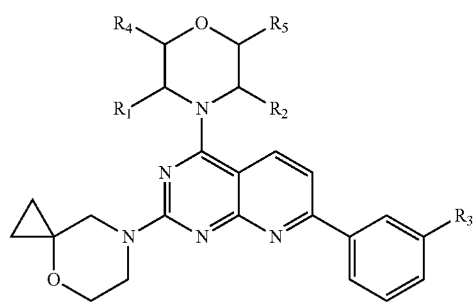
(I-2)
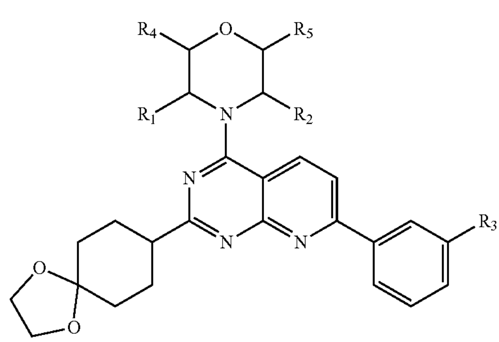
-continued
(I-3)
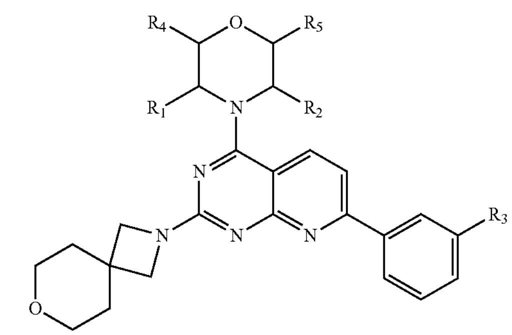
(I-4)
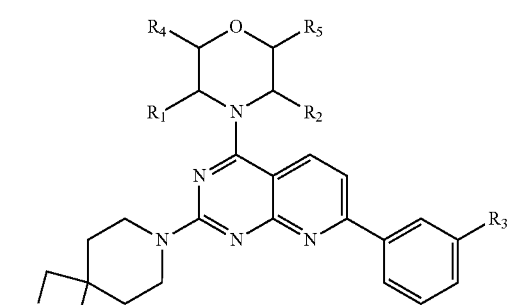
(I-5)
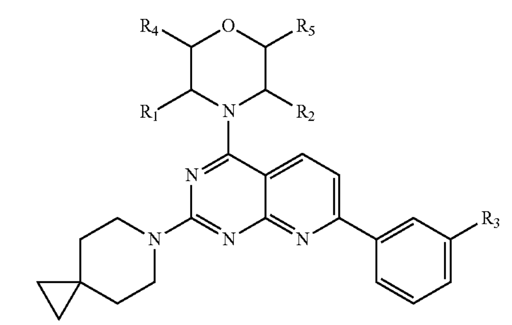
(I-6)
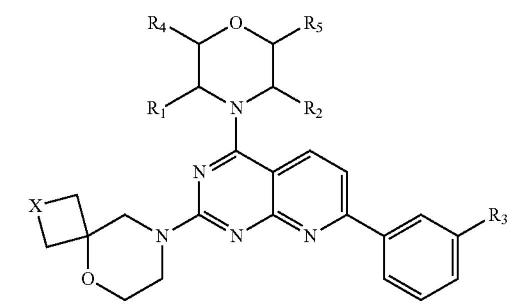
(I-7)
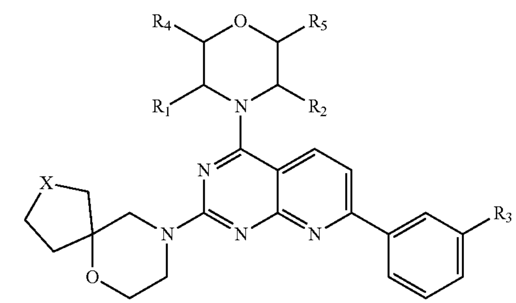

-continued
(I-8)
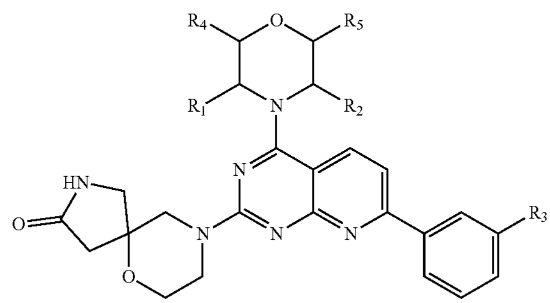
(I-9)
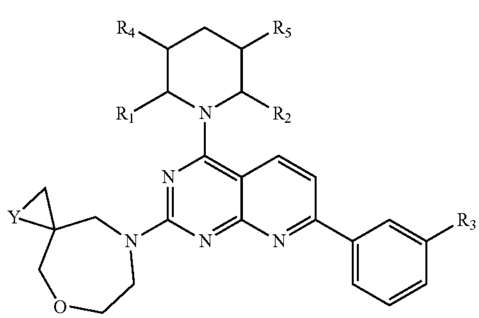
(IV-1)
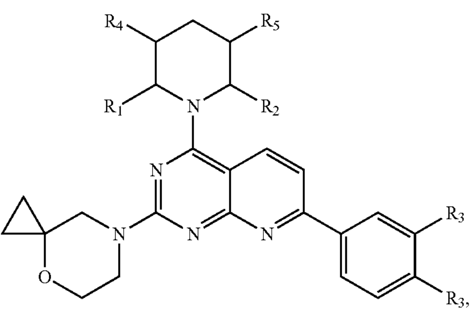
wherein $R_1$, $R_2$, $R_3$, $R_4$ and $R_5$ are as defined above, and X is selected from —$CH_2$—, —NH—, —O—,
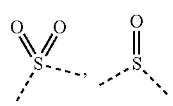
and —S—.
The present disclosure also has some embodiments derived from any combination of the variables described above.
The invention also provides a compound as shown below, a pharmaceutical acceptable salt thereof or an isomer thereof,
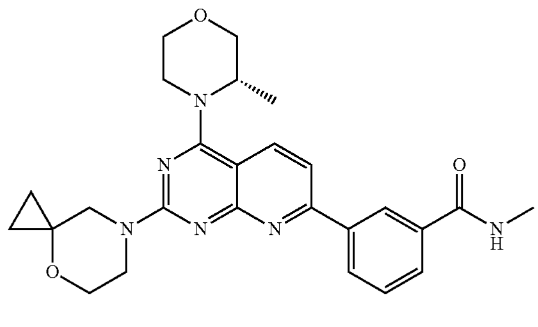
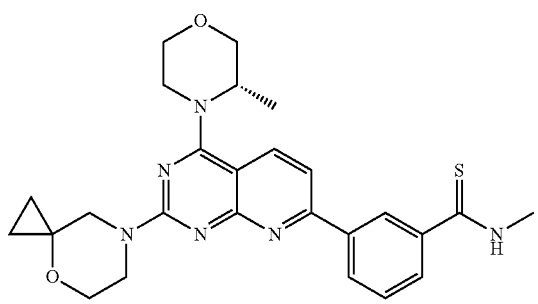
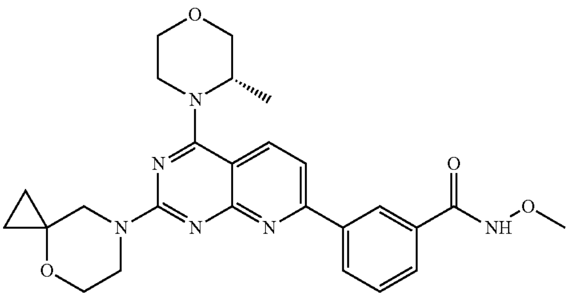
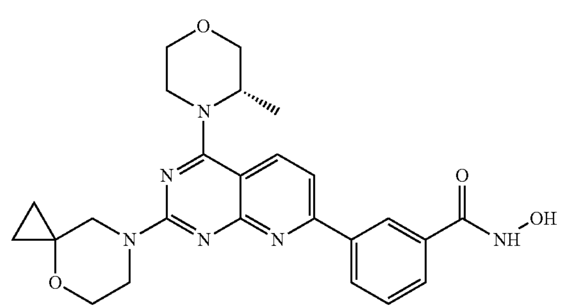
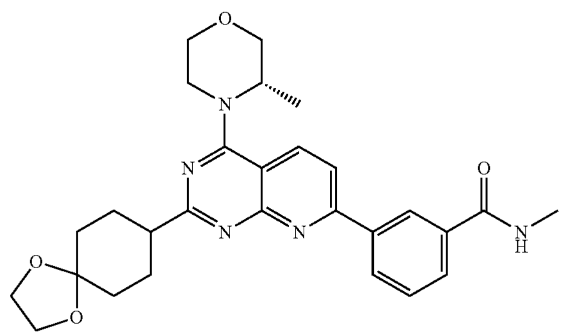

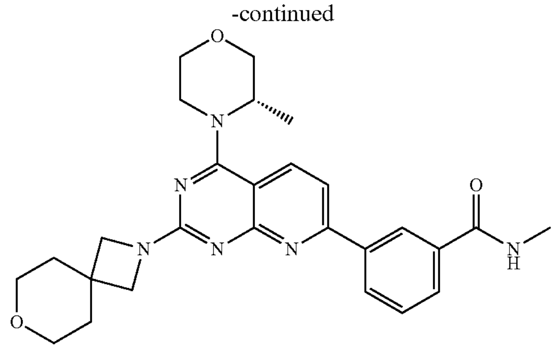
O
N
N
N
N
N
O
N
H
O
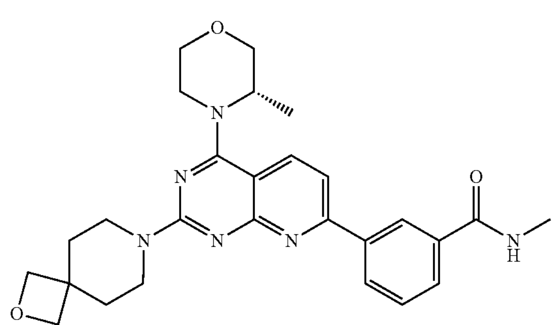
O
N
N
N
N
N
O
N
H
O
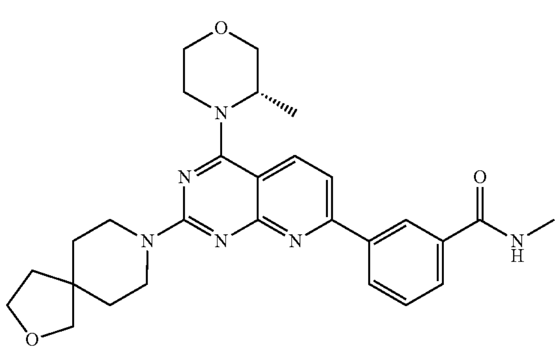
O
N
N
N
N
N
O
N
H
O
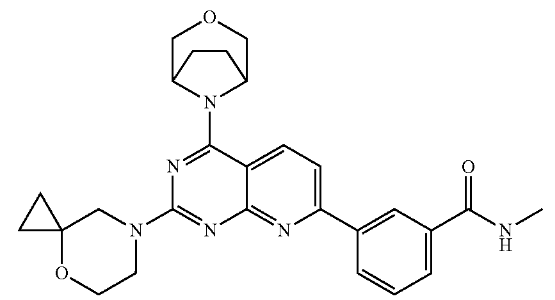
O
N
N
N
N
N
O
N
H
O
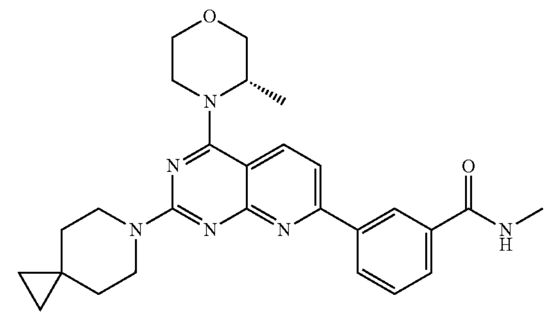
O
N
N
N
N
N
O
N
H
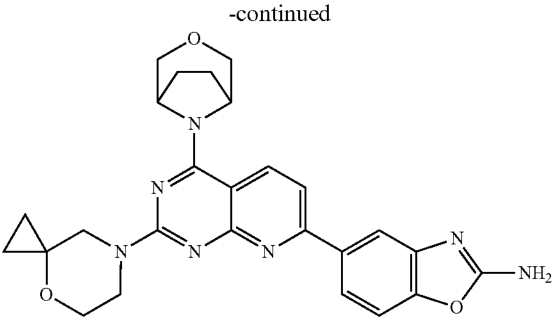
O
N
N
N
N
N
N
NH2
O
O
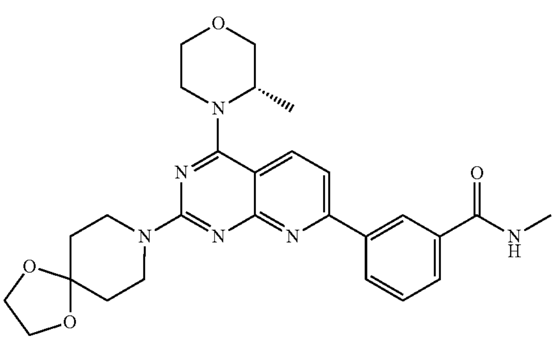
O
N
N
N
N
N
O
N
H
O
O
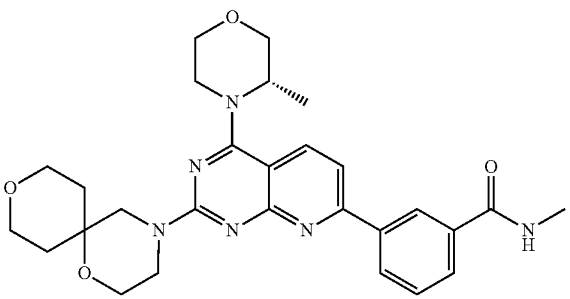
O
N
N
N
N
N
O
N
H
O
O
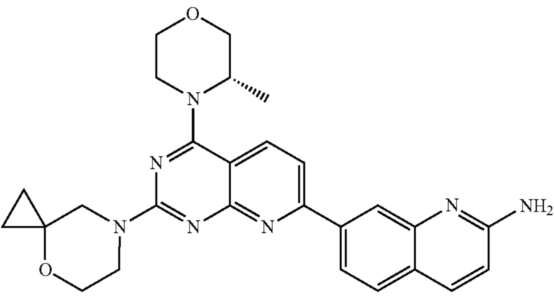
O
N
N
N
N
N
N
NH2
O
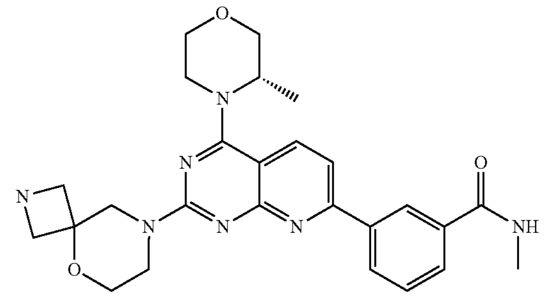
O
N
N
N
N
N
N
O
NH
O -continued
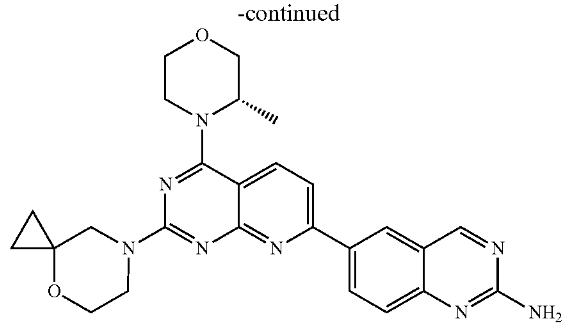
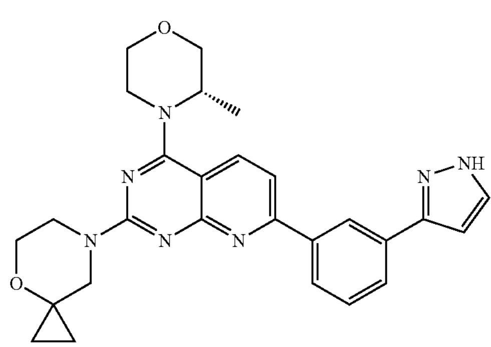
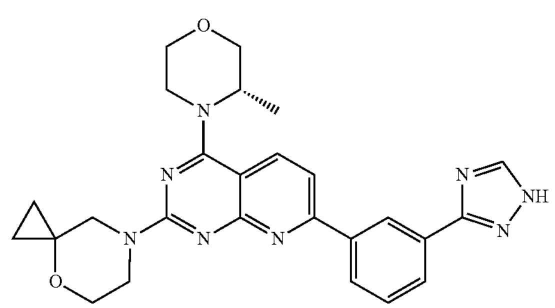
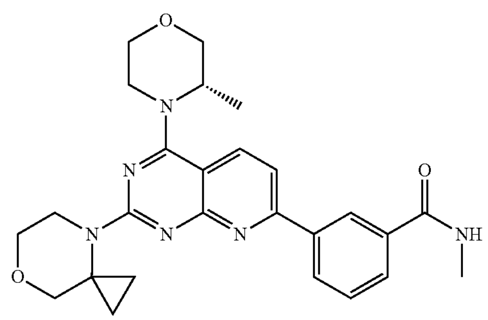
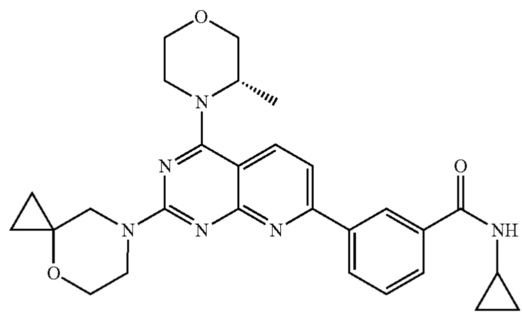
-continued
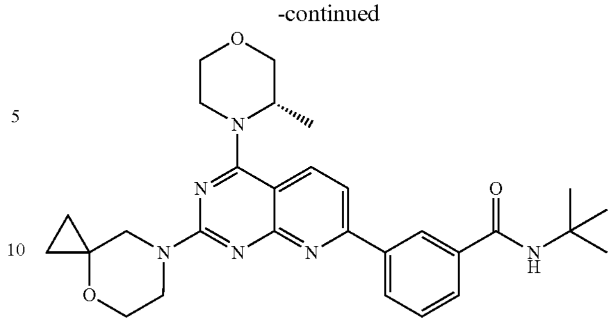
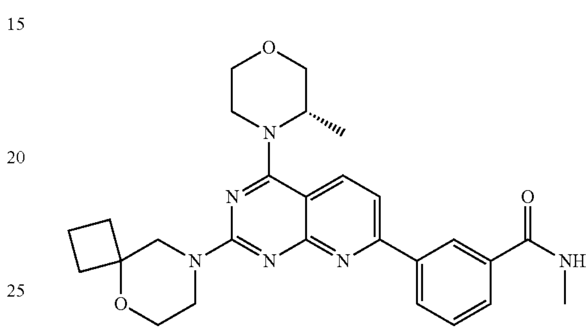
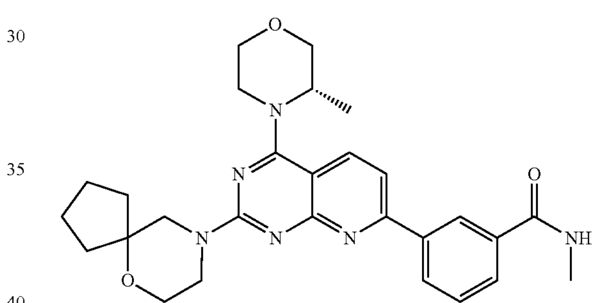
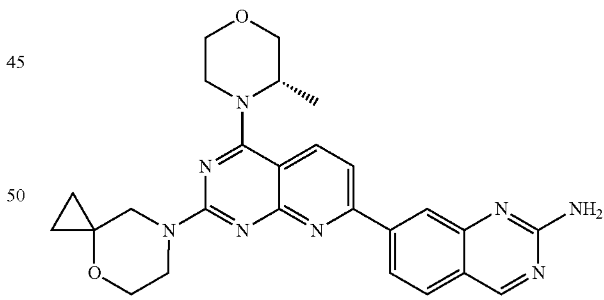
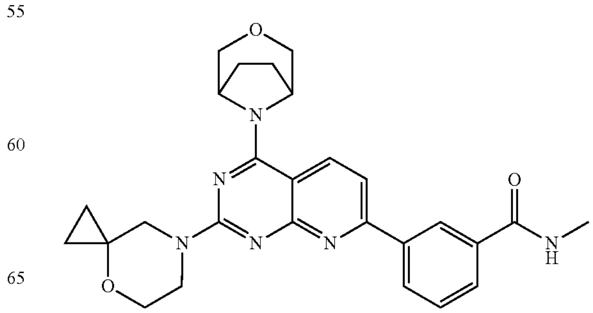

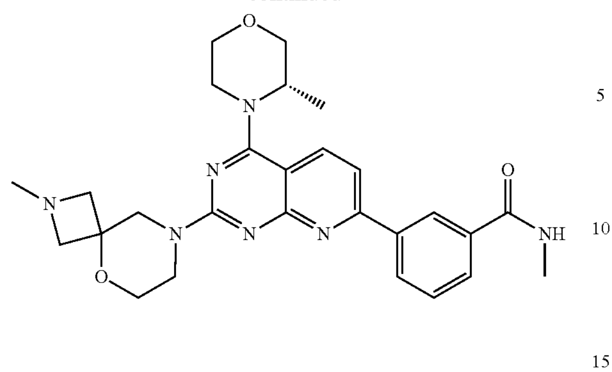
O
N
N
N
N
N
NH
O
O
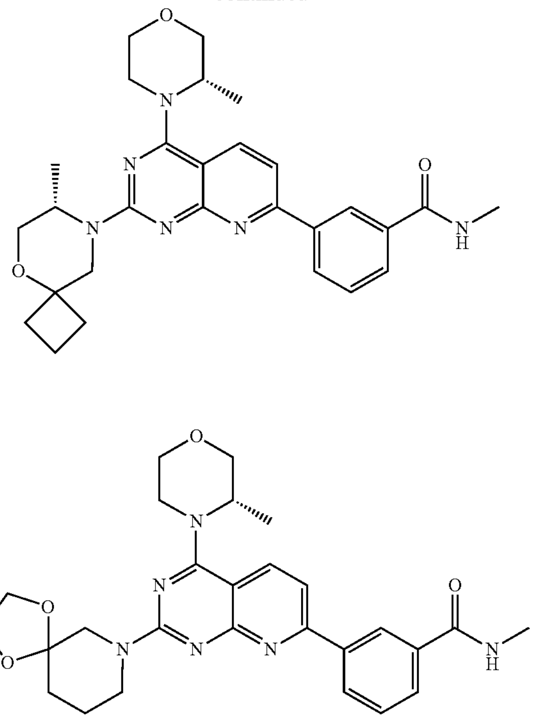
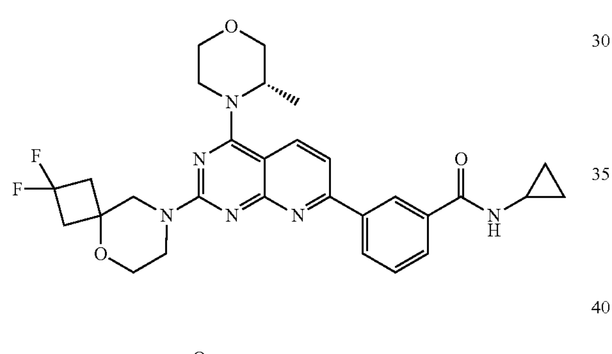
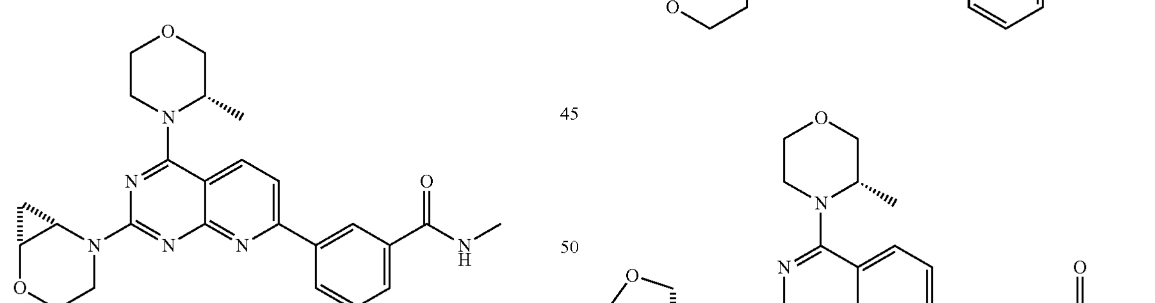
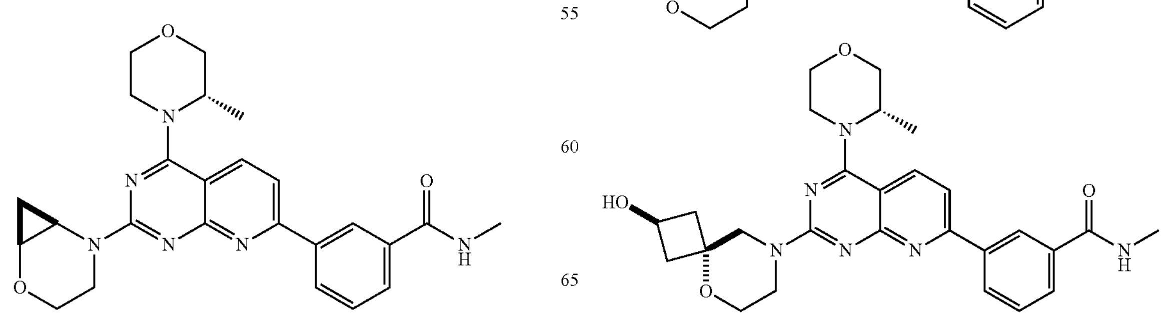
HO

-continued
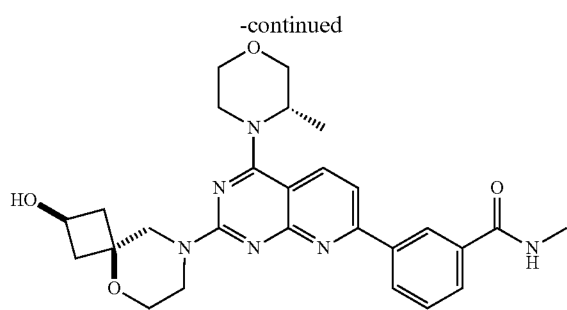
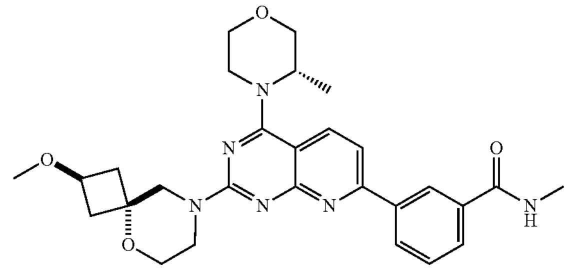
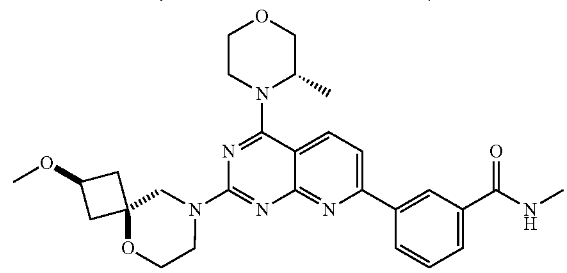
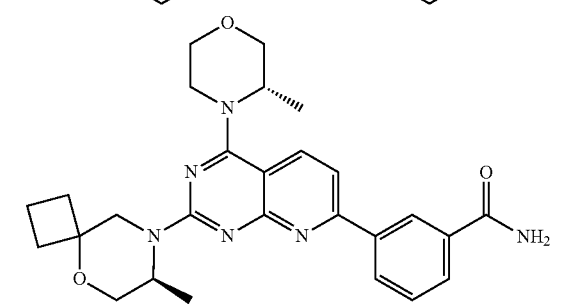
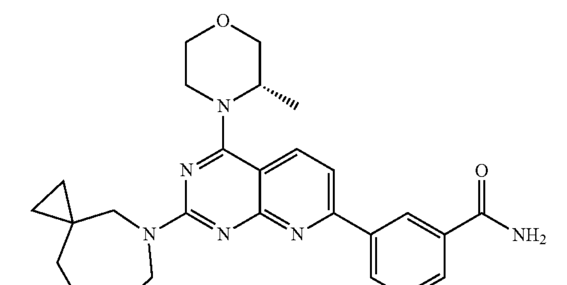
-continued
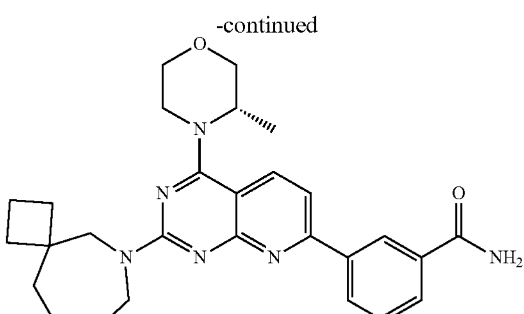
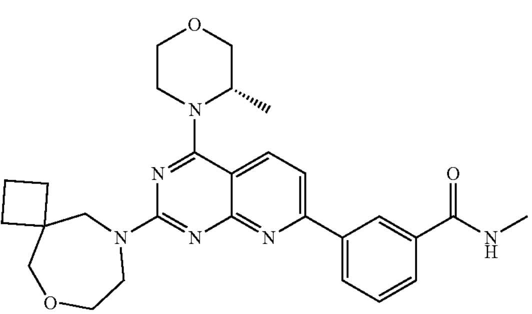
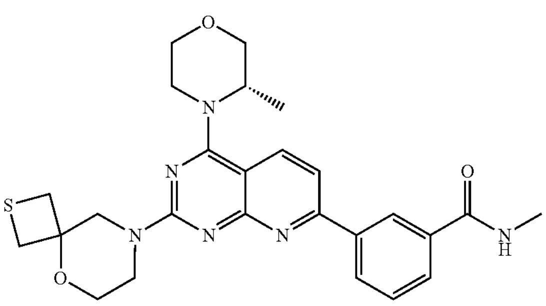
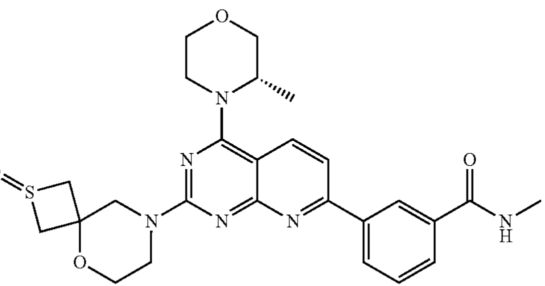

-continued
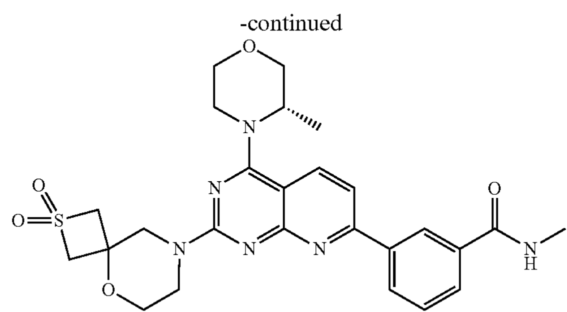
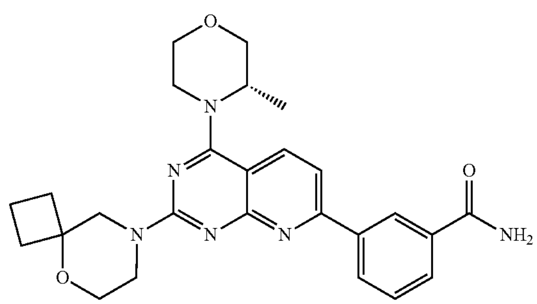
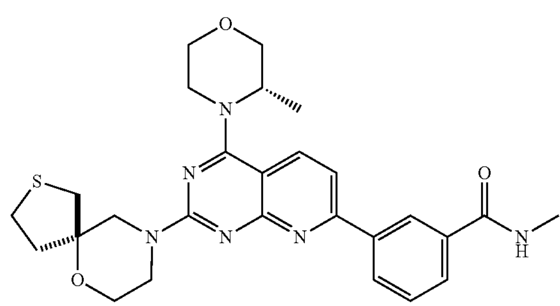
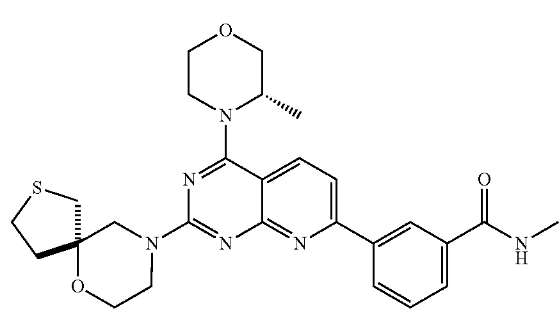
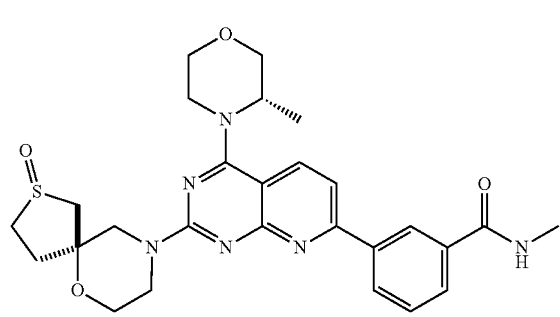
-continued
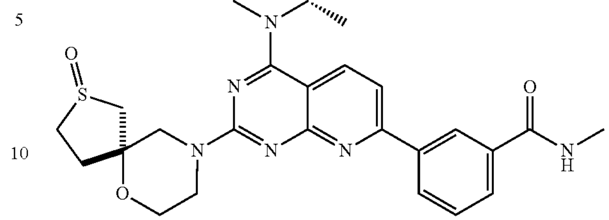
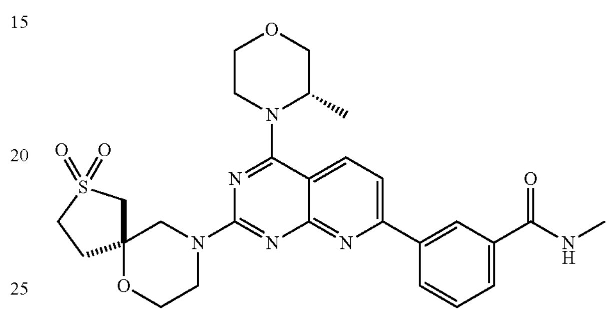
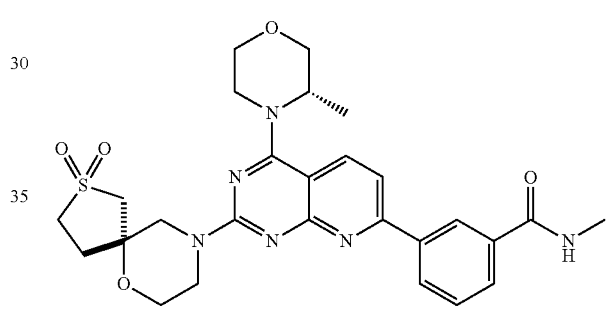
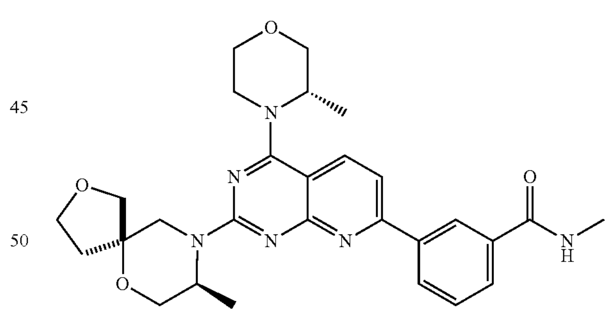
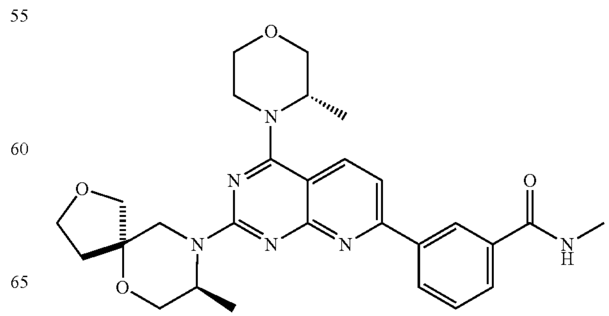

-continued
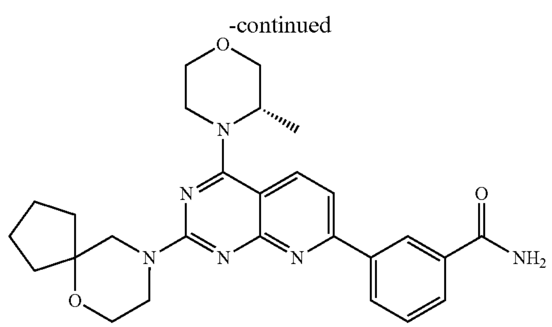
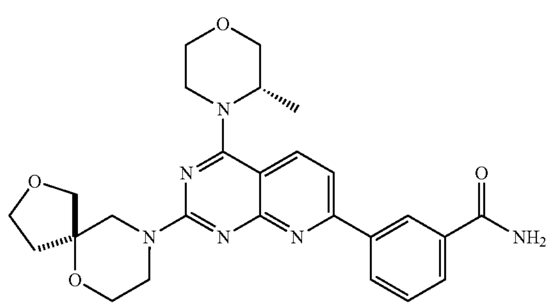
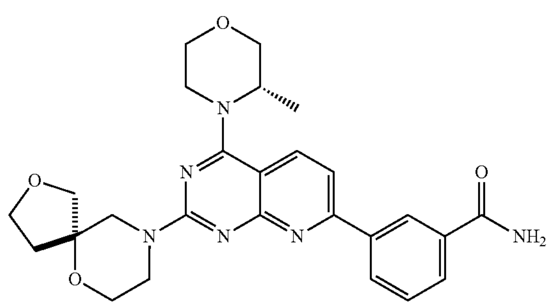
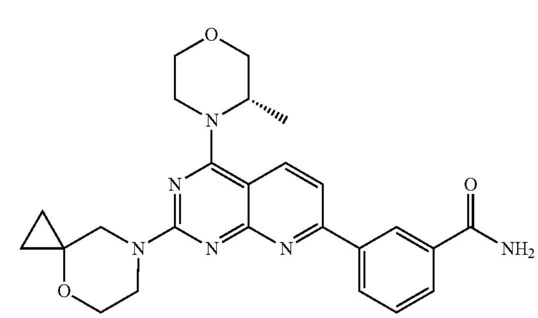
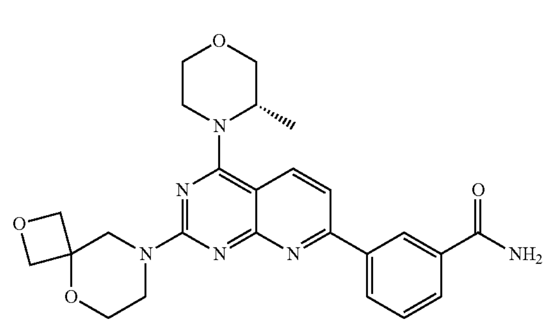
-continued
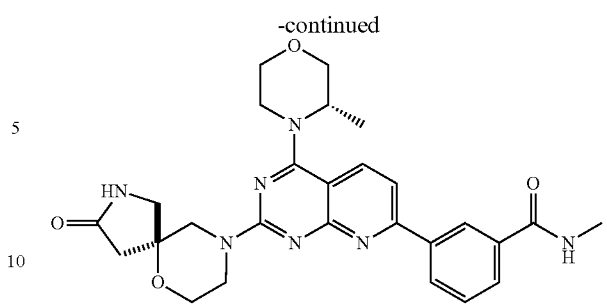
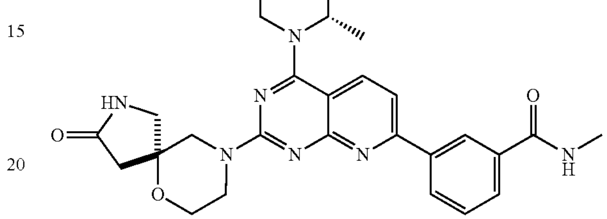
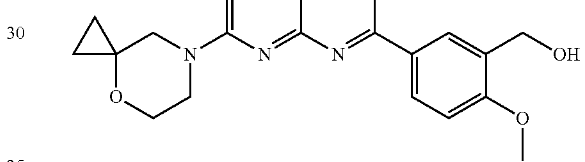
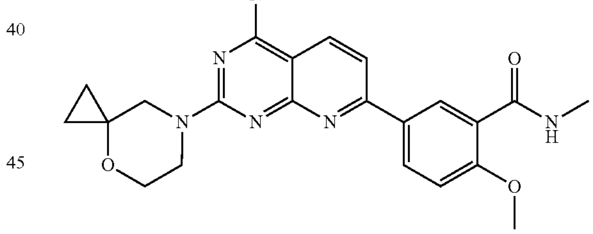
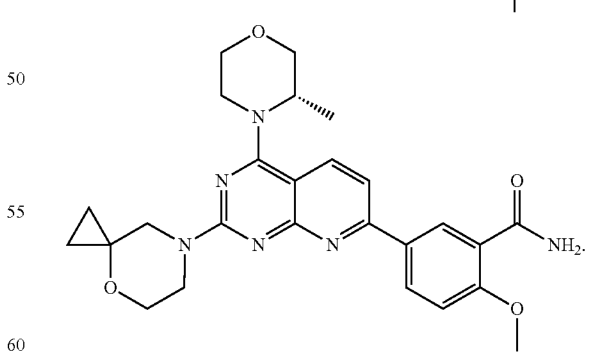
The present disclosure also provides a pharmaceutical composition, which comprises a therapeutically effective amount of the compound, the pharmaceutically acceptable salt thereof or the isomer thereof described above as an active ingredient, and a pharmaceutically acceptable carrier.

The present disclosure also provides a use of the compound, the pharmaceutically acceptable salt thereof or the isomer thereof described above or the pharmaceutical composition described above in the manufacture of a medicament for treating mTORC1/2 dual complex-related diseases.

The present disclosure also provides a use of the compound, the pharmaceutically acceptable salt thereof or the isomer thereof described above or the pharmaceutical composition described above in the manufacture of a medicament for treating breast cancer, breast cancer, head and neck cancer, and colorectal cancer.

Technical Effect:

The compounds of the present disclosure were tested for mTORC½ kinase activity, and the data show that the compounds of the present disclosure have significant or even unexpected mTOR kinase inhibitory activity, which are superior to the current clinical compound AZD2014.

The compounds of the present disclosure have obvious proliferative inhibitory activity against MCF-7, N87 and OE-21 cells, and have certain proliferative inhibitory activity against HT-29 cells.

PK results show that the compounds of the present disclosure have a bioavailability of near 100%, and are excellent developable molecules for oral administration.

In the MCF-7 transplanted tumor model, some compounds have the same efficacy as AZD2014. The compounds of the present disclosure have the potential to become inhibitors against a variety of tumors.

Definition and Description

Unless otherwise indicated, the following terms and phrases used herein are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present disclosure that contain both basic and acidic functional groups can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis- and trans-isomers, (−)- and (+)-enantiomers, (R)- and (S)-enantiomers, diastereomers, (D)-isomers, (L)-isomers, and racemic and other mixtures thereof, such as enantiomers or diastereomers enriched mixtures, all of which are within the scope of the present disclosure. Additional asymmetric carbon atoms may be present in substituents such as alkyl. All these isomers and their mixtures are included within the scope of the present disclosure.

Unless otherwise indicated, the terms "enantiomers" or "optical isomers" refer to stereoisomers which are mirror images of each other.

Unless otherwise indicated, the terms "cis/trans-isomer" or "geometric isomer" are caused by the inability of a double bond or a single bond of a ring-forming carbon atom to rotate freely.

Unless otherwise indicated, the term "diastereomer" refers to a stereoisomer in which a molecule has two or more chiral centers, and there is non-mirror image relationship between molecules.

Unless otherwise indicated, a wedged solid bond ( ) and a wedged dashed bond ( ) represent the absolute configuration of a stereocenter, a straight solid bond ( ) and a straight dashed bond ( ) represent the relative configuration of a stereocenter, a wave line ( ) represents a wedged solid bond ( ) or a wedged dashed bond ( ), or a wave line ( ) represents a straight solid bond ( ) or a straight dashed bond ( ).

The compounds of the disclosure may be specific. Unless otherwise indicated, the term "tautomer" or "tautomeric form" means that at room temperature, the isomers of different functional groups are in dynamic equilibrium and can be quickly converted to each other. If tautomer is possible (e.g. in solution), the chemical equilibrium of the tautomer can be reached. For example, proton tautomer (also known as prototropic tautomer) include interconversions via proton migration, such as keto-enol isomerization and imine-enamine isomerization. Valence tautomer includes interconversion formed by recombination of some bonding electrons. A specific example of the keto-enol tautomerization is the interconversion between two tautomers of pentane-2,4-dione and 4-hydroxypent-3-en-2-one.

Unless otherwise indicated, the term “enriched in an isomer”, “isomer enriched”, “enriched in an enantiomer” or “enantiomer enriched” refers to that the content of the isomer or enantiomer is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise indicated, the terms “isomer excess” or “enantiomer excess” refer to the difference between the relative percentages of two isomers or two enantiomers. For example, if the content of one isomer or enantiomer is 90%, and the content of the other isomer or enantiomer is 10%, the isomer or enantiomeric excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compounds of the present disclosure may contain atomic isotopes in unnatural proportions on one or more of the atoms constituting the compound. For example, the compound can be radiolabeled with a radioactive isotope, such as tritium ($^{3}H$), iodine-125 ($^{125}I$) or C-14 ($^{14}C$). As another example, deuterated drugs can be obtained by replacing hydrogen by deuterium. The bond between deuterium and carbon is stronger than the bond between ordinary hydrogen and carbon. Compared with non-deuterated drugs, deuterated drugs have the advantages of reduced toxic and side effects, increased drug stability, enhanced efficacy, prolonged biological half-life of drugs, and the like. Transformations of all isotopic compositions of the compounds of the present disclosure, whether radioactive or not, are included within the scope of the disclosure. The term “pharmaceutically acceptable carrier” refers to any agent or carrier medium which is capable of delivering an effective amount of the active substance of the present disclosure, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to those skilled in the cosmetic field or the topical pharmaceutical field.

“Optional” or “optionally” means that the subsequent event or condition may occur but not requisite, that the term includes the instance in which the event or condition occurs and the instance in which the event or condition does not occur.

The term “substituted” means one or more than one hydrogen atom(s) on a specific atom are substituted by the substituent, including deuterium and hydrogen variants, as long as the valence of the specific atom is normal and the substituted compound is stable. When the substituent is an oxygen (i.e. =O), it means two hydrogen atoms are substituted. Positions on an aromatic ring cannot be substituted by a ketone. The term “optionally substituted” means an atom can be substituted by a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —$(CRR)_0$—, it means that the linking group is a single bond.

When one of the variables is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a substituent is attachable to more than one atom on a ring, such substituent can be bonded to any atom of the ring. For example, the structural unit

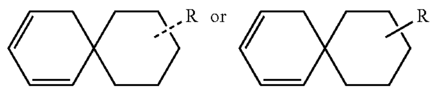

means that the substituent R can be located at any position on cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring. When the enumerative linking group does not indicate the direction for linking, the direction for linking is arbitrary, for example, the linking group L contained in

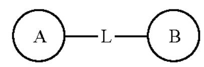

is -M-W-, then -M-W- can link ring A and ring B to form

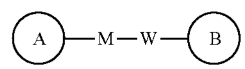

in the direction same as left-to-right reading order, and form

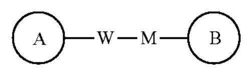

in the direction contrary to left-to-right reading order. A combination of the linking group, substituent and/or variants thereof is allowed only when such combination can result in a stable compound.

Unless otherwise specified, the term "heterocyclo" refers to a stable monocyclic, bicyclic or tricyclic ring containing a heteroatom or a heteroatom group, which are saturated, and contain carbon atoms and 1, 2, 3 or 4 ring heteroatoms respectively selected from N, O and S. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms respectively selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)p, p is 1 or 2). It is worth noting that the total number of S and O atom of an aromatic heterocycle is not more than one. A bridged ring is formed when one or more than one atom (i.e., C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Unless otherwise specified, the term "5-6 membered heterocycloalkyl" by itself or in combination with other terms, refers to a saturated cyclic group consisting of 5 to 6 ring atoms, respectively, of which 1, 2, 3 or 4 ring atoms are independently selected from O, S and N heteroatoms, the rest are carbon atoms, wherein the nitrogen atom is optionally quatemized, and the nitrogen and sulfur heteroatoms are optionally oxidized (i.e. NO and S(O), p is 1 or 2). It includes both monocyclic and bicyclic systems, wherein the bicyclic system includes a spiro ring, a fused ring, and a bridge ring. In addition, for the "5-6 membered heterocycloalkyl", a heteroatom may occupy connection position of the heterocycloalkyl to the rest of the molecule. The 5-6 membered heterocycloalkyl includes 5-membered and 6-membered heterocycloalkyl. Examples of 5-6 membered heterocycloalkyl include, but are not limited to, pyrrolidinyl, pyrazolidinyl, imidazolidinyl, tetrahydrothiophenyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl or homopiperidinyl and the like.

Unless otherwise specified, the terms "6-10 membered heteroaryl ring" and "6-10 membered heteroaryl" of the present disclosure can be used interchangeably. The term "6-10 membered heteroaryl" refers to a cyclic group consisting of 6 to 10 ring atoms with a 7-conjugated electron system, wherein 1, 2, 3 or 4 ring atoms are heteroatoms respectively selected from O, S and N, the rest are carbon atoms. It can be monocyclic, fused bicyclic, or fused tricyclic system, wherein each ring is aromatic. The nitrogen atom is optionally quatemized, and the nitrogen and sulfur heteroatoms are optionally oxidized (i.e. NO and $S(O)_P$, p is 1 or 2). The 6-10 membered heteroaryl can be connected to the rest part of the molecule via heteroatom or carbon atom. The 6-10 membered heteroaryl includes 6-8 membered, 6-7 membered, 6-9 membered, 6 membered, and 10 membered heteroaryl. Examples of the 6-10 membered heteroaryl include, but are not limited to, furanyl (including 2-furanyl and 3-furanyl, etc.), pyridyl (including 2-pyridyl, 3-pyridyl, 4-pyridyl, etc.), pyrazinyl, pyrimidinyl (including 2-pyrimidinyl and 4-pyrimidinyl, etc.), benzthiazolyl (including 5-benzothiazolyl, etc.), purinyl, benzimidazolyl (including 2-benzimidazolyl, etc.), benzoxazolyl, indolyl (including 5-indolyl, etc.), isoquinolinyl (including 1-isoquinolinyl and 5-isoquinolinyl, etc.), quinoxalinyl (including 2-quinoxalinyl and 5-quinoxalinyl, etc.) or quinolinyl (including 3-quinolinyl and 6-quinolinyl, etc.).

Unless otherwise specified, the terms "5-6 membered heteroaryl ring" and "5-6 membered heteroaryl" of the present disclosure can be used interchangeably. The term "5-6 membered heteroaryl" refers to a cyclic group consisting of 5 to 6 ring atoms with a 7-conjugated electron system, wherein 1, 2, 3 or 4 ring atoms are heteroatoms respectively selected from O, S and N, the rest are carbon atoms. The nitrogen atom is optionally quatemized, and the nitrogen and sulfur heteroatoms are optionally oxidized (i.e. NO and S(O), p is 1 or 2). The 5-6 membered heteroaryl can be connected to the rest part of the molecule via heteroatom or carbon atom. The 5-6 membered heteroaryl includes 5 membered and 6 membered heteroaryl. Examples of the 5-6 membered heteroaryl include, but are not limited to, pyrrolyl (including N-pyrrolyl, 2-pyrrolyl and 3-pyrrolyl etc.), pyrazolyl (including 2-pyrazolyl and 3-pyrazolyl etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furanyl (including 2-furanyl and 3-furanyl, etc.), thienyl (including 2-thienyl and 3-thienyl, etc.), pyridyl (including 2-pyridyl, 3-pyridyl and 4-pyridyl, etc.), pyrazinyl or pyrimidyl (including 2-pyrimidyl and 4-pyrimidyl, etc.).

Unless otherwise specified, "$C_{3-6}$ cycloalkyl" refers to a saturated cyclic hydrocarbyl consisting of 3 to 6 carbon atoms, which is a monocyclic and bicyclic system, and the $C_{3-6}$ cycloalkyl includes $C_{3-5}$, $C_{4-5}$ and $C_{5-6}$ cycloalkyl, etc.; it can be monovalent, divalent or polyvalent. Examples of $C_{3-6}$ cycloalkyl include, but are not limited to, cyclopropyl, cyclobutyl, cyclopentyl, cyclohexyl, and the like.

In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen heteroatom is optionally quaternized. The heteroatom or heteroatom group can be located at any internal position of a heterohydrocarbyl, including the position where the hydrocarbyl connects to the rest part of the molecule. However, the terms "alkoxy", "alkylamino" and "alkylthio" (or thioalkoxy) are used by the conventional expressions and refer to an alkyl group that is connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, and —$CH_2$—$CH_2$—$S(O)_2$—$CH_3$. Up to two consecutive heteroatoms can be present, such as, —$CH_2$—NH—$OCH_3$.

Unless otherwise specified, the term "alkyl" refers to a linear chain or branched saturated hydrocarbon group, can be mono-substituted (e.g. —$CH_2F$) or poly-substituted (e.g. —$CF_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl, etc.; it may be monovalent (such as methyl), divalent (such as methylene) or multivalent (such as methine). Examples of $C_{1-3}$ alkyl include, but are not limited to, methyl (Me), ethyl (Et), propyl (including n-propyl and isopropyl), and the like.

Unless otherwise specified, the term "$C_{1-3}$ alkoxy" refers to those alkyl containing 1 to 3 carbon atoms that are connected to the rest of the molecule by one oxygen atom. The $C_{1-3}$ alkoxy group includes $C_{1-2}$, $C_{2-3}$, $C_3$ and $C_2$ alkoxy. Examples of $C_{1-3}$ alkoxy include, but are not limited to, methoxy, ethoxy, propoxy (including n-propoxy and isopropoxy) and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo ($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, N, O and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, $C_{n-n+m}$ or $C_n$–$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; in the same way, n to n+m means that the number of atoms in the ring is n to n+m, for example, 3-12 membered rings include 3 member ring, 4-membered ring, 5-membered ring, 6-membered ring, 7-membered ring, 8-membered ring, 9-membered ring, 10-membered ring, 11-membered ring, and 12-membered ring, also includes any range from n to n+m, for example, 3-12 membered rings include 3-6 member ring, 3-9 member ring, 5-6 member ring, 5-7 member ring, 6-7 member ring, 6-8 member ring, and 6-10 member ring, and the like.

The compounds of the present disclosure can be prepared by a variety of synthetic methods well known to those skilled in the art, including the specific embodiments listed below, the embodiments formed by combining the specific embodiments listed below with other chemical synthesis methods, and equivalent embodiments well known to those skilled in the art, preferred embodiments include, but are not limited to, the embodiments of the present disclosure.

The compounds of the present disclosure may have various uses or indications, including but not limited to, the specific uses or indications listed in this application.

The solvent used in the present disclosure is commercially available.

Each embodiment of the present disclosure involves neutral purification for high performance liquid chromatography purification.

The present invention employs the following abbreviations: aq represents water; HATU represents O-(7-azabenzotriazol-1-yl)-N,N,N,N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equal or equivalent; CDI represents carbonyl diimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amino protecting group; BOC represents tert-butylcarbonyl, which is an amino protecting group; HOAc represents acetic acid; $NaCNBH_3$ represents sodium cyanoborohydride; r.t. represents room temperature; O/N represents overnight; TH represents tetrahydrofuran; $Boc_2O$ represents di-tert-butyldicarbonate; TFA represents trifluoroacetic acid; DIPEA represents diisopropylethylamine; $SOCl_2$ represents thionyl chloride; $CS_2$ represents carbon disulfide; TsOH represents p-toluenesulfonic acid; NFSI represents N-fluoro-N-(phenylsulfonyl)benzenesulfonamide; n-$Bu_4NF$ represents tetrabutylammonium fluoride; iPrOH represents 2-propanol; mp represents melting point; LDA represents lithium diisopropylamide; $Pd(PPh_3)_4$ represents tetrakis(triphenylphosphine) palladium; IV represents intravenous injection; PO represents oral administration.

Compounds are named according to conventional naming principles in the art or by ChemDraw® software, the commercially available compounds use their vendor directory names.

DETAILED DESCRIPTION OF THE PREFERRED EMBODIMENT

The present disclosure will be specifically described below by way of embodiments, but the scope of the present disclosure is not limited thereto. The present disclosure has been described in detail herein, and the embodiment of the present disclosure has been disclosed herein. Various modifications and changes may be made to the embodiment of the present disclosure without departing from the spirit and scope of the invention, which will be apparent to the skilled in the art.

Embodiment 1

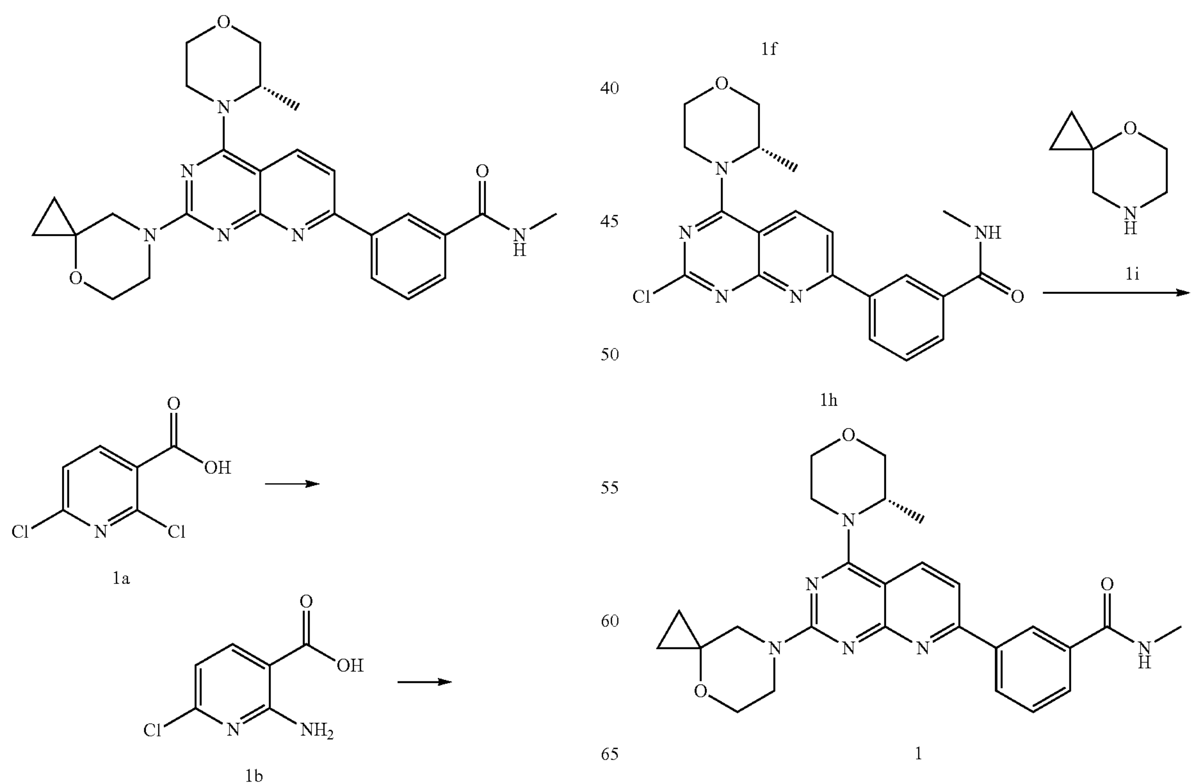

-continued

1c

1d

1e

1f

1g

1h

1i

1

First Step

Compound 1a (20.0 g, 104 mmol, 1.00 eq) and concentrated ammonium hydroxide (200 mL, 1.45 mol, 14.0 eq) were sealed in an autoclave, and stirred at 130° C. for 24 hours under a pressure of about 0.9 MPa. The reaction solution was concentrated to give compound 1b.

MS-ESI calculated for $[M+H]^+$: 173 and 175, found: 173 and 175.

$^1$H NMR (400 MHz, DMSO-$d_6$) δ: 8.03 (d, J=8.0 Hz, 1H), 7.56 (br s, 2H), 6.61 (d, J=8.0 Hz, 1H).

Second Step

Compound 1b (17.0 g, 98.5 mmol, 1.00 eq), ammonium chloride (10.5 g, 197 mmol, 2.00 eq), 1-hydroxybenzotriazole (13.3 g, 98.5 mmol, 1.00 eq), 1-(3-dimethylaminopropyl)-3-ethylcarbodiimide hydrochloride (18.9 g, 98.5 mmol, 1.00 eq) and diisopropylethylamine (38.2 g, 296 mmol, 3.00 eq) were dissolved in N, N-dimethylformamide (200.0 mL). The mixture was stirred at 20° C. for 16 hours. After completion of the reaction, the solvent was removed by rotary evaporation under reduced pressure, followed by addition of water (200 mL) and extraction with ethyl acetate (200 mL×3). The combined organic phase was dried with anhydrous sodium sulfate, filtered, and subjected to column chromatography (1:1 petroleum ether/ethyl acetate, $R_f$=0.4) to give a compound, which was slurried with ethyl acetate (50 mL) for ten minutes to give compound 1c.

$^1$H NMR (400 MHz, DMSO-$d_6$) δ: 7.96 (d, J=8.0 Hz, 2H), 7.62 (br s, 2H), 7.40 (br s, 1H), 6.61 (d, J=8.0 Hz, 1H).

Third Step

Compound 1c (8.00 g, 46.6 mmol, 1.00 eq) and oxalyl chloride (7.1 g, 56.0 mmol, 4.9 mL, 1.00 eq) were sequentially added to toluene (200 mL). The mixture was stirred at 110° C. for 15 hours, then cooled to room temperature, filtered and dried to give compound 1d.

$^1$H NMR (400 MHz, DMSO-$d_6$) δ: 8.24 (d, J=8.0 Hz, 1H), 7.30 (d, J=8.0 Hz, 1H).

Fourth Step

Compound 1d (6.00 g, 30.4 mmol, 1.00 eq) and diisopropylethylamine (11.8 g, 91.1 mmol, 15.9 mL, 3.00 eq) were sequentially added to toluene (100 mL). The mixture was stirred at 70° C. for half an hour, and cooled to room temperature. Phosphorus oxychloride (14.0 g, 91.1 mmol, 8.5 mL, 3.00 eq) was dropwise added into the obtained mixture. The mixture was stirred at 100° C. for 2 hours, cooled to room temperature, concentrated, and purified by column chromatography (3:1 petroleum ether/ethyl acetate, $R_f$=0.4) to give compound 1e.

$^1$H NMR (400 MHz, DMSO-$d_6$) δ: 8.45 (d, J=8.0 Hz, 1H), 7.63 (d, J=8.3 Hz, 1H).

Fifth Step

Compound 1e (1.90 g, 8.10 mmol, 1.00 eq), (S)-2-methylmorpholine (819 mg, 8.10 mmol, 1.00 eq) and diisopropylethylamine (2.09 g, 16.2 mmol, 2.83 mL, 2.00 eq) were dissolved in dichloromethane (50 mL), and the resulting solution was reacted at 25° C. for 2 hours. After completion of the reaction, the reaction solution was concentrated and subjected to column chromatography (3:1 petroleum ether/ethyl acetate) to give compound 1f.

$^1$H NMR (400 MHz, DMSO-$d_6$) δ: 8.47 (d, J=8.8 Hz, 1H), 7.55 (d, J=8.8 Hz, 1H), 4.71-4.72 (m, 1H), 4.12-4.09 (m, 1H), 3.92-3.91 (m, 1H), 3.84-3.74 (m, 1H), 3.73-3.64 (m, 2H), 3.54-3.53 (m, 1H), 1.46 (d, J=6.8 Hz, 3H).

Sixth Step

Compound 1f (1.2 g, 4.01 mmol, 1.00 eq), compound 1g (1.15 g, 4.41 mmol, 1.10 eq), tetrakis(triphenylphosphine) palladium (232 mg, 200 μmol, 0.05 eq) and potassium carbonate (1.66 g, 12.0 mmol, 3.00 eq) were dissolved in water (24 mL) and 1,4-dioxane (120 mL), and the mixture was reacted at 60° C. for 5 hours under nitrogen protection. After completion of the reaction, the reaction solution was concentrated to remove solvent, diluted with water (30 mL), and extracted with ethyl acetate (50 mL×2). The combined organic phase was dried over anhydrous sodium sulfate, filtered, and subjected to rotary evaporation under reduced pressure to dryness, and purified by column chromatography (100% ethyl acetate) to give compound 1h.

$^1$H NMR (400 MHz, DMSO-$d_6$) δ: 8.71 (s, 1H), 8.67 (d, J=4.8 Hz, 1H), 8.55 (d, J=8.8 Hz, 1H), 8.39 (d, J=8.0 Hz, 1H), 8.14 (d, J=8.8 Hz, 1H), 8.01 (d, J=8.0 Hz, 1H), 7.68 (t, J=7.6 Hz, 1H), 4.75 (d, J=6.4 Hz, 1H), 4.17-4.15 (m, 1H), 3.94-3.92 (m, 1H), 3.87-3.77 (m, 1H), 3.72 (s, 2H), 3.59-3.57 (m, 1H), 2.86-2.84 (m, 3H), 1.49 (d, J=6.8 Hz, 3H).

Seventh Step

Compound 1h (50 mg, 126 μmol, 1 eq), 1i (18.8 mg, 126 μmol, 1 eq) and DIPEA (16.2 mg, 126 μmol, 21.89 μL, 1 eq) were dissolved in DMSO (3 mL). The reaction solution was reacted at 70° C. for 20 hours. After completion of the reaction, the reaction solution was purified by high performance liquid chromatography to give compound 1.

MS-ESI calculated for $[M+H]^+$: 475, found: 475.

$^1$H NMR (400 MHz, $CD_3OD$) δ: 8.62 (s, 1H), 8.32-8.30 (m, 2H), 7.96 (d, J=7.2 Hz, 1H), 7.72-7.61 (m, 2H), 4.52 (br s, 1H), 4.09-3.92 (m, 6H), 3.91-3.82 (m, 3H), 3.76-3.74 (m, 3H), 2.99 (s, 3H), 1.49 (d, J=6.8 Hz, 3H), 0.81 (s, 2H), 0.71 (s, 2H).

Embodiment 2

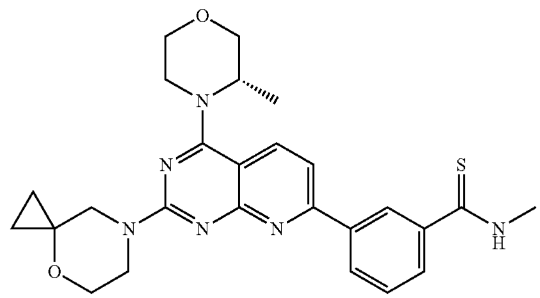

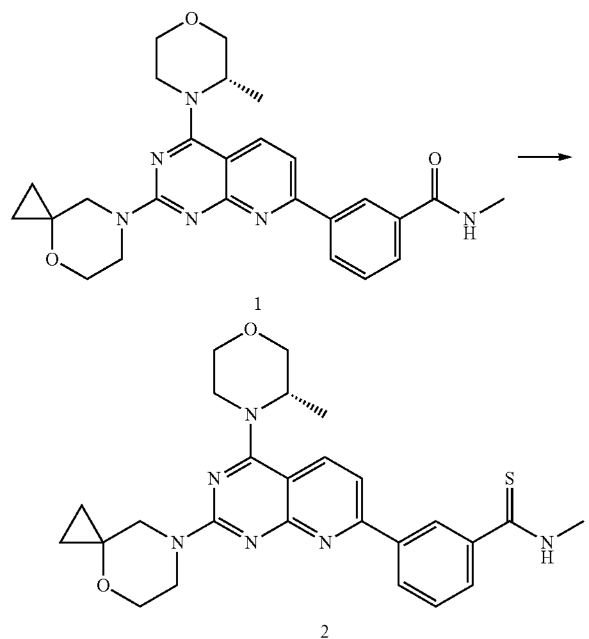

Compound 1 (40 mg, 84.3 μmol, 1.00 eq) was dissolved in xylene (2 mL) at 130° C., and then Lawesson's reagent (37.5 mg, 92.7 μmol, 1.10 eq) was added to the above reaction solution in batches. Nitrogen replacement was performed for three times, and then the reaction was carried out at 130° C. under nitrogen protection for 17 hours. After completion of the reaction, the reaction solution was subjected to rotary evaporation under reduced pressure to remove solvent. The crude product was added with water (10 mL) and extracted with dichloromethane (10 mL×3). The organic phases were combined and dried with anhydrous sodium sulfate, filtered, and subjected to rotary evaporation under reduced pressure to dryness. The residue was separated by preparative thin layer chromatography (100% ethyl acetate). The crude product was separated by preparative liquid chromatography to give compound 2.

MS-ESI calculated for $[M+H]^+$: 491, found: 491.

$^1$H NMR (400 MHz, $CDCl_3$) δ: 8.47 (s, 1H), 8.15 (s, 1H), 8.05 (d, J=7.8 Hz, 1H), 8.02-7.95 (m, 2H), 7.47-7.36 (m, 2H), 4.30 (s, 1H), 4.04-3.83 (m, 5H), 3.80-3.78 (m, 4H), 3.73-3.60 (m, 3H), 3.33 (d, J=4.8 Hz, 3H), 1.41 (d, J=6.8 Hz, 3H), 0.80-0.74 (m, 2H), 0.60-0.59 (m, 2H).

Embodiment 3

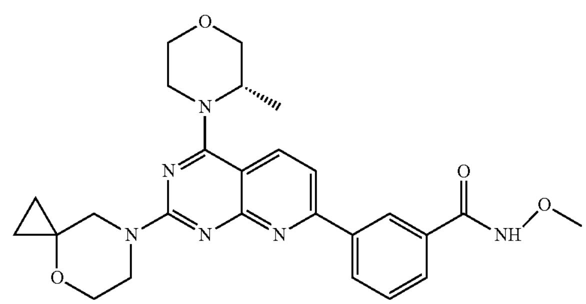

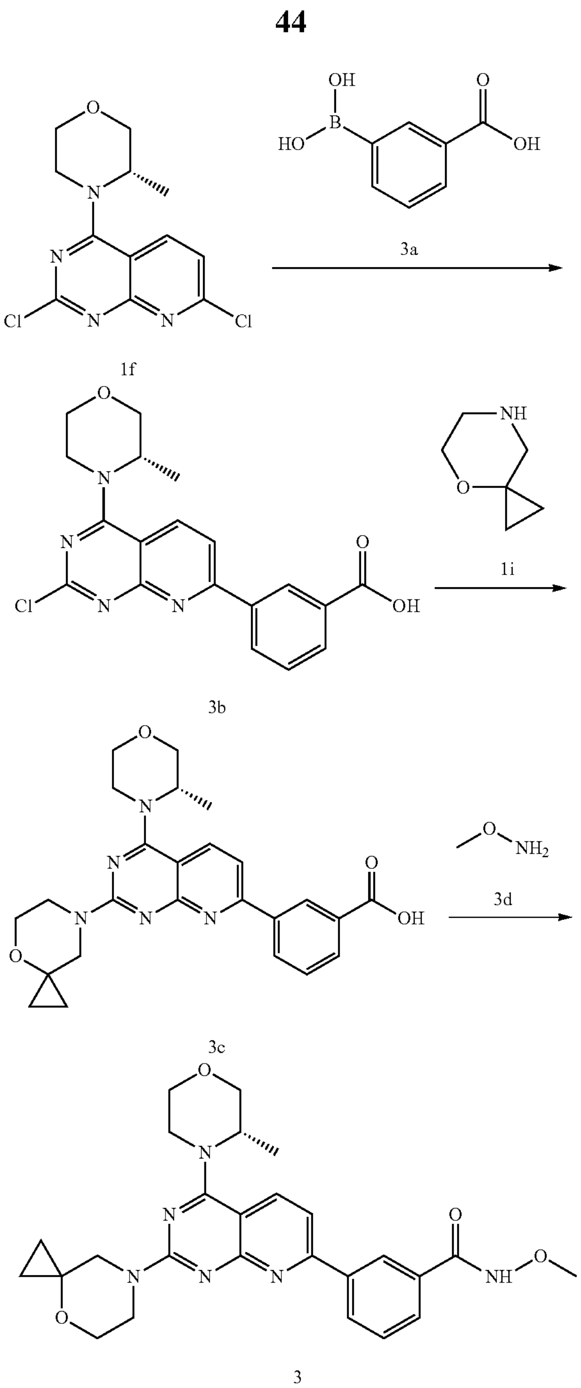

First Step

Compound 1f (0.5 g, 1.37 mmol, 1 eq), 3a (246 mg, 1.37 mmol, 1 eq), tetrakis (triphenylphosphine) palladium (79.2 mg, 68.53 μmol, 0.05 eq) and anhydrous sodium carbonate (436 mg, 4.11 mmol, 3 eq) were dissolved in dioxane (6.0 mL) and water (2.0 mL). Nitrogen replacement was performed for three times. The reaction was carried out under nitrogen protection at 70° C. for 3 hours. After completion of the reaction, the reaction solution was subjected to rotary evaporation under reduced pressure to remove solvent. The remaining solid was diluted with water (20 mL) and ethyl acetate (10 mL×3), filtered, and partitioned. The obtained organic phases were combined, dried over anhydrous sodium sulfate, filtered, and subjected to rotary evaporation to dryness, and purified by column chromatography (3:1 petroleum ether/ethyl acetate) to give compound 3b.

Second Step

Compound 3b (180 mg, 375 μmol, 1 eq), 1i (56.0 mg, 375 μmol, 1 eq, HCl) and DIPEA (145 mg, 1.12 mmol, 196 μL, 3 eq) were dissolved in DMSO (3 mL), and then the mixture was reacted at 70° C. for 15 hours. After completion of the reaction, 3c was directly used in the reaction of next step without treatment.

Third Step

Compound 3c (30.0 mg, 65.0 μmol, 1 mL, 1 eq), 3d (10.9 mg, 130 μmol, 2 eq, HCl), DIPEA (25.2 mg, 195 μmol, 34.0 μL, 3 eq) and HATU (49.4 mg, 130 μmol, 2 eq) were dissolved in DMSO (2 mL) and then the mixture was reacted at 27° C. for 20 hours. After completion of the reaction, the reaction solution was subjected to high performance liquid chromatography to give compound 3.

MS-ESI calculated for $[M+H]^+$: 491, found: 491.

$^1$H NMR: (400 MHz, $CDCl_3$) δ: 9.29 (s, 1H), 8.49 (s, 1H), 8.13 (br d, J=7.6 Hz, 1H), 7.98 (d, J=8.4 Hz, 1H), 7.8 (d, J=7.6 Hz, 1H), 7.49 (t, J=7.6 Hz, 1H), 7.37-7.46 (m, 1H), 4.22-4.37 (m, 1H), 3.89-4.06 (m, 3H), 3.75-3.89 (m, 9H), 3.60-3.73 (m, 3H), 1.41 (d, J=6.4 Hz, 3H), 0.74-0.81 (m, 2H), 0.61 (br s, 2H).

Embodiment 4

4

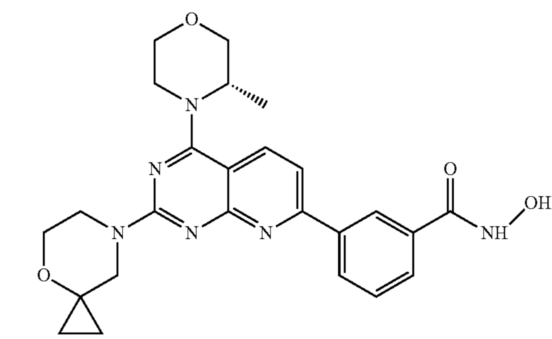

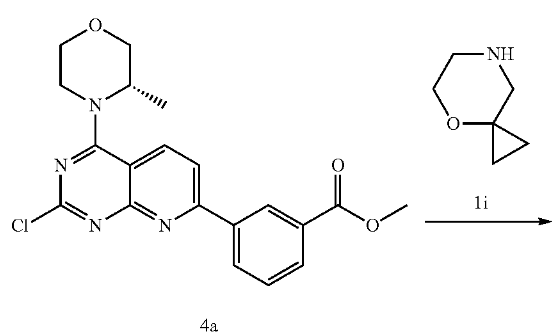

4a

-continued

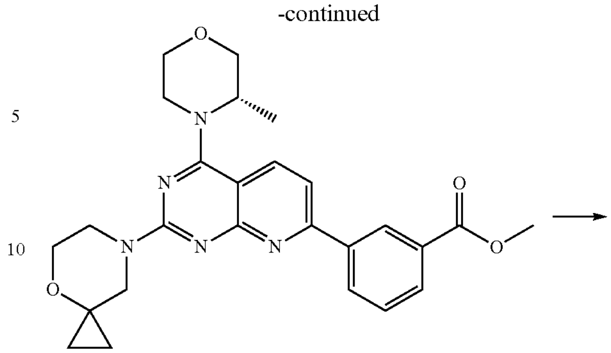

4b

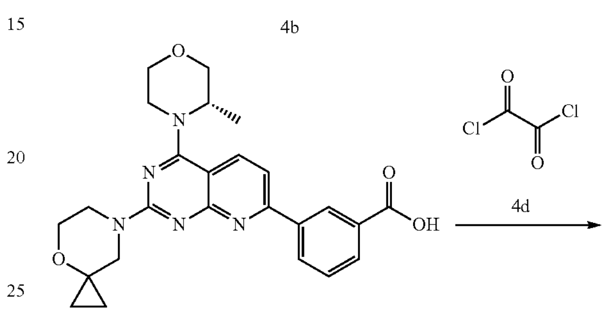

4c

4f

4e

4

First Step

Compound 4a (180 mg, 375 μmol, 1 eq), 1i (56.0 mg, 375 μmol, 1 eq, HCl) and DIPEA (145 mg, 1.12 mmol, 196 μL, 3 eq) were dissolved in DMSO (3 mL), and then the mixture was reacted at 70° C. for 15 hours. After completion of the reaction, compound 4b was obtained, which was directly used in the reaction of next step.

MS-ESI calculated for $[M+H]^+$: 476, found: 476.

Second Step

Compound 4b (178 mg, 374.31 μmol, 1 eq) and LiOH (23.56 mg, 561.47 μmol, 1.5 eq) were dissolved in dimethyl sulfoxide (3 mL), and the mixture was reacted at room temperature for 24 hours. LC-MS detection found that compound 3 was not obtained. Sodium hydroxide (29.95 mg, 748.63 μmol, 2 eq) was added to the reaction solution, and the reaction was continued for 20 hours. After completion of the reaction, the resulting mixture was directly purified by high performance liquid chromatography to give compound 4c.

Third Step

Compound 4c (20 mg, 42.9 μmol, 1 eq), 4d (5.99 mg, 47.2 μmol, 4.13 μL, 1.1 eq) and DMF (314 g, 4.29 μmol, 0.33 μL, 0.1 eq) were dissolved in dichloromethane (2 mL), and the resulting solution was reacted at room temperature for an hour. After completion of the reaction, compound 4e was obtained, which was directly used in the reaction of next step without treatment.

Fourth Step

Compound 4f (60 mg, 125.01 μmol, 1 eq) was added to a solution of 4e (86.9 mg, 1.25 mmol, 10 eq, HCl) and DIPEA (194 mg, 1.50 mmol, 261 L, 12 eq) in dichloromethane (2 mL), then the mixture was reacted at room temperature for 2 hours.

The resulting solution was purified by high performance liquid chromatography to give 4.

MS-ESI calculated for $[M+H]^+$: 477, found: 477.

$^1H$ NMR (400 MHz, $CD_3OD$) δ: 8.57 (s, 1H), 8.34-8.31 (m, 2H), 7.90 (d, J=7.6 Hz, 1H), 7.57-7.78 (m, 2H), 4.62-4.60 (m, 3H), 4.04-4.02 (m, 2H), 4.01-3.92 (m, 3H), 3.87-3.85 (m, 3H), 3.78-3.76 (m, 2H), 1.51 (d, J=6.8 Hz, 3H), 0.93-0.61 (m, 4H).

Embodiment 5

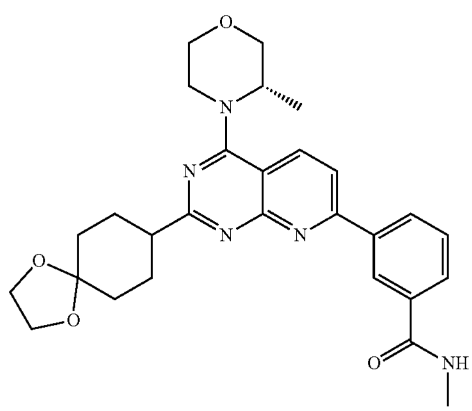

5

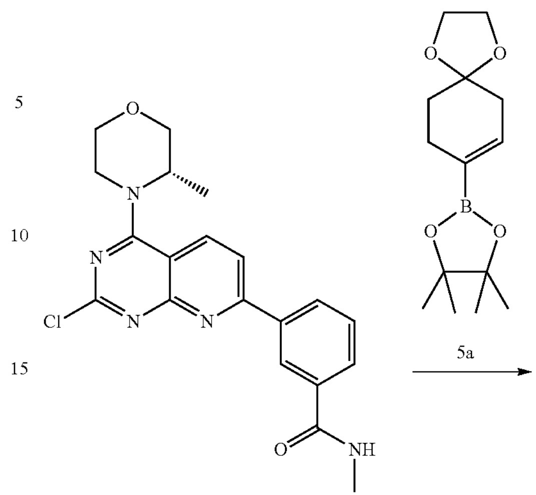

1h

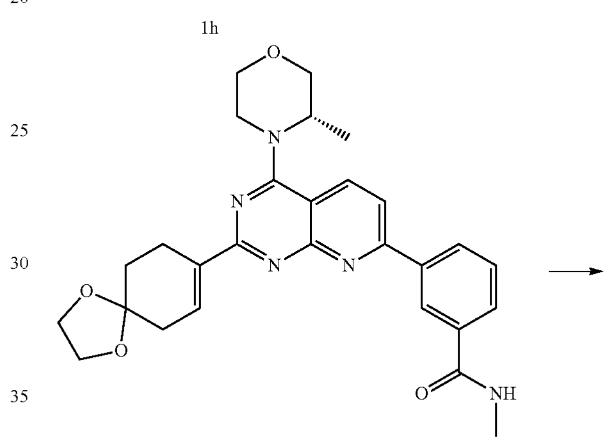

5b

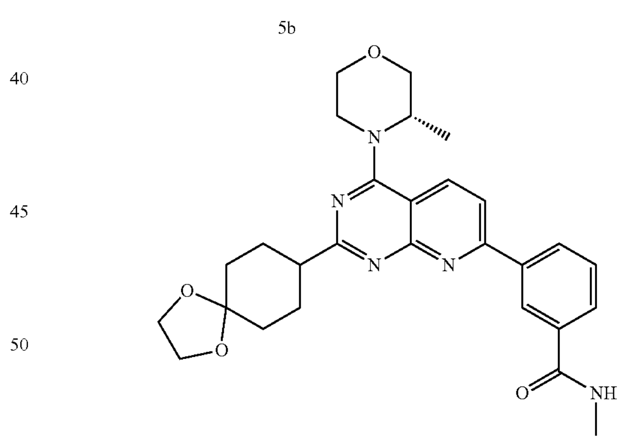

5

First Step 1h (300 mg, 754 μmol, 1.00 eq), 5a (301 mg, 1.13 mmol, 1.50 eq), tetrakis(triphenylphosphine) palladium (43.6 mg, 37.7 mol, 0.05 eq) and sodium carbonate (240 mg, 2.26 mmol, 3.00 eq) were dissolved in water (3 mL) and 1,4-dioxane (10 mL). The reaction was carried out at 90° C. for 16 hours under nitrogen protection. After completion of the reaction, the reaction solution was concentrated to remove solvent, diluted with water (10 mL), and extracted with ethyl acetate (20 mL×3). The organic phases were combined, dried over anhydrous sodium sulfate, filtered, subjected to rotary evaporation under reduced pressure to dryness, and purified by column chromatography (100% ethyl acetate, $R_f$=0.4) to give a yellow solid (200 mg) with a purity of 63.8% and a yield of 27%. 40 mg thereof was separated and purified by preparative high performance liquid chromatography to give compound 5b.

MS-ESI calculated for $[M+H]^+$: 502, found: 502.

$^1$H NMR (400 MHz, $CD_3OD$) δ: 8.70 (s, 1H), 8.44 (d, J=8.8 Hz, 1H), 8.41 (br d, J=8.0 Hz, 1H), 8.02-7.92 (m, 2H), 7.66 (t, J=8.0 Hz, 1H), 7.35-7.25 (m, 1H), 4.68-4.66 (m, 1H), 4.21-4.210 (m, 1H), 4.05-3.96 (m, 5H), 3.90-3.72 (m, 4H), 3.00 (s, 3H), 2.92 (br s, 2H), 2.56 (s, 2H), 1.94 (t, J=6.4 Hz, 2H), 1.53 (d, J=6.4 Hz, 3H).

Second Step

Palladium on carbon (10 mg, content 10%, moisture: 50%) was added to a solution of 5b (80 mg, 160 μmol, 1.00 eq) in methanol (10 mL), and hydrogen replacement was performed for three times. The obtained mixture was reacted under hydrogen atmosphere (15 psi) at 20° C. for 16 hours, and filtered. The filter cake was washed with 10 mL methanol, and the filtrate was concentrated. The crude product was separated and purified by preparative high performance liquid chromatography to give compound 5.

MS-ESI calculated for $[M+H]^+$: 504, found: 504.

$^1$H NMR (400 MHz, $CD_3OD$) δ: 8.73 (s, 1H), 8.48 (d, J=8.4 Hz, 1H), 8.45 (br d, J=8.0 Hz, 1H), 8.02 (d, J=8.4 Hz, 1H), 7.98 (br d, J=8.0 Hz, 1H), 7.66 (t, J=8.0 Hz, 1H), 4.78-4.76 (m, 1H), 4.26-4.24 (m, 1H), 4.05-3.94 (m, 5H), 3.89-3.70 (m, 4H), 3.00 (s, 3H), 2.94-2.82 (m, 1H), 2.12-1.99 (m, 4H), 1.92-1.90 (m, 2H), 1.78-1.67 (m, 2H), 1.57 (d, J=6.8 Hz, 3H).

Embodiment 6

-continued

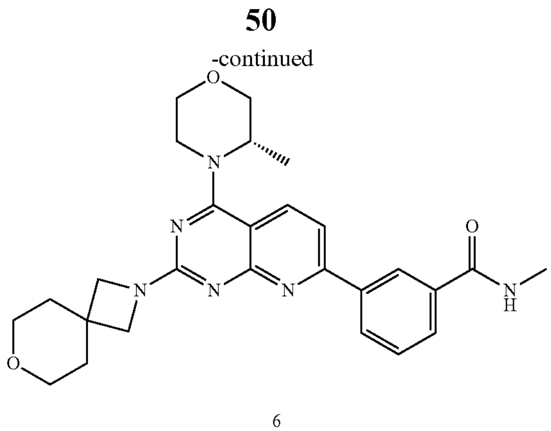

First Step

Compound 1h (50.0 mg, 126 μmol, 1.00 eq), compound 6a (32.5 mg, 189 μmol, 1.50 eq, 0.5 equivalent oxalate), and N, N-diisopropylethylamine (48.7 mg, 377 μmol, 3.00 eq) were dissolved in dimethyl sulfoxide (1.00 mL), and then the reaction solution was stirred at 70° C. for 16 hours. After completion of the reaction, the reaction solution was purified by preparative high performance liquid chromatography to give compound 6.

MS-ESI calculated for $[M+H]^+$: 489, found: 489.

$^1$H NMR (400 MHz, DMSO-$d_6$) δ: 8.64 (s, 2H), 8.31 (d, J=7.6 Hz, 1H), 8.24 (d, J=8.4 Hz, 1H), 7.95 (d, J=7.6 Hz, 1H), 7.69 (d, J=8.4 Hz, 1H), 7.62 (t, J=7.6 Hz, 1H), 4.47-4.45 (m, 1H), 3.95-3.82 (m, 6H), 3.79-3.70 (m, 1H), 3.69-3.50 (m, 7H), 2.84 (d, J=4.8 Hz, 3H), 1.76 (br t, J=4.8 Hz, 4H), 1.38 (d, J=6.8 Hz, 3H).

Embodiment 7

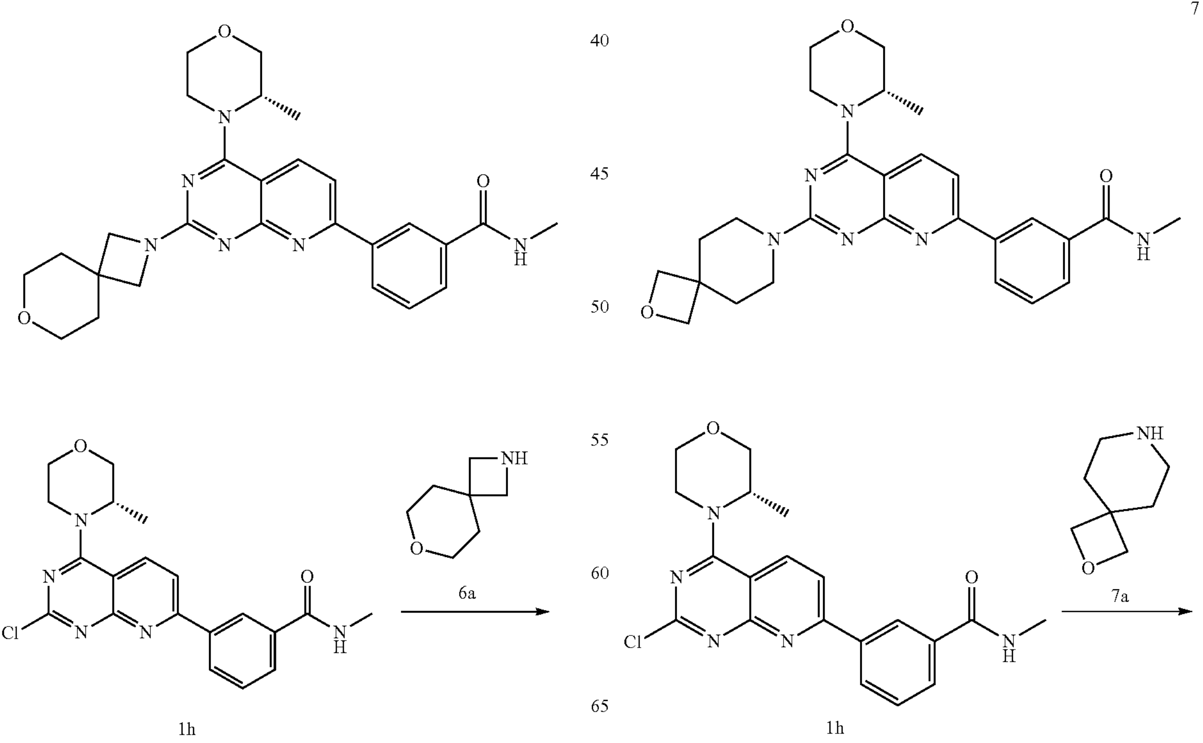

-continued

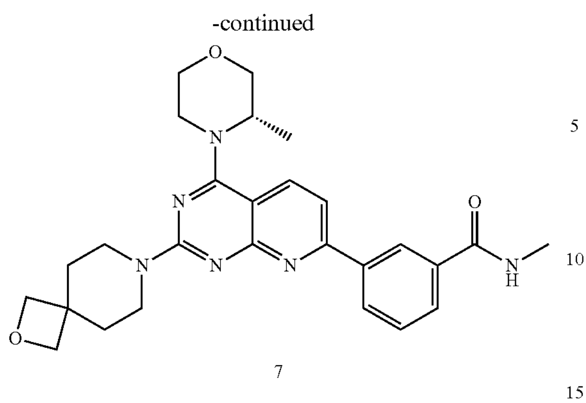

7

Compound 1h (50.0 mg, 126 μmol, 1.00 eq), compound 7a (32.5 mg, 189 μmol, 1.50 eq, 0.5 equivalent oxalate) and diisopropylethylamine (48.7 mg, 377 μmol, 3.00 eq) were dissolved in dimethyl sulfoxide (1.00 mL). The reaction solution was then stirred at 70° C. for 16 hours. After completion of the reaction, the reaction solution was purified by preparative high performance liquid chromatography to give compound 7.

MS-ESI calculated for $[M+H]^+$:489, found: 489.

$^1$H NMR (400 MHz, DMSO-$d_6$) δ: 8.70-8.60 (m, 2H), 8.30 (br d, J=8.0 Hz, 1H), 8.22 (d, J=8.4 Hz, 1H), 7.95 (d, J=8.0 Hz, 1H), 7.68 (d, J=8.4 Hz, 1H), 7.62 (t, J=8.0 Hz, 1H), 4.47-4.27 (m, 5H), 3.96-3.56 (m, 10H), 2.84 (d, J=4.4 Hz, 3H), 1.83 (br t, J=5.2 Hz, 4H), 1.37 (d, J=6.8 Hz, 3H).

Embodiment 8

8

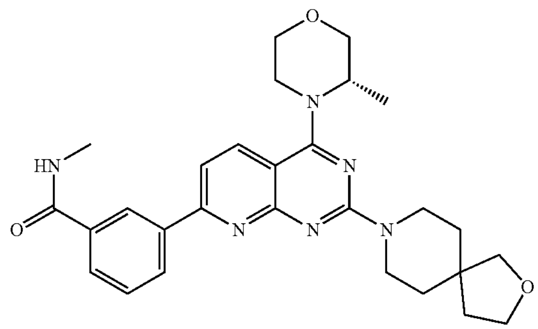

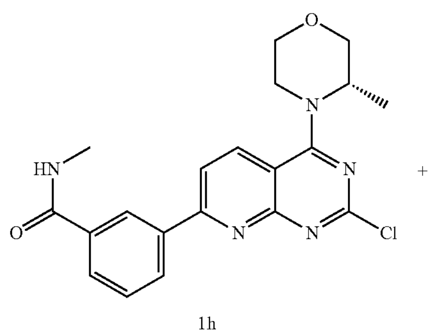

1h

-continued

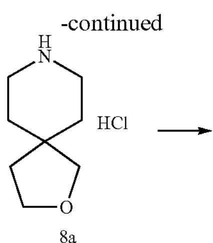

8a

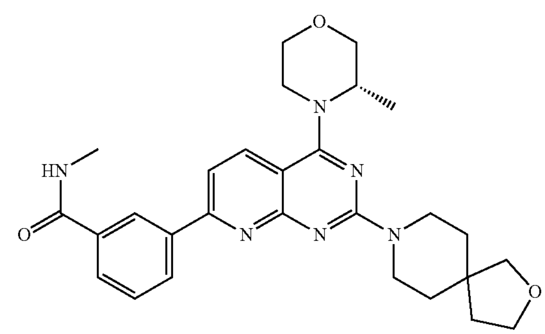

8

Compound 1h (20 mg, 50.3 μmol, 1.00 eq), 8a (13.4 mg, 75.4 μmol, 1.50 eq, HCl) and N, N-diisopropylethylamine (19.5 mg, 151 μmol, 26.3 μL, 3.00 eq) were dissolved in dimethyl sulfoxide (1 mL), and the mixed solution was allowed to react at 70° C. for 40 hours. After completion of the reaction, the reaction solution was purified by high performance liquid chromatography to give compound 8.

MS-ESI calculated for $[M+H]^+$: 503, found: 503.

$^1$H NMR (400 MHz, $CD_3OD$) δ: 8.62 (s, 1H), 8.33 (d, J=8.0 Hz, 1H), 8.26 (d, J=8.0 Hz, 1H), 7.95 (d, J=8.0 Hz, 1H), 7.67-7.61 (m, 2H), 4.51 (br d, J=7.03 Hz, 1H), 4.13-4.05 (m, 2H), 4.02-3.85 (m, 7H), 3.82-3.69 (m, 3H), 3.65 (s, 2H), 2.99 (s, 3H), 1.92 (t, J=7.2 Hz, 2H), 1.69 (t, J=5.6 Hz, 4H), 1.48 (d, J=6.8 Hz, 3H).

Embodiment 9

9

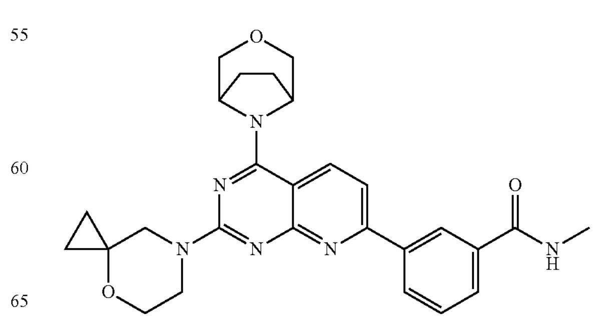

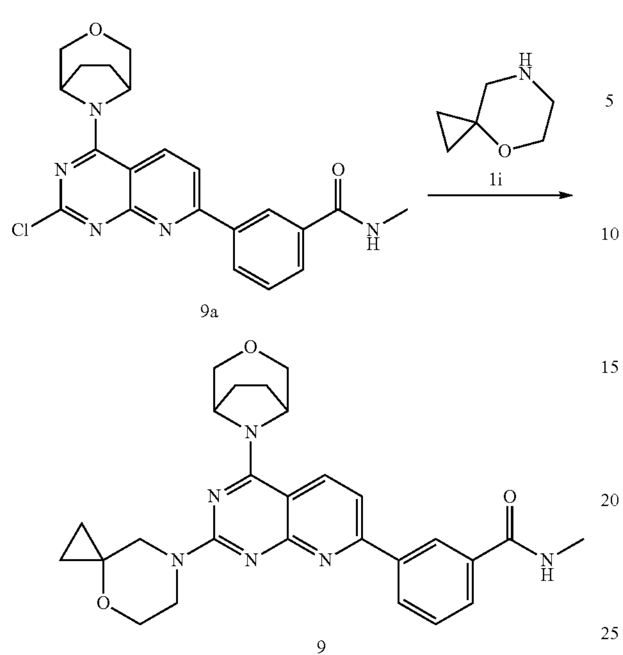

Compound 9a (100 mg, 175 μmol, 1 eq), 1i (26.28 mg, 175.67 μmol, 1 eq, HCl) and DIPEA (68.1 mg, 527 μmol, 91.8 μL, 3 eq) were dissolved in DMSO (5 mL), and then the mixture was reacted at 70° C. for 18 hours. After completion of the reaction, the reaction solution was diluted with water (10 mL), then extracted with ethyl acetate (15 mL×5), and partitioned. The combined organic phases were dried over anhydrous sodium sulfate, filtered and subjected to rotary evaporation to dryness. The residue was purified by high performance liquid chromatography to give compound 9.

MS-ESI calculated for $[M+H]^+$: 487, found: 487.

$^1$H NMR (400 MHz, $CDCl_3$) δ: 8.63 (s, 1H), 8.22 (d, J=8.0 Hz, 1H), 8.14 (d, J=8.0 Hz, 1H), 7.98 (d, J=8.0 Hz, 1H), 7.50-7.61 (m, 2H), 6.56 (s, 1H), 4.59 (s, 2H), 3.69-4.23 (m, 10H), 3.07 (d, J=4.8 Hz, 3H), 2.06-2.20 (m, 2H), 1.98-2.06 (m, 2H), 0.90 (s, 2H), 0.69 (s, 2H).

Embodiment 10

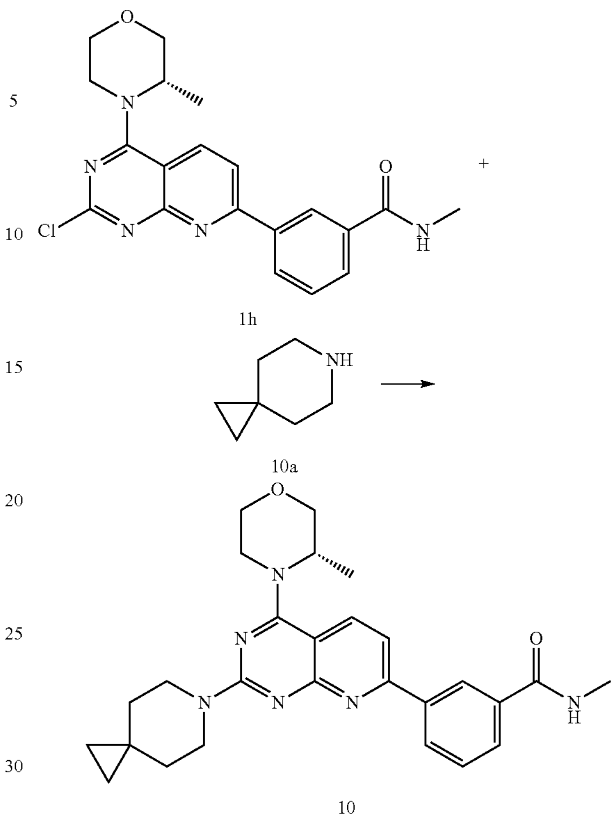

Compound 1h (50.0 mg, 126 μmol, 1.00 eq), 10a (20.9 mg, 188 μmol, 1.50 eq) and triethylamine (38.2 mg, 377 μmol, 52.3 μL, 3.00 eq) were dissolved in dimethyl sulfoxide (1.00 mL). Nitrogen replacement was performed for three times, and the reaction solution was stirred at 70° C. for 12 hours. After completion of the reaction, the reaction solution was purified by high performance liquid chromatography to give compound 10.

MS-ESI calculated for $[M+H]^+$:473, found: 473.

$^1$H NMR (400 MHz, $CD_3OD$) δ: 8.61 (s, 1H), 8.32 (d, J=8.0 Hz, 1H), 8.23 (d, J=8.4 Hz, 1H), 7.95 (d, J=8.0 Hz, 1H), 7.59-7.66 (m, 2H), 4.49-4.47 (m, 1H), 4.00-4.07 (m, 4H), 4.00-3.92 (m, 2H), 3.89-3.87 (m, 1H), 3.82-3.67 (m, 3H), 2.99 (s, 3H), 1.49-1.46 (m, 7H), 0.43 (s, 4H).

Embodiment 11

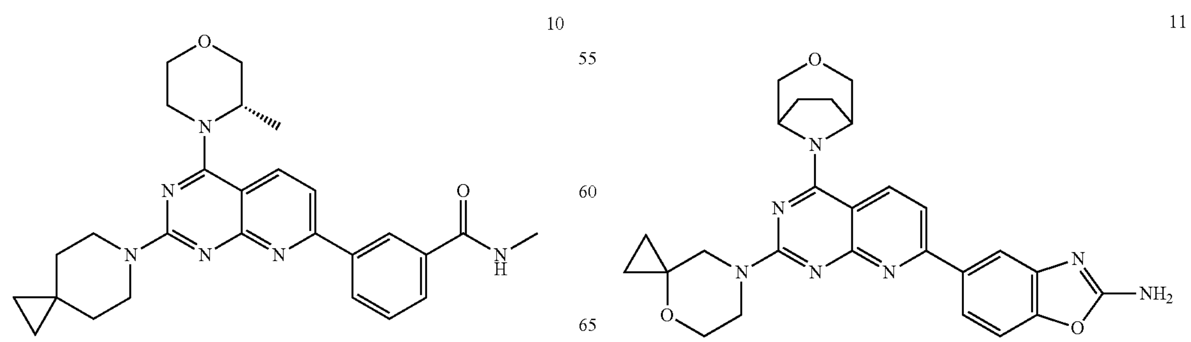

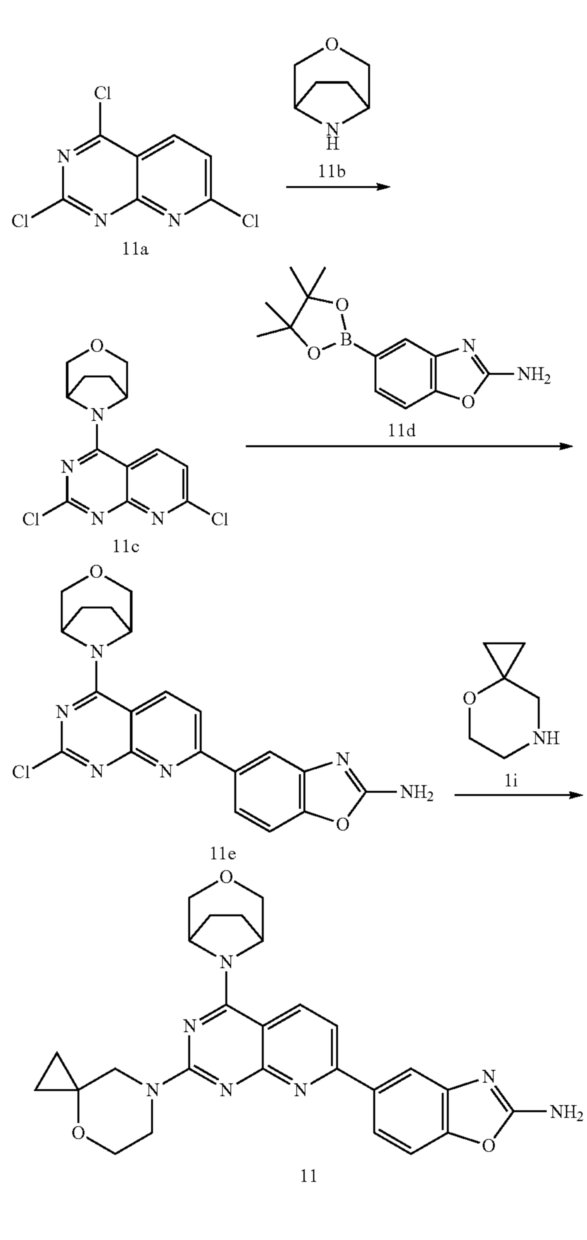

First Step

Compound 11a (1.0 g, 3.41 mmol, 1 eq) and lib (510 mg, 3.41 mmol, 1 eq, HCl) were dissolved in anhydrous dichloromethane (80 mL), followed by addition of DIPEA (441 mg, 3.41 mmol, 594 μL, 1 eq). The mixed solution was allowed to react at 20° C. for 18 hours. After completion of the reaction, the reaction solution was concentrated under reduced pressure, and the filter residue was purified by preparative thin layer chromatography (1:1 petroleum ether/ethyl acetate) to give compound 11c.

MS-ESI calculated for $[M+H]^+$: 311, 312 and 313, found: 311, 312 and 313.

$^1$H NMR (400 MHz, $CDCl_3$) δ: 8.14 (d, J=8.8 Hz, 1H), 7.36 (d, J=8.8 Hz, 1H), 4.84 (s, 2H), 3.97 (d, J=11.2 Hz, 2H), 3.83 (d, J=11.2 Hz, 2H), 2.24-2.16 (m, 2H), 2.10-2.01 (m, 2H).

Second Step

Compound 11c (200 mg, 643 μmol, 1 eq), 11d (167 mg, 643 μmol, 1 eq), $K_2CO_3$ (266 mg, 1.93 mmol, 3 eq) and Pd$(PPh_3)_4$ (37.1 mg, 32.1 μmol, 0.05 eq) were dissolved in anhydrous dioxane (30 mL) and water (6 mL). Nitrogen replacement was performed for three times, and the mixed solution was allowed to react at 90° C. for 2 hours under nitrogen atmosphere. After completion of the reaction, the reaction solution was concentrated under reduced pressure, and then added with 20 mL water, and extracted with ethyl acetate (20 mL×3). The organic phase was dried over anhydrous sodium sulfate, filtered, and the filtrate was concentrated under reduced pressure, and the filter residue was purified by plate chromatography (100% ethyl acetate) to give compound 11e.

MS-ESI calculated for $[M+H]^+$: 409 and 411, found: 409 and 411.

Third Step

Compound 1e (120 mg, 294 μmol, 1 eq), 1i (33.2 mg, 222 μmol, HCl) and DIPEA (37.9 mg, 294 μmol, 51.1 μL, 1 eq) were dissolved in DMSO (6 mL), and the mixed solution was allowed to react at 70° C. for 17 hours under nitrogen atmosphere. After completion of the reaction, the reaction solution was purified by high performance liquid chromatography to give compound 11.

MS-ESI calculated for $[M+H]^+$:486, found: 486.

$^1$H NMR (400 MHz, $CD_3OD$) δ: 8.38 (d, J=8.4 Hz, 1H), 8.24 (br s, 1H), 8.03 (d, J=1.2 Hz, 1H), 7.94-7.89 (m, 1H), 7.71 (d, J=8.4 Hz, 1H), 7.43 (d, J=8.4 Hz, 1H), 4.83 (s, 1H), 4.06-3.97 (m, 4H), 3.94 (s, 2H), 3.87 (t, J=4.8 Hz, 2H), 3.80 (br d, J=10.4 Hz, 2H), 2.17-2.00 (m, 4H), 0.86-0.80 (m, 2H), 0.76-0.70 (m, 2H).

Embodiment 12

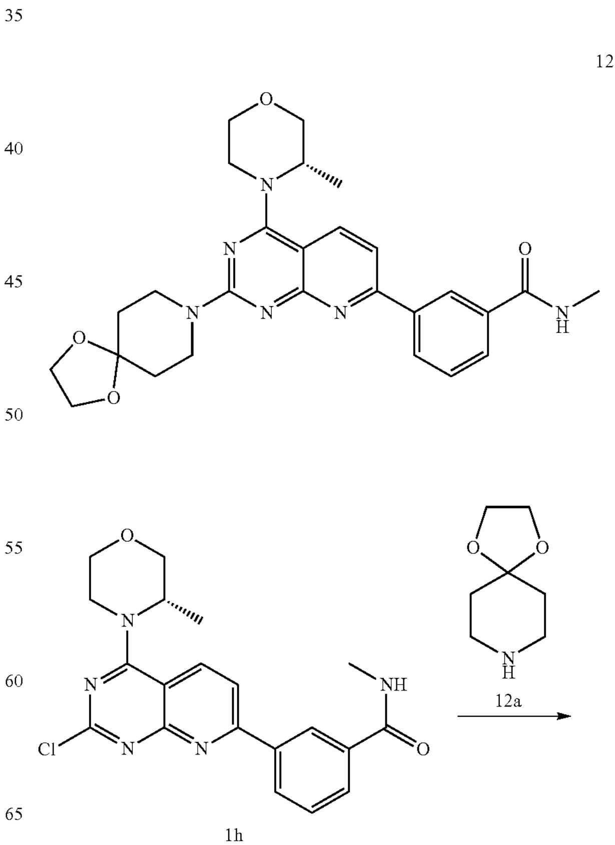

-continued

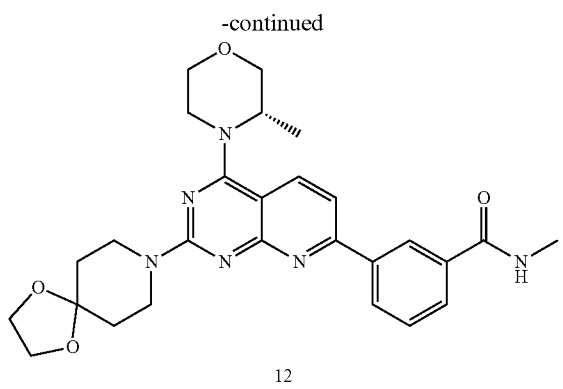

Compound 1h (80 mg, 201 μmol, 1 eq), 12a (28.8 mg, 201 μmol, 25.7 μL, 1 eq), and diisopropylethylamine (26.0 mg, 201 μmol, 35.0 μL, 1 eq) were dissolved in dimethyl sulfoxide (4.00 mL), the mixed solution was allowed to react at 70° C. for 1.5 hours. After completion of the reaction, the reaction solution was purified by high performance liquid chromatography to give compound 12.

MS-ESI calculated for $[M+H]^+$: 505, found: 505.

$^1$H NMR (400 MHz, $CD_3OD$) δ: 8.62-8.60 (m, 1H), 8.31 (d, J=8.0 Hz, 1H), 8.24 (d, J=8.4 Hz, 1H), 7.95 (d, J=8.0 Hz, 1H), 7.65-7.60 (m, 2H), 4.50 (br d, J=6.8 Hz, 1H), 4.09-4.02 (m, 8H), 4.00-3.93 (m, 2H), 3.90-3.84 (m, 1H), 3.81-3.68 (m, 3H), 2.99 (s, 3H), 1.80-1.74 (m, 4H), 1.48 (d, J=6.8 Hz, 3H).

Embodiment 13

13

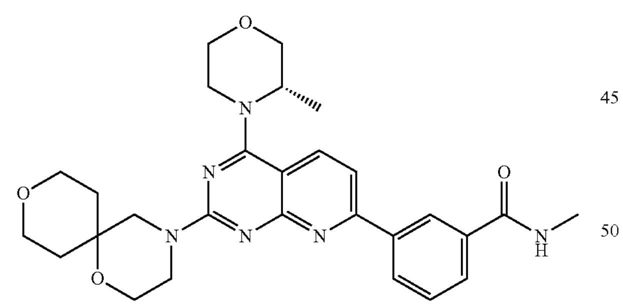

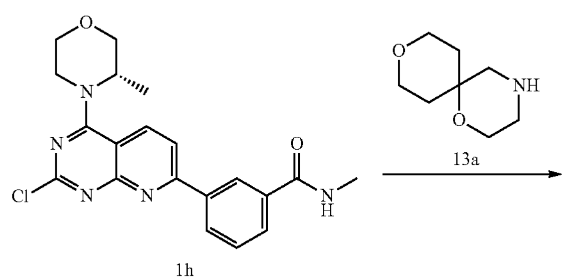

-continued

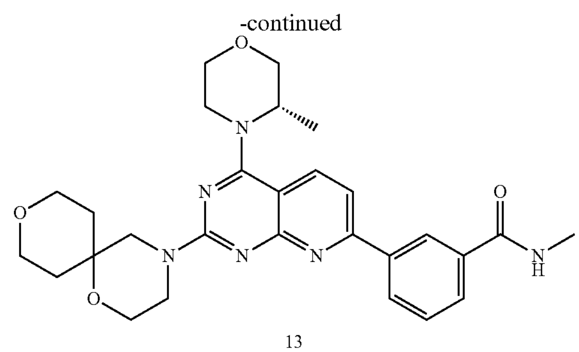

Compound 1h (50.0 mg, 126 μmol, 1 eq), 13a (19.8 mg, 126 μmol, 1 eq) and N, N-diisopropylethylamine (48.7 mg, 377 μmol, 65.7 μL, 3 eq) were dissolved in dimethyl sulfoxide (2 mL), and the mixture was reacted at 70° C. for 16 hours. After completion of the reaction, the reaction solution was purified by high performance liquid chromatography to give compound 13.

MS-ESI calculated for [M+H]: 519, found: 519.

$^1$H NMR (400 MHz, $CDCl_3$) δ: 8.63 (s, 1H), 8.24 (d, J=8.00 Hz, 1H), 8.06 (d, J=8.00 Hz, 1H), 7.98 (d, J=8.00 Hz, 1H), 7.49-7.64 (m, 2H), 6.52 (br s, 1H), 4.40 (br d, J=6.8 Hz, 1H), 4.02 (br d, J=10.8 Hz, 3H), 3.83-3.94 (m, 6H), 3.66-3.83 (m, 7H), 3.08 (d, J=4.8 Hz, 3H), 1.80-1.93 (m, 2H), 1.73 (br s, 2H), 1.50 (d, J=6.8 Hz, 3H).

Embodiment 14

14

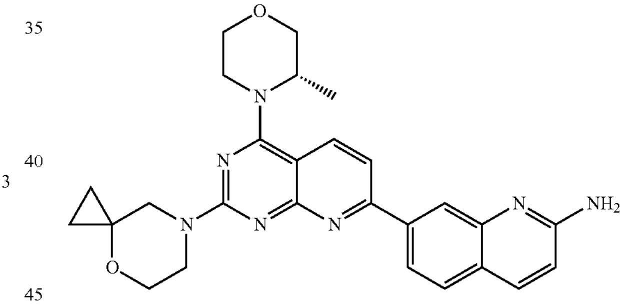

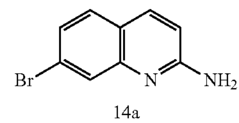

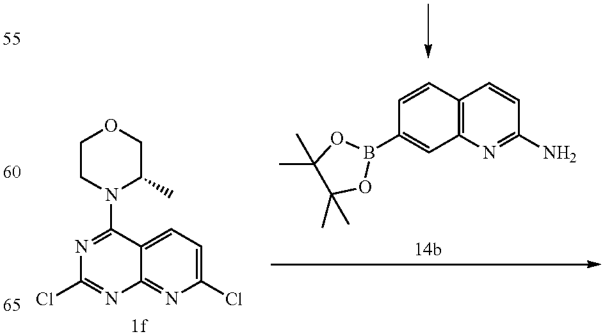

-continued

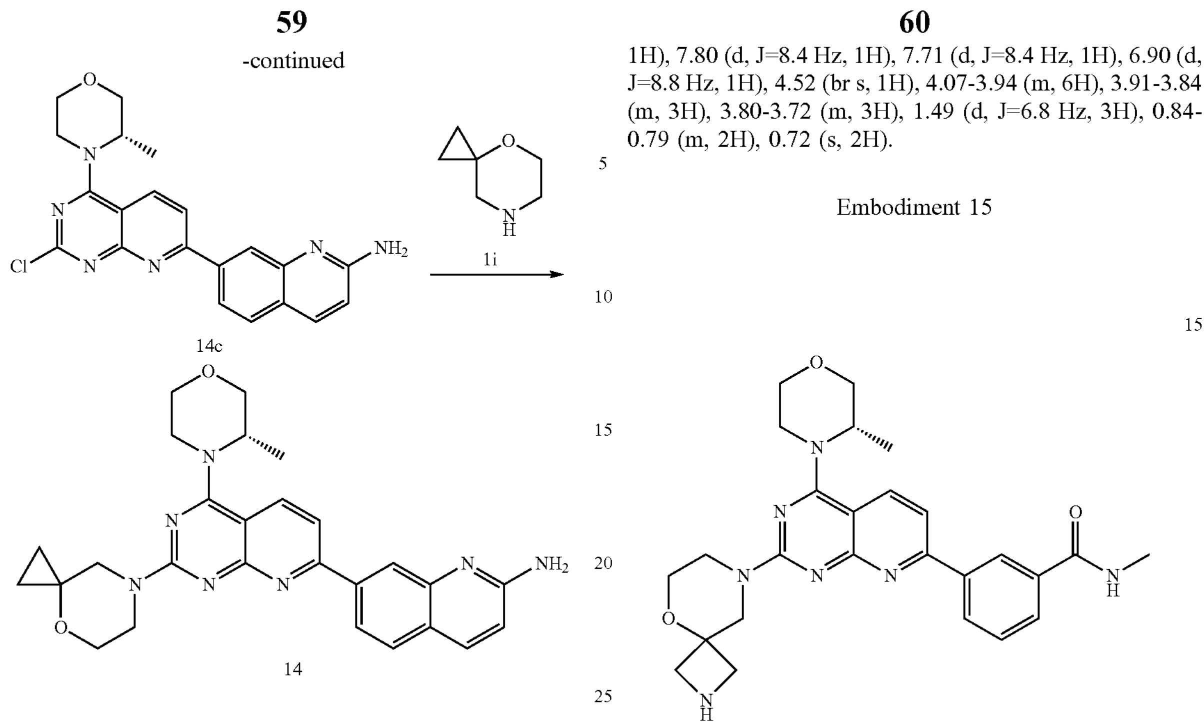

First Step

Compound 14a (0.08 g, 359 μmol, 1 eq), pinacol diborate (109 mg, 430 μmol, 1.2 eq), Pd(dppf)$Cl_2$ (10.5 mg, 14.4 μmol, 0.04 eq) and potassium acetate (106 mg, 1.08 mmol, 3 eq) were dissolved in 20 mL anhydrous dioxane, and the mixed solution was allowed to react at 90° C. for 22 hours under nitrogen protection. After completion of the reaction, the reaction solution was concentrated to give 14b.

MS-ESI calculated for $[M+H]^+$: 270, found: 270.

Second Step

Compound 1f (0.1 g, 334 μmol, 1 eq), 14b (99.3 mg, 367 μmol, 1.1 eq), tetrakis(triphenylphosphine) palladium (19.3 mg, 16.7 μmol, 0.05 eq) and potassium carbonate (139 mg, 1.00 mmol, 3 eq) were dissolved in anhydrous dioxane (20 mL) and water (4 mL), and the mixed solution was allowed to react under nitrogen protection at 70° C. for 3.5 hours. After the reaction was complete and the reaction solution was cooled, 10 mL water and 60 mL (20 mL×3) ethyl acetate were added to the reaction solution for extraction. Then, the organic phase was dried over anhydrous sodium sulfate, concentrated, and purified by column chromatography to give 14c.

MS-ESI calculated for $[M+H]^+$: 407, and 409, found: 407, and 409.

Third Step

Compound 14c (0.04 g, 93.4 μmol, 1 eq), 1i (13.9 mg, 93.4 μmol, 1 eq, HCl) and diisopropylamine (12.1 mg, 93.4 μmol, 16.3 μL, 1 eq) were dissolved in dimethyl sulfoxide (3 mL). The reaction solution was allowed to react at 70° C. for 17 hours. After completion of the reaction, the reaction solution was purified by high performance liquid chromatography to give compound 14.

MS-ESI calculated for $[M+H]^+$: 484, found: 484.

$^1$H NMR (400 MHz, $CD_3OD$) δ: 8.30 (d, J=8.4 Hz, 1H), 8.21 (s, 1H), 8.08 (dd, J=1.6, 8.4 Hz, 1H), 8.01 (d, J=9.2 Hz, 1H), 7.80 (d, J=8.4 Hz, 1H), 7.71 (d, J=8.4 Hz, 1H), 6.90 (d, J=8.8 Hz, 1H), 4.52 (br s, 1H), 4.07-3.94 (m, 6H), 3.91-3.84 (m, 3H), 3.80-3.72 (m, 3H), 1.49 (d, J=6.8 Hz, 3H), 0.84-0.79 (m, 2H), 0.72 (s, 2H).

Embodiment 15

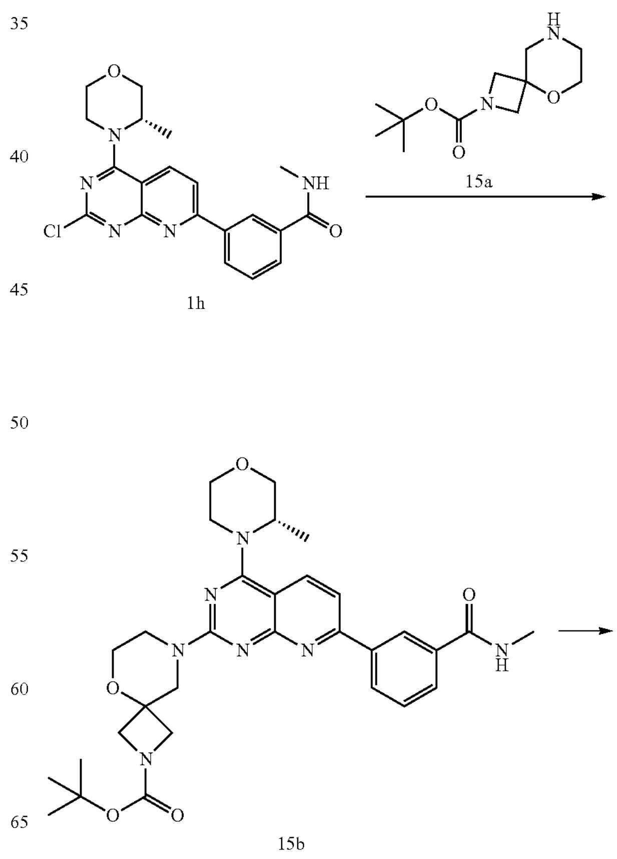

-continued

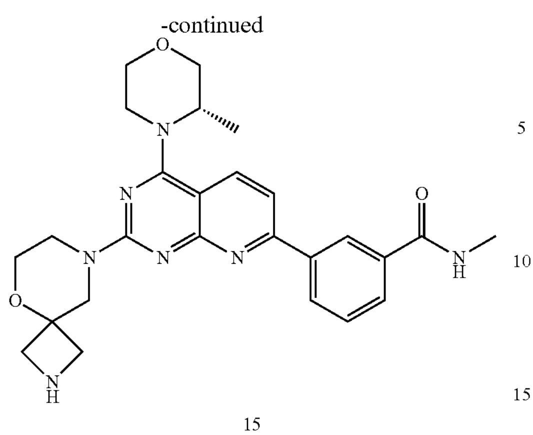

First Step

Compound 1h (70 mg, 176 μmol, 1 eq), 15a (40.2 mg, 176 μmol, 1 eq) and diisopropylethylamine (22.7 mg, 176 μmol, 30.7 μL, 1 eq) were dissolved in dimethyl sulfoxide (5 mL). The mixed solution was allowed to react at 70° C. for 17 hours. After the reaction was complete and the reaction solution was cooled, 10 mL water and 30 mL ethyl acetate were added to the reaction solution for extraction. Then, the organic phase was added with water to extract excess dimethyl sulfoxide. The organic phase was dried over anhydrous sodium sulfate, concentrated, and subjected to planar chromatography (0/1 petroleum ether/ethyl acetate) to give compound 15b.

MS-ESI calculated for $[M+H]^+$:590, found: 590.

Second Step

Compound 15b (100 mg, 169 μmol, 1 eq) was dissolved in ethyl acetate (3 mL). The obtained solution was added with hydrochloric acid/ethyl acetate (4 M, 3 mL, 70.8 eq), and allowed to react at 20° C. for 3 hours. After completion of the reaction, the reaction solution was concentrated, and extracted with 10 mL water and 45 mL ethyl acetate (15 mL×3). The organic phase was dried over anhydrous sodium sulfate, and concentrated. A small amount of the reaction solution was purified by high performance liquid chromatography to give compound 15.

MS-ESI calculated for $[M+H]^+$: 490, found: 490.

$^1$H NMR (400 MHz, $CD_3OD$) δ: 8.62 (s, 1H), 8.36-8.29 (m, 2H), 7.96 (d, J=7.8 Hz, 1H), 7.69 (d, J=8.4 Hz, 1H), 7.64 (t, J=7.8 Hz, 1H), 4.62 (br d, J=6.4 Hz, 1H), 4.19-3.86 (m, 7H), 3.81-3.72 (m, 5H), 3.65 (br d, J=9.2 Hz, 2H), 3.53 (br d, J=8.0 Hz, 2H), 2.99 (s, 3H), 1.51 (d, J=6.8 Hz, 3H).

Embodiment 16

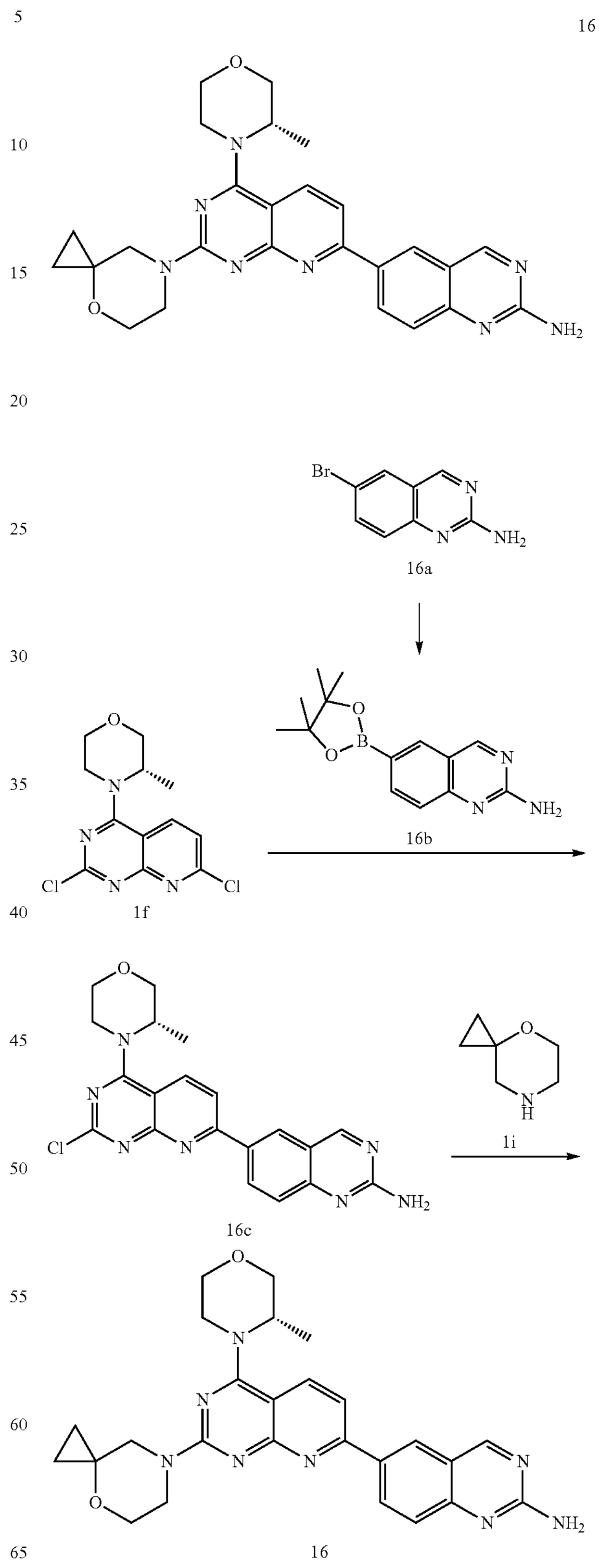

First Step

Compound 16a (0.1 g, 446 μmol, 1 eq), pinacol borate (136 mg, 536 μmol, 1.2 eq), Pd(dppf)$Cl_2$ (13.1 mg, 17.9 μmol, 0.04 eq) and potassium acetate (131 mg, 1.34 mmol, 3 eq) were dissolved in 10 mL anhydrous dioxane, and the mixed solution was allowed to react at 90° C. for 2.5 hours under nitrogen protection. The reaction was stopped when it was detected by mass spectrometry that 30% of the product was obtained. Then, the reaction solution was concentrated to give compound 16b.

MS-ESI calculated for $[M+H]^+$: 272, found: 272.

Second Step

Compound 1f (0.1 g, 334 μmol, 1 eq), 16b (90.6 mg, 334 μmol, 1 eq), tetrakis(triphenylphosphine) palladium (19.3 mg, 16.7 μmol, 0.05 eq) and potassium carbonate (139 mg, 1.00 mmol, 3 eq) were dissolved in anhydrous dioxane (20 mL) and water (4 mL), and the mixed solution was allowed to react at 70° C. for 15 hours under nitrogen protection. When the reaction was complete and the reaction solution was cooled, 10 mL water and 60 mL (20 mL×3) ethyl acetate were added to the reaction solution for extraction. Then the organic phase was dried over anhydrous sodium sulfate, concentrated, and separated by column chromatography (methanol/ethyl acetate) to give compound 16c.

MS-ESI calculated for $[M+H]^+$: 408 and 410, found: 408 and 410.

Third Step

Compound 16c (0.1 g, 153 μmol, 1 eq), 1i (22.9 mg, 153 μmol, 1 eq, HCl) and diisopropylamine (19.7 mg, 153 μmol, 26.6 μL, 1 eq) were dissolved in dimethyl sulfoxide (4 mL), the reaction solution was allowed to react at 70° C. for 15 hours. After completion of the reaction, the reaction solution was purified by high performance liquid chromatography to give compound 16.

MS-ESI calculated for $[M+H]^+$: 485, found: 485.

$^1$H NMR (400 MHz, $CD_3OD$) δ: 9.21 (s, 1H), 8.61-8.55 (m, 2H), 8.23 (d, J=8.4 Hz, 1H), 7.69 (d, J=8.4 Hz, 1H), 7.61 (d, J=9.6 Hz, 1H), 4.50 (br d, J=6.8 Hz, 1H), 4.04 (q, J=4.4 Hz, 2H), 4.00-3.92 (m, 4H), 3.90-3.84 (m, 3H), 3.80-3.69 (m, 3H), 1.48 (d, J=6.8 Hz, 3H), 0.86-0.78 (m, 2H), 0.75-0.69 (m, 2H).

Embodiment 17

17

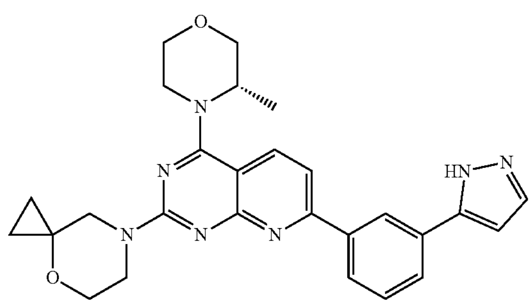

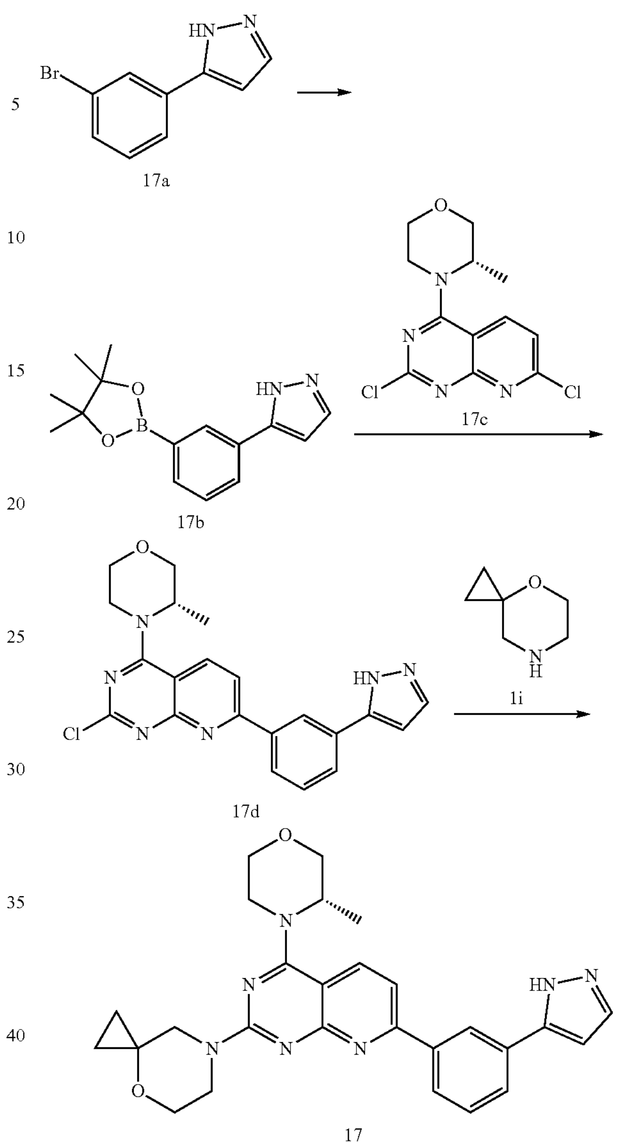

First Step

Compound 17a (100 mg, 448 μmol, 1.0 eq), bis(pinacolato)diboron (125 mg, 493 μmol, 1.1 eq), potassium acetate (132 mg, 1.34 mmol, 3.0 eq) and Pd(dppf)$Cl_2$ (16.4 mg, 22.4 μmol, 0.05 eq) were dissolved in anhydrous dioxane (5 mL), followed by ventilation for three times. The mixed solution was allowed to react at 100° C. for 17 hours under nitrogen atmosphere. After completion of the reaction, the reaction solution was directly used in the next step.

MS-ESI calculated for $[M+H]^+$: 271, found: 271.

Second Step

Compound 17c (134 mg, 448 μmol, 1.0 eq), tetrakis (triphenylphosphine) palladium (25.9 mg, 22.4 μmol, 0.05 eq) and sodium carbonate (143 mg, 1.34 mmol, 3.0 eq) were added to the reaction solution containing compound 17b, the mixture was dissolved in water (2 mL) and 1,4-dioxane (5 mL). The reaction was carried out at 70° C. for 4 hours under nitrogen protection. After completion of the reaction, the reaction solution was concentrated to remove solvent, diluted with water (10 mL), extracted with ethyl acetate (10 mL×3). The organic phases were combined, dried over anhydrous sodium sulfate, filtered, and subjected to rotary evaporation under reduced pressure to dryness, and purified by planar chromatography (pure ethyl acetate) to give 17d.

MS-ESI calculated for $[M+H]^+$: 407 and 409, found: 407 and 409.

$^1$H NMR (400 MHz, $CDCl_3$) δ: 8.60 (s, 1H), 8.14 (d, J=8.8 Hz, 1H), 8.10 (br d, J=7.8 Hz, 1H), 7.85 (d, J=7.8 Hz, 1H), 7.79 (d, J=8.8 Hz, 1H), 7.62 (d, J=2.0 Hz, 1H), 7.54-7.45 (m, 1H), 6.68 (d, J=2.0 Hz, 1H), 4.62 (br d, J=4.3 Hz, 1H), 4.15 (br d, J=12.5 Hz, 1H), 3.98-3.92 (m, 1H), 3.81-3.67 (m, 4H), 1.53 (d, J=6.8 Hz, 3H).

Third Step

Compound 17d (30 mg, 58.3 μmol, 1.00 eq), 1i (13.1 mg, 87.5 μmol, 1.50 eq) and DIPEA (22.6 mg, 175 μmol, 3.00 eq) were dissolved in DMSO (3 mL). The mixed solution was allowed to react at 70° C. for 17 hours. After completion of the reaction, the reaction solution was purified by high performance liquid chromatography to give compound 17.

MS-ESI calculated for $[M+H]^+$: 484, found: 484.

$^1$H NMR (400 MHz, $CDCl_3$) δ: 8.48 (s, 1H), 8.02 (d, J=8.0 Hz, 1H), 7.97 (d, J=8.3 Hz, 1H), 7.79 (br d, J=7.8 Hz, 1H), 7.59 (d, J=2.3 Hz, 1H), 7.49-7.42 (m, 2H), 6.67 (d, J=2.0 Hz, 1H), 4.30 (br s, 1H), 4.01-3.56 (m, 12H), 1.40 (d, J=6.8 Hz, 3H), 0.79-0.73 (m, 2H), 0.61 (br s, 2H).

Embodiments 18-1&18-2

18-1 or 18-2

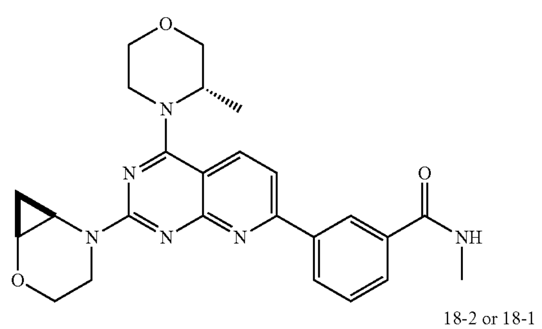

18-2 or 18-1

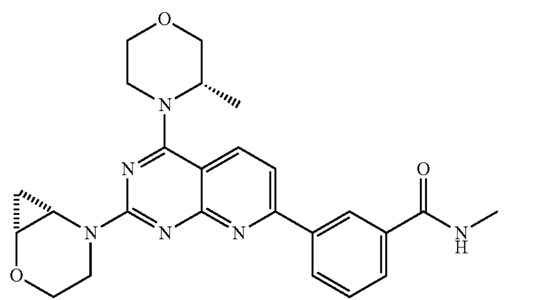

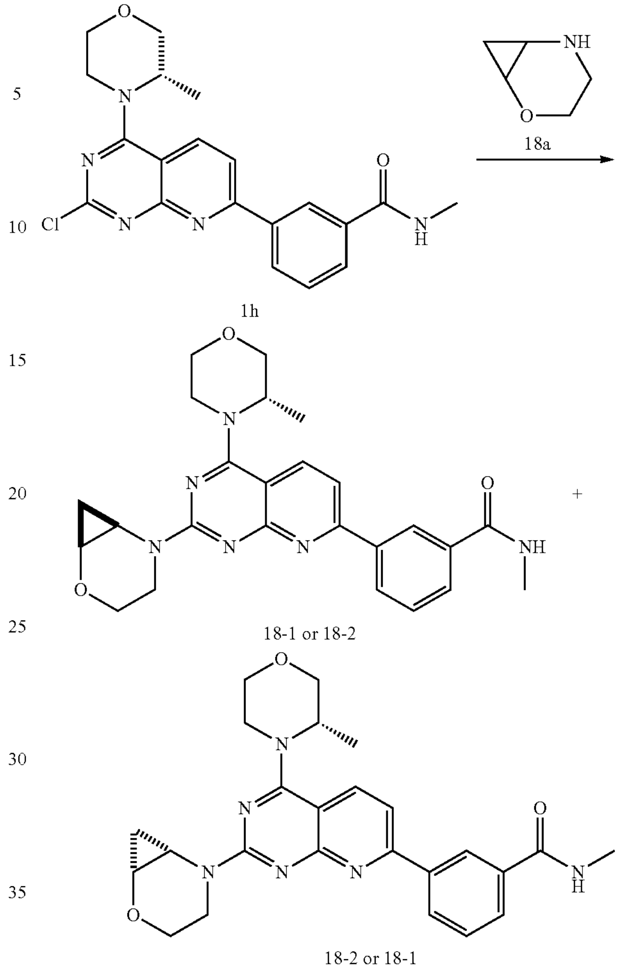

Compound 1h 100 mg, 251 μmol, 1 eq), 18a 34.1 mg, 251 μmol, 1 eq, HCl) and N, N-diisopropylethylamine (97.5 mg, 754 μmol, 131 μL, 3 eq) were dissolved in dimethyl sulfoxide (2 mL) and the mixture was reacted at 70° C. for 18 hours. After completion of the reaction, the reaction solution was purified by high performance liquid chromatography to give racemate, 50 mg of which was subjected to chiral separation to give compounds 18-1 and 18-2.

MS-ESI calculated for $[M+H]^+$: 461, found: 461.

Peak position of compound 18-1: 3.032 min (chiral column: AD-3 150×4.6 mm, mobile phase: 40% ethanol (0.05% diethylamine)+carbon dioxide, flow rate: 2.5 mL/min, column temperature: 40° C.).

18-1 NMR: $^1$H NMR (400 MHz, $CDCl_3$) δ: 8.58 (br s, 1H), 7.84-8.23 (m, 3H), 7.41-7.59 (m, 2H), 6.52 (s, 1H), 4.39 (br s, 1H), 3.63-4.02 (m, 10H), 3.04-3.63 (m, 2H), 2.99 (d, J=4.8 Hz, 3H), 1.46 (s, 3H), 0.57-0.92 (m, 2H).

Peak position of compound 18-2: 3.587 min (chiral column: AD-3 150×4.6 mm, mobile phase: 40% ethanol (0.05% diethylamine)+carbon dioxide, flow rate: 2.5 mL/min, column temperature: 40° C.).

18-2 NMR: $^1$H NMR (400 MHz, $CDCl_3$) δ: 8.49-8.82 (m, 1H), 7.82-8.23 (m, 3H), 7.42-7.58 (m, 2H), 6.53 (br s, 1H), 4.39 (br s, 1H), 3.60-4.06 (m, 10H), 3.03-3.60 (m, 2H), 2.99 (d, J=4.8 Hz, 3H), 1.46 (s, 3H), 0.54-0.99 (m, 2H).

Embodiment 19

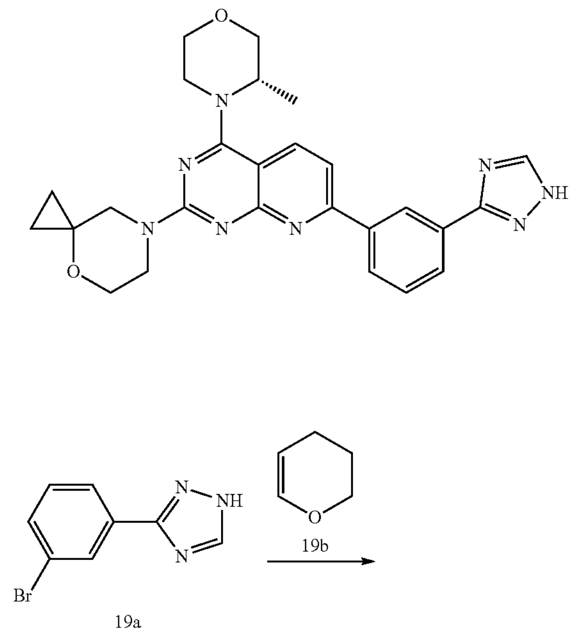

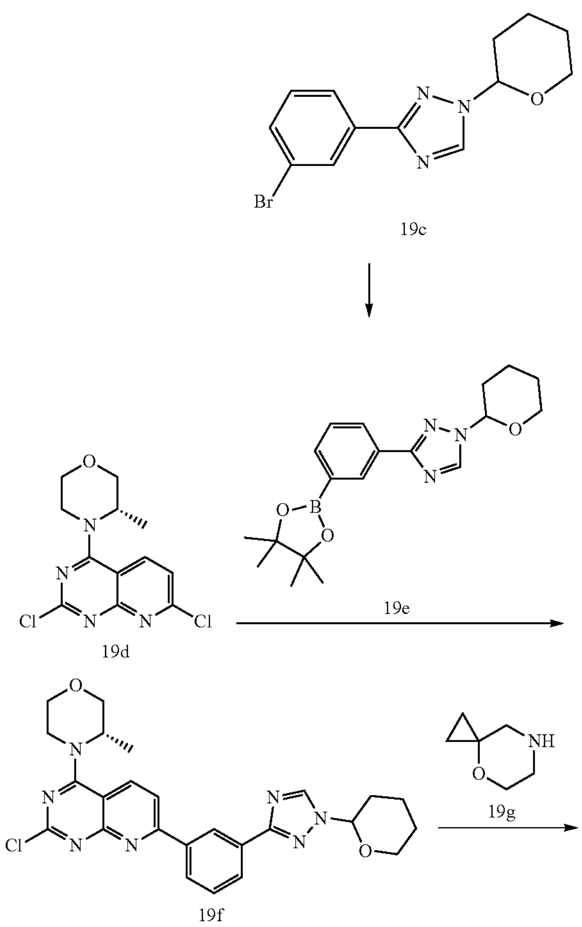

-continued

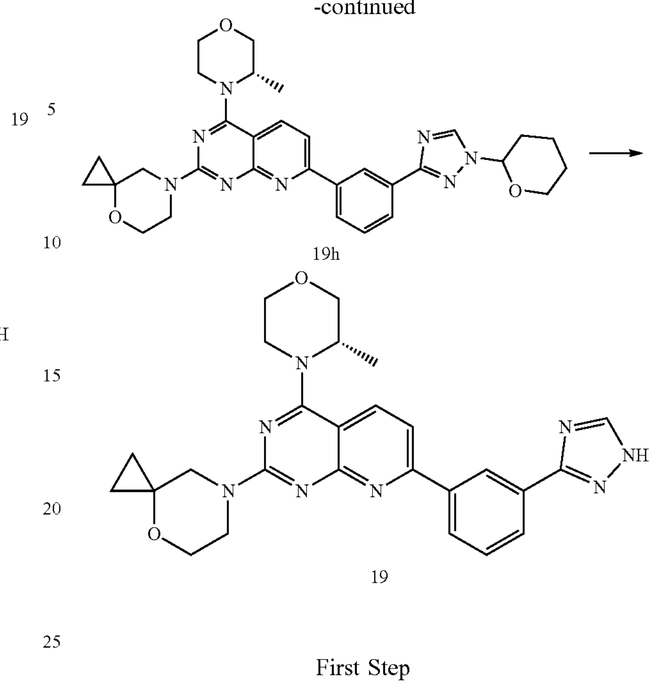

First Step

Compound 19a (50 mg, 223 μmol, 1 eq), compound 19b (37.5 mg, 446 μmol, 40.8 μL, 2 eq), and p-toluenesulfonic acid (2.14 mg, 22.3 μmol, 1.59 μL, 0.1 eq) were dissolved in tetrahydrofuran (2 mL), and the mixture was reacted at 75° C. for 3 hours under nitrogen protection. After completion of the reaction, the reaction solution was concentrated to remove solvent, diluted with water (40 mL), added with saturated sodium bicarbonate solution (10 mL), extracted with ethyl acetate (20 mL×3). The organic phases were combined, dried over anhydrous sodium sulfate, filtered, and subjected to rotary evaporation under reduced pressure to dryness, and compound 19c was obtained.

MS-ESI calculated for $[M+H]^+$308 and 310, found: 308 and 310.

Second Step

Compound 19c (70 mg, 227 mol, 1 eq), bis(pinacolato) diboron (57.7 mg, 227 mol, 1 eq), Pd (dppf)$Cl_2$ (8.31 mg, 11.4 μmol, 0.05 eq), and sodium acetate (66.9 mg, 681 μmol, 3 eq) were dissolved in 1,4-dioxane (3 mL), and the mixture was reacted at 100° C. for 16 hours under nitrogen protection. After completion of the reaction, 19e was obtained, which was directly used in the next step without treatment.

MS-ESI calculated for $[M+H]^+$: 356, found: 356.

Third Step

Compound 19d (80.7 mg, 227 μmol, 1 eq), compound 19e (68.0 mg, 227 μmol, 1 eq), tetrakis(triphenylphosphine) palladium (13.1 mg, 11.4 μmol, 0.05 eq) and sodium carbonate (72.2 mg, 681 μmol, 3 eq) were dissolved in water (1 mL) and 1,4-dioxane (3 mL), and the mixture was reacted at 90° C. for 4 hours under nitrogen protection. After completion of the reaction, the reaction solution was concentrated to remove solvent, diluted with water (30 mL), and extracted with ethyl acetate (20 mL×3). The organic phases were combined, dried over anhydrous sodium sulfate, filtered, subjected to rotary evaporation under reduced pressure to dryness, and purified by column chromatography (100% ethyl acetate) to give 19f.

MS-ESI calculated for $[M+H]^+$: 492 and 494, found: 492 and 494.

Fourth Step

Compound 19f (90 mg, 166 μmol, 1 eq), 19g (24.9 mg, 166 μmol, 1 eq, HCl) and DIPEA (64.6 mg, 499 μmol, 87.0 μL, 3 eq) were dissolved in DMSO (2 mL). The mixed solution was allowed to react at 70° C. for 16 hours. After completion of the reaction, 19h was obtained, which was directly used in the reaction of next step without treatment.

MS-ESI calculated for $[M+H]^+$: 569, found: 569.

Fifth Step

HCl (6 M, 166.48 μL, 6 eq) was added to a solution of compound 19h (94.7 mg, 166 μmol, 1 eq) in DMSO (2 mL). The mixed solution was allowed to react at 20° C. for 66 hours. After completion of the reaction, the reaction solution was purified by high performance liquid chromatography to give 19.

MS-ESI calculated for $[M+H]^+$:485, found: 485.

$^1$H NMR (400 MHz, $CDCl_3$) δ: 8.88 (s, 1H), 8.02-8.35 (m, 4H), 7.42-7.77 (m, 3H), 4.40 (br s, 1H), 4.01 (br d, J=10.4 Hz, 3H), 3.82-3.95 (m, 6H), 3.65-3.82 (m, 3H), 1.50 (d, J=6.8 Hz, 3H), 0.83 (s, 2H), 0.59-0.69 (m, 2H).

Embodiment 20

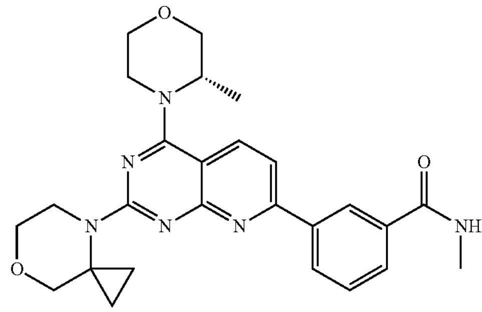

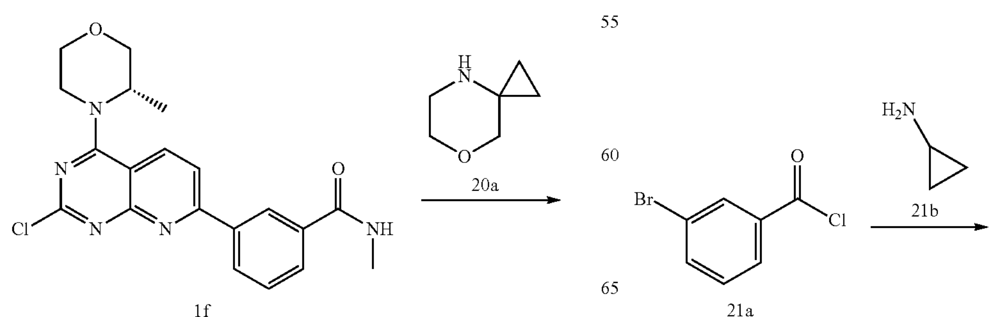

-continued

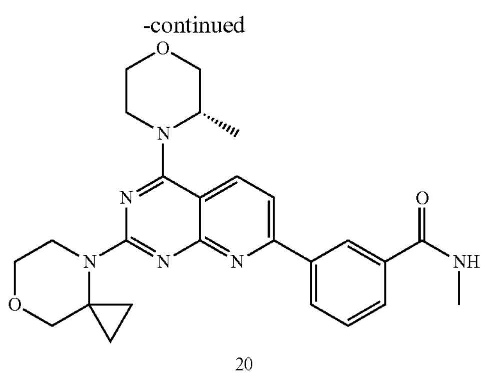

Compound 1f (60 mg, 151 μmol, 1 eq) and 20a (22.6 mg, 151 μmol, 1 eq) were dissolved in 0.8 mL tetrahydrofuran, followed by addition of potassium tert-butoxide (29.0 mg, 302 μmol, 2 eq) and Ruphos-Pd-G3(12.6 mg, 15.1 μmol, 0.1 eq). The reaction solution was subjected to nitrogen replacement for 2 minutes, and allowed to react at 80° C. for an hour. After completion of the reaction, 1 mL water was added to the reaction solution, and the reaction solution was purified by high performance liquid chromatography to give 20.

$^1$H NMR (400 MHz, $CDCl_3$) δ: 8.18 (s, 1H), 8.09 (d, J=8.0 Hz, 2H), 7.62-7.53 (m, 2H), 7.21 (s, 1H), 4.51-4.18 (m, 3H), 4.08-3.95 (m, 2H), 3.90-3.75 (m, 6H), 3.64 (s, 2H), 3.08 (d, J=5.0 Hz, 3H), 1.31 (s, 3H), 1.09-1.02 (m, 2H), 0.90 (s, 2H).

Embodiment 21

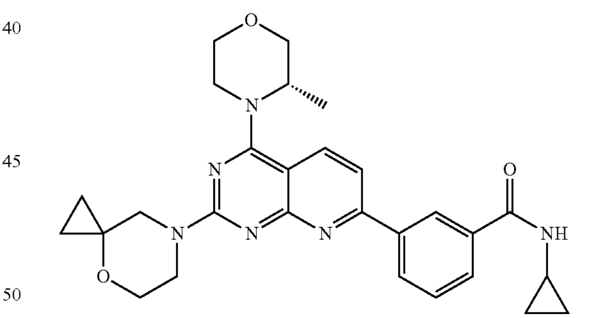

-continued

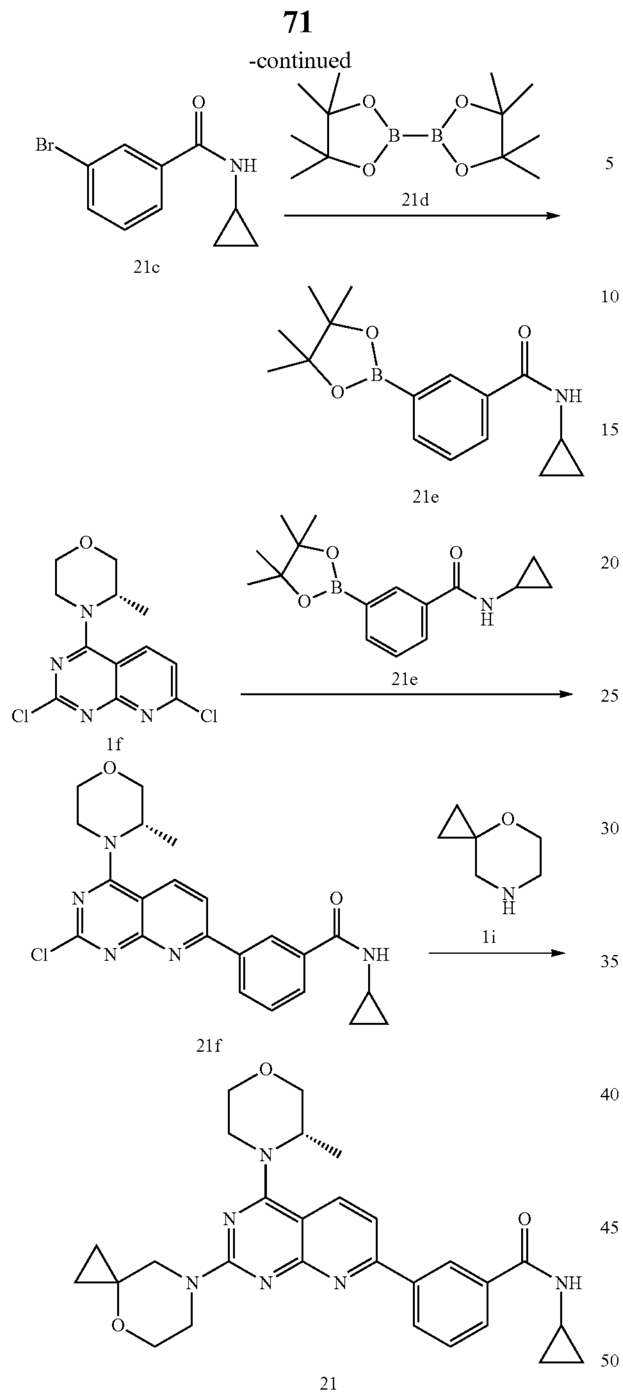

First Step

Compound 21a (5.46 g, 24.9 mmol, 3.27 mL, 1 eq) and sodium bicarbonate (6.27 g, 74.6 mmol, 2.90 mL, 3 eq) were dissolved in anhydrous tetrahydrofuran (80 mL), and then 21b (4.26 g, 74.6 mmol, 5.17 mL, 3 eq) was added dropwise. The mixed solution was allowed to react at 20° C. for 16 hours under nitrogen protection. After completion of the reaction, the reaction solution was filtered, and then the filtrate was concentrated to give 21c.

Second Step

Compound 21c (0.3 g, 1.25 mmol, 1 eq), 21d (476 mg, 1.87 mmol, 1.5 eq), $Pd(dppf)Cl_2$ (36.6 mg, 50.0 μmol, 0.04 eq) and potassium acetate (368 mg, 3.75 mmol, 3 eq) were dissolved in anhydrous dioxane (25 mL), and the mixed solution was allowed to react at 90° C. for 2 hours under nitrogen protection. After the reaction was complete and the reaction solution was cooled, the reaction solution was concentrated under reduced pressure, followed by addition of 15 mL water and 60 mL (20 mL×3) ethyl acetate for extraction. The organic phase was then dried over anhydrous sodium sulfate, concentrated, and purified by column chromatography (42.5%-petroleum ether/ethyl acetate) to give 21e.

MS-ESI calculated for $[M+H]^+$: 288, found: 288.

$^1$H NMR (400 MHz, $CDCl_3$) δ: 7.95-7.89 (m, 2H), 7.85 (d, J=7.6 Hz, 1H), 7.42-7.33 (m, 1H), 2.83 (qt, J=3.6, 7.07 Hz, 1H), 1.28 (s, 12H), 0.83-0.76 (m, 2H), 0.54-0.59 (m, 2H).

Third Step

Compound 1f (0.1 g, 334 μmol, 1 eq), 21e (125 mg, 435 μmol, 1.3 eq), diisopropylamine tetrakis(triphenylphosphine) palladium (23.2 mg, 20.1 μmol, 0.06 eq) and potassium carbonate (139 mg, 1.00 mmol, 3 eq) were dissolved in anhydrous dioxane (10 mL) and water (2 mL), and the reaction solution was allowed to react at 70° C. for 4 hours. After completion of the reaction, the reaction solution was concentrated under reduced pressure, and then purified by column chromatography (20.2%-methanol/ethyl acetate) to give 21f.

MS-ESI calculated for $[M+H]^+$: 424 and 426, found: 424 and 426.

Fourth Step

Compound 21f (0.09 g, 212 μmol, 1 eq), 1i (31.8 mg, 212 μmol, 1 eq, HCl) and diisopropylamine (27.4 mg, 212 μmol, 37.0 μL, 1 eq) were dissolved in dimethyl sulfoxide (4 mL), the reaction solution was allowed to react at 70° C. for 15 hours. After completion of the reaction, the reaction solution was purified by high performance liquid chromatography to give 21.

MS-ESI calculated for $[M+H]^+$: 501, found: 501.

$^1$H NMR (400 MHz, $CD_3OD$) δ: 8.60 (s, 1H), 8.31 (d, J=8 Hz, 1H), 8.28 (d, J=8.4 Hz, 1H), 4.52 (br d, J=6.0 Hz, 1H), 4.07-3.93 (m, 6H), 3.89-3.83 (m, 3H), 3.80-3.71 (m, 3H), 2.92-2.91 (m, 1H), 1.48 (d, J=6.8 Hz, 3H), 0.90-0.79 (m, 4H), 0.74-0.68 (m, 4H).

Embodiment 22

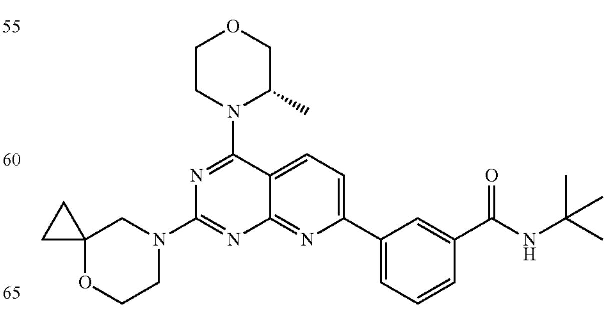

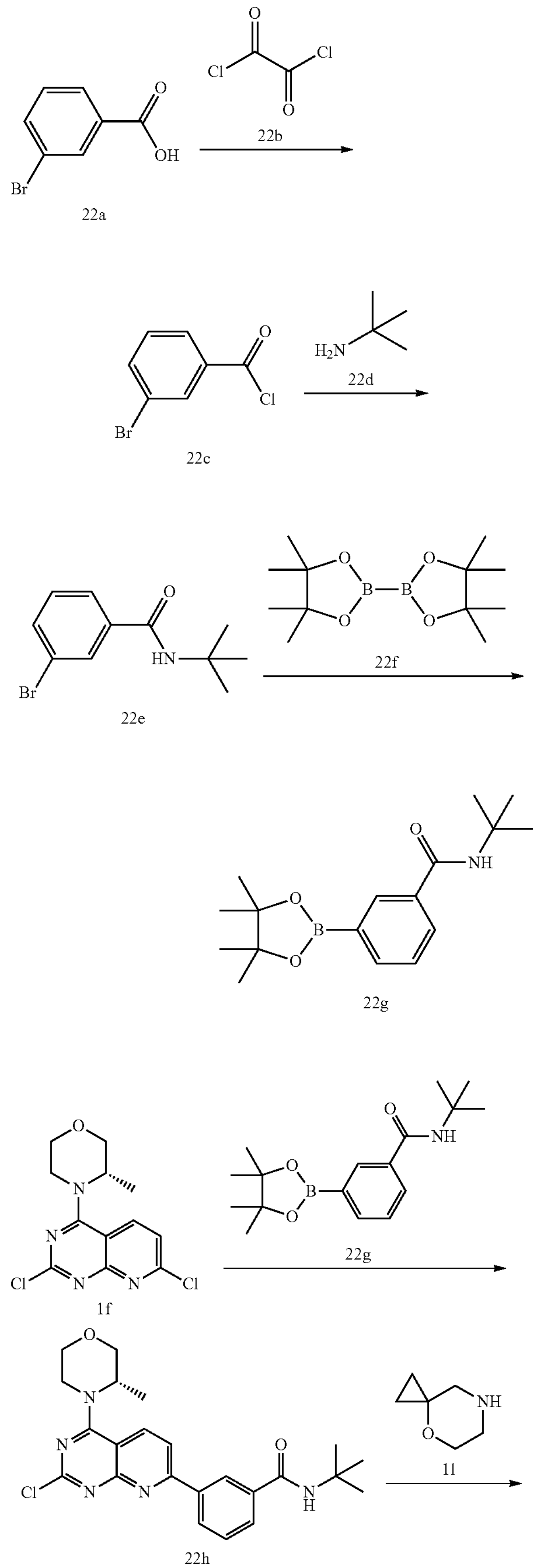

-continued

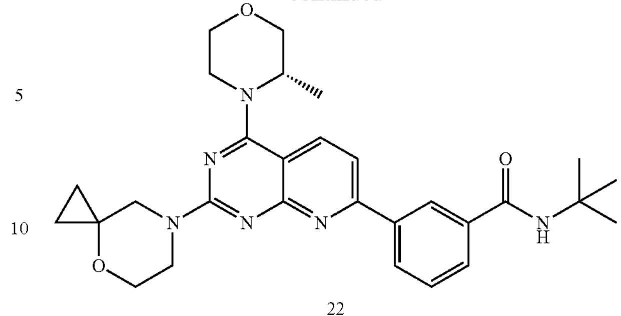

First Step

Compound 22a (5 g, 24.9 mmol, 1 eq) and compound 22b (3.79 g, 29.9 mmol, 2.61 mL, 1.2 eq) were dissolved in dichloromethane (50 mL), and DMF (18.2 mg, 249 mol, 19.1 μL, 0.01 eq) was added dropwise. The reaction solution was allowed to react at room temperature for 2 hours. After completion of the reaction, compound 22c was obtained.

Second Step

Compound 22c (5.46 g, 29 mmol, 1 eq), compound 22d (7.28 g, 99.5 mmol, 10.5 mL, 4 eq) and DIPEA (12.9 g, 99.5 mmol, 17.3 mL, 4 eq) were dissolved in dichloromethane (50 mL), and the mixture was reacted at room temperature for 5 hours. After completion of the reaction, the reaction solution was washed with water (50 mL×3). The organic phase was dried over anhydrous sodium sulfate, filtered, and subjected to rotary evaporation under reduced pressure to dryness to give 22e.

MS-ESI calculated for $[M+H]^+$: 256 and 258, found: 256 and 258.

Third Step

Compound 22e (300 mg, 1.17 mmol, 1 eq), compound 22f (356.9 mg, 1.41 mmol, 1.2 eq), potassium acetate (344 mg, 3.51 mmol, 3 eq) and Pd (dppf)$Cl_2$ (42.9 mg, 58.6 μmol, 0.05 eq) were dissolved in 1,4-dioxane (10 mL). The reaction solution was allowed to react at 90° C. for 4 hours under nitrogen protection. After completion of the reaction, the reaction solution was concentrated to remove solvent, diluted with water (30 mL), extracted with ethyl acetate (20 mL×3), and the organic phases were combined, dried over anhydrous sodium sulfate, filtered, subjected to rotary evaporation under reduced pressure to dryness, and purified by column chromatography (40% ethyl acetate) to give 22g.

MS-ESI calculated for $[M+H]^+$: 304, found: 304.

Fourth Step

Compound 1f (98.7 mg, 330 μmol, 1 eq), 22g (100 mg, 330 μmol, 1 eq), sodium carbonate (105 mg, 989 μmol, 3 eq) and tetrakis(triphenylphosphine) palladium (19.1 mg, 16.5 μmol, 0.05 eq) were dissolved in 1,4-dioxane (3 mL) and water (1 mL). The reaction solution was allowed to react at 90° C. for 5 hours under nitrogen protection. After completion of the reaction, the reaction solution was concentrated to remove solvent, diluted with water (20 mL), and extracted with ethyl acetate (20 mL×3). The organic phases were combined, dried over anhydrous sodium sulfate, filtered, subjected to rotary evaporation under reduced pressure to dryness, and purified by column chromatography (100% ethyl acetate) to give 22h.

MS-ESI calculated for $[M+H]^+$: 440 and 442, found: 440 and 442.

Fifth Step

Compound 22h (60.0 mg, 136 μmol, 1 eq), 1i (20.4 mg, 136 μmol, 1 eq, HCl) and DIPEA (52.9 mg, 409 μmol, 71.3 μL, 3 eq) were dissolved in DMSO (3 mL). The mixed solution was allowed to react at 70° C. for 15 hours and purified by high performance liquid chromatography to give 22.

MS-ESI calculated for $[M+H]^+$: 517, found: 517.

$^1$H NMR (400 MHz, $CDCl_3$) δ: 8.53 (s, 1H), 8.19 (d, J=8.0 Hz, 1H), 8.06 (d, J=8.6 Hz, 1H), 7.94 (d, J=7.8 Hz, 1H), 7.45-7.64 (m, 2H), 6.28 (br s, 1H), 4.32-4.48 (m, 1H), 3.62-4.24 (m, 12H), 1.43-1.61 (m, 12H), 0.58-0.95 (m, 4H).

Embodiment 23

23

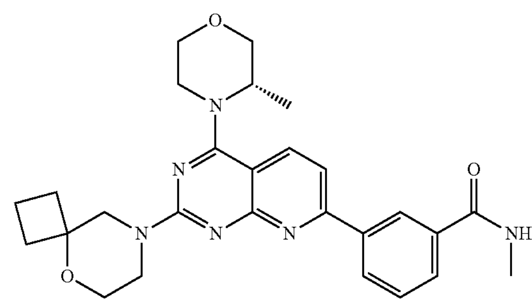

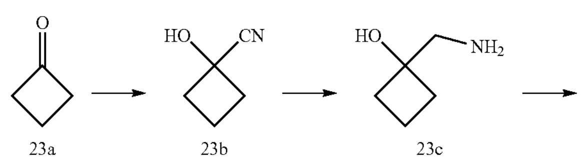

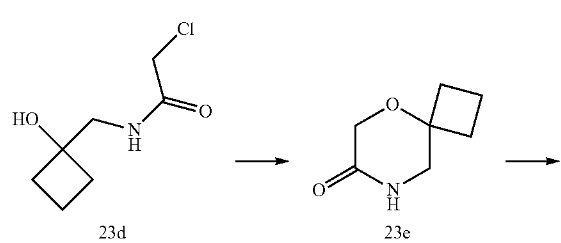

-continued

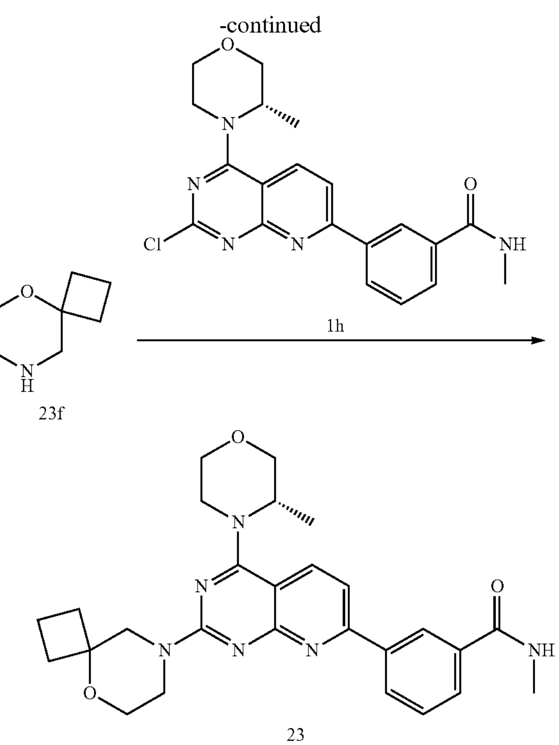

First Step

Compound 23a (23.0 g, 328 mmol, 24.5 mL, 1.0 eq) and zinc diiodide (5.20 g, 16.4 mmol, 0.05 eq) were dissolved in 200 mL dichloromethane. The internal temperature thereof was lowered to 0° C. Trimethylsilyl cyanide (39.1 g, 393 mmol, 49 mL, 1.2 eq) was added. The reaction solution was allowed to react at 25° C. for 18 hours. After completion of the reaction, the reaction solution was concentrated, followed by addition of 50 mL acetonitrile and 50 mL hydrochloric acid aqueous solution (1M). The reaction solution was stirred for 5 minutes at 25° C., and extracted with ethyl acetate. The organic phase was dried, filtered, and concentrated by evaporation. The obtained residue was purified by silica gel chromatography (petroleum ether/ethyl acetate=100:1-1:1) to give 23b.

$^1$H NMR (400 MHz, $CDCl_3$) δ: 4.30 (s, 1H), 2.62-2.59 (m, 2H), 2.33-2.30 (m, 2H), 1.95-1.79 (m, 2H).

Second Step 23b (16.0 g, 164 mmol, 1 eq) was added into a solution of lithium aluminum hydride (9.38 g, 247 mmol, 1.5 eq) in tetrahydrofuran (300 mL) at 0° C., and the mixture was allowed to react at 20° C. for 18 hours. After completion of the reaction, water (9.38 mL), 15% sodium hydroxide (9.38 mL) and water (28.1 mL) were sequentially added to the reaction solution, stirred for 15 minutes, filtered, and concentrated to give 23c.

$^1$H NMR (400 MHz, $CDCl_3$) δ: 2.72 (s, 2H), 2.12-1.76 (m, 7H), 1.7-1.63 (m, 1H), 1.49-1.33 (m, 1H).

Third Step

Chloroacetyl chloride (2.23 g, 19.8 mmol, 1.6 mL, 1.0 eq) was added into a solution of 23c (2.0 g, 19.8 mmol, 1 eq) and diisopropylethylamine (4.0 g, 31.0 mmol, 5.4 mL, 1.6 eq) in dichloromethane (20.0 mL) at 0° C. The reaction solution was reacted at 20° C. for 2 hours. After completion of the reaction, the reaction solution was concentrated and the residue was purified by silica gel chromatography (petroleum ether/ethyl acetate=100:1-1:1) to give 23d.

$^1$H NMR (400 MHz, $CDCl_3$) δ: 6.99 (s, 1H), 4.17-4.02 (m, 2H), 3.50 (d, J=6.0 Hz, 2H), 2.71 (s, 1H), 2.14-1.98 (m, 4H), 1.81-1.71 (m, 1H), 1.64-1.49 (m, 1H).

Fourth Step

Compound 23d (2.2 g, 12.4 mmol, 1 eq) was added to anhydrous tetrahydrofuran (100 mL). The internal temperature thereof was lowered to 0° C., and sodium hydride (1.49 g, 37.2 mmol, 60% purity, 3 eq) was added. The reaction solution was reacted at 20° C. for 18 hours. After completion of the reaction, water (15.0 mL) was added to the reaction solution. The reaction solution was extracted with ethyl acetate (20 mL×3), and the organic phases were combined, dried, filtered, and concentrated to give 23e.

$^1$H NMR (400 MHz, $CDCl_3$) δ: 6.96 (s, 1H), 4.15 (s, 2H), 3.44-3.35 (m, 2H), 2.27-2.16 (m, 2H), 2.09-2.01 (m, 2H), 1.95-1.86 (m, 1H), 1.74-1.63 (m, 1H).

Fifth Step 23e (1.2 g, 8.5 mmol, 1 eq) was added to a solution of lithium aluminium hydride (645 mg, 17 mmol, 2 eq) in tetrahydrofuran (30 mL) at 0° C., and the mixture was allowed to react at 20° C. for 18 hours. After completion of the reaction, water (0.7 mL), 15% sodium hydroxide (0.7 mL) and water (2.1 mL) were sequentially added to the reaction solution, stirred for 15 minutes, filtered, and concentrated to give 23f.

$^1$H NMR (400 MHz, $CDCl_3$) δ: 3.61-3.51 (m, 2H), 2.87-2.76 (m, 4H), 2.03-1.97 (m, 4H), 1.86-1.82 (m, 1H), 1.62-1.54 (m, 1H).

Sixth Step

Compound 23f (53 mg, 414 μmol, 1.1 eq), 1h (150 mg, 377 μmol, 1 eq) and DIPEA (48 mg, 377 μmol, 66 μL, 1 eq) were dissolved in DMSO (4 mL). The mixed solution was allowed to react at 70° C. for 18 hours. After completion of the reaction, and the reaction solution was purified by high performance liquid chromatography to give 23.

MS-ESI calculated for $[M+H]^+$: 489, found: 489.

$^1$H NMR (400 MHz, $CDCl_3$) δ: 8.63 (s, 1H), 8.22 (d, J=7.6 Hz, 1H), 8.05 (d, J=8.4 Hz, 1H), 7.97 (d, J=7.6 Hz, 1H), 7.65-7.41 (m, 2H), 6.53 (br s, 1H), 4.40 (d, J=6.8 Hz, 1H), 4.12-3.95 (m, 3H), 3.93-3.83 (m, 4H), 3.83-3.68 (m, 5H), 3.06 (d, J=4.8 Hz, 3H), 2.07-2.04 (m, 4H), 1.91-1.80 (m, 1H), 1.77-1.70 (m, 1H), 1.50 (d, J=6.8 Hz, 3H).

Embodiment 24

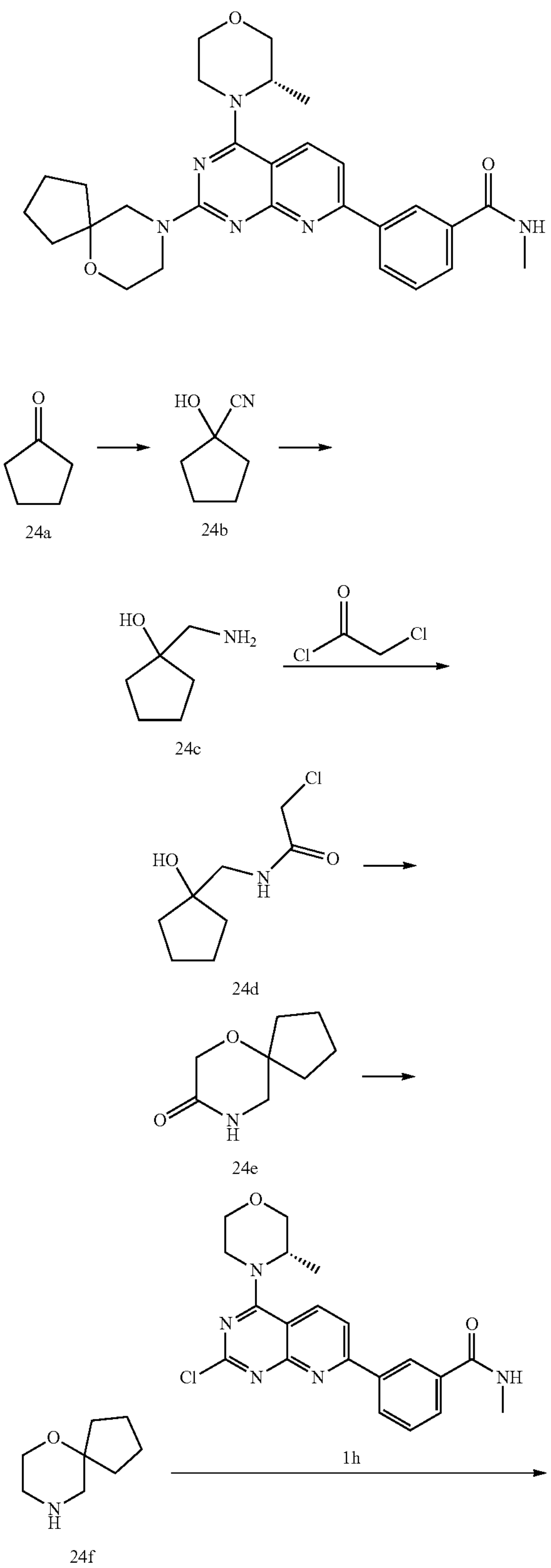

-continued

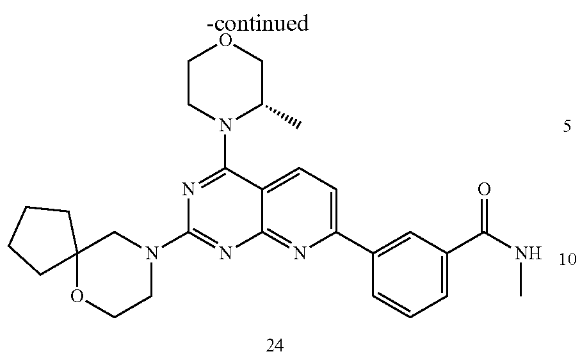

24

First Step

Compound 24a (23.0 g, 273 mmol, 24.2 mL, 1 eq) and zinc diiodide (4.36 g, 13.7 mmol, 0.05 eq) were dissolved in 200 mL dichloromethane. The internal temperature thereof was cooled to 0° C. Trimethylsilyl cyanide (32.6 g, 328 mmol, 41.1 mL, 1.2 eq) was added. The reaction solution was allowed to react at 25° C. for 18 hours. After completion of the reaction, the reaction solution was concentrated, followed by addition of 50 mL acetonitrile and 50 mL hydrochloric acid aqueous solution (1M). The reaction solution was stirred for 5 minutes at 25° C., and extracted with ethyl acetate. The organic phase was dried, filtered, concentrated by evaporation. The obtained residue was purified by silica gel chromatography (petroleum ether/ethyl acetate=100:1-1:1) to give 24b.

$^1$H NMR (400 MHz, $CDCl_3$) δ: 3.27-3.20 (m, 1H), 2.10-2.06 (m, 4H), 1.87-1.80 (m, 4H).

Second Step 24b (16.0 g, 164 mmol, 1 eq) was added into a solution of lithium aluminum hydride (8.19 g, 216 mmol, 1.5 eq) in tetrahydrofuran (300 mL) at 0° C., and the mixture was allowed to react at 20° C. for 18 hours. After completion of the reaction, water (8.19 mL), 15% sodium hydroxide (8.19 mL) and water (25 mL) were sequentially added to the reaction solution, stirred for 15 minutes, filtered, and concentrated to give 24c.

$^1$H NMR (400 MHz, $CDCl_3$) δ: 2.74 (s, 2H), 1.90-1.55 (m, 9H), 1.54-1.47 (m, 2H).

Third Step

Chloroacetyl chloride (1.96 g, 17.4 mmol, 1.38 mL, 1.0 eq) was added into a solution of 24c (2.0 g, 17.4 mmol, 1 eq) and diisopropylethylamine (3.37 g, 26.1 mmol, 4.54 mL, 1.5 eq) in dichloromethane (20 mL) at 0° C. The reaction solution was reacted at 20° C. for 2 hours. After completion of the reaction, the reaction was concentrated and the residue was purified by silica gel chromatography (petroleum ether/ethyl acetate=100:1-1:1) to give 24d.

$^1$H NMR (400 MHz, $CDCl_3$) δ: 7.03 (s, 1H), 4.09 (s, 2H), 3.44 (d, J=5.6 Hz, 2H), 2.00 (s, 1H), 1.89-1.77 (m, 2H), 1.67-1.64 (m, 6H).

Fourth Step

Compound 24d (2.6 g, 13.6 mmol, 1 eq) was added to anhydrous tetrahydrofuran (100 mL). The internal temperature thereof was lowered to 0° C., and sodium hydride (1.63 g, 40.7 mmol, 60%, 3 eq) was added. The reaction solution was allowed to react at 20° C. for 18 hours. After completion of the reaction, water (15.0 mL) was added to the reaction solution. The reaction solution was extracted with ethyl acetate (20 mL×3), and the organic phases were combined, dried, filtered, and concentrated to give 24e.

$^1$H NMR (400 MHz, $CDCl_3$) δ: 6.79 (s, 1H), 4.19 (s, 2H), 3.38-3.33 (m, 2H), 1.74-1.64 (m, 8H).

Fifth Step 24e (1.8 g, 11.6 mmol, 1 eq) was added to a solution of lithium aluminium hydride (880.32 mg, 23.2 mmol, 2 eq) in tetrahydrofuran (50 mL) at 0° C., and the mixture was allowed to react at 20° C. for 18 hours. After completion of the reaction, water (0.9 mL), 15% sodium hydroxide (0.9 mL) and water (2.7 mL) were sequentially added to the reaction solution, stirred for 15 minutes, filtered, and concentrated to give crude product 24f.

Sixth Step

Compound 24f (159 mg, 1.13 mmol, 3 eq), 1h (150 mg, 377 μmol, 1 eq) and DIPEA (97.5 mg, 754 μmol, 131 μL, 2 eq) were dissolved in DMSO (4 mL). The mixed solution was allowed to react at 70° C. for 18 hours. After completion of the reaction, and the reaction solution was purified by high performance liquid chromatography to give 24.

MS-ESI calculated for $[M+H]^+$: 503, found: 503.

$^1$H NMR (400 MHz, $CDCl_3$) δ: 8.62 (s, 1H), 8.22 (d, J=8.0 Hz, 1H), 8.05 (d, J=8.4 Hz, 1H), 7.97 (d, J=8.0 Hz, 1H), 7.57 (t, J=8.0 Hz, 1H), 7.51 (d, J=8.4 Hz, 1H), 6.46 (s, 1H), 4.38 (d, J=5.6 Hz, 1H), 4.00 (d, J=10.8 Hz, 2H), 3.93-3.64 (m, 10H), 3.06 (d, J=4.8 Hz, 3H), 1.85-1.70 (m, 6H), 1.64 (s, 2H), 1.49 (d, J=6.8 Hz, 3H).

25

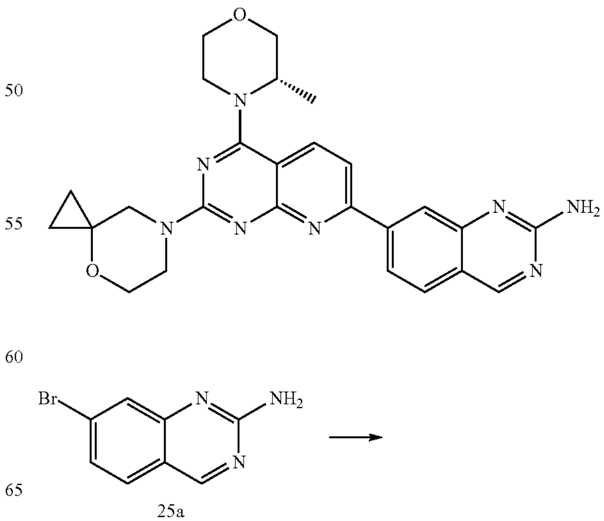

25a

-continued

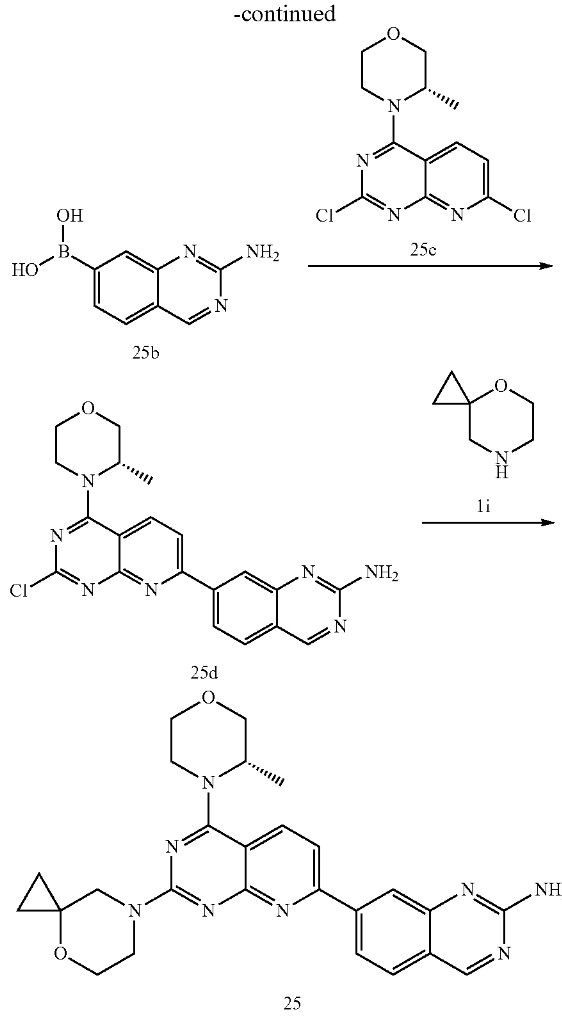

First Step

Compound 25a (100 mg, 446 µmol, 1.0 eq), bis(pinacolato)diboron (136 mg, 536 µmol, 1.2 eq), potassium acetate (131 mg, 1.34 mmol, 3.0 eq) and Pd(dppf)$Cl_2$ (16.4 mg, 22.4 µmol, 0.05 eq) were dissolved in anhydrous dioxane (5 mL), followed by ventilation for three times. The mixed solution was allowed to react at 90° C. for 16 hours under nitrogen atmosphere. After completion of the reaction, a reaction solution containing 25b was obtained, which was directly used in the next step.

MS-ESI calculated for $[M+H]^+$:190, found: 190.

Second Step

The solution containing compound 25b was added with compound 25c (133 mg, 446 µmol, 1.0 eq), tetrakis(triphenylphosphine) palladium (25.8 mg, 22.3 µmol, 0.05 eq), and sodium carbonate (142 mg, 1.34 mmol, 3.0 eq) dissolved in water (2 mL) and 1,4-dioxane (5 mL). The reaction solution was allowed to react at 80° C. for 17 hours under nitrogen protection. After completion of the reaction, the reaction solution was concentrated to remove solvent, diluted with water (10 mL), extracted with ethyl acetate (20 mL×3). The organic phases were combined, dried over anhydrous sodium sulfate, filtered, subjected to rotary evaporation under reduced pressure to dryness, and purified by column chromatography (1:10 methanol/dichloromethane) to give 25d.

MS-ESI calculated for $[M+H]^+$408, and 410, found: 408 and 410.

Third Step

Compound 25d (30 mg, 73.5 µmol, 1.00 eq), 1i (10.0 mg, 66.8 µmol, 1.00 eq) and DIPEA (28.5 mg, 221 µmol, 3.00 eq) were dissolved in DMSO (2 mL). The mixed solution was allowed to react at 70° C. for 17 hours. After completion of the reaction, and the reaction solution was purified by high performance liquid chromatography to obtain compound 25.

MS-ESI calculated for $[M+H]^+$: 485, found: 485.

$^1$H NMR (400 MHz, $CDCl_3$) δ: 9.01 (s, 1H), 8.22 (br d, J=8.0 Hz, 1H), 8.09 (s, 1H), 8.01 (d, J=8.4 Hz, 1H), 7.75 (d, J=8.4 Hz, 1H), 7.50 (d, J=8.4 Hz, 1H), 5.18 (s, 2H), 4.31 (br s, 1H), 4.02-3.54 (m, 12H), 1.41 (d, J=6.4 Hz, 3H), 0.77 (s, 2H), 0.61 (br s, 2H).

Embodiment 26

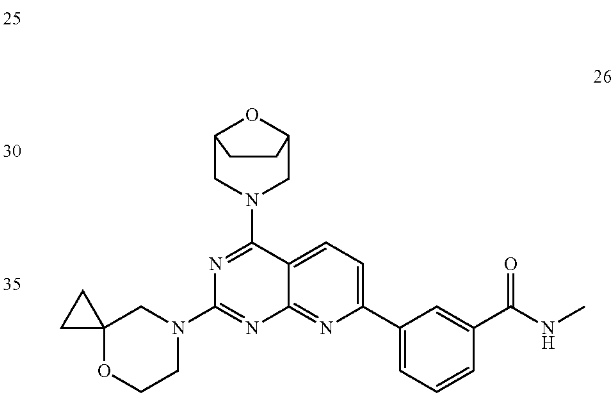

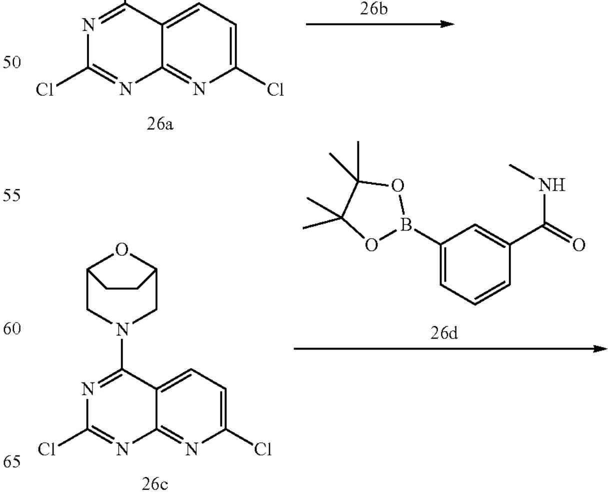

-continued

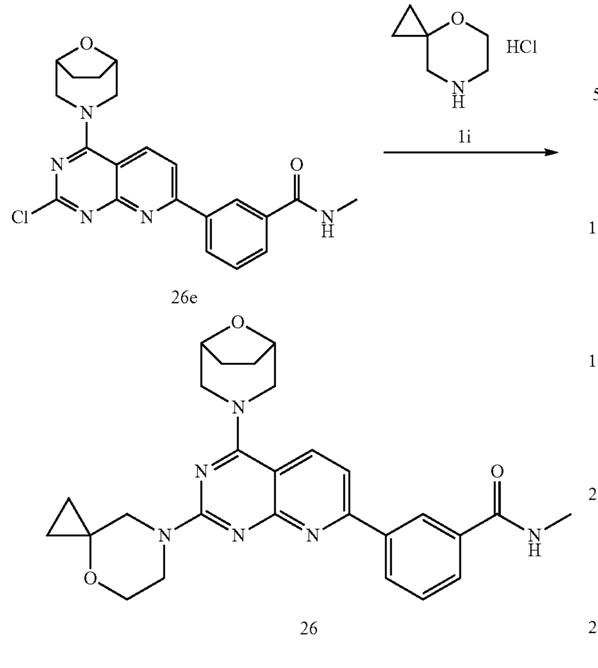

First Step

Compound 26a (150 mg, 639 μmol, 1.00 eq), compound 26b (57.4 mg, 639 μmol, 1.00 eq) and diisopropylethylamine (248 mg, 1.92 mmol, 2.83 mL, 3.00 eq) were dissolved in dichloromethane (10 mL), and the mixture was allowed to react at 20° C. for 2 hours. After completion of the reaction, the reaction solution was concentrated and purified by column chromatography (1:5 methanol/dichloromethane) to give 26c.

Second Step

Compound 26c (0.12 g, 386 μmol, 1.00 eq), compound 26d (90.6 mg, 347 μmol, 0.90 eq), tetrakis (triphenylphosphine) palladium (22.3 mg, 19.3 μmol, 0.05 eq) and sodium carbonate (123 mg, 1.16 mmol, 3.00 eq) were dissolved in water (3 mL) and 1,4-dioxane (10 mL), and the mixture was allowed to react at 80° C. for 16 hours under nitrogen protection. After completion of the reaction, the reaction solution was concentrated to remove solvent, diluted with water (10 mL), extracted with ethyl acetate (20 mL×3). The organic phases were combined, dried over anhydrous sodium sulfate, filtered, and subjected to rotary evaporation under reduced pressure to remove solvent, and purified by column chromatography (1.5 methanol/dichloromethane) to give 26e.

Third Step

Compound 26e (70 mg, 171 μmol, 1.00 eq), 1i (30.7 mg, 205 μmol, 1.20 eq) and DIPEA (66.2 mg, 512 mol, 89 μL, 3.00 eq) were dissolved in DMSO (3 mL). The mixed solution was allowed to react at 70° C. for 17 hours. After completion of the reaction, the reaction solution was purified by high performance liquid chromatography to give 26.

MS-ESI calculated for $[M+H]^+$: 487, found: 487.

$^1$H NMR (400 MHz, $CDCl_3$) δ: 8.62 (s, 1H), 8.21 (d, J=7.8 Hz, 1H), 8.06 (d, J=8.4 Hz, 1H), 7.98 (d, J=7.8 Hz, 1H), 7.56 (t, J=7.8 Hz, 1H), 7.49 (d, J=8.4 Hz, 1H), 6.59 (br s, 1H), 4.48 (br s, 2H), 4.13 (br d, J=12.8 Hz, 2H), 4.06 (br s, 2H), 3.94 (br s, 2H), 3.90-3.84 (m, 2H), 3.62 (br d, J=11.6 Hz, 2H), 3.06 (d, J=4.8 Hz, 3H), 2.06-1.90 (m, 4H), 0.89-0.82 (m, 2H), 0.69 (s, 2H).

Embodiment 27

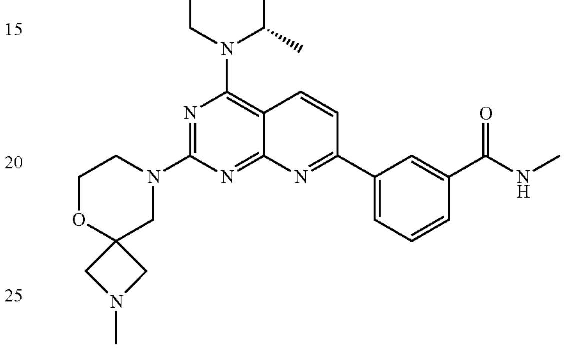

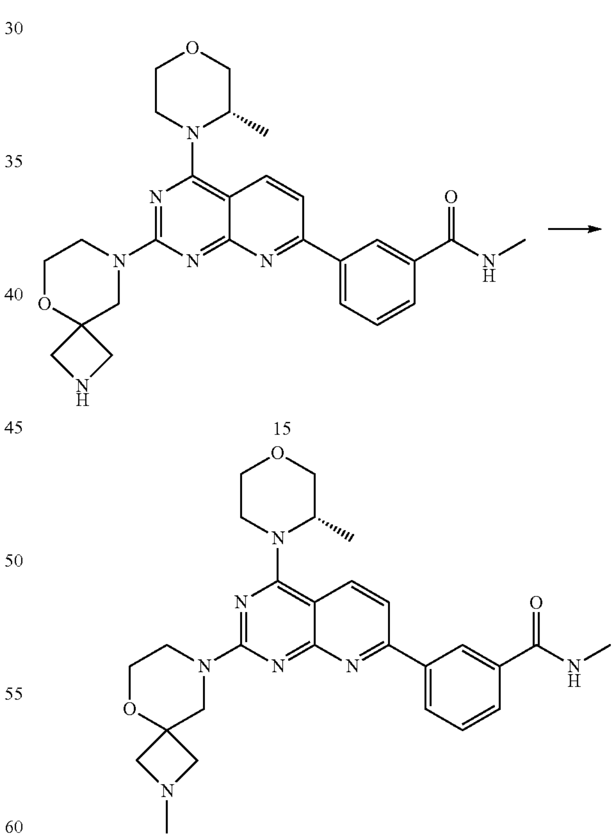

Compound 15 (150 mg, 306 μmol, 1 eq) and formaldehyde (11.96 mg, 398 mol, 11.0 μL, 1.3 eq) were dissolved in dichloroethane (10 mL) and acetic acid (2 mL), followed by addition of sodium cyanoborohydride (38.5 mg, 613 μmol, 2 eq). The mixed solution was allowed to react at 20° C. for 18 hours. After completion of the reaction, and the reaction solution was cooled, the reaction solution was concentrated under reduced pressure, and the obtained residue was purified by high performance liquid chromatography to give 27.

MS-ESI calculated for $[M+H]^+$: 504, found: 504.

$^1H$ NMR (400 MHz, $CD_3OD$) δ: 8.63 (s, 1H), 8.36-8.30 (m, 2H), 7.96 (d, J=8.0 Hz, 1H), 7.71 (d, J=8.6 Hz, 1H), 7.65 (t, J=7.8 Hz, 1H), 4.63 (br s, 2H), 4.17-3.85 (m, 7H), 3.83-3.67 (m, 8H), 2.99 (s, 3H), 2.61 (s, 3H), 1.51 (d, J=6.8 Hz, 3H).

Embodiment 28

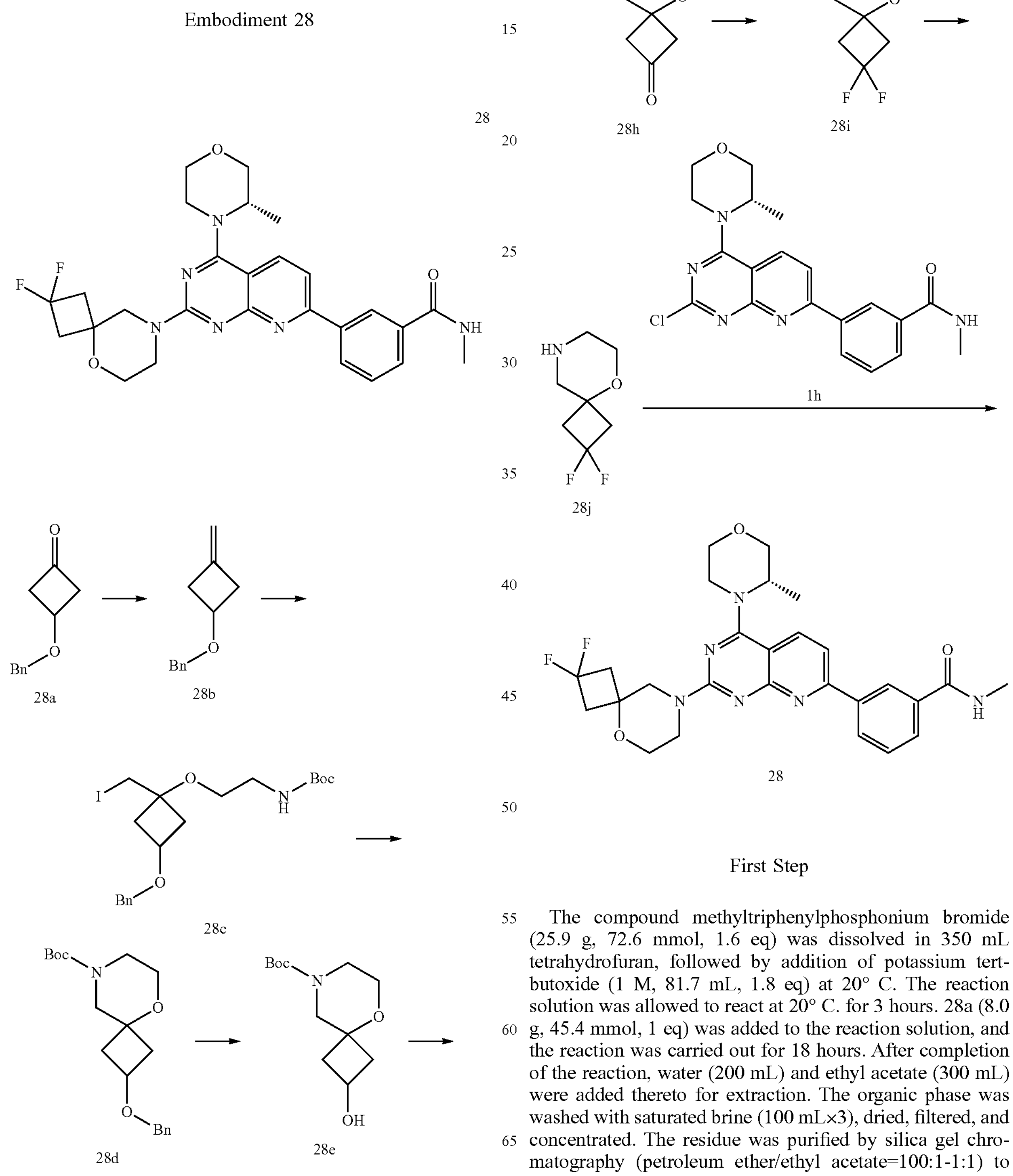

First Step

The compound methyltriphenylphosphonium bromide (25.9 g, 72.6 mmol, 1.6 eq) was dissolved in 350 mL tetrahydrofuran, followed by addition of potassium tert-butoxide (1 M, 81.7 mL, 1.8 eq) at 20° C. The reaction solution was allowed to react at 20° C. for 3 hours. 28a (8.0 g, 45.4 mmol, 1 eq) was added to the reaction solution, and the reaction was carried out for 18 hours. After completion of the reaction, water (200 mL) and ethyl acetate (300 mL) were added thereto for extraction. The organic phase was washed with saturated brine (100 mL×3), dried, filtered, and concentrated. The residue was purified by silica gel chromatography (petroleum ether/ethyl acetate=100:1-1:1) to give 28b.

$^{1}H$ NMR (400 MHz, $CDCl_3$) δ: 7.36-7.31 (m, 5H), 4.87-4.85 (m, 2H), 4.46 (s, 2H), 4.45-4.08 (m, 1H), 2.89-2.86 (m, 2H), 2.78-2.73 (m, 2H).

Second Step

NIS (2.32 g, 10.3 mmol, 1.2 eq) was added to a solution of 28b (1.5 g, 8.61 mmol, 640 μL, 1 eq) and tert-butyl N-(2-hydroxyethyl) formate (1.67 g, 10.3 mmol, 1.60 mL, 1.2 eq) in acetonitrile (14 mL), and the mixture was allowed to react at 20° C. for 4 hours. After completion of the reaction, the reaction solution was sequentially added with water (20 mL) and ethyl acetate (30 mL) for extraction, dried, filtered, and concentrated. The residue was purified by silica gel chromatography (petroleum ether/ethyl acetate=100:1-1:1) to give 28c.

$^{1}H$ NMR (400 MHz, $CDCl_3$) δ: 7.33-7.30 (m, 5H), 5.01-4.97 (m, 1H), 4.44-4.43 (m, 2H), 3.79-3.71 (m, 1H), 3.33-3.32 (m, 3H), 2.45-2.40 (m, 5H), 2.03-2.02 (m, 1H), 1.46 (s, 9H).

Third Step

Compound 28c (1.8 g, 3.90 mmol, 1 eq) was added to anhydrous tetrahydrofuran (50 mL). The internal temperature was lowered to 0° C., followed by addition of sodium hydride (312 mg, 7.80 mmol, 60%, 2 eq). The reaction solution was reacted at 20° C. for 18 hours. After completion of the reaction, the reaction solution was extracted with water (50.0 mL) and ethyl acetate (50 mL). The organic phases were combined, dried, filtered, and concentrated. The residue was purified by silica gel chromatography (petroleum ether/ethyl acetate=100:1-1:1) to give 28d.

$^{1}H$ NMR (400 MHz, $CDCl_3$) δ: 7.33-7.20 (m, 5H), 4.63-4.09 (m, 3H), 3.52-3.50 (m, 2H), 3.37 (s, 1H), 3.30 (s, 2H), 3.18 (s, 1H), 2.35 (s, 1H), 2.28-2.15 (m, 1H), 1.97-1.85 (m, 2H), 1.43-1.28 (m, 9H).

Fourth Step

Compound 28d (2.6 g, 13.6 mmol, 1 eq) was added to ethyl acetate (15 mL), and wet palladium on carbon (0.1 g, 10%) was added thereto. Nitrogen replacement was performed for three times. The reaction solution was allowed to react at 25° C. for 2 hours under this atmosphere (15 psi). After completion of the reaction, the reaction solution was filtered, and concentrated to give 28e. The crude product was directly used in the next step.

Fifth Step

HCl/EtOAc (4 M, 10 mL, 27 eq) was added to a reaction flask containing 28e (360 mg, 1.48 mmol, 1 eq) and ethyl acetate (4 mL), and the mixture was reacted at 20° C. for 2 hours. After completion of the reaction, the reaction solution was concentrated to give crude product 28f, which was directly used in the next step.

Sixth Step

Compound 28f (210 mg, 1.47 mmol, 1 eq) and DIPEA (381 mg, 2.95 mmol, 513 μL, 2 eq) were dissolved in dichloromethane (5 mL), and benzyl chloroformate (302 mg, 1.77 mmol, 251 μL, 1.2 eq) was added to the reaction solution. The mixture was reacted at 20° C. for 18 hours. After completion of the reaction, the reaction solution was added with water (30.0 mL) and ethyl acetate (20 mL×3) for extraction. The organic phases were combined, dried, filtered, and concentrated, and the residue was purified by silica gel chromatography (petroleum ether/ethyl acetate=100:1-1:1) to give 28g.

$^{1}H$ NMR (400 MHz, $CDCl_3$) δ: 7.43-7.29 (m, 5H), 5.23-5.10 (m, 2H), 4.55-4.10 (m, 1H), 3.61 (s, 2H), 3.55 (s, 1H), 3.47-3.45 (m, 2H), 3.34 (s, 1H), 2.60-2.30 (m, 2H), 1.95-1.93 (m, 2H).

Seventh Step

Compound 28g (320 mg, 1.15 mmol, 1 eq) was dissolved in dichloromethane (5 mL), and DMP (636 mg, 1.50 mmol, 1.3 eq) was added to the reaction solution.

The reaction was carried out at 20° C. for 2 hours. After completion of the reaction, the reaction solution was concentrated, and the residue was purified by silica gel chromatography (petroleum ether/ethyl acetate=100:1-1:1) to give 28h.

$^{1}H$ NMR (400 MHz, $CDCl_3$) δ: 7.46-7.30 (m, 5H), 5.16 (s, 2H), 3.71 (s, 2H), 3.62 (s, 2H), 3.58-3.52 (m, 2H), 3.15-3.07 (m, 2H), 2.98 (s, 2H).

Eighth Step

Compound 28h (200 mg, 727 μmol, 1 eq) was dissolved in dichloromethane (1 mL), and N, N-diethylsulfur trifluoride (703 mg, 4.36 mmol, 576 μL, 6 eq) was added into the reaction solution. The reaction solution was carried out at 20° C. for 18 hours. After completion of the reaction, the reaction solution was added with water (40.0 mL) and dichloromethane (30 mL×3). The organic phases were combined, dried, filtered, concentrated, and the residue was purified by silica gel column chromatography (petroleum ether/ethyl acetate=100:1-1:1) to give 28i.

Ninth Step

Compound 28i (180 mg, 606 μmol, 1 eq) was added to methanol (5 mL), and wet palladium on carbon (0.01 g, 10%) was added thereto. Hydrogen replacement was performed for three times, and the reaction was carried out at 20° C. for 2 hours under this atmosphere (15 psi). After completion of the reaction, the reaction solution was filtered, and concentrated to give 28j. The crude product was directly used in the next step.

Tenth Step

Compound 28j (42 mg, 257 μmol, 1 eq), 1h (102 mg, 257 μmol, 1 eq) and N, N-diisopropylethylamine (66.5 mg, 514 μmol, 89.7 μL, 2 eq) were dissolved in DMSO (1 mL) and the obtained mixed solution was allowed to react at 70° C. for 18 hours. After completion of the reaction, the reaction solution was purified by high performance liquid chromatography to give 28.

MS-ESI calculated for $[M+H]^+$: 525, found: 525.

$^{1}H$ NMR (400 MHz, $CDCl_3$) δ: 8.54 (s, 1H), 8.15 (d, J=8.0 Hz, 1H), 7.99 (d, J=8.4 Hz, 1H), 7.89 (d, J=8.0 Hz, 1H), 7.54-7.41 (m, 2H), 6.38 (br s, 1H), 4.36 (br s, 1H), 4.06-3.84 (m, 6H), 3.79-3.53 (m, 6H), 2.99 (d, J=4.8 Hz, 3H), 2.73-2.46 (m, 4H), 1.44 (d, J=6.8 Hz, 3H).

Embodiment 29

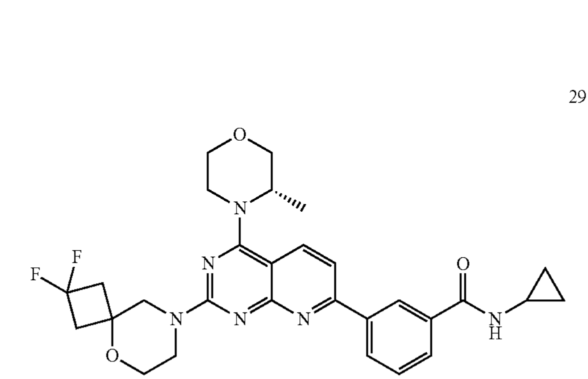 [SMILES: C[C@H]1COCCN1c1nc(N2CCOC3(C2)CC(F)(F)C3)nc2nc(-c3cccc(C(=O)NC4CC4)c3)ccc12]

29

29a

29b

29

Compound 29a (109 mg, 257 μmol, 1 eq), 29b (42 mg, 257 μmol, 1 eq) and N, N-diisopropylethylamine (66.5 mg, 514.82 μmol, 89.7 μL, 2 eq) were dissolved in DMSO (1 mL), the mixed solution was allowed to react at 70° C. for 18 hours. After completion of the reaction, the reaction solution was purified by high performance liquid chromatography to give 29.

MS-ESI calculated for $[M+H]^+$: 551, found: 551.

$^1$H NMR (400 MHz, $CDCl_3$) δ: 8.57 (s, 1H), 8.20 (d, J=8.0 Hz, 1H), 8.07 (d, J=8.4 Hz, 1H), 7.98 (d, J=8.0 Hz, 1H), 7.61-7.47 (m, 2H), 6.56 (s, 1H), 4.43 (d, J=6.4 Hz, 1H), 4.12-4.05 (m, 2H), 4.03-3.92 (m, 4H), 3.88-3.83 (m, 1H), 3.80-3.70 (m, 5H), 3.01-2.92 (m, 1H), 2.76-2.57 (m, 4H), 1.53-1.50 (m, 3H), 0.98-0.87 (m, 2H), 0.76-0.60 (m, 2H).

Embodiment 30

30

30a 30b 30c

30d 30e 30f 1h 30f

-continued

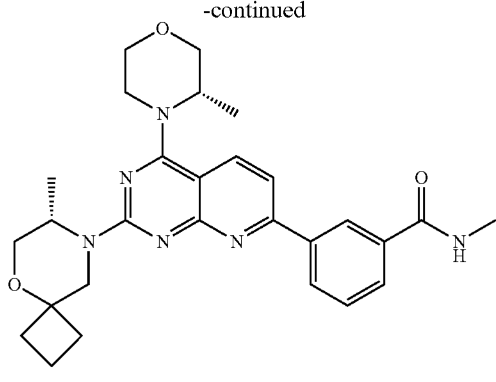

30

First Step

Methyltriphenylphosphonium bromide (102 g, 285 mmol, 2 eq) and potassium tert-butoxide (1 M, 257 mL, 1.8 eq) were dissolved in tetrahydrofuran (500 mL), the mixture was reacted at room temperature for an hour, followed by addition of compound 30a (10.0 g, 143 mmol, 10.7 mL, 1 eq). After reacting at room temperature for 17 hours, and the reaction mixture was distilled at 80° C. to give compound 30b distillate.

$^1$H NMR (400 MHz, $CDCl_3$) δ: 4.51 (dt, J=1.13, 2.32 Hz, 2H), 3.71-3.48 (m, 2H), 2.61-2.46 (m, 2H), 1.81-1.74 (m, 2H).

Second Step

Compound 30b (30.0 g, 17.6 mmol, 1 eq), compound 30c (3.70 g, 21.1 mmol, 1.2 eq), N-iodosuccinimide (4.76 g, 21.1 mmol, 1.2 eq) were dissolved in tetrahydrofuran (10.0 mL), the mixture was reacted at room temperature for 24 hours. After completion of the reaction, the reaction solution was concentrated to remove solvent, diluted with water (100 mL), and extracted with ethyl acetate (50.0 mL×3). The organic phase was dried over anhydrous sodium sulfate, filtered, subjected to rotary evaporation under reduced pressure to dryness, and purified by column chromatography (20% ethyl acetate) to give compound 30d.

MS-ESI calculated for $[M+H]^+$: 370, found: 270.

Third Step

Compound 30d (30.9 g, 2.44 mmol, 1 eq), sodium hydride (195 mg, 4.87 mmol, 60% purity, 2 eq) were dissolved in tetrahydrofuran (10.0 mL), and the mixture was reacted at 65° C. for 16 hours. After completion of the reaction, the reaction was terminated by addition of water (50.0 mL), extracted with ethyl acetate (50.0 mL×3). The organic phases were combined, dried over anhydrous sodium sulfate, filtered, and subjected to rotary evaporation under reduced pressure to dryness, and compound 30e was obtained.

MS-ESI calculated for $[M+H]^+$:242, found: 142.

Fourth Step

Compound 30e (0.18 g, 746 μmol, 1 eq) was dissolved in hydrochloric acid/ethyl acetate (20.0 mL), and the mixture was reacted and stirred for 5 hours. After completion of the reaction, the reaction solution was subjected to rotary evaporation to remove solvent, and 30f was obtained.

MS-ESI calculated for $[M+H]^+$: 142, found: 142.

Fifth Step

Compound 1h (141 mg, 354 μmol, 0.25 eq), 30f (200 mg, 1.42 mmol, 1 eq, HCl), and DIPEA (549 mg, 4.25 mmol, 740 μL, 3 eq) were dissolved in DMSO (5.00 mL). The mixed solution was allowed to react at 70° C. for 16 hours, and purified by high performance liquid chromatography to give 30.

MS-ESI calculated for $[M+H]^+$: 503, found: 503.

$^1$H NMR (400 MHz, $CDCl_3$) δ: 8.65 (s, 1H), 8.22 (br d, J=7.8 Hz, 1H), 8.07 (d, J=8.4 Hz, 1H), 7.99 (br d, J=7.8 Hz, 1H), 7.63-7.48 (m, 2H), 6.56 (br s, 1H), 4.81 (br d, J=13.6 Hz, 2H), 4.42 (br d, J=5.6 Hz, 1H), 4.08-3.97 (m, 1H), 3.96-3.67 (m, 6H), 3.58 (d, J=11.6 Hz, 1H), 3.18 (br d, J=13.2 Hz, 1H), 3.08 (d, J=4.8 Hz, 3H), 2.26-1.93 (m, 4H), 1.93-1.77 (m, 2H), 1.52 (d, J=6.8 Hz, 3H), 1.36 (br d, J=6.8 Hz, 3H).

Embodiment 31

31

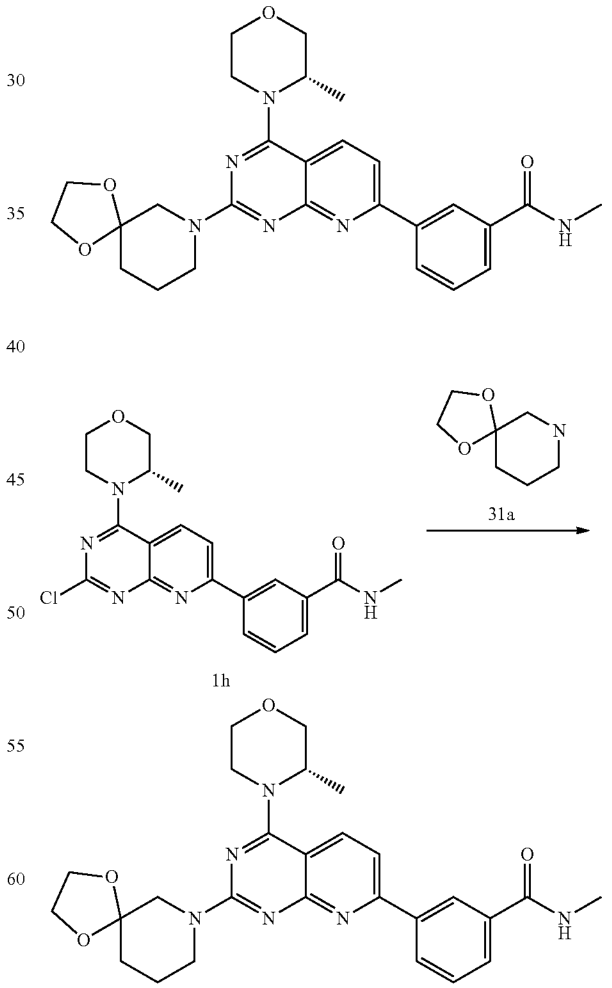

First Step

Compound 1h (100 mg, 251 μmol, 1.00 eq), 31a (36.0 mg, 251 μmol, 1.00 eq), and DIPEA (97.5 mg, 754 μmol, 131 μL, 3.00 eq) were dissolved in DMSO (3.00 mL). The mixed solution was allowed to react at 90° C. for 18 hours. After completion of the reaction, the reaction solution was purified by high performance liquid chromatography to give 31.

MS-ESI calculated value $[M+H]^+$: 505, found: 505.

$^1$H NMR (400 MHz, $CDCl_3$) δ: 8.57 (br s, 1H), 8.11 (br d, J=7.2 Hz, 1H), 7.95 (br d, J=8.4 Hz, 1H), 7.91 (br d, J=8.0, 1H), 7.48 (br t, J=8.0, 1H), 7.41 (br d, J=8.4 Hz, 1H), 6.53 (br s, 1H), 4.31 (br s, 1H), 4.01-3.52 (m, 14H), 2.99 (d, J=4.8 Hz, 3H), 1.67 (br s, 4H), 1.41 (br d, J=6.8 Hz, 3H).

Embodiment 32-1&32-2

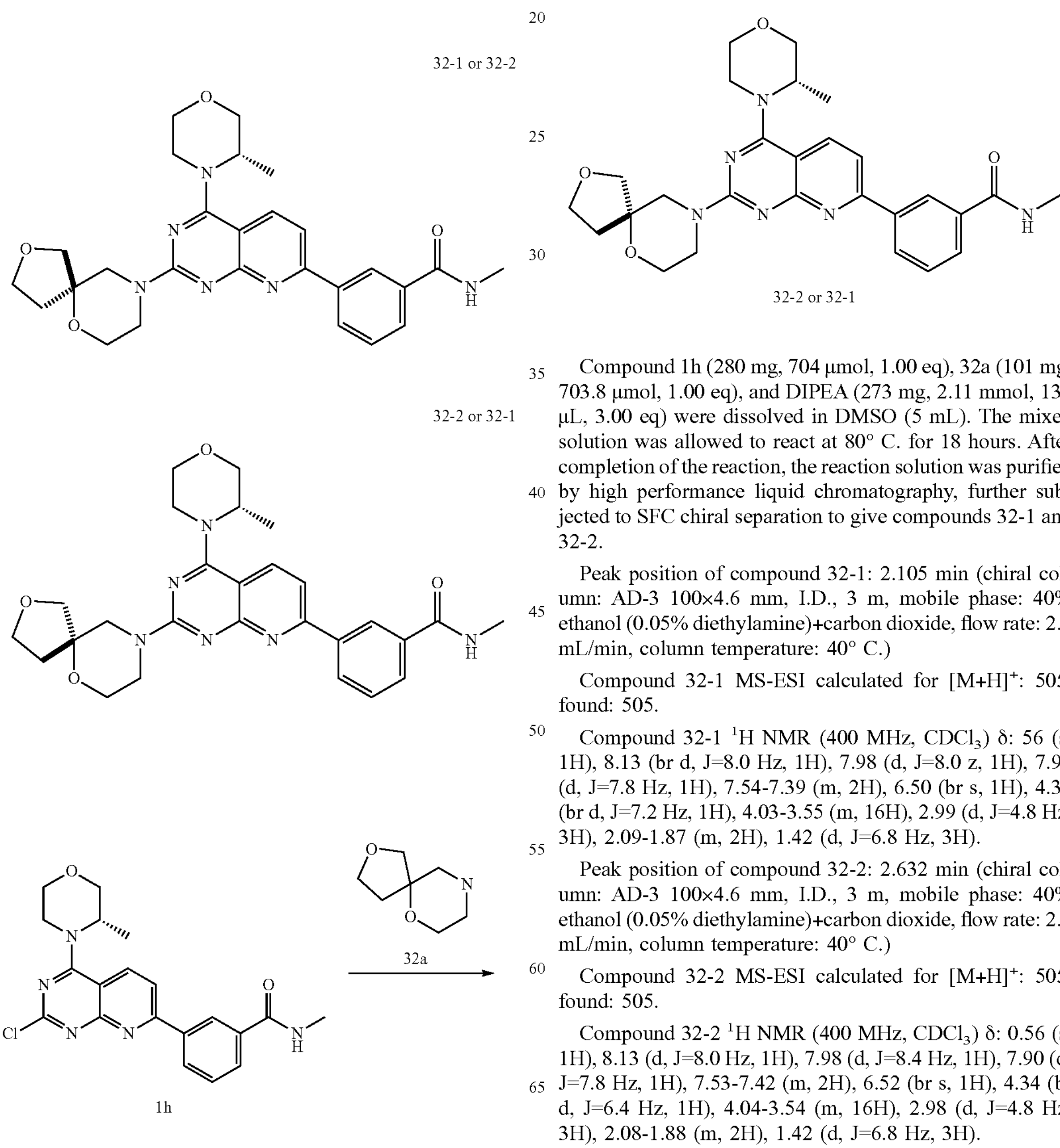

32-1 or 32-2

32-2 or 32-1

1h

32a

-continued 32-1 or 32-2

32-2 or 32-1

Compound 1h (280 mg, 704 μmol, 1.00 eq), 32a (101 mg, 703.8 μmol, 1.00 eq), and DIPEA (273 mg, 2.11 mmol, 131 μL, 3.00 eq) were dissolved in DMSO (5 mL). The mixed solution was allowed to react at 80° C. for 18 hours. After completion of the reaction, the reaction solution was purified by high performance liquid chromatography, further subjected to SFC chiral separation to give compounds 32-1 and 32-2.

Peak position of compound 32-1: 2.105 min (chiral column: AD-3 100×4.6 mm, I.D., 3 m, mobile phase: 40% ethanol (0.05% diethylamine)+carbon dioxide, flow rate: 2.8 mL/min, column temperature: 40° C.)

Compound 32-1 MS-ESI calculated for $[M+H]^+$: 505, found: 505.

Compound 32-1 $^1$H NMR (400 MHz, $CDCl_3$) δ: 56 (s, 1H), 8.13 (br d, J=8.0 Hz, 1H), 7.98 (d, J=8.0 z, 1H), 7.90 (d, J=7.8 Hz, 1H), 7.54-7.39 (m, 2H), 6.50 (br s, 1H), 4.34 (br d, J=7.2 Hz, 1H), 4.03-3.55 (m, 16H), 2.99 (d, J=4.8 Hz, 3H), 2.09-1.87 (m, 2H), 1.42 (d, J=6.8 Hz, 3H).

Peak position of compound 32-2: 2.632 min (chiral column: AD-3 100×4.6 mm, I.D., 3 m, mobile phase: 40% ethanol (0.05% diethylamine)+carbon dioxide, flow rate: 2.8 mL/min, column temperature: 40° C.)

Compound 32-2 MS-ESI calculated for $[M+H]^+$: 505, found: 505.

Compound 32-2 $^1$H NMR (400 MHz, $CDCl_3$) δ: 0.56 (s, 1H), 8.13 (d, J=8.0 Hz, 1H), 7.98 (d, J=8.4 Hz, 1H), 7.90 (d, J=7.8 Hz, 1H), 7.53-7.42 (m, 2H), 6.52 (br s, 1H), 4.34 (br d, J=6.4 Hz, 1H), 4.04-3.54 (m, 16H), 2.98 (d, J=4.8 Hz, 3H), 2.08-1.88 (m, 2H), 1.42 (d, J=6.8 Hz, 3H).

Embodiment 33-1&33-2

33-1 or 33-2

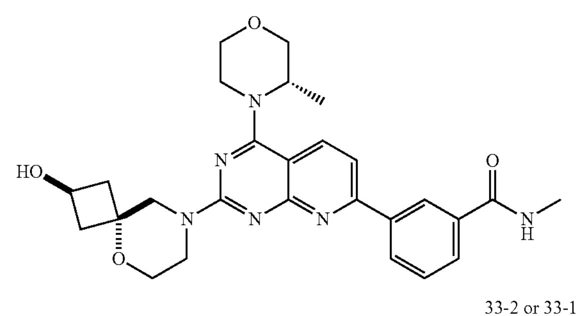

33-2 or 33-1

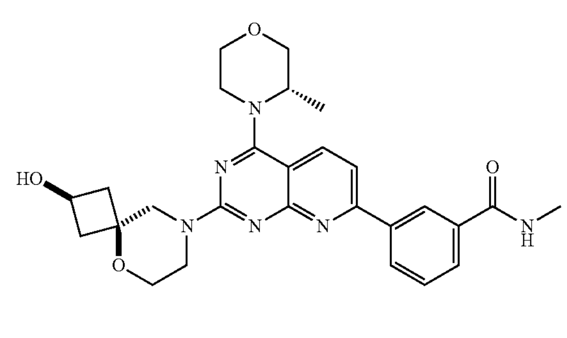

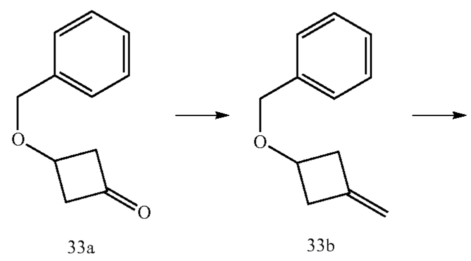

33a

33b

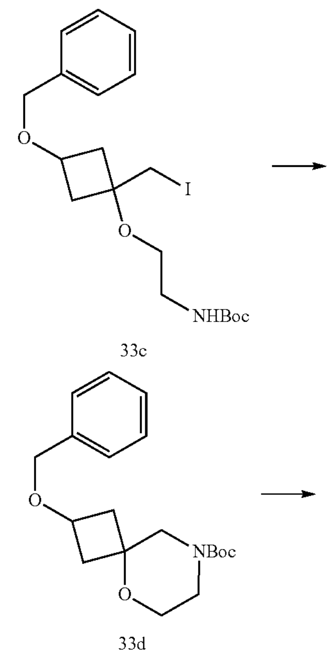

33c

33d

-continued

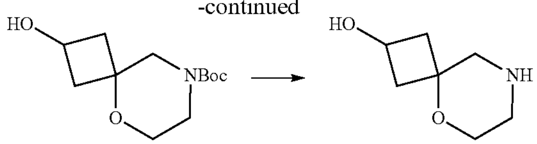

33e

33f

1h

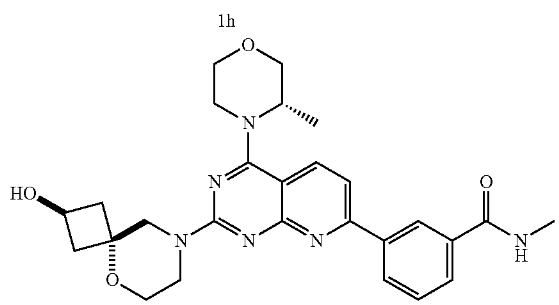

33-1 or 33-2

33-2 or 33-1

First Step

The compound methyltriphenylphosphonium bromide (32.4 g, 90.8 mmol, 1.6 eq) was dissolved in a solution of potassium tert-butoxide (11.5 g, 102 mmol, 1.8 eq) in anhydrous tetrahydrofuran (400 mL) at room temperature (20° C.). The mixed solution was allowed to react at room temperature for 3 hours, and then 33a (10.0 g, 56.8 mmol, 1 eq) was added dropwise to the solution, and the mixed solution was allowed to react at 20° C. for 17 hours. After completion of the reaction, TLC detection showed that new compound spot appeared. The reaction solution was added with water (100 mL), and extracted with ethyl acetate (200 mL×3). The organic phase was treated with anhydrous sodium sulfate, concentrated under reduced pressure, and purified by column chromatography (50%-ethyl acetate/petroleum ether) to give 33b.

$^1$H NMR (400 MHz, $CDCl_3$) δ: 7.23-7.13 (m, 5H), 4.74 (br s, 2H), 4.34-4.27 (m, 2H), 4.00-3.92 (m, 1H), 2.80-2.71 (m, 2H), 2.68-2.58 (m, 2H).

Second Step

Compound 33b (8.7 g, 49.9 mmol, 1 eq) and N-Boc ethanolamine (9.66 g, 59.9 mmol, 9.29 mL, 1.2 eq) were dissolved in acetonitrile (90.0 mL), followed by addition of N-iodosuccinimide (13.5 g, 59.9 mmol, 1.2 eq). The mixed solution was allowed to react at 20° C. for 18 hours. After completion of the reaction, TLC detection showed that new compound spot appeared. The reaction solution was added with water (30.0 mL), extracted with ethyl acetate (30 mL×2). The organic phase was treated with anhydrous sodium sulfate, concentrated under reduced pressure, and purified by column chromatography (35.5%-ethyl acetate/petroleum ether) to give 33c.

$^1$H NMR (400 MHz, $CDCl_3$) δ: 7.37-7.32 (m, 5H), 5.03 (br d, J=10.8 Hz, 1H), 4.44 (d, J=9.6 Hz, 2H), 3.79-3.67 (m, 1H), 3.34 (br d, J=5.6 Hz, 3H), 2.59-2.37 (m, 3H), 2.31-2.11 (m, 2H), 2.08-1.98 (m, 1H), 1.52-1.42 (m, 9H).

Third Step

Compound 33c (4 g, 8.67 mmol, 1 eq) was dissolved in N, N-dimethylacetamide (160 mL), and then sodium hydride (694 mg, 60% purity, 2 eq) was added to the obtained solution in ice bath. The reaction solution was allowed to react at 20° C. for 17 hours. After completion of the reaction, the reaction solution was poured into a saturated ammonium chloride aqueous solution (30 mL), added with water (60.0 mL), extracted with ethyl acetate (50 mL×3). The organic phase was treated with anhydrous sodium sulfate, concentrated under reduced pressure, and purified by column chromatography (30%-ethyl acetate/petroleum ether) to give 33d.

$^1$H NMR (400 MHz, $CDCl_3$) δ: 7.38-7.32 (m, 5H), 4.47-4.40 (m, 2H), 4.23-4.15 (m, 1H), 3.62-3.53 (m, 2H), 3.45 (s, 1H), 3.41-3.32 (m, 2H), 3.25 (s, 1H), 2.43 (br s, 1H), 2.35-2.27 (m, 1H), 2.04 (s, 2H), 1.46 (d, J=5.2 Hz, 9H).

Fourth Step

Compound 33d (1.00 g, 3.00 mmol, 1 eq) was dissolved in methanol (30.0 mL), and then palladium hydroxide (421 mg, 20% purity, 0.2 eq) was added to the solution under nitrogen atmosphere. Hydrogen replacement was performed for several times. The reaction solution was allowed to react at 50° C. for 50 hours under hydrogen atmosphere of 50 psi. After completion of the reaction, the reaction solution was filtered, and the filtrate was concentrated under reduced pressure to give 33e.

$^1$H NMR (400 MHz, $CDCl_3$) δ: 4.06-3.87 (m, 1H), 3.51 (br s, 2H), 3.42-3.36 (m, 2H), 3.34-3.26 (m, 2H), 3.21-3.14 (m, 1H), 2.47-2.38 (m, 1H), 2.35-2.25 (m, 1H), 1.92-1.79 (m, 2H), 1.39 (s, 9H).

Fifth Step

Compound 33e (0.28 g, 1.15 mmol, 1 eq) was dissolved in ethyl acetate (10.0 mL), and then hydrochloric acid/ethyl acetate (4 M, 10 mL, 34.8 eq) was added to the solution. The reaction solution was allowed to react at 20° C. for 6 hours. After completion of the reaction, the reaction solution was concentrated under reduced pressure to give 33f.

Sixth Step

Compound 1h (0.3 g, 754 μmol, 1 eq) was dissolved in dimethyl sulfoxide (10.0 mL), and then N, N-diisopropylethylamine (292 mg, 2.26 mmol, 3 eq) and 33f (162 mg, 902 μmol, 1.20 eq, HCl) were added to the solution. The reaction solution was allowed to react at 70° C. for 25 hours. After completion of the reaction, water (12 mL) was added to the reaction solution, and extracted with ethyl acetate (10.0 mL×3). The organic phase was treated with anhydrous sodium sulfate, concentrated under reduced pressure, purified by column chromatography (12.8%-methanol/dichloromethane), and subjected to chiral resolution to give 33-1 and 33-2.

Peak position of compound 33-1: 1.672 min (chiral column: AD-3 100×4.6 mm, I.D., 3 m, mobile phase: 40% isopropanol (0.05% diethylamine)+carbon dioxide, flow rate: 2.8 mL/min, column temperature: 40° C.)

Compound 33-1 MS-ESI calculated for $[M+H]^+$: 505, found: 505.

Compound 33-1 $^1$H NMR (400 MHz, $CD_3OD$) δ: 8.62 (s, 1H), 8.34 (d, J=8.4 Hz, 1H), 8.29 (d, J=8.4 Hz, 1H), 7.96 (d, J=8.4 Hz, 1H), 7.68 (d, J=8.4 Hz, 1H), 7.66-7.62 (m, 1H), 4.54 (br d, J=7.2 Hz, 1H), 4.12 (br s, 1H), 4.04-3.93 (m, 3H), 3.93-3.70 (m, 10H), 3.02-2.97 (m, 3H), 2.56-2.52 (m, 2H), 1.96-1.92 (m, 2H), 1.51 (d, J=6.8 Hz, 3H).

Peak position of compound 33-2: 3.338 min (chiral column: AD-3 100×4.6 mm, I.D., 3 m, mobile phase: 40% isopropanol (0.05% diethylamine)+carbon dioxide, flow rate: 2.8 mL/min, column temperature: 40° C.)

Compound 33-2: MS-ESI calculated for $[M+H]^+$: 505, found: 505.

Compound 33-2 $^1$H NMR (400 MHz, $CD_3OD$) δ: 8.62 (s, 1H), 8.33 (d, J=7.8 Hz, 1H), 8.28 (d, J=8.4 Hz, 1H), 7.96 (d, J=7.8 Hz, 1H), 7.67 (d, J=8.4 Hz, 1H), 7.66-7.62 (m, 1H), 4.57 (br d, J=7.2 Hz, 1H), 4.44-4.36 (m, 1H), 4.08-3.95 (m, 4H), 3.95-3.85 (m, 3H), 3.82-3.70 (m, 5H), 2.99 (s, 3H), 2.43-2.40 (m, 2H), 2.04-1.95 (m, 2H), 1.51 (d, J=6.8 Hz, 3H).

Embodiment 34-1&34-2

34-1 or 34-2

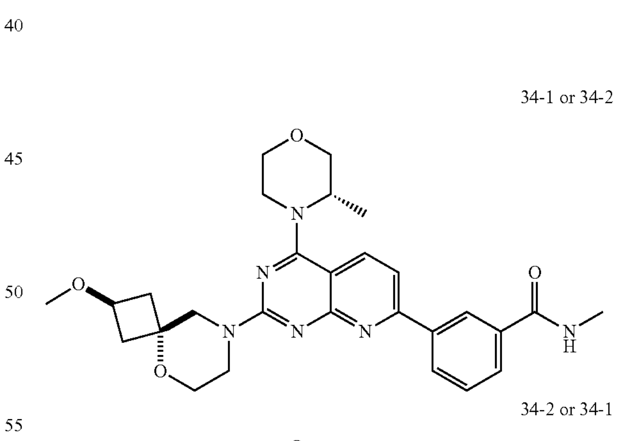

34-2 or 34-1

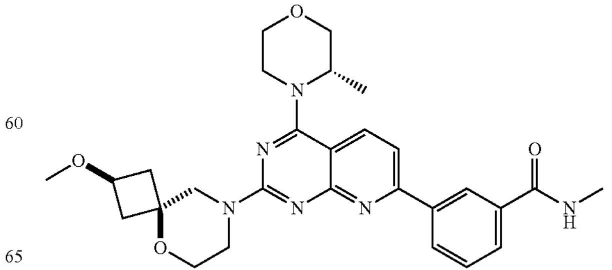

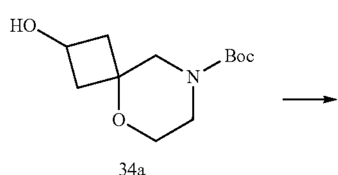

34a

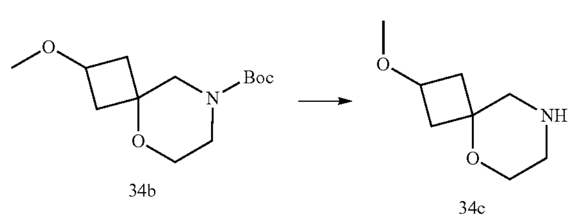

34b 34c

34c

1h 34-1 or 34-2

34-2 or 34-1

First Step

Compound 34a (0.27 g, 1.11 mmol, 1 eq) was dissolved in anhydrous tetrahydrofuran (20.0 mL). The obtain mixed solution was carefully added with sodium hydride (133 mg, 60% purity, 3 eq) and iodomethane (1.19 g, 522 μL, 7.55 eq) at 0° C. The reaction solution was gradually warmed to room temperature, and the mixture was reacted at room temperature for 3 hours. After completion of the reaction, TLC detection showed that new compound spot appeared. The reaction solution was concentrated under reduced pressure to give 34b.

Second Step

Compound 34b (0.10 g, 389 μmol, 1 eq) was dissolved in ethyl acetate (8 mL). The obtained solution was added with hydrochloric acid/ethyl acetate (4 M, 8.0 mL, 82.34 eq). The mixed solution was allowed to react at 20° C. for 18 hours. After completion of the reaction TLC detection showed that new compound spot appeared. The reaction solution was concentrated under reduced pressure to give 34c.

Third Step

Compound 1h (0.1 g, 251 μmol, 1 eq) was dissolved in dimethyl sulfoxide (5.00 mL). The obtained solution was added with N, N-diisopropylethylamine (65.0 mg, 87.6 μL, 2 eq) and 34c (73.0 mg, 377 μmol, 1.5 eq, HCl). The reaction solution was allowed to react at 70° C. for 22 hours. After completion of the reaction, water (20.0 mL) was added to the reaction solution, and extracted with ethyl acetate (15.0 mL×3). The organic phase was treated with anhydrous sodium sulfate, concentrated under reduced pressure, purified by column chromatography (100%-ethyl acetate/petroleum ether), and subjected to chiral resolution to give 34-1 and 34-2.

Peak position of compound 34-1:2.407 minute (chiral column: OD-3 50×4.6 mm, I.D., 3 μm, mobile phase: A: $CO_2$, B: ethanol (0.05% diethylamine), the content of B was maintained at 5% for 0.2 minute, then increased from 5% to 40% gradient within 1.4 min, then maintained at 40% for 1.05 min, and finally maintained at 5% for 0.35 min, flow rate: 4 mL/min, column temperature: 40° C.)

Compound 34-1 MS-ESI calculated for $[M+H]^+$: 519, found: 519.

Compound 34-1 $^1$H NMR (400 MHz, $CD_3OD$) δ: 8.64-8.60 (m, 1H), 8.34 (d, J=8.4 Hz, 1H), 8.29 (d, J=8.4 Hz, 1H), 7.96 (dd, J=1.2, 8.0 Hz, 1H), 7.68 (d, J=8.4 Hz, 1H), 7.66-7.61 (m, 1H), 4.55 (br d, J=7.2 Hz, 1H), 4.06-3.93 (m, 3H), 3.92-3.70 (m, 10H), 3.28 (s, 3H), 2.99 (s, 3H), 2.56-2.48 (m, 2H), 1.96-1.86 (m, 2H), 1.51 (d, J=6.8 Hz, 3H).

Peak position of compound 34-2: 1.807 minute (chiral column: OD-3 50×4.6 mm, I.D., 3 μm, mobile phase: A: $CO_2$, B: ethanol (0.05% diethylamine), the content of B was maintained at 5% for 0.2 min, then increased from 5% to 40% gradient within 1.4 min, then maintained at 40% for 1.05 min, and finally maintained at 5% for 0.35 min, flow rate: 4 mL/min, column temperature: 40° C.)

Compound 34-2 MS-ESI calculated for $[M+H]^+$: 519, found: 519.

Compound 34-2 $^1$H NMR (400 MHz, $CD_3OD$) δ: 8.62 (s, 1H), 8.33 (d, J=8.03 Hz, 1H), 8.29 (d, J=8.4 Hz, 1H), 7.96 (d, J=8.4 Hz, 1H), 7.68 (d, J=8.4 Hz, 1H), 7.66-7.62 (m, 1H), 4.57 (br d, J=6.0 Hz, 1H), 4.08-3.97 (m, 5H), 3.94-3.2 (m, 8H), 3.27 (s, 3H), 2.99 (s, 3H), 2.39-2.27 (m, 2H), 2.09-2.01 (m, 2H), 1.51 (d, J=6.8 Hz, 3H).

Embodiment 35

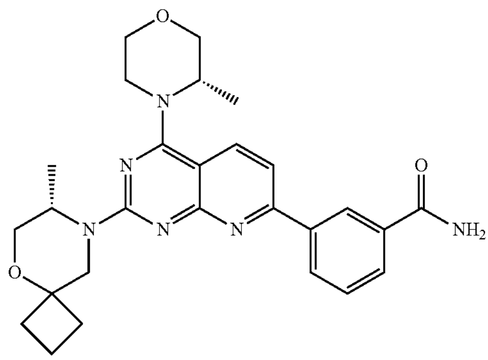

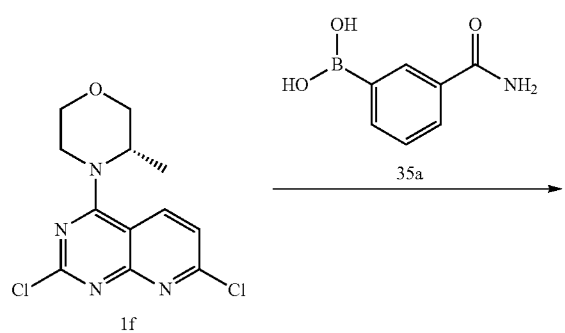

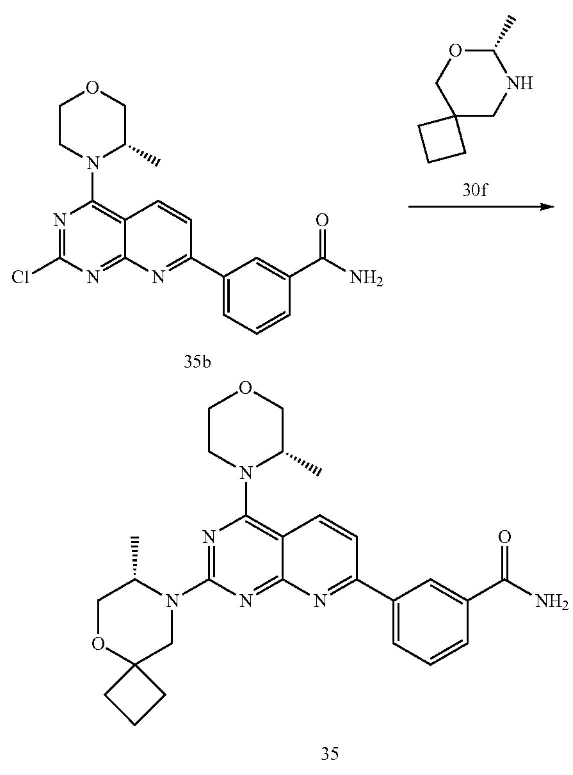

First Step

Compound 1f (2 g, 6.0 mmol, 1 eq), 35a (993 mg, 6.0 mmol, 1 eq), sodium carbonate (1.9 g, 18.1 mmol, 3 eq), dichlorobis(triphenylphosphine) palladium (211 mg, 301 μmol, 0.05 eq) were dissolved in anhydrous dioxane (35 mL) and water (7.0 mL), and the obtained solution was reacted at 70° C. for 19 hours under nitrogen atmosphere. After completion of the reaction, the reaction solution was concentrated under reduced pressure, then added with water (15 mL), and extracted with ethyl acetate (20 mL×3). The organic phase was treated with anhydrous sodium sulfate, collected under reduced pressure, and purified by column chromatography (methanol/ethyl acetate; $R_f$=0.28) to give 35b.

MS-ESI calculated for $[M+H]^+$384 and 386, found: 384 and 386.

Second Step

Compound 35b (0.1 g, 261 μmol, 1 eq), 30f (73.6 mg, 414 μmol, 1.6 eq), N, N-diisopropylethylamine (33.7 mg, 261 μmol, 1 eq) were dissolved in dimethyl sulfoxide (5.00 mL). The reaction solution was allowed to react at 70° C. for 40 hours. After completion of the reaction, the reaction solution was filtered and purified by high performance liquid chromatography to give 35.

MS-ESI calculated for $[M+H]^+$: 489, found: 489.

$^1$H NMR (400 MHz, $CD_3OD$) δ: 8.70 (s, 1H), 8.36 (d, J=8.0 Hz, 1H), 8.30 (d, J=8.8 Hz, 1H), 8.04 (d, J=8.0 Hz, 1H), 7.68 (d, J=8.8 Hz, 1H), 7.68-7.64 (m, 1H), 4.88 (s, 2H), 4.56 (d, J=6.4 Hz, 1H), 4.04-3.96 (m, 2H), 3.90 (dd, J=2.8, 11.6 Hz, 1H), 3.84 (dd, J=3.2, 11.6 Hz, 1H), 3.77-3.75 (m, 3H), 3.59 (d, J=11.6 Hz, 1H), 3.14 (dd, J=1.6, 13.6 Hz, 1H), 2.20-2.08 (m, 2H), 2.08-1.96 (m, 2H), 1.92-1.76 (m, 2H), 1.50 (d, J=6.8 Hz, 3H), 1.36 (d, J=6.8 Hz, 3H).

Embodiment 36

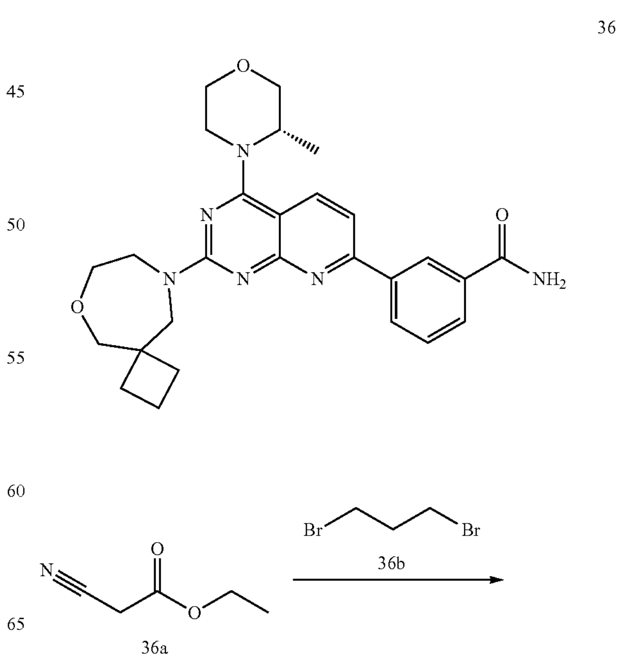

-continued

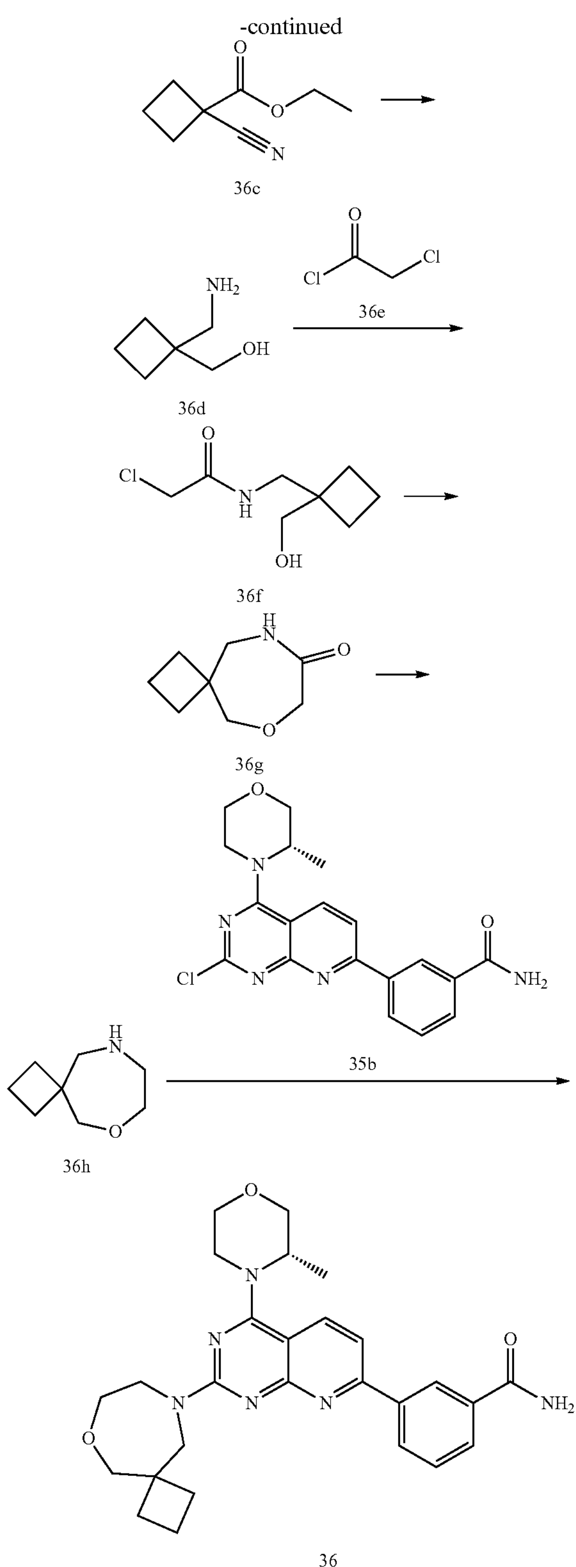

First Step

Sodium (3.66 g, 159 mmol, 3.77 mL, 2 eq) was dissolved in ethanol (147 mL). 36a (9 g, 79.6 mmol, 8.49 mL, 1 eq) was added, followed by addition of compound 36b (16.1 g, 79.6 mmol, 8.11 mL, 1 eq). The mixed solution was allowed to react at 80° C. for 3 hours, then subjected to rotary evaporation to remove ethanol, poured into water (500 mL), extracted with ethyl acetate (100 mL), dried over anhydrous sodium sulfate, filtered, subjected to rotary evaporation under reduced pressure to dryness, and purified by column chromatography (20% ethyl acetate) to give compound 36c.

$^1$H NMR (400 MHz, $CDCl_3$) δ: 4.26-4.14 (m, 2H), 2.67-2.56 (m, 4H), 2.20-2.04 (m, 2H), 1.28-1.25 (m, 3H).

Second Step

Lithium aluminum hydride (1.98 g, 52.2 mmol, 2 eq) was dissolved in tetrahydrofuran (100 mL), compound 36c (4.00 g, 26.1 mmol, 1 eq) was added, and the mixed solution was allowed to react at 45° C. for 18 hours. After completion of the reaction, water (2.00 mL), 15% NaOH (2.00 mL), and water (6.00 mL) were sequentially added at 0-20° C. to terminate the reaction. Then the mixture was stirred for 0.5 hours, filtered, and subjected to rotary evaporation under reduced pressure to dryness to give compound 36d.

$^1$H NMR (400 MHz, $CDCl_3$) δ: 3.75 (s, 2H), 2.97 (s, 2H), 1.93-1.73 (m, 6H).

Third Step

Compound 36d (0.5 g, 4.34 mmol, 1 eq) was dissolved in dichloromethane (10.0 mL), sodium carbonate (920 mg, 8.68 mmol, 2 eq) and compound 36e (539 mg, 4.77 mmol, 380 μL, 1.1 eq) were added. The mixed solution was allowed to react at 20° C. for an hour. After the completion of the reaction, the reaction solution was subjected to rotary evaporation under reduced pressure to dryness, and purified by column chromatography (20% methanol/dichloromethane) to give compound 36f.

$^1$H NMR (400 MHz, $CDCl_3$) δ: 7.00 (s, 1H), 4.11-4.08 (m, 3H), 3.54-4.54 (m, 5H), 3.04-3.01 (m, 1H), 1.98-1.94 (m, 2H), 1.82-1.75 (m, 4H).

Fourth Step

Compound 36f (0.22 g, 1.15 mmol, 1 eq) was dissolved in tetrahydrofuran (22.0 mL), and sodium hydride (138 mg, 3.44 mmol, 60%, 3 eq) was added. The mixed solution was reacted at 20° C. for an hour. After completion of the reaction, the reaction solution was subjected to rotary evaporation under reduced pressure to dryness, and purified by column chromatography (20% methanol/dichloromethane) to give compound 36g.

MS-ESI calculated for $[M+H]^+$: 156, found: 156.

Fifth Step

Compound 36g (0.35 g, 2.26 mmol, 1 eq) was dissolved in tetrahydrofuran (10.0 mL), lithium aluminum hydride (257 mg, 6.77 mmol, 3 eq) was added. The mixed solution was allowed to react at 25° C. for 18 hours. After completion of the reaction, water (0.26 mL), 15% NaOH (0.26 mL), and water (0.78 mL) were sequentially added at 0-20° C. to terminate the reaction. The reaction solution was stirred for 0.5 hour, filtered, and subjected to rotary evaporation under reduced pressure to dryness to give compound 36h.

MS-ESI calculated for $[M+H]^+$: 142, found: 142.

Sixth Step

Compound 36h (0.1 g, 261 μmol, 1 eq), 35b (55.18 mg, 391 μmol, 1.5 eq), DIPEA (101 mg, 782 μmol, 136 μL, 3 eq)

were dissolved in DMSO (3.00 mL). The mixed solution was allowed to react at 70° C. for 16 hours and purified by high performance liquid chromatography to give 36.

MS-ESI calculated for $[M+H]^+$: 489, found: 489.

$^1$H NMR (400 MHz, $CDCl_3$) δ: 8.70 (br s, 1H), 8.24 (br d, J=7.6 Hz, 1H), 8.08-7.03 (m, 2H), 7.59 (t, J=7.6 Hz, 1H), 7.49 (d, J=8.4 Hz, 1H), 6.70 (br s, 1H), 5.76 (br s, 1H), 4.40 (br s, 1H), 4.16 (br d, J=12.4 Hz, 2H), 4.02 (br s, 2H), 3.99-3.81 (m, 5H), 3.81-3.61 (m, 5H), 1.92 (br s, 6H), 1.49 (d, J=6.8 Hz, 3H).

Embodiment 37

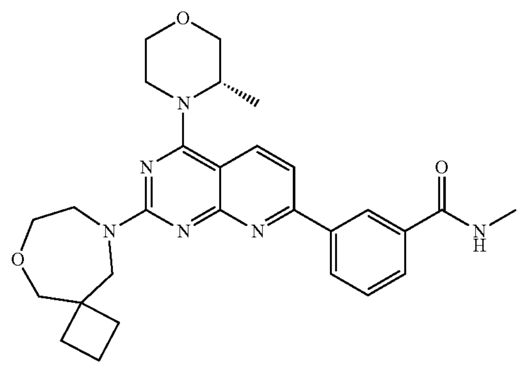

Compound 1h (0.1 g, 251 μmol, 1 eq), 36h (53.2 mg, 377 μmol, 1.5 eq), DIPEA (97.5 mg, 754 μmol, 131 μL, 3 eq) were dissolved in DMSO (5.00 mL). The mixed solution was allowed to react at 70° C. for 16 hours, and purified by high performance liquid chromatography to give 37.

MS-ESI calculated for $[M+H]^+$: 503, found: 503.

$^1$H NMR (400 MHz, $CDCl_3$) δ: 8.64 (br s, 1H), 8.19 (br d, J=7.2 Hz, 1H), 8.06 (br d, J=8.4 Hz, 1H), 7.98 (br d, J=7.6 Hz, 1H), 7.57 (t, J=7.6 Hz, 1H), 7.49 (d, J=8.4 Hz, 1H), 6.70 (br s, 1H), 4.40 (br s, 1H), 4.16 (br d, J=12.0 Hz, 2H), 4.02 (br s, 2H), 3.96-3.84 (m, 4H), 3.84-3.59 (m, 6H), 3.07 (d, J=4.8 Hz, 3H), 2.11-1.84 (m, 6H), 1.49 (d, J=6.8 Hz, 3H).

Embodiment 38

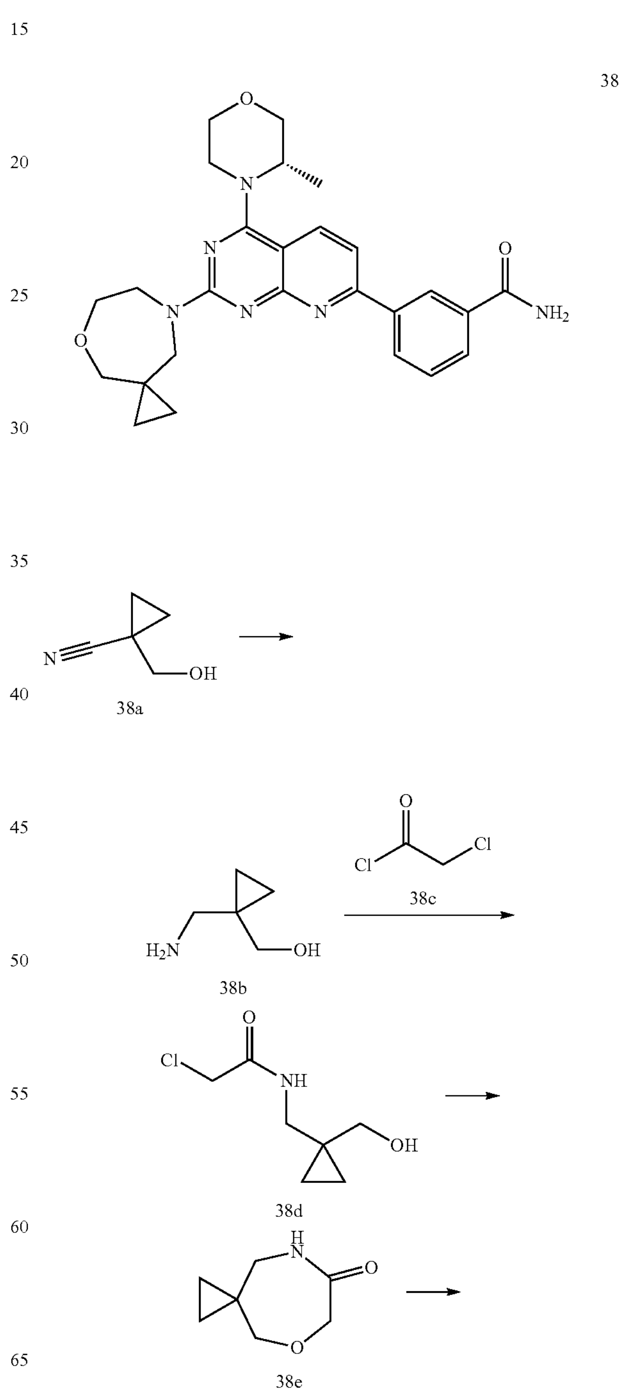

-continued

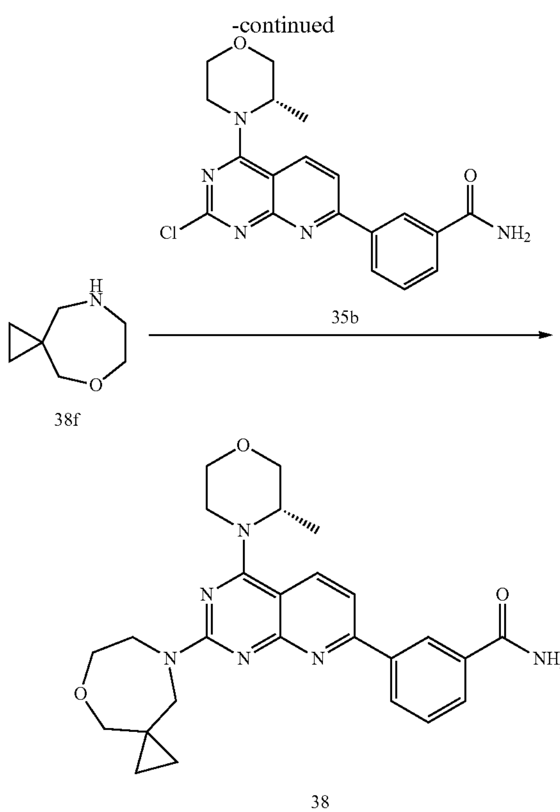

First Step

Lithium aluminum hydride (3.91 g, 103 mmol, 2 eq) was dissolved in tetrahydrofuran (100 mL), and compound 38a (5.00 g, 51.5 mmol, 3.37 mL, 1 eq) was added. The mixed solution was allowed to react at 45° C. for 18 hours. After completion of the reaction, water (4.00 mL), 15% NaOH (4.00 mL), and water (8.00 mL) were sequentially added at 0-20° C. to terminate the reaction. The mixture was stirred for 0.5 hour, filtered, and subjected to rotary evaporation under reduced pressure to give 38b.

MS-ESI calculated for $[M+H]^+$:102, found: 102.

Second Step

Compound 38b (4 g, 39.6 mmol, 1 eq) was dissolved in dichloromethane (10.0 mL), sodium carbonate (8.38 g, 79.1 mmol, 2 eq) and compound 38c (4.47 g, 39.6 mmol, 3.15 mL, 1.0 eq) were added. The mixed solution was allowed to react at 20° C. for an hour. After completion of the reaction, the reaction solution was subjected to rotary evaporation under reduced pressure to dryness, and purified by column chromatography (20% methanol/dichloromethane) to give compound 38d.

MS-ESI calculated for $[M+H]^+$: 178, found: 178.

$^1$H NMR (400 MHz, $CDCl_3$) δ: 7.27 (s, 1H), 4.09 (s, 2H), 3.44 (d, J=5.2 Hz, 2H), 3.32 (d, J=5.6 Hz, 2H), 2.83-2.81 (m, 1H), 0.52 (d, J=3.6 Hz, 4H).

Third Step

Compound 38d (4.70 g, 26.5 mmol, 1 eq) was dissolved in tetrahydrofuran (470 mL), and sodium hydride (3.18 g, 79.4 mmol, 60% purity, 3 eq) was added. The mixed solution was allowed to react at 20° C. for an hour. After the completion of the reaction, the reaction solution was added with hydrochloric acid to adjust the pH to 7, dried over anhydrous sodium sulfate to give compound 38e.

MS-ESI calculated for $[M+H]^+$: 142, found: 142.

Fourth Step

Compound 38e (0.5 g, 3.54 mmol, 1 eq) was dissolved in tetrahydrofuran (10 mL), and lithium aluminum hydride (269 mg, 7.08 mmol, 2 eq) was added. The mixed solution was allowed to react at 20° C. for an hour. After the completion of the reaction, water (0.26 mL), 15% NaOH (0.26 mL), and water (0.78 mL) were sequentially added at 0-20° C. to terminate the reaction. The reaction solution was stirred for 0.5 hour, filtered, and subjected to rotary evaporation under reduced pressure to dryness to give compound 38f.

MS-ESI calculated for $[M+H]^+$: 128, found: 128.

Fifth Step

Compound 38f (48.2 mg, 126 μmol, 1 eq), 35b (159.84 mg, 1.26 mmol, 10 eq), DIPEA (48.7 mg, 377 μmol, 65.7 μL, 3 eq) were dissolved in DMSO (5.00 mL). The mixed solution was allowed to react at 70° C. for 16 hours, and purified by high performance liquid chromatography to give 38.

MS-ESI calculated for $[M+H]^+$: 475, found: 475.

$^1$H NMR (400 MHz, $CDCl_3$) δ: 8.69 (br s, 1H), 8.25 (br d, J=7.2 Hz, 1H), 8.06-8.03 (m, 2H), 7.71-7.40 (m, 2H), 6.63 (br s, 1H), 5.80 (br s, 1H), 4.48-4.17 (m, 3H), 4.07-3.94 (m, 2H), 3.87 (br s, 4H), 3.83-3.62 (m, 4H), 3.55 (s, 2H), 1.48 (br d, J=6.4 Hz, 3H), 0.85-0.31 (m, 4H).

Embodiment 39

39

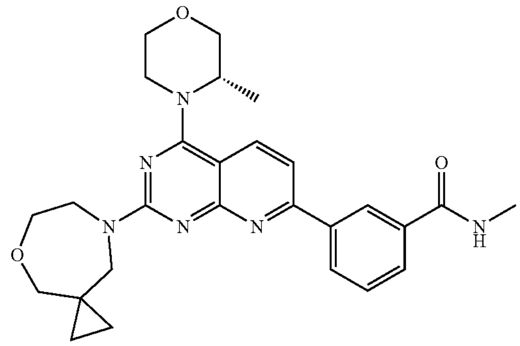

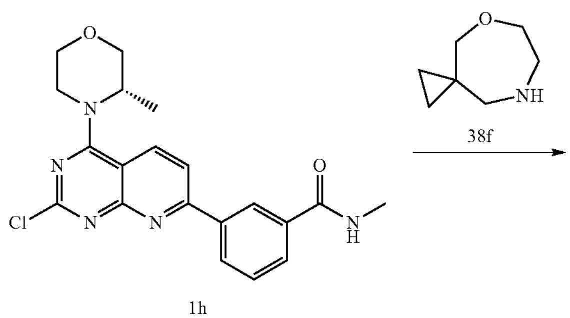

-continued

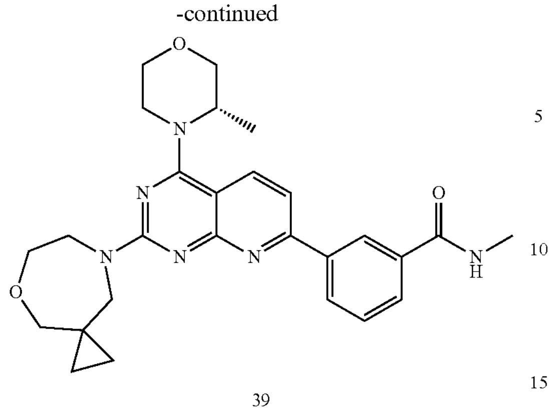

First Step

Compound 38f (141 mg, 354 μmol, 0.25 eq), 1h (200 mg, 1.42 mmol, 1 eq, HCl), DIPEA (549 mg, 4.25 mmol, 740 μL, 3 eq) were dissolved in DMSO (5.00 mL). The mixed solution was allowed to react at 70° C. for 16 hours, and purified by high performance liquid chromatography to give 39.

MS-ESI calculated for $[M+H]^+$: 489, found: 489.

$^1$H NMR (400 MHz, $CDCl_3$) δ: 8.64 (br s, 1H), 8.21 (br d, J=7.6 Hz, 1H), 8.06 (d, J=8.4 Hz, 1H), 7.99 (br d, J=7.6 Hz, 1H), 7.58 (t, J=7.6 Hz, 1H), 7.50 (br d, J=8.4 Hz, 1H), 6.59 (br s, 1H), 4.38 (br d, J=6.8 Hz, 1H), 4.34-4.12 (m, 2H), 4.07-3.96 (m, 2H), 3.96-3.81 (m, 5H), 3.81-3.61 (m, 3H), 3.56 (s, 2H), 3.08 (d, J=4.8 Hz, 3H), 1.49 (br d, J=6.8 Hz, 3H), 0.80-0.54 (m, 4H).

Embodiment 40

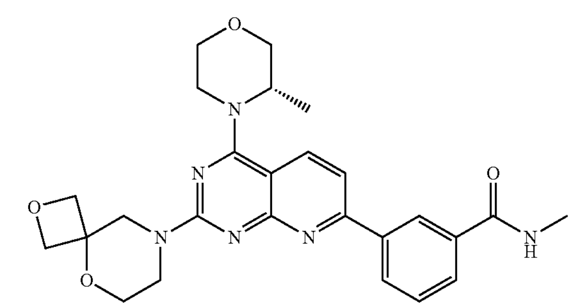

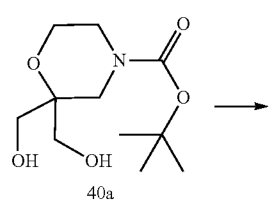

-continued

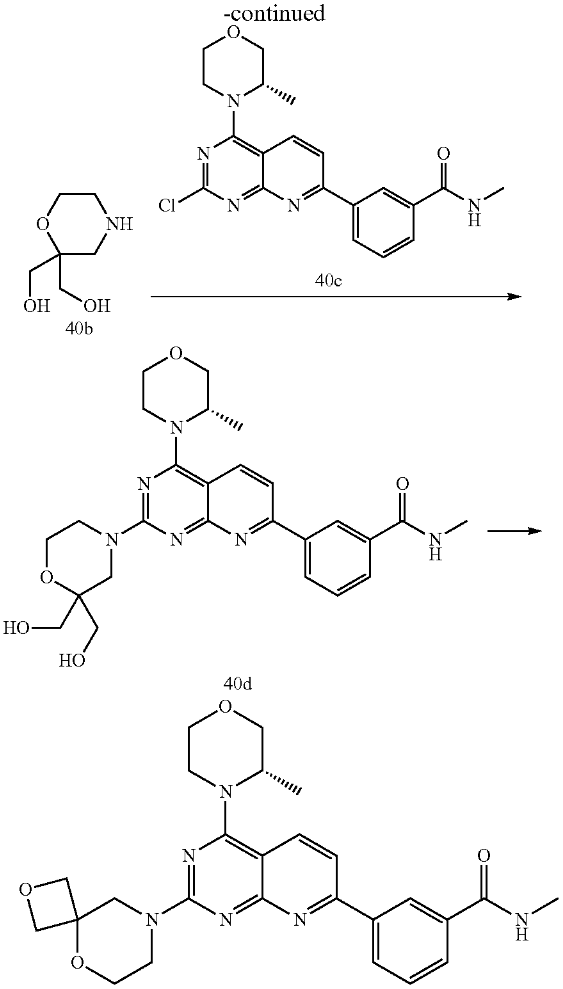

First Step

Compound 40a (0.28 g, 1.13 mmol, 1 eq) was dissolved in trifluoroacetic acid (5.00 mL) and dichloromethane (10.0 mL). The reaction solution was stirred and reacted at room temperature for 2 hours. After the completion of the reaction, the reaction solution was subjected to rotary evaporation under reduced pressure to dryness, and 40b was obtained.

MS-ESI calculated for $[M+H]^+$: 148, found: 148.

Second Step

Compound 40b (300 mg, 1.15 mmol, 1 eq, TFA), compound 40c (320 mg, 804 mol, 0.7 eq), DIPEA (445 mg, 3.45 mmol, 600 μL, 4 eq) were dissolved in dimethyl sulfoxide (5.00 mL), and the mixture was reacted at 70° C. for 16 hours. After completion of the reaction, the reaction solution was purified by high performance liquid chromatography to give 40d.

MS-ESI calculated for $[M+H]^+$: 509, found: 509.

Third Step

Compound 40d (100 mg, 197 μmol, 1 eq), p-toluenesulfonyl chloride (37.5 mg, 197 μmol, 1 eq) and sodium hydride (15.7 mg, 393 μmol, 60%, 2 eq) were dissolved in DMF (10.0 mL), the mixture was reacted at room temperature for 16 hours. After completion of the reaction, the reaction solution was purified by high performance liquid chromatography to give 40.

MS-ESI calculated for $[M+H]^+$: 491, found: 491.

$^1$H NMR (400 MHz, $CDCl_3$) δ: 8.65 (s, 1H), 8.23 (br d, J=7.8 Hz, 1H), 8.09 (d, J=8.4 Hz, 1H), 7.99 (br d, J=7.8 Hz, 1H), 7.62-7.53 (m, 2H), 6.60 (br s, 1H), 4.66 (d, J=6.4 Hz, 2H), 4.57-4.41 (m, 3H), 4.32-4.14 (m, 2H), 4.08-3.85 (m, 5H), 3.83-3.75 (m, 5H), 3.08 (d, J=4.8 Hz, 3H), 1.52 (d, J=6.8 Hz, 3H).

Embodiment 41

41

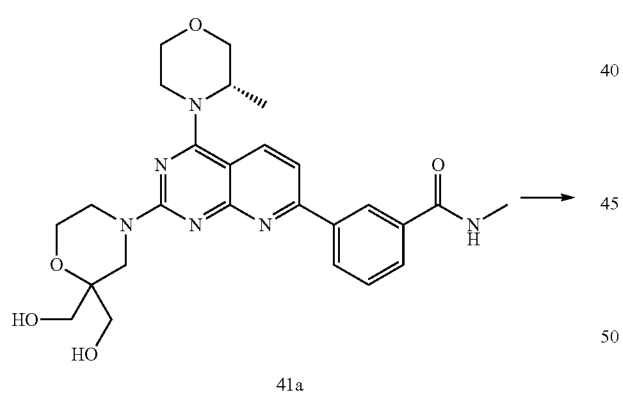

41a

-continued

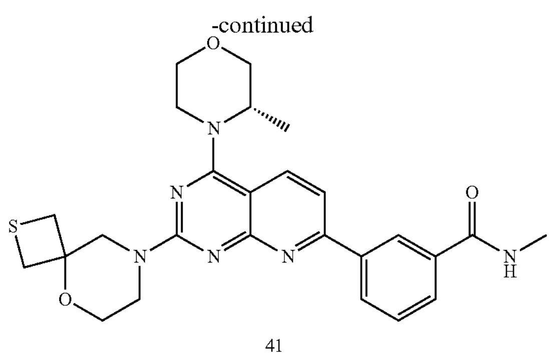

41

First Step

Compound 41a (70.0 mg, 138 μmol, 1 eq), methanesulfonyl chloride (0.8 g, 6.98 mmol, 541 μL, 50.7 eq) and triethylamine (27.9 mg, 275 μmol, 38.3 μL, 2 eq) were dissolved in dichloromethane (10.0 mL), and the mixture was reacted at room temperature for 16 hours. After completion of the reaction, the reaction solution was subjected to rotary evaporation under reduced pressure to dryness, and compound 41b was obtained.

MS-ESI calculated for $[M+H]^+$: 665, found: 665.

Second Step

Compound 41b (59.9 mg, 90.26 μmol, 1 eq), tetra-n-butylammonium iodide (3.33 mg, 9.03 μmol, 0.1 eq), sodium sulfide (21.1 mg, 271 μmol, 11.4 μL, 3 eq) were dissolved in N, N'-dimethylformamide (5.00 mL), and the mixture was reacted at 70° C. for 18 hours under nitrogen protection. After completion of the reaction, the reaction solution was washed with water (50.0 mL×3), and purified by high performance liquid chromatography to give 41.

MS-ESI calculated for $[M+H]^+$: 507, found: 507.

$^1$H NMR (400 MHz, $CDCl_3$) δ: 8.67 (br s, 1H), 8.20 (br d, J=8.0 Hz, 1H), 8.10-8.03 (m, 1H), 7.99 (br d, J=8.0 Hz, 1H), 7.60-7.52 (m, 2H), 6.64 (br s, 1H), 4.46 (br d, J=5.6 Hz, 1H), 4.42-4.33 (m, 1H), 4.19 (br d, J=13.2 Hz, 1H), 4.09-3.91 (m, 3H), 3.91-3.69 (m, 7H), 3.42 (br d, J=10.0 Hz, 2H), 3.06 (d, J=4.8 Hz, 3H), 3.00 (br d, J=8.0 Hz, 2H), 1.53 (br d, J=6.8 Hz, 3H).

Embodiment 42

42

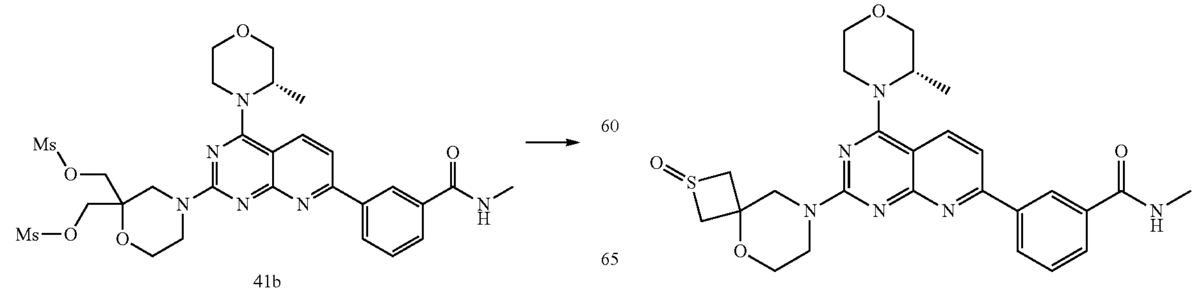

41b

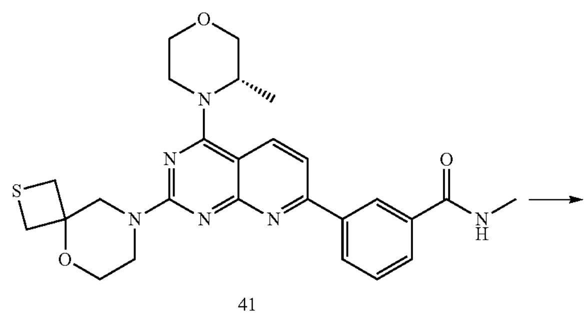
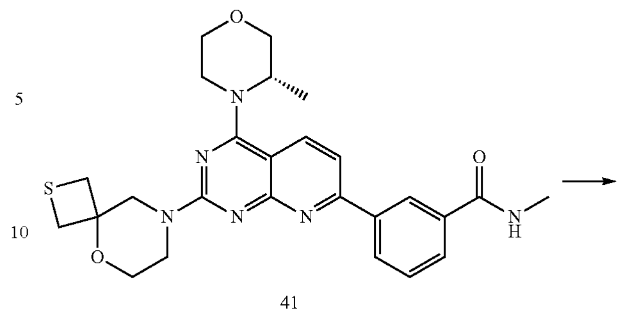
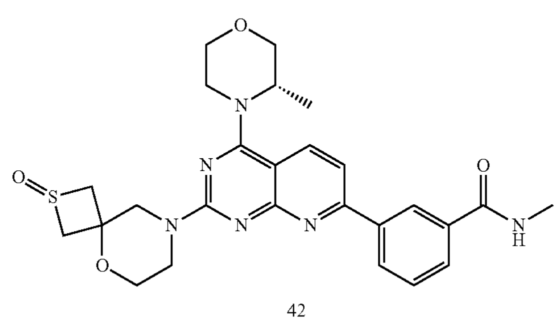
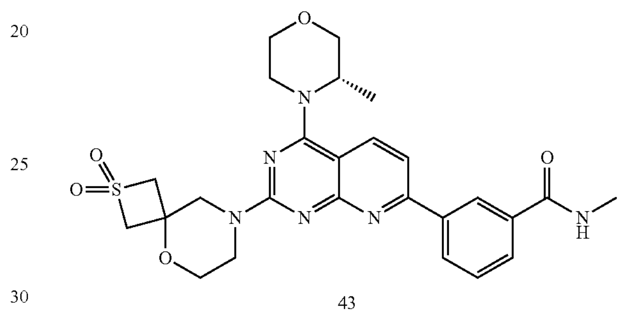

Compound 41 (70.0 mg, 138 μmol, 1 eq) was dissolved in methanol (20.0 mL), an aqueous solution (10.0 mL) of potassium monopersulfate (84.9 mg, 138 μmol, 1 eq) was added dropwise. The reaction was carried out at room temperature for an hour. After the completion of the reaction, the reaction solution was purified by high performance liquid chromatography to give 42.

MS-ESI calculated for $[M+H]^+$: 523, found: 523.

$^1$H NMR (400 MHz, $CDCl_3$) δ: 8.72-7.51 (m, 1H), 8.11 (br d, J=7.2 Hz, 1H), 8.00 (d, J=8.4 Hz, 1H), 7.93 (br d, J=7.8 Hz, 1H), 7.55-7.43 (m, 2H), 4.49-4.33 (m, 1H), 4.20 (s, 2H), 3.94 (br d, J=8.4 Hz, 3H), 3.82-3.74 (m, 1H), 3.74-3.60 (m, 5H), 3.52 (br d, J=13.6 Hz, 2H), 3.28-3.06 (m, 2H), 3.00-2.94 (m, 3H), 1.44 (d, J=6.8 Hz, 3H).

Embodiment 43

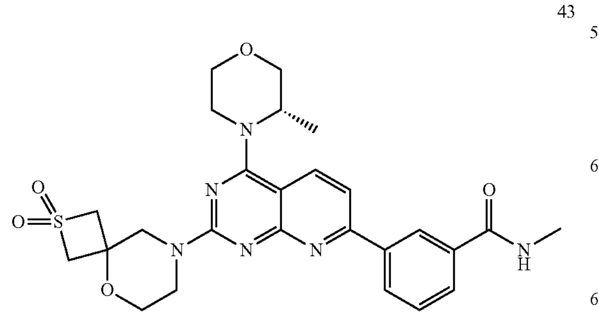
43

Compound 41 (120 mg, 237 μmol, 1 eq) was dissolved in methanol (5.00 mL), an aqueous solution (5.00 mL) of potassium monopersulfate (291 mg, 474 μmol, 2 eq) was added dropwise. The reaction was carried out at room temperature for 30 hours.

After completion of the reaction, the reaction solution was purified by high performance liquid chromatography to give 43.

MS-ESI calculated for $[M+H]^+$: 539, found: 539.

$^1$H NMR (400 MHz, $CDCl_3$) δ: 8.58 (br s, 1H), 8.14 (br d, J=8.0 Hz, 1H), 8.02 (d, J=8.4 Hz, 1H), 7.91 (br d, J=7.6 Hz, 1H), 7.60-7.44 (m, 2H), 6.57 (br s, 1H), 4.42 (br d, J=6.0 Hz, 1H), 4.27-3.85 (m, 10H), 3.82-3.60 (m, 6H), 2.99 (d, J=4.8 Hz, 3H), 1.46 (d, J=6.8 Hz, 3H).

Embodiment 44

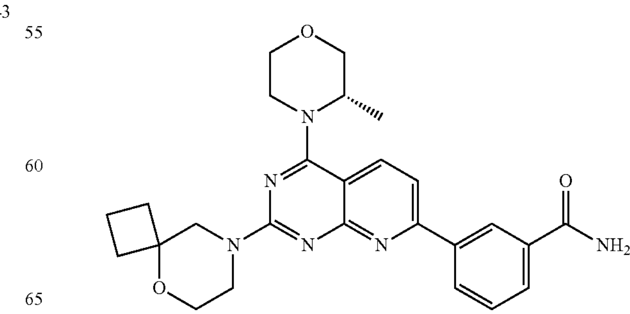
44

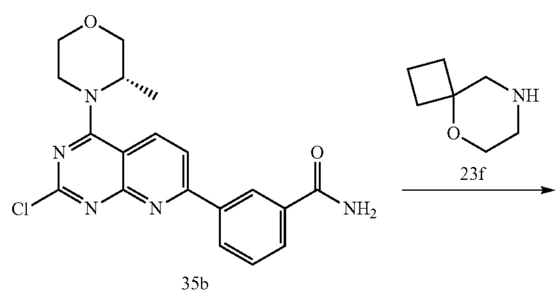

-continued 45-2 or 45-1

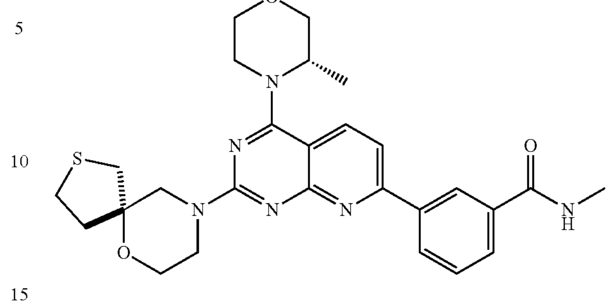

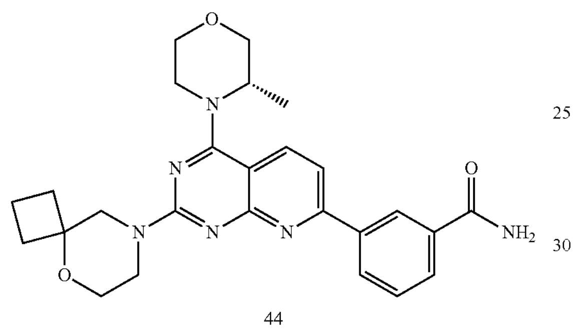

Compound 35b (150 mg, 391 μmol, 1 eq), 23f (128 mg, 782 μmol, 1 eq) and DIPEA (152 mg, 1.17 mmol, 3 eq) were dissolved in DMSO (3.00 mL), and the mixed solution was allowed to react at 90° C. for 20 hours. After completion of the reaction, the reaction solution was purified by high performance liquid chromatography to give 44.

MS-ESI calculated for $[M+H]^+$: 475, found: 475.

$^1$H NMR (400 MHz, $CDCl_3$) δ: 8.66 (br s, 1H), 8.18 (br d, J=7.6 Hz, 1H), 7.99 (d, J=8.4 Hz, 1H), 7.95 (br d, J=7.6 Hz, 1H), 7.51 (t, J=7.6 Hz, 1H), 7.46 (br d, J=8.4 Hz, 1H), 6.72-6.11 (m, 1H), 5.64 (br s, 1H), 4.35 (br s, 1H), 3.95-3.57 (m, 11H), 2.07-1.77 (m, 7H), 1.45 (br d, J=6.8 Hz, 3H).

Embodiment 45-1&45-2

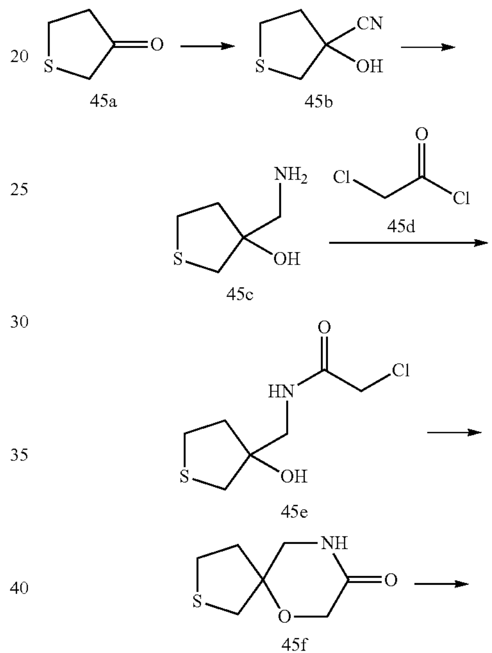

45-1 or 45-2

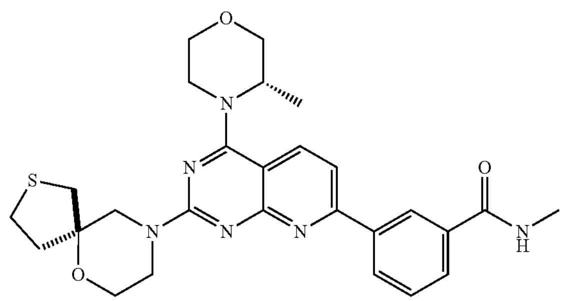

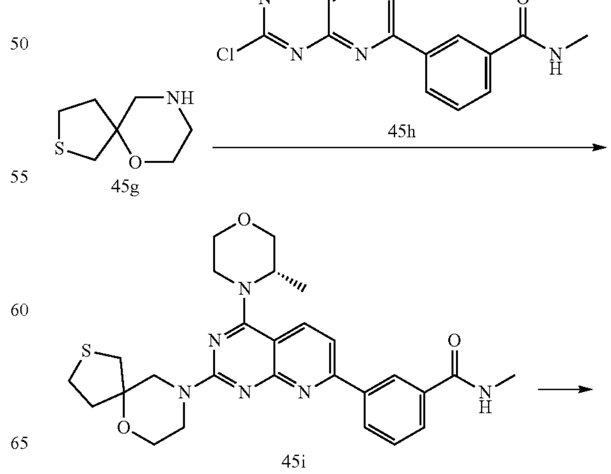

-continued

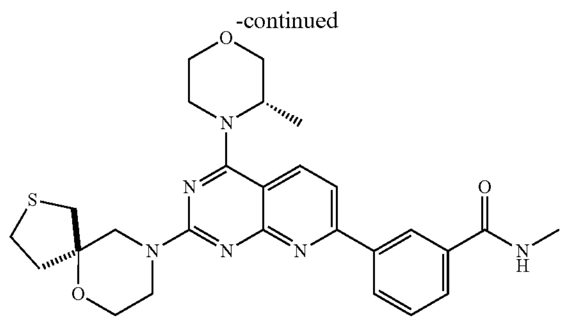

45-1 or 45-2

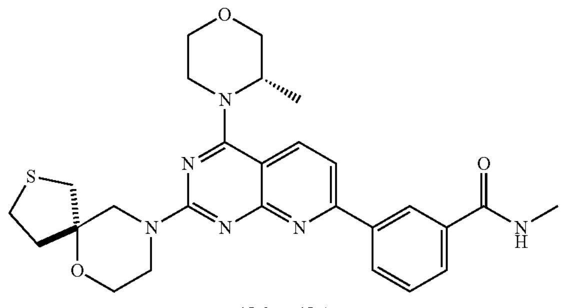

45-2 or 45-1

First Step

TMSCN (18.9 g, 191 mmol, 1.5 eq) and boron trifluoride ether complex (18.1 g, 127 mmol, 1.0 eq) were sequentially added to a solution of compound 45a (13.0 g, 127 mmol, 1.0 eq) in dichloromethane (250 mL), and the mixture was reacted at 20° C. for 15 hours. After completion of the reaction, the reaction solution was concentrated, purified by column chromatography (2:1 petroleum ether/ethyl acetate) to give 45b.

$^{1}$H NMR (400 MHz, $CDCl_3$) δ: 3.34 (d, J=12.0 Hz, 1H), 3.19 (s, 1H), 3.16 (dd, J=1.6, 12.0 Hz, 1H), 3.13-3.01 (m, 2H), 2.59-2.47 (m, 1H), 2.32 (td, J=8.8, 12.8 Hz, 1H).

Second Step

Borane-tetrahydrofuran complex (1 M, 157 mL, 1.5 eq) was added dropwise to a solution of compound 45b in tetrahydrofuran (200 mL) at 0° C. The mixed solution was allowed to react at 20° C. for 17 hours. 10 mL methanol was added to the reaction solution to terminate the reaction. The reaction solution was concentrated to give 45c, and the crude product was directly used in the next step.

Third Step

Compound 45d (8.48 g, 75.1 mmol, 1.0 eq) was added dropwise to a solution of compound 45c (10.0 g, 75.1 mmol, 1.0 eq) and diisopropylethylamine (19.4 g, 150 mmol, 2.0 eq) in dichloromethane (150 mL) at 0° C. The mixed solution was allowed to react at 20° C. for 3 hours. 5 mL water was added to the reaction solution to terminate the reaction. The reaction solution was concentrated, and purified by column chromatography (100% ethyl acetate) to give 45e.

$^{1}$H NMR (400 MHz, $CDCl_3$) δ: 7.12-6.88 (m, 1H), 4.06-3.99 (m, 2H), 3.55 (d, J=6.0 Hz, 2H), 3.01-2.84 (m, 3H), 2.82 (d, J=11.2 Hz, 1H), 2.68 (dd, J=1.6, 11.6 Hz, 1H), 2.08-1.99 (m, 1H), 1.81 (td, J=9.2, 13.2 Hz, 1H).

Fourth Step

Potassium tert-butoxide (9.63 g, 85.8 mmol, 3.0 eq) was added to a solution of compound 45e (6.0 g, 28.6 mmol, 1.0 eq) in tetrahydrofuran (500 mL) at 0° C. The mixed solution was allowed to react at 20° C. for 2 hours. The reaction solution was concentrated, and purified by column chromatography (1:10 methanol/ethyl acetate) to give 45f.

$^{1}$H NMR (400 MHz, $CDCl_3$) δ: 6.43 (br s, 1H), 4.26 (s, 2H), 3.59-3.39 (m, 2H), 3.13-3.00 (m, 2H), 2.96-2.78 (m, 2H), 2.47-2.32 (m, 1H), 2.02-1.88 (m, 1H).

Fifth Step

Lithium aluminum hydride (329 mg, 8.66 mmol, 1.5 eq) was added to a solution of compound 45f (1.0 g, 5.77 mmol, 1.0 eq) in anhydrous tetrahydrofuran (30.0 mL) at 0° C. The mixed solution was allowed to react at 20° C. for an hour. 0.3 mL water, 0.3 mL 15% aqueous solution of sodium hydroxide, and 1 mL water were sequentially added to the reaction solution and filtered. The filter cake was rinsed with 10 mL ethyl acetate. The filtrate was concentrated to give 45 g. The crude product was directly used in the next step.

Sixth Step

Compound 45g (92.1 mg, 578 μmol, 2.3 eq), 45h (100 mg, 251 μmol, 1.00 eq), DIPEA (97.5 mg, 754 μmol, 3.00 eq) were dissolved in DMSO (3.00 mL). The mixed solution was allowed to react at 80° C. for 18 hours. After completion of the reaction, the reaction solution was diluted with water (10.0 mL) and extracted with ethyl acetate (20.0 mL×3). The combined organic phase was dried over anhydrous sodium sulfate, filtered, and subjected to rotary evaporation under reduced pressure to dryness, and purified by preparative thin layer chromatography (100% ethyl acetate) to give 45i, which was further subjected to SFC chiral separation to give compounds 45-1 and 45-2.

Compound 45-1 MS-ESI calculated for $[M+H]^+$: 521, found: 521.

Peak position of compound 45-1: 0.950 min (chiral column: AD-3 50×4.6 mm, I.D., 3 m, mobile phase: 40% ethanol (0.05% diethylamine)+carbon dioxide, flow rate: 4 mL/min, column temperature: 40° C.).

Compound 45-1 $^{1}$H NMR (400 MHz, $CDCl_3$) δ: 8.57 (s, 1H), 8.13 (br d, J=7.6 Hz, 1H), 7.98 (d, J=8.4 Hz, 1H), 7.90 (d, J=8.0 Hz, 1H), 7.52-7.42 (m, 2H), 6.57 (br s, 1H), 4.35 (br d, J=6.8 Hz, 1H), 4.22 (d, J=13.2 Hz, 1H), 4.13 (br s, 1H), 3.95-3.61 (m, 10H), 2.98 (d, J=4.8 Hz, 3H), 2.97-2.78 (m, 4H), 2.21 (td, J=6.0, 12.4 Hz, 1H), 1.99-1.88 (m, 1H), 1.43 (d, J=6.8 Hz, 3H).

Compound 45-2 MS-ESI calculated for $[M+H]^+$: 521, found: 521.

Peak position of compound 45-2: 1.168 min (chiral column: AD-3 50×4.6 mm, I.D., 3 m, mobile phase: 40% ethanol (0.05% diethylamine)+carbon dioxide, flow rate: 4 mL/min, column temperature: 40° C.).

Compound 45-2 $^{1}$H NMR (400 MHz, $CDCl_3$) δ: 8.57 (s, 1H), 8.13 (br d, J=7.6 Hz, 1H), 7.98 (d, J=8.4 Hz, 1H), 7.90 (d, J=8.0 Hz, 1H), 7.52-7.43 (m, 2H), 6.54 (br s, 1H), 4.34 (br d, J=6.8 Hz, 1H), 4.23 (br d, J=13.2 Hz, 1H), 4.17 (br s, 1H), 3.95-3.60 (m, 10H), 2.99 (d, J=4.8 Hz, 3H), 2.97-2.76 (m, 4H), 2.20 (td, J=6.0, 12.4 Hz, 1H), 2.00-1.89 (m, 1H), 1.42 (d, J=6.8 Hz, 3H).

Embodiment 46-1&46-2

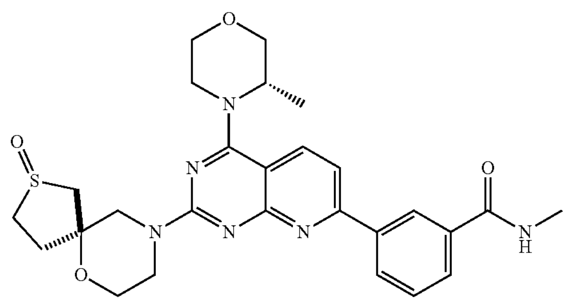

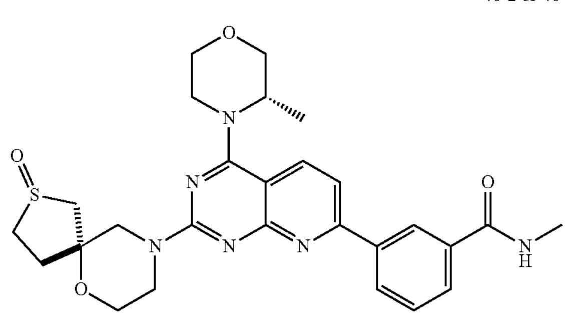

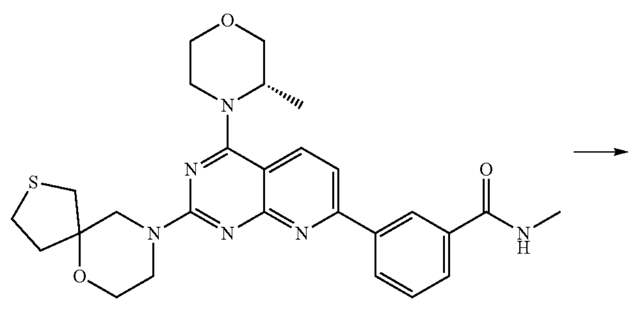
46a

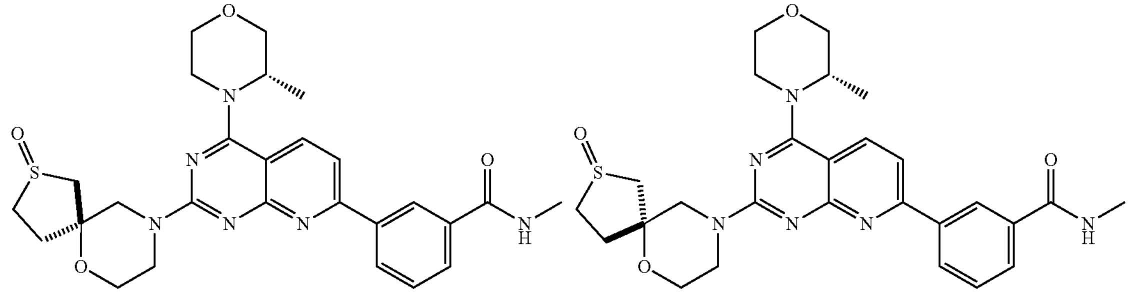

An aqueous solution (40.0 mL) of potassium monopersulfate (402 mg, 653 mol, 0.85 eq) was added dropwise to a solution of compound 46a (400 mg, 768 μmol, 1.0 eq) in methanol (60.0 mL). The reaction was carried out at 25° C. for 1.5 hours, and terminated by addition of 10 mL saturated solution of sodium thiosulfate. The reaction solution was concentrated to a volume of about 50 mL, and extracted with ethyl acetate (30 mL×3). The combined organic phases were dried over anhydrous sodium sulfate, filtered, and subjected to rotary evaporation under reduced pressure to dryness, and purified by column chromatography (1:10 methanol/ethyl acetate) to give racemate, which was further subjected to SFC chiral separation to give compounds 46-1 and 46-2.

Peak position of compound 46-1: 5.297 minutes (chiral column: AD-3 150×4.6 mm, I.D., 3 m, mobile phase: 40% methanol (0.05% diethylamine)+carbon dioxide, flow rate: 2.5 mL/min, column temperature: 40° C.).

Compound 46-1 MS-ESI calculated for $[M+H]^+$537, found: 537.

Compound 46-1 $^1$H NMR (400 MHz, $CDCl_3$) δ: 8.69 (br s, 1H), 8.13-7.91 (m, 3H), 7.53-7.40 (m, 2H), 4.46-4.22 (br d, J=6.8 Hz, 2H), 4.14 (br d, J=12.2 Hz, 1H), 3.97-3.62 (m, 10H), 3.17 (br s, 1H), 2.97 (d, J=4.8 Hz, 6H), 2.68 (br d, J=6.4 Hz, 1H), 2.49-2.38 (m, 1H), 1.43 (d, J=6.8 Hz, 3H).

Peak position of compound 46-2: 6.265 minutes (chiral column: AD-3 150×4.6 mm, I.D., 3 μm, mobile phase: 40% methanol (0.05% diethylamine)+carbon dioxide, flow rate: 2.5 mL/min, column temperature: 40° C.).

Compound 46-2 MS-ESI calculated for $[M+H]^+$: 537, found: 537.

Compound 46-2 $^1$H NMR (400 MHz, $CDCl_3$) δ: 8.70 (br s, 1H), 8.13-7.91 (m, 3H), 7.55-7.39 (m, 2H), 4.45-4.22 (m, 2H), 4.20-4.08 (m, 1H), 3.94-3.63 (m, 10H), 3.17 (br s, 1H), 2.97 (d, J=4.8 Hz, 6H), 2.78-2.61 (m, 1H), 2.44 (br d, J=14.1 Hz, 1H), 1.41 (d, J=6.8 Hz, 3H).

Embodiments 47-1&47-2

47-1 or 47-2

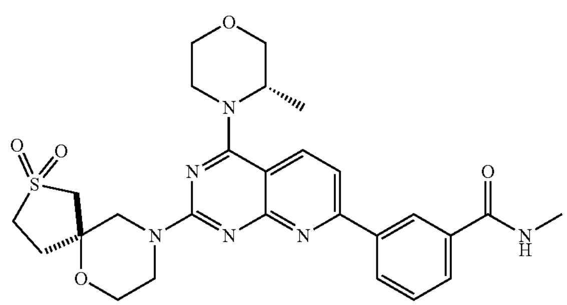

47-2 or 47-1

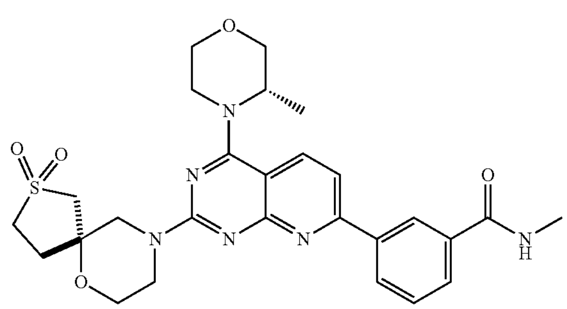

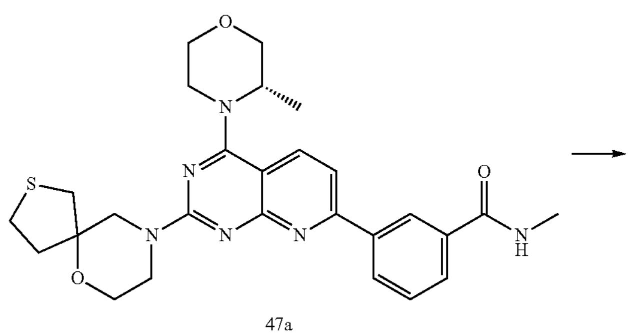

47a

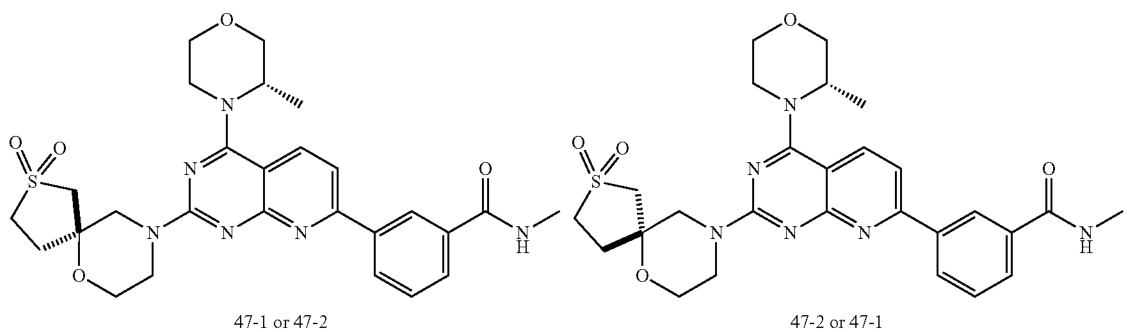

47-1 or 47-2 47-2 or 47-1

An aqueous solution (30.0 mL) of potassium monopersulfate (779 mg, 1.27 mmol, 3.3 eq) was added dropwise to a solution of compound 47a (200 mg, 384 μmol, 1.0 eq) in methanol (30.0 mL). The reaction was carried out at 25° C. for 5 hours, and terminated by addition of 10 mL saturated solution of sodium thiosulfate. The reaction solution was concentrated to a volume of about 40 mL, and extracted with dichloromethane (50.0 mL×4). The combined organic phase was dried over anhydrous sodium sulfate, filtered, and subjected to rotary evaporation under reduced pressure to dryness, and purified by preparative thin layer chromatography (1:20 methanol/dichloromethane) to give a racemic intermediate, which was further subjected to SFC chiral separation to give compounds 47-1 and 47-2.

Compound 47-1 MS-ESI calculated for $[M+H]^+$: 553, found: 553.

Peak position of compound 47-1: 1.617 min (chiral column: AD-3 50×4.6 mm, I.D., 3 m, mobile phase: 40% ethanol (0.05% diethylamine)+carbon dioxide, flow rate: 4 mL/min, column temperature: 40° C.).

Compound 47-1 $^1$H NMR (400 MHz, $CDCl_3$) δ: 8.65 (s, 1H), 8.23 (d, J=8.0 Hz, 1H), 8.10 (d, J=8.4 Hz, 1H), 7.99 (d, J=8.0 Hz, 1H), 7.64-7.55 (m, 2H), 6.58 (br s, 1H), 4.66-4.34 (m, 3H), 4.07-3.55 (m, 10H), 3.45-3.18 (m, 4H), 3.08 (d, J=4.8 Hz, 3H), 2.57-2.45 (m, 1H), 2.38-2.26 (m, 1H), 1.53 (d, J=6.8 Hz, 3H).

Compound 47-2 MS-ESI calculated for $[M+H]^+$: 553, found: 553.

Peak position of compound 47-2: 2.000 min (chiral column: AD-3 50×4.6 mm, I.D., 3 μm, mobile phase: 40% ethanol (0.05% diethylamine)+carbon dioxide, flow rate: 4 mL/min, column temperature: 40° C.).

Compound 47-2 $^1$H NMR (400 MHz, $CDCl_3$) δ: 8.65 (s, 1H), 8.23 (d, J=8.0 Hz, 1H), 8.10 (d, J=8.4 Hz, 1H), 7.99 (d, J=8.0 Hz, 1H), 7.64-7.55 (m, 2H), 6.58 (br s, 1H), 4.66-4.34 (m, 3H), 4.07-3.55 (m, 10H), 3.45-3.18 (m, 4H), 3.08 (d, J=4.8 Hz, 3H), 2.57-2.45 (m, 1H), 2.38-2.26 (m, 1H), 1.53 (d, J=6.8 Hz, 3H).

Embodiments 48-1&48-2

-continued

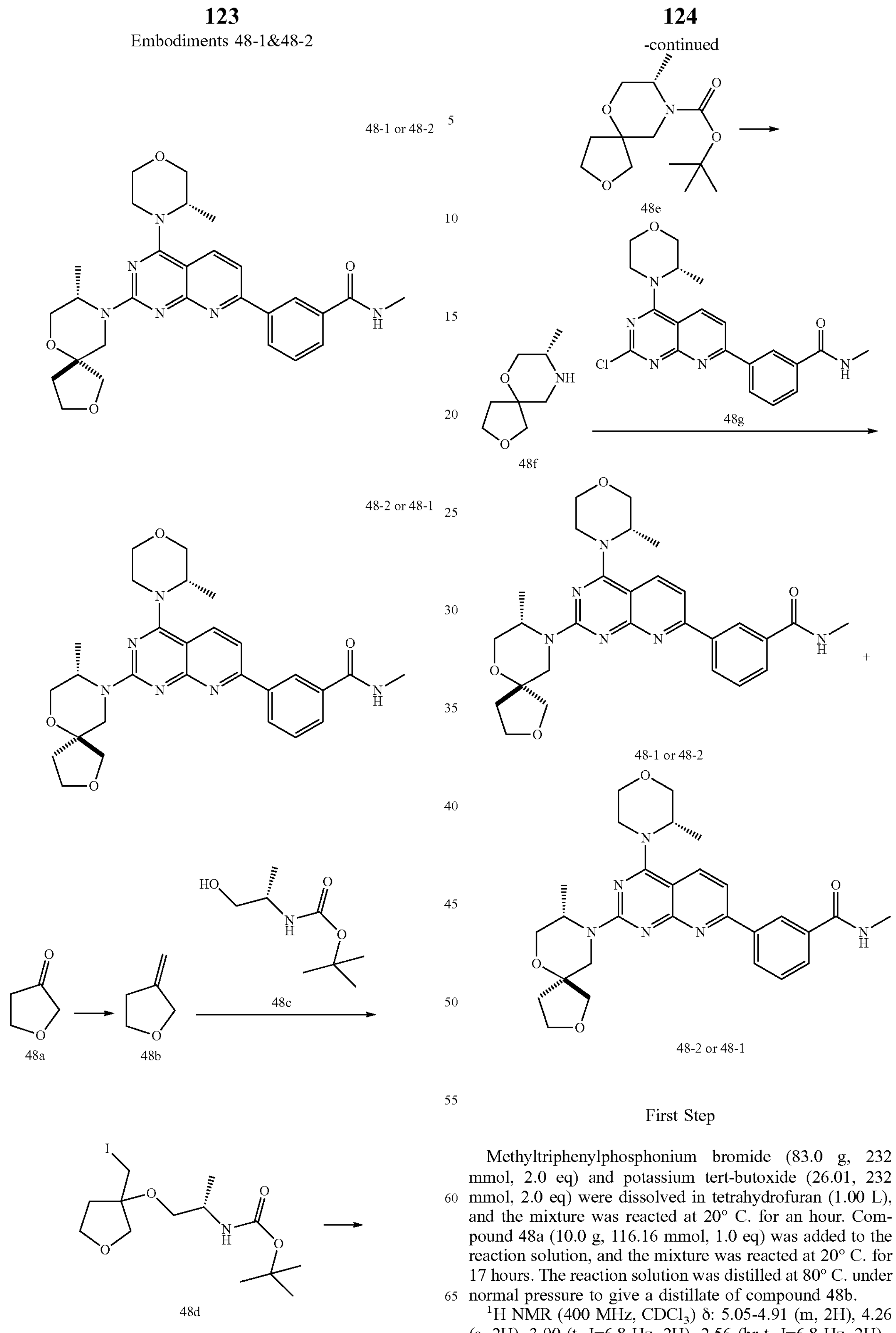

First Step

Methyltriphenylphosphonium bromide (83.0 g, 232 mmol, 2.0 eq) and potassium tert-butoxide (26.01, 232 mmol, 2.0 eq) were dissolved in tetrahydrofuran (1.00 L), and the mixture was reacted at 20° C. for an hour. Compound 48a (10.0 g, 116.16 mmol, 1.0 eq) was added to the reaction solution, and the mixture was reacted at 20° C. for 17 hours. The reaction solution was distilled at 80° C. under normal pressure to give a distillate of compound 48b.

$^{1}$H NMR (400 MHz, $CDCl_3$) δ: 5.05-4.91 (m, 2H), 4.26 (s, 2H), 3.90 (t, J=6.8 Hz, 2H), 2.56 (br t, J=6.8 Hz, 2H).

Second Step

Compound 48b (6.00 g, 28.5 mmol, 4% purity, 1 eq), compound 48c (5.0 g, 28.5 mmol, 1.0 eq), and N-iodosuccinimide (6.42 g, 28.5 mmol, 1.0 eq) were dissolved in tetrahydrofuran (80.0 mL), and the mixture was reacted at 60° C. for 17 hours. After completion of the reaction, the reaction was terminated by 100 mL saturated aqueous solution of sodium thiosulfate. The reaction solution was extracted with ethyl acetate (150 mL×3), and the organic phase was dried over anhydrous sodium sulfate, filtered, subjected to rotary evaporation under reduced pressure to dryness, and purified by column chromatography (1:1 ethyl acetate/petroleum ether) to give compound 48d.

MS-ESI calculated for $[M+H]^+$: 386, found: 386.

Third Step

Compound 48d (0.2 g, 519 μmol, 1.0 eq) and sodium hydride (41.5 mg, 1.04 mmol, 60% purity, 2.0 eq) were dissolved in N, N-dimethylformamide (10.0 mL), and the mixture was reacted at 25° C. for 16 hours. After completion of the reaction, the reaction was terminated by addition of water (1.00 mL). The reaction solution was concentrated, diluted with 10.0 mL water, extracted with ethyl acetate (10.0 mL×3). The organic phases were combined, dried over anhydrous sodium sulfate, filtered, and subjected to rotary evaporation under reduced pressure to dryness to give 48e.

Fourth Step

Compound 48e (0.15 g, 583 μmol, 1 eq) was dissolved in hydrochloric acid/ethyl acetate (10.0 mL, 2M), and the mixture was reacted at 25° C. for 17 hours under stirring. After completion of the reaction, the reaction solution was subjected to rotary evaporation under reduced pressure to dryness to give 48f.

Fifth Step

Compound 48f (90.0 mg, 465 μmol, 1.85 eq), compound 48g (100 mg, 251 mol, 1.0 eq), and DIPEA (97.5 mg, 754 μmol, 3.0 eq) were dissolved in DMSO (5.00 mL). The mixed solution was allowed to react at 80° C. for 18 hours, and purified by high performance liquid chromatography to give a racemate, which was further subjected to SFC chiral separation to give compounds 48-1 and 48-2.

Peak position of compound 48-1: 3.301 minutes (chiral column: AS-H 150×4.6 mm, I.D., 5 μm, mobile phase: A: $CO_2$, B: ethanol (0.05% diethylamine), the content of B was maintained at 5% for 0.5 min, then increased from 5% to 40% gradient within 3.5 min, then maintained at 40% for 2.5 min, and finally maintained at 5% for 1.5 min, flow rate: 3 mL/min, column temperature: 40° C.).

Compound 48-1 MS-ESI calculated for $[M+H]^+$: 519, found: 519.

Compound 48-1 $^1H$ NMR (400 MHz, $CDCl_3$) δ: 8.54 (s, 1H), 8.13 (d, J=8.0 Hz, 1H), 7.99 (d, J=8.4 Hz, 1H), 7.89 (d, J=8.0 Hz, 1H), 7.49 (t, J=8.0 Hz, 1H), 7.45 (d, J=8.4 Hz, 1H), 6.50 (br s, 1H), 4.93 (br s, 1H), 4.59 (br d, J=13.2 Hz, 1H), 4.33 (br d, J=6.4 Hz, 1H), 3.94-3.54 (m, 12H), 3.23 (d, J=13.6 Hz, 1H), 2.99 (d, J=5.2 Hz, 3H), 2.14-2.00 (m, 1H), 1.98-1.88 (m, 1H), 1.42 (d, J=6.8 Hz, 3H), 1.29 (br d, J=6.4 Hz, 3H).

Peak position of compound 48-2: 3.608 min (chiral column: AS-H 150×4.6 mm, I.D., 5 μm, mobile phase: A: $CO_2$, B: ethanol (0.05% diethylamine), the content of B was maintained at 5% for 0.5 min, then increased from 5% to 40% gradient within 3.5 min, then maintained at 40% for 2.5 min, and finally maintained at 5% for 1.5 min, flow rate: 3 mL/min, column temperature: 40° C.).

Compound 48-2 MS-ESI calculated for $[M+H]^+$: 519, found: 519.

Compound 48-2 $^1H$ NMR (400 MHz, $CDCl_3$) δ: 8.54 (s, 1H), 8.13 (d, J=8.0 Hz, 1H), 7.99 (d, J=8.4 Hz, 1H), 7.89 (d, J=8.0 Hz, 1H), 7.49 (t, J=8.0 Hz, 1H), 7.45 (d, J=8.4 Hz, 1H), 6.50 (br s, 1H), 4.93 (br s, 1H), 4.59 (br d, J=13.2 Hz, 1H), 4.33 (br d, J=6.4 Hz, 1H), 3.94-3.54 (m, 12H), 3.23 (d, J=13.6 Hz, 1H), 2.99 (d, J=5.2 Hz, 3H), 2.14-2.00 (m, 1H), 1.98-1.88 (m, 1H), 1.42 (d, J=6.8 Hz, 3H), 1.29 (br d, J=6.4 Hz, 3H).

Embodiment 49

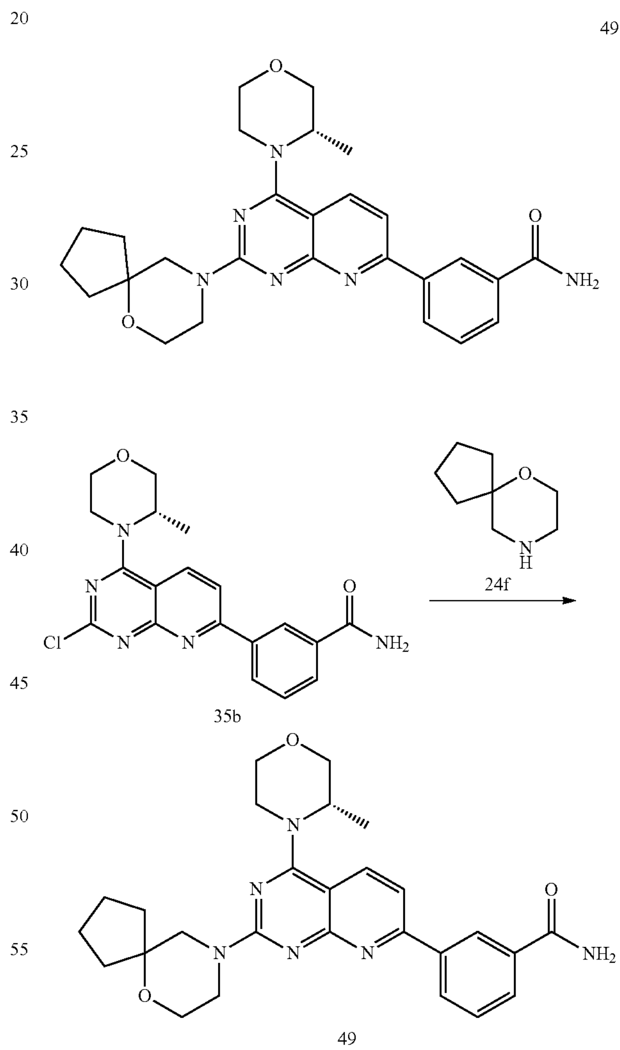

Compound 35b (100 mg, 261 μmol, 1.00 eq), 24f (92.6 mg, 522 μmol, 2.00 eq), DIPEA (101 mg, 782 μmol, 136 μL, 3.00 eq) were dissolved in DMSO (2.00 mL). The mixed solution was allowed to react at 80° C. for 40 hours. After completion of the reaction, the reaction solution was purified by high performance liquid chromatography to give 49.

MS-ESI calculated for $[M+H]^+$: 489, found: 489.

$^{1}$H NMR (400 MHz, $CDCl_3$) δ: 8.62 (s, 1H), 8.18 (br d, J=7.6 Hz, 1H), 7.97 (d, J=8.4 Hz, 1H), 7.93 (br d, J=8.0 Hz, 1H), 7.51 (t, J=8.0 Hz, 1H), 7.43 (d, J=8.4 Hz, 1H), 6.52 (br s, 1H), 5.63 (br s, 1H), 4.29 (br s, 1H), 3.95-3.57 (m, 12H), 1.70 (br d, J=8.4 Hz, 8H), 1.41 (d, J=6.8 Hz, 3H).

Embodiments 50-1&50-2

50-1 or 50-2

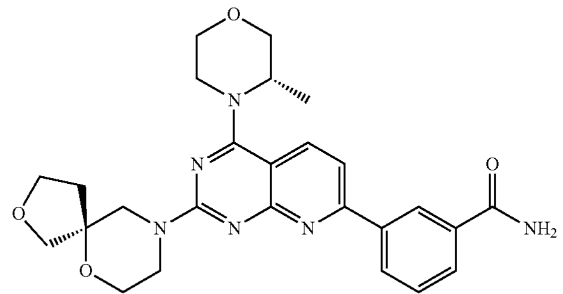

50-2 or 50-1

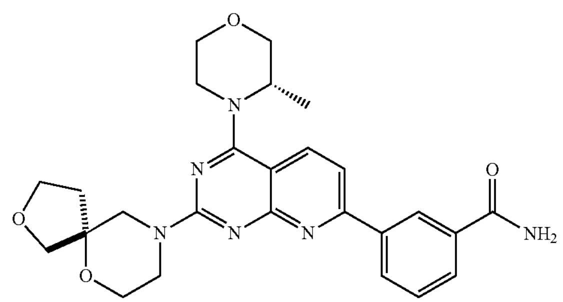

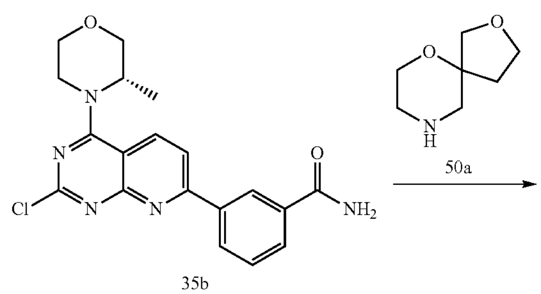

35b

50a

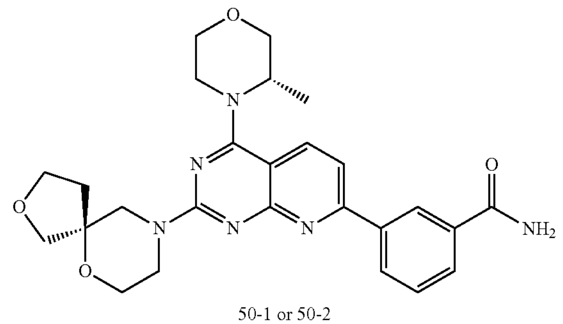

50-1 or 50-2

-continued

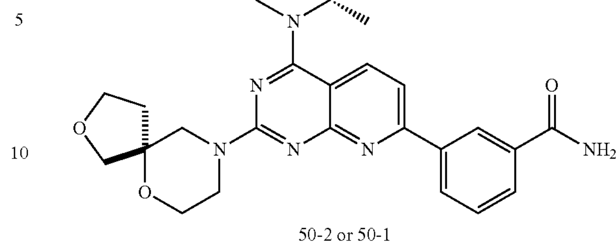

50-2 or 50-1

Compound 35b (80.0 mg, 208 μmol, 1.00 eq), 50a (44.9 mg, 250 μmol, 1.20 eq) and DIPEA (80.8 mg, 625 μmol, 109 μL, 3 eq) were dissolved in DMSO (2.00 mL). The mixed solution was allowed to react at 80° C. for 22 hours. After completion of the reaction, the reaction solution was purified by high performance liquid chromatography to give a racemate, which was further subjected to SFC chiral separation to give 50-1 and 50-2.

Peak position of 50-1: 3.491 min (chiral column: OJ-3 100×4.6 mm, I.D., 3 m, mobile phase: A: $CO_2$, B: methanol (0.05% diethylamine), the content of B was increased from 5% to 40% gradient within 4.5 min, then maintained at 5% for 1.0 min, flow rate: 2.8 mL/min, column temperature: 40° C.).

50-1 MS-ESI calculated for $[M+H]^+$: 491, found: 491.

50-1 $^{1}$H NMR (400 MHz, $CDCl_3$) δ: 8.63 (s, 1H), 8.18 (br d, J=8.0 Hz, 1H), 7.99 (d, J=8.4 Hz, 1H), 7.94 (d, J=80 Hz, 1H), 7.51 (t, J=7.2 Hz, 1H), 7.46 (d, J=8.0 Hz, 1H), 6.61 (br s, 1H), 5.69 (br s, 1H), 4.33 (br d, J=6.4 Hz, 1H), 3.97-3.59 (m, 16H), 2.07-1.85 (m, 2H), 1.41 (d, J=6.8 Hz, 3H).

Peak position of 50-2: 3.846 min (chiral column: OJ-3 100×4.6 mm, I.D., 3 m, mobile phase: A: $CO_2$, B: methanol (0.05% diethylamine), the content of B was increased from 5% to 40% gradient within 4.5 min, and then maintained at 5% for 1.0 min, flow rate: 2.8 mL/min, column temperature: 40° C.).

50-2 MS-ESI calculated for $[M+H]^+$: 491, found: 491.

50-2 $^{1}$H NMR (400 MHz, $CDCl_3$) δ: 8.63 (s, 1H), 8.18 (br d, J=8.0 Hz, 1H), 7.99 (d, J=8.4 Hz, 1H), 7.94 (d, J=80 Hz, 1H), 7.51 (t, J=7.2 Hz, 1H), 7.46 (d, J=8.0 Hz, 1H), 6.61 (br s, 1H), 5.69 (br s, 1H), 4.33 (br d, J=6.4 Hz, 1H), 3.97-3.59 (m, 16H), 2.07-1.85 (m, 2H), 1.41 (d, J=6.8 Hz, 3H).

Embodiment 51

51

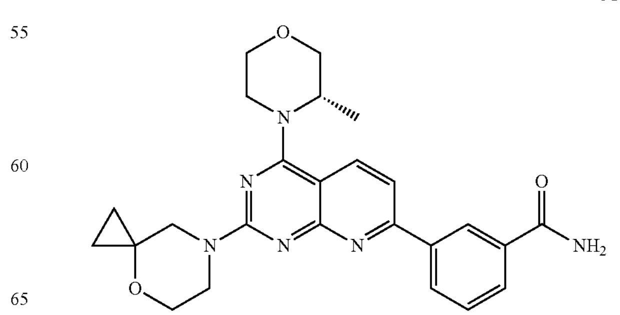

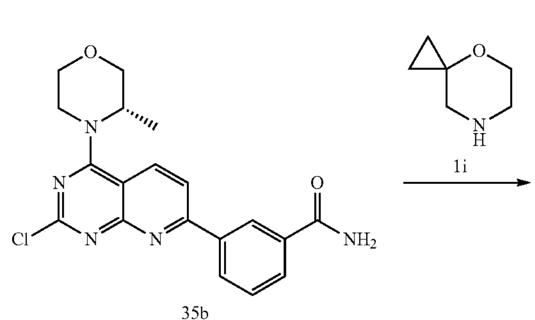

-continued

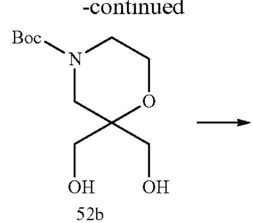

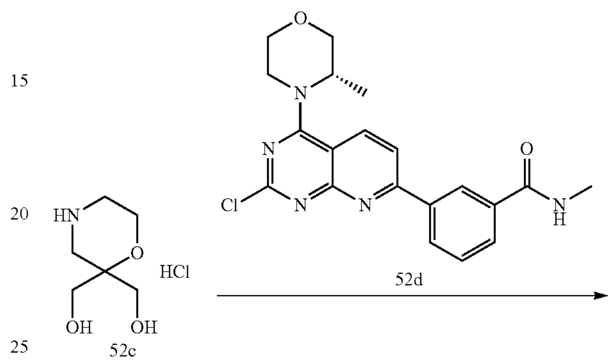

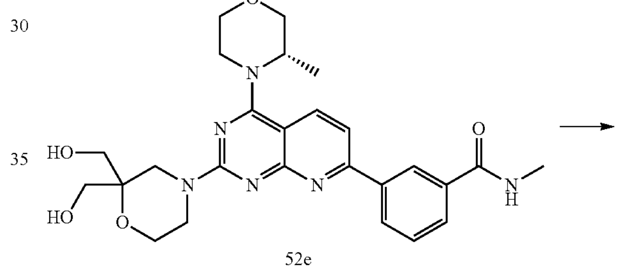

Compound 35b (100 mg, 261 μmol, 1.00 eq), 1i (46.8 mg, 313 μmol, 1.20 eq), and DIPEA (101 mg, 782 μmol, 136 μL, 3.00 eq) were dissolved in DMSO (2.00 mL). The mixed solution was allowed to react at 80° C. for 18 hours. After completion of the reaction, the reaction solution was purified by high performance liquid chromatography to give 51.

MS-ESI calculated value $[M+H]^+$: 461, found: 461.

$^1$H NMR (400 MHz, $CDCl_3$) δ: 8.60 (s, 1H), 8.18 (br d, J=8.0 Hz, 1H), 7.98 (d, J=8.4 Hz, 1H), 7.92 (br d, J=8.0 Hz, 1H), 7.51 (t, J=8.0 Hz, 1H), 7.43 (d, J=8.4 Hz, 1H), 6.46 (br s, 1H), 5.62 (br s, 1H), 4.30 (br s, 1H), 4.05-3.59 (m, 12H), 1.40 (d, J=6.8 Hz, 3H), 0.80-0.73 (m, 2H), 0.61 (br s, 2H).

Embodiment 52

52

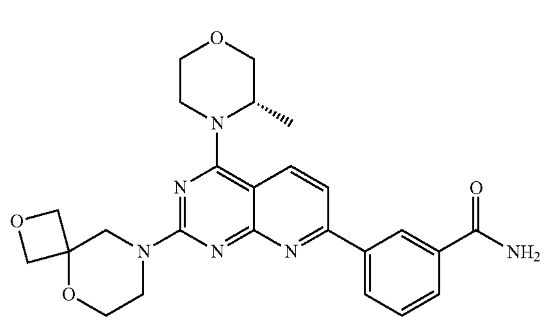

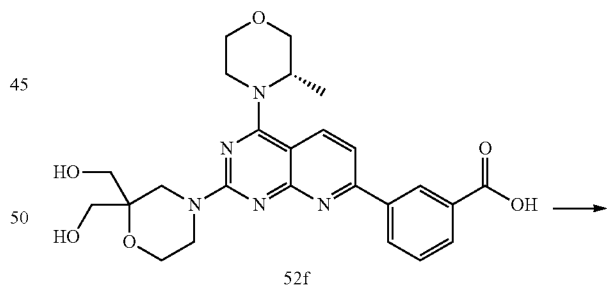

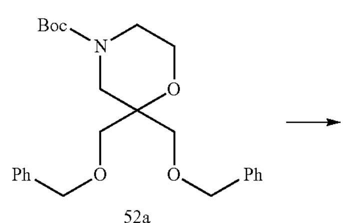

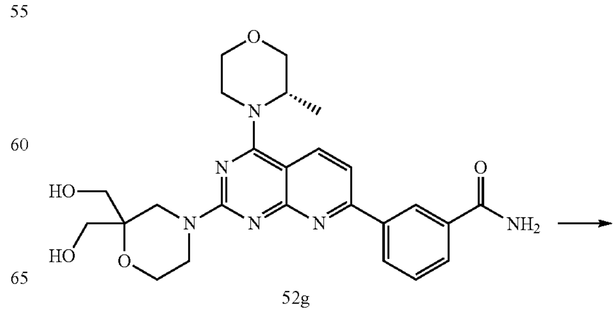

-continued

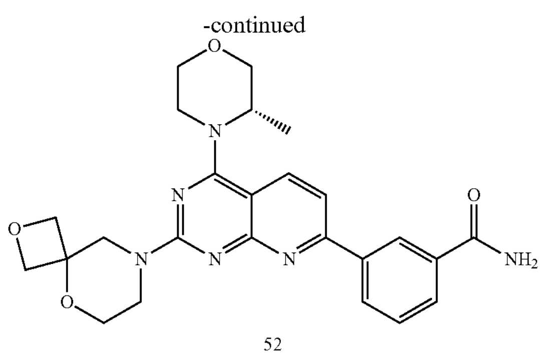

First Step

Compound 52a (900 mg, 2.11 mmol, 1 eq) was dissolved in methanol (20.0 mL), and palladium hydroxide (591 mg, 421 μmol, 0.2 eq) was added thereto. The mixed solution was allowed to react at 50° C. for 42 hours under 50 psi hydrogen atmosphere, then filtered, subjected to rotary evaporation under reduced pressure to dryness to give compound 52b.

$^1$H NMR (400 MHz, $CDCl_3$) δ: 3.80-3.58 (m, 6H), 3.52-3.50 (m, 1H), 3.51 (s, 1H), 3.50-3.38 (m, 4H), 1.49 (s, 9H).

Second Step

Compound 52b (500 mg, 2.02 mmol, 1 eq) dissolved in hydrochloric acid-ethyl acetate solution (20.0 mL, 2 M), the mixture was allowed to react at 25° C. for an hour. After completion of the reaction, the reaction solution was subjected to rotary evaporation under reduced pressure to dryness, and a crude product of compound 52c was obtained.

$^1$H NMR (400 MHz, $CD_3OD$) δ: 4.15-4.10 (m, 2H), 3.71-3.63 (m, 4H), 3.31 (s, 2H), 3.23-3.17 (m, 2H).

Third Step

Compound 52c (350 mg, 1.91 mmol, 1 eq), 52d (531 mg, 1.33 mmol, 0.7 eq), and DIPEA (668 mg, 5.17 mmol, 0.9 mL, 2.71 eq) were dissolved in DMSO (7.00 mL). The mixed solution was allowed to react at 80° C. for 23 hours, and purified by high performance liquid chromatography to give 52e.

MS-ESI calculated for $[M+H]^+$509, found: 509.

$^1$H NMR (400 MHz, $CDCl_3$) δ: 8.61 (s, 1H), 8.21 (br d, J=8.0 Hz, 1H), 8.08 (d, J=8.4 Hz, 1H), 7.99 (d, J=8.0 Hz, 1H), 7.60-7.54 (m, 2H), 4.46 (br d, J=4.8 Hz, 1H), 4.34-3.45 (m, 19H), 3.07 (d, J=4.8 Hz, 3H), 1.52 (d, J=6.8 Hz, 3H).

Fourth Step

Compound 52e (300 mg, 590 μmol, 1 eq) was dissolved in ethanol (15.0 mL) and water (15.0 mL), sodium hydroxide (118 mg, 2.95 mmol, 5 eq) was added thereto. The mixed solution was allowed to react at 105° C. for 285 hours, and purified by high performance liquid chromatography to give a yellow solid 52f.

MS-ESI calculated for $[M+H]^+$: 496, found: 496.

$^1$H NMR (400 MHz, DMSO-$d_6$) δ: 8.78 (s, 1H), 8.28 (br d, J=8.0 Hz, 1H), 8.23 (d, J=8.4 Hz, 1H), 8.05 (br d, J=8.0 Hz, 1H), 7.68 (d, J=8.4 Hz, 1H), 7.58 (t, J=8.0 Hz, 1H), 4.66-4.39 (m, 3H), 3.96-3.41 (m, 14H), 1.38 (d, J=6.8 Hz, 3H).

Fifth Step

Compound 52f (78 mg, 157 μmol, 1 eq), ammonium chloride (33.7 mg, 630 mol, 4 eq), DIPEA (81.4 mg, 630 μmol, 110 μL, 4 eq), EDCI (60.4 mg, 315 μmol, 2 eq), and HOBt (42.5 mg, 315 μmol, 2 eq) were dissolved in dichloromethane (10.0 mL). The mixed solution was allowed to react at 30° C. for 16 hours. After completion of the reaction, water (3 mL) was added to terminate the reaction. The reaction solution was concentrated to remove solvent, diluted with water (20.0 mL) and extracted with ethyl acetate (20.0 mL×3) and methanol (5.00 mL). The combined organic phase was dried over anhydrous sodium sulfate, filtered, and subjected to rotary evaporation under reduced pressure to dryness, and 52 g was obtained.

MS-ESI calculated for $[M+H]^+$495, found: 495.

Sixth Step

Compound 52g (87.4 mg, 177 μmol, 1 eq), TosCl (50.5 mg, 265 μmol, 1.5 eq), and sodium hydride (35.3 mg, 884 μmol, 60% purity, 5 eq) were dissolved in DMF (4.00 mL). The mixed solution was allowed to react at 30° C. for 24 hours, and purified by high performance liquid chromatography to give 52.

MS-ESI calculated for $[M+H]^+$477, found: 477.

$^1$H NMR (400 MHz, $CDCl_3$) δ: 8.62 (s, 1H), 8.19 (br d, J=8.0 Hz, 1H), 8.00 (d, J=8.4 Hz, 1H), 7.94 (br d, J=8.0 Hz, 1H), 7.54-7.45 (m, 2H), 6.54 (br s, 1H), 5.73 (br s, 1H), 4.57 (d, J=6.8 Hz, 2H), 4.47-4.35 (m, 3H), 4.21-4.07 (m, 2H), 3.96-3.65 (m, 10H), 1.43 (d, J=6.8 Hz, 3H).

Embodiments 53-1&53-2

53-1 or 53-2

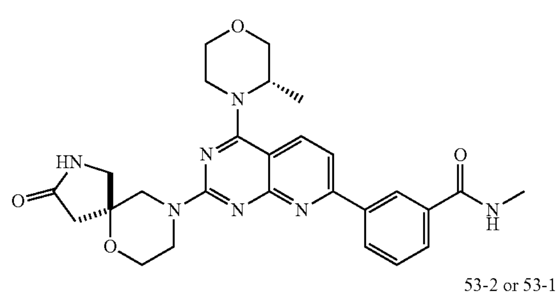

53-2 or 53-1

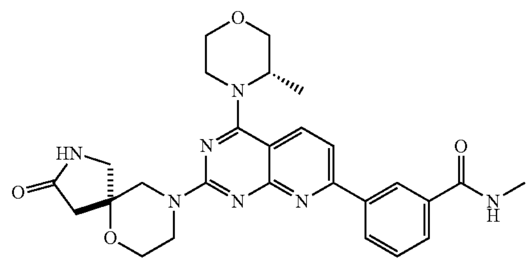

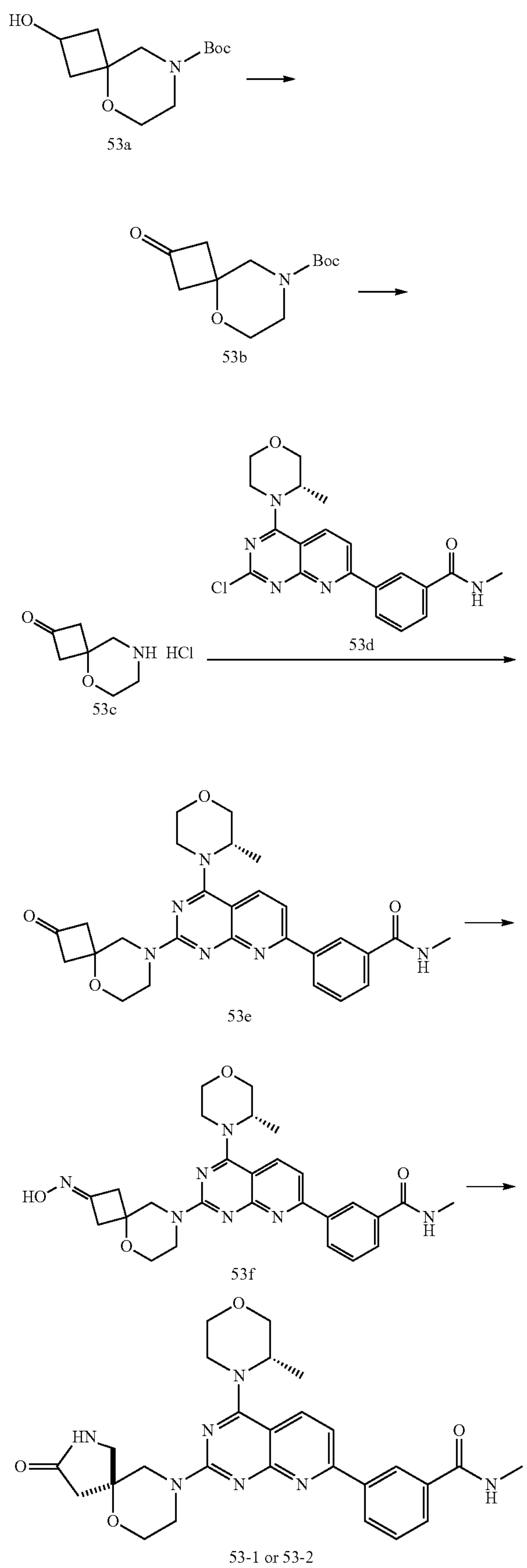

-continued

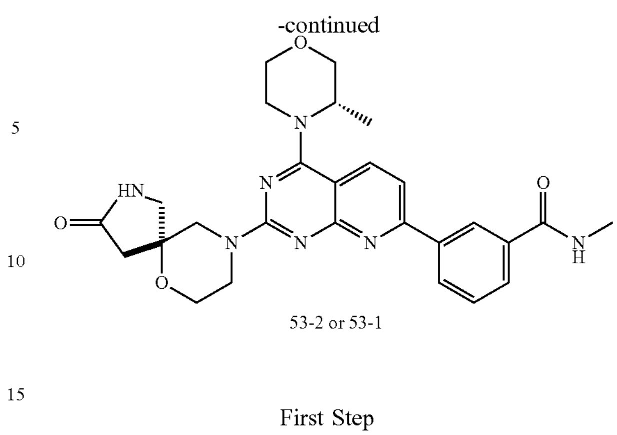

First Step

Dess-martin periodinane (1.31 g, 3.08 mmol, 1.5 eq) was added to a solution of compound 53a (0.5 g, 2.06 mmol, 1.0 eq) in dichloromethane (5 mL) at 0° C., and the mixture was reacted at 25° C. for 4 hours. The reaction solution was concentrated. The crude product was diluted with 10.0 mL of 1 M sodium hydroxide solution, extracted with ethyl acetate (20.0 mL×3). The organic phase was dried over anhydrous sodium sulfate, filtered, subjected to rotary evaporation under reduced pressure to dryness, and purified by column chromatography (1:4 ethyl acetate/petroleum ether) to give 53b.

$^{1}$H NMR (400 MHz, $CDCl_3$) δ: 3.71 (br t, J=4.8 Hz, 2H), 3.55 (s, 2H), 3.50 (br d, J=4.8 Hz, 2H), 3.21-3.08 (m, 2H), 3.06-2.91 (m, 2H), 1.49 (s, 9H).

Second Step

Compound 53b (0.25 g, 1.04 mmol, 1 eq) was dissolved in hydrochloric acid/ethyl acetate (10.0 mL, 2M), and the mixture was reacted at 30° C. for 15 hours under stirring. After completion of the reaction, the reaction solution was subjected to rotary evaporation under reduced pressure to dryness, and 53c was obtained. The crude product was directly used in the next step.

Third Step

Compound 53d (400 mg, 1.01 mmol, 1.0 eq), compound 53c (200 mg, 1.13 mmol, 1.12 eq), and DIPEA (390 mg, 302 μmol, 3.0 eq) were dissolved in DMSO (10.0 mL). The mixed solution was allowed to react at 80° C. for 17 hours, diluted with 20.0 mL water, extracted with ethyl acetate (20 mL×3). The organic phase was dried over anhydrous sodium sulfate, filtered, subjected to rotary evaporation under reduced pressure to dryness, and purified by column chromatography (100% ethyl acetate) to give 53e.

$^{1}$H NMR (400 MHz, $CDCl_3$) δ: 8.53 (s, 1H), 8.15 (d, J=8.0 Hz, 1H), 7.99 (d, J=8.4 Hz, 1H), 7.89 (d, J=8.0 Hz, 1H), 7.52-7.48 (m, 1H), 7.48-7.44 (m, 1H), 6.41 (br s, 1H), 4.34 (br d, J=7.2 Hz, 1H), 4.03-3.90 (m, 4H), 3.82-3.59 (m, 8H), 3.13-3.00 (m, 4H), 2.99 (d, J=4.8 Hz, 3H), 1.42 (d, J=6.8 Hz, 3H).

Fourth Step

Hydroxylamine hydrochloride (41.5 mg, 596.9 μmol, 3 eq) was added to a solution of compound 53e (100 mg, 199 μmmol, 1.0 eq) in methanol (3.00 mL), and the mixture was stirred at 70° C. for an hour. The reaction solution was concentrated. The crude product was diluted with 5 mL water, and extracted with ethyl acetate (10.0 mL×3). The organic phase was dried over anhydrous sodium sulfate, filtered, and subjected to rotary evaporation under reduced pressure to dryness, and purified by preparative thin layer chromatography (100% ethyl acetate) to give 53f.

Fifth Step

Sodium hydroxide (101 mg, 2.51 mmol, 10.0 eq), p-toluenesulfonyl chloride (479 mg, 2.51 mmol, 10.0 eq) were sequentially added to a solution of compound 53f (130 mg, 251 μmol, 1.0 eq) in acetone (40 mL) and water (4 mL), the mixture was reacted at 30° C. for 16 hours. The reaction solution was concentrated. The crude product was diluted with 10 mL of water and washed with ethyl acetate (20 mL×3). The organic phase was discarded. The aqueous phase was concentrated and purified by preparative thin layer chromatography (1:10 methanol/ethyl acetate) to give a racemate, which was further subjected to SFC chiral separation to give compounds 53-1 and 53-2.

Peak position of compound 53-1: 2.589 min (chiral column: AS-3 150×4.6 mm, mobile phase: A: $CO_2$, B: methanol (0.05% diethylamine), flow rate: 25 mL/min, column temperature: 40° C.).

Compound 53-1 MS-ESI calculated for $[M+H]^+$: 518, found: 518.

Compound 53-1 $^1H$ NMR (400 MHz, $CDCl_3$) δ: 8.55 (s, 1H), 8.13 (d, J=8.0 Hz, 1H), 7.99 (d, J=8.4 Hz, 1H), 7.90 (d, J=8.0 Hz, 1H), 7.53-7.43 (m, 2H), 6.52 (br s, 1H), 5.55 (br s, 1H), 4.34 (br d, J=6.4 Hz, 1H), 3.97-3.58 (m, 12H), 3.45-3.37 (m, 2H), 2.98 (d, J=5.2 Hz, 3H), 2.56-2.41 (m, 2H), 1.42 (d, J=6.8 Hz, 3H).

Peak position of compound 53-2: 5.877 min (chiral column: AS-3 150×4.6 mm, mobile phase: A: $CO_2$, B: methanol (0.05% diethylamine), flow rate: 25 mL/min, column temperature: 40° C.).

Compound 53-2 MS-ESI calculated for $[M+H]^+$: 518, found: 518.

Compound 53 $^1H$ NMR (400 MHz, $CDCl_3$) δ: 8.55 (s, 1H), 8.13 (d, J=8.0 Hz, 1H), 7.99 (d, J=8.4 Hz, 1H), 7.90 (d, J=8.0 Hz, 1H), 7.53-7.43 (m, 2H), 6.52 (br s, 1H), 5.55 (br s, 1H), 4.34 (br d, J=6.4 Hz, 1H), 3.97-3.58 (m, 12H), 3.45-3.37 (m, 2H), 2.98 (d, J=5.2 Hz, 3H), 2.56-2.41 (m, 2H), 1.42 (d, J=6.8 Hz, 3H).

Embodiment 54

54

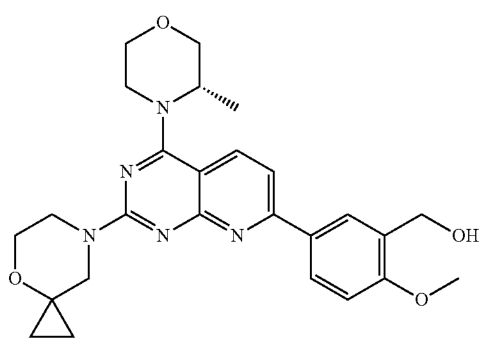

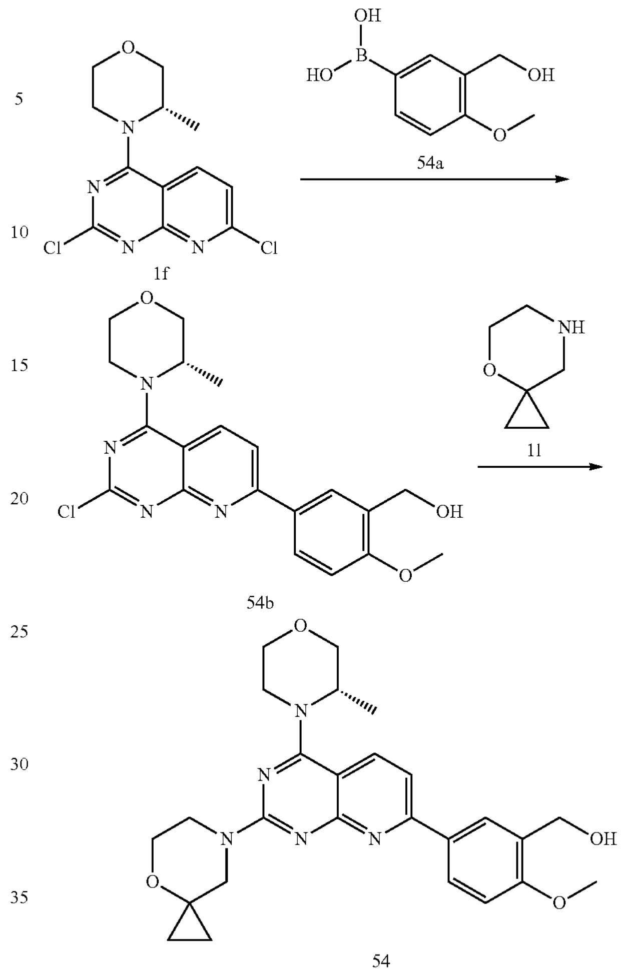

First Step

Compound 1f (150 mg, 501 μmol, 1.00 eq), 54a (82.1 mg, 451 μmol, 0.90 eq), bis(triphenylphosphine) palladium dichloride (17.6 mg, 25.1 μmol, 0.05 eq) and sodium carbonate (106 mg, 1.0 mmol, 2.00 eq) were dissolved in water (2.00 mL) and 1,4-dioxane (4.00 mL), and the mixture was reacted at 70° C. for 15.5 hours under nitrogen protection. After completion of the reaction, the reaction solution was concentrated to remove solvent, diluted with water (5 mL) and extracted with ethyl acetate (10.0 mL×3). The combined organic phase was dried over anhydrous sodium sulfate, filtered, and subjected to rotary evaporation under reduced pressure to dryness, and 54b was obtained.

Second Step

Compound 54b (100 mg, 249 μmol, 1.00 eq), 1i (33.9 mg, 299 μmol, 1.2 eq) and DIPEA (96.7 mg, 748 μmol, 130 μl, 3 eq) were dissolved in DMSO (3.00 mL). The mixed solution was allowed to react at 80° C. for 17 hours. After completion of the reaction, the reaction solution was purified by high performance liquid chromatography to give 54.

MS-ESI calculated for $[M+H]^+$: 478, found: 478.

$^1H$ NMR (400 MHz, $CDCl_3$) δ: 8.20-8.13 (m, 2H), 8.00 (d, J=8.4 Hz, 1H), 7.45 (d, J=8.4 Hz, 1H), 7.01 (d, J=8.4 Hz,

1H), 4.79 (s, 2H), 4.36 (br s, 1H), 4.08-3.63 (m, 15H), 1.47 (d, J=6.4 Hz, 3H), 0.85 (s, 2H), 0.70 (br s, 2H).

Embodiment 55

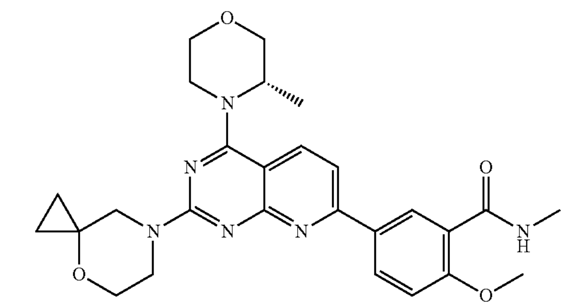

55

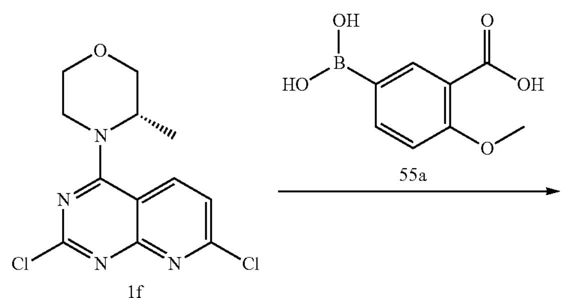

1f

55a

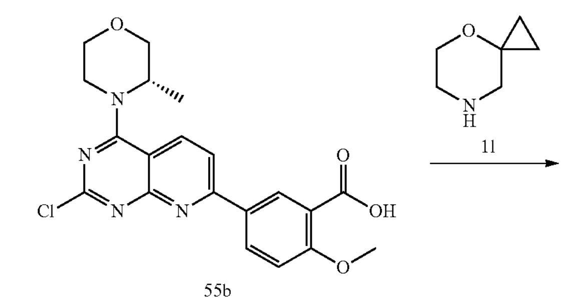

55b

1i

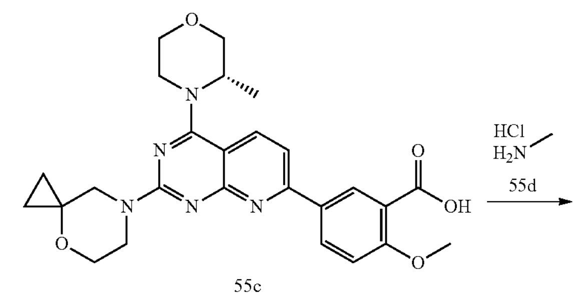

55c

55d

-continued

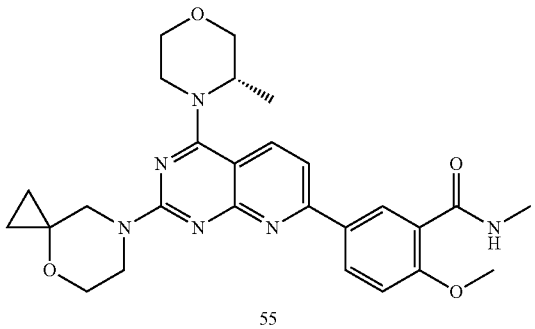

55

First Step

Compound 1f (100 mg, 334 μmol, 1.00 eq), compound 55a (65.5 mg, 334 mol, 1.00 eq), bis(triphenylphosphine) palladium dichloride (11.7 mg, 16.7 μmol, 0.05 eq) and sodium carbonate (70.9 mg, 669 μmol, 2.00 eq) were dissolved in water (1.00 mL) and 1,4-dioxane (3.00 mL), and the mixture was reacted at 80° C. for 15 hours under nitrogen protection. After completion of the reaction, the reaction solution was concentrated to remove solvent, diluter with water (15.0 mL) and extracted with ethyl acetate (50.0 mL×3). The combined organic phase was dried over anhydrous sodium sulfate, filtered, and subjected to rotary evaporation under reduced pressure to dryness, and 55b was obtained.

Second Step

Compound 55b (168 mg, 404 μmol, 1.00 eq), 1i (54.4 mg, 364 μmol, 0.90 eq) and DIPEA (157 mg, 1.21 mmol, 211 μL, 3.00 eq) were dissolved in DMSO (3.00 mL). The mixed solution was allowed to react at 80° C. for 15 hours. After completion of the reaction, the reaction solution was concentrated to remove solvent to give 55c. The crude product was directly used in the next step.

Third Step

Compound 55c (99.0 mg, 201 μmol, 1.00 eq), 55d (24.5 mg, 363 μmol, 1.80 eq), DIPEA (104 mg, 806 μmol, 140 μL, 4.00 eq), EDCI (57.9 mg, 302 μmol, 1.50 eq), and HOBt (40.8 mg, 302 μmol, 1.50 eq) were dissolved in DMSO (4.00 mL). The mixed solution was allowed to react at 30° C. for 22 hours. After completion of the reaction, the reaction solution was purified by high performance liquid chromatography to give 55.

MS-ESI calculated for $[M+H]^+$: 505, found: 505.

$^1$H NMR (400 MHz, $CDCl_3$) δ: 8.75 (br s, 1H), 8.51 (br d, J=8.0 Hz, 1H), 7.94 (br d, J=8.4 Hz, 1H), 7.76 (br s, 1H), 7.50 (br d, J=8.4 Hz, 1H), 7.03 (br d, J=8.4 Hz, 1H), 4.29 (br s, 1H), 3.97 (s, 3H), 3.96-3.51 (m, 12H), 2.98 (br d, J=4.4 Hz, 3H), 1.38 (br d, J=6.8 Hz, 3H), 0.76 (br s, 2H), 0.61 (br s, 2H).

Embodiment 56

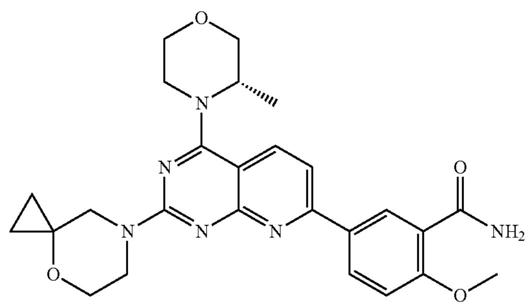

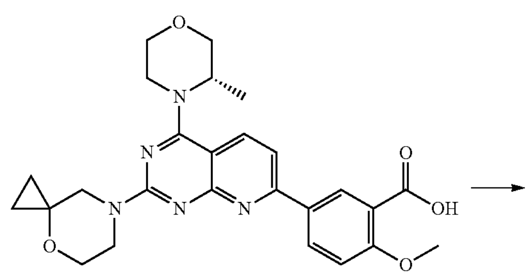

55c

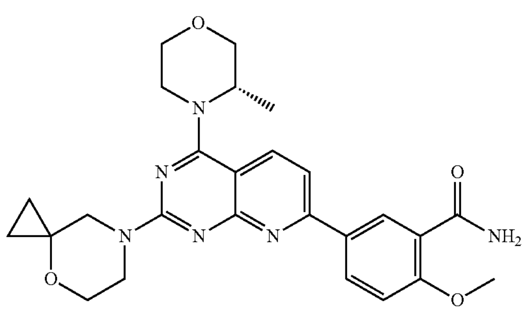

56

Compound 56c (99.0 mg, 201 μmol, 1.00 eq), ammonium chloride (43.1 mg, 806 μmol, 4.00 eq), DIPEA (104 mg, 806 μmol, 140 μL, 4.00 eq), EDCI (57.9 mg, 302 mol, 1.50 eq), and HOBt (40.8 mg, 302 μmol, 1.50 eq) was dissolved in DMSO (4.00 mL). The mixed solution was allowed to react at 30° C. for 22 hours. After completion of the reaction, the reaction solution was purified by high performance liquid chromatography to give 56.

MS-ESI calculated for $[M+H]^+$: 491, found: 491.

$^1H$ NMR (400 MHz, $CDCl_3$) δ: 8.76 (d, J=2.4 Hz, 1H), 8.55 (dd, J=2.4, 8.8 Hz, 1H), 7.93 (d, J=8.8 Hz, 1H), 7.67 (br s, 1H), 7.50 (d, J=8.8 Hz, 1H), 7.06 (d, J=8.8 Hz, 1H), 5.75 (br s, 1H), 4.28 (br d, J=5.6 Hz, 1H), 3.99 (s, 3H), 3.97-3.36 (m, 12H), 1.38 (d, J=6.8 Hz, 3H), 0.79-0.73 (m, 2H), 0.61 (br s, 2H).

Experimental Embodiment 1: In Vitro Evaluation of mTOR Kinase Inhibitory Activity Experimental Materials:

This experiment was performed by DiscoverX. All materials and methods were obtained from DiscoverX.

Experimental Operation:

Kinase activity analysis.

1. Labeled mTOR kinase was stably expressed in HEK-293 cells.

2. Streptavidin magnetic beads were treated with biotinylated small molecule ligands at room temperature for 30 minutes to produce affinity resin for kinase analysis;

3. Ligand beads were blocked with excess biotin and washed with buffer (1% bovine serum albumin, 20 mL 0.05% Tween, 1 mL dithiothreitol) to remove unbound ligand and non-specifically bound ligand;

4. The assembly of kinase and ligand and affinity beads, and the binding reaction between the compound and the three were performed in buffer (20% blocking buffer, 0.17x phosphate buffer, 0.05% Tween 20, 6 mL dithiothreitol);

5. The test compounds were dissolved in dimethyl sulfoxide;

6. All test compounds were dissolved in DMSO, and then directly diluted to a concentration of 0.9%.

7. The solution was placed in a 384-well polypropylene plate, wherein the volume of each well was 0.02 mL;

8. The plate was shaked for an hour at room temperature;

9. The plate was washed with buffer (1× PBS, 0.05% Tween 20);

10. The affinity beads were resuspended in buffer (1× PBS, 0.05% Tween 20, 0.5 μm non-biotin affinity ligand) and incubated at room temperature for 30 minutes;

11. The kinase concentration in the eluate was deteced by qPCR.

Experimental Results:

TABLE 1

The activity test results of mTORC1 and mTORC2 kinase complex

| Test compound (the compound prepared by each embodiment) | mTORC1 and mTORC2 kinase complex inhibitory activity Kd (nM) |
|---|---|
| Embodiment 1 | 0.85 |
| Embodiment 2 | 0.15 |
| Embodiment 3 | 0.32 |
| Embodiment 4 | 0.22 |
| Embodiment 5 | 0.66 |
| Embodiment 6 | 12 |
| Embodiment 7 | 6.4 |
| Embodiment 8 | 5.9 |
| Embodiment 9 | 0.34 |
| Embodiment 10 | 7.8 |
| Embodiment 11 | 1.2 |
| Embodiment 12 | 0.75 |
| Embodiment 13 | 0.64 |
| Embodiment 14 | 0.25 |
| Embodiment 15 | 3.3 |
| Embodiment 16 | 1.5 |
| Embodiment 17 | 3.4 |
| Embodiment 18-1 | 3 |

TABLE 1-continued

The activity test results of mTORC1 and mTORC2 kinase complex

| Test compound (the compound prepared by each embodiment) | mTORC1 and mTORC2 kinase complex inhibitory activity Kd (nM) |
|---|---|
| Embodiment 18-2 | 0.5 |
| Embodiment 19 | 3 |
| Embodiment 20 | 0.97 |
| Embodiment 21 | 0.47 |
| Embodiment 22 | 1.5 |
| Embodiment 23 | 0.38 |
| Embodiment 24 | 0.41 |
| Embodiment 25 | 1.4 |
| Embodiment 26 | 1 |
| Embodiment 27 | 6.6 |
| Embodiment 28 | 1.4 |
| Embodiment 29 | 2.7 |
| Embodiment 30 | 0.44 |
| Embodiment 31 | 5 |
| Embodiment 32-1 | 0.79 |
| Embodiment 32-2 | 1.5 |
| Embodiment 33-1 | 0.78 |
| Embodiment 33-2 | 0.38 |
| Embodiment 34-1 | 1 |
| Embodiment 34-2 | 0.73 |
| Embodiment 35 | 0.4 |
| Embodiment 36 | ND |
| Embodiment 37 | ND |
| Embodiment 38 | ND |
| Embodiment 39 | ND |
| Embodiment 40 | 0.78 |
| Embodiment 41 | 0.94 |
| Embodiment 42 | 0.93 |
| Embodiment 43 | 12 |
| Embodiment 44 | 0.24 |
| Embodiment 45-1 | 0.5 |
| Embodiment 45-2 | 1.7 |
| Embodiment 46-1 | 1 |
| Embodiment 46-2 | 4.9 |
| Embodiment 47-1 | 7.9 |
| Embodiment 47-2 | 7.9 |
| Embodiment 48-1 | 1.8 |
| Embodiment 48-2 | 0.7 |
| Embodiment 49 | 0.3 |
| Embodiment 50-1 | 1.9 |
| Embodiment 50-2 | 0.7 |
| Embodiment 51 | 0.3 |
| Embodiment 52 | 0.8 |
| Embodiment 53-1 | 1.1 |
| Embodiment 53-2 | 1.8 |
| Embodiment 54 | ND |
| Embodiment 55 | ND |
| Embodiment 56 | ND |

"ND" refers to undetected.

Conclusion: the compounds of the present invention have significant or unexpected mTOR kinase inhibitory activity.

Experimental Embodiment 2: Evaluation of Cell Proliferation Inhibitory Activity Experiment objective: To detect cell proliferation inhibitory activity of the tested compounds.

Experimental principle: The luciferase in the Cell-Titer-Glo reagent produces oxyluciferin using luciferin, oxygen and ATP as reaction substrates, and releases energy in the form of light. Since the reaction of luciferase requires ATP, the total amount of light generated by the reaction is proportional to the total amount of ATP that reflects cell viability.

Experimental Materials:

Cell lines: MCF-7 cell line (ATCC-CRL-22), HT-29 cell line (ATCC-HTB-38), OE21 (ECACC-96062201), NCI-N87 cell line (ATCC-CRL-5822)

Cell culture medium: (RPMI 1640 culture medium (Invitrogen #1868546; 10% serum Invitrogen #1804958; L-glutamine 1×, Invitrogen #1830863; dual antibiotic Hyclone #J170012))

Cell Titer-Glo® Luminescent Cell Viability Assay Kit (Promega #G7573)

384-well cell culture plate (Greiner #E15103MA)

Compound plate (LABCYTE #0006346665)

$CO_2$ incubator (Thermo #371)

Vi-cell cell counter (Beckman Coulter)

Locomotive pipette (Eppendorf)

Transfer pipette (Greiner)

Pipetting gun (Eppendorf)

Multifunctional enzyme marker (Envision Reader)

ECHO Liquid-handling workstation (Labcyte-ECHO555)

Experimental steps and methods:

2.1. First Day:

The cells were inoculated in a 384- or 96-well plate with a density of 1000 cells per well and 25 μL per well according to the instructions of the cell inoculating plate. The edge wells were not inoculated with cells, and was supplemented with 25 L PBS.

2.2. Zeroth Day:

(i) The mother solution of the compound was 10 mM, and diluted with DMSO to an initial concentration of 4 mM. The compound was added to the compound mother solution, 9 μL per well.

(ii) The compound was diluted with ECHO liquid-handling workstation. Each well of the cell plate was added with 125 nL compound. Each well of the cell wells in $2^{nd}$ column and $23^{rd}$ column was added with 125 nL DMSO, and each of the PBS wells in $1^{st}$ column and $24^{th}$ column was added with 125 nL DMSO.

(iii) Each well of the cell plate was supplemented with 25 μL culture medium, the final volume in each well of the cell plate was 50 μL, the concentration of compound was 1 μM, 3 times dilution, 10 concentrations, each concentration was duplicated in left and right wells, the final DMSO concentration was 0.25%.

2.3. After addition of the compound, centrifugation was performed at 1000 rpm for 1 min, and the cell plate was placed in a 37° C., 5% $CO_2$ incubator for 3 days.

2.4. Third Day:

The cell plate was taken out from the incubator and equilibrated at room temperature for 30 minutes. 25 μL Cell-Titer-Glo reagent was added to each well, shaken for one minute to mix thoroughly, centrifuged at 1000 rpm for 1 minute. After 10 minutes, the plate was read on PerkinElmer Envision with a fluorescence reading time was set at 0.2 second.

Test results: The test results are shown in Table 2

TABLE 2

Screening test results of in vitro cell proliferation inhibitory activity of the compound of the present invention

| Compound | MCF-7 cell $IC_{50}$ (nM) | HT-29 cell $IC_{50}$ (nM) | OE21 cell $IC_{50}$ (nM) | N87 cell $IC_{50}$ (nM) |
|---|---|---|---|---|
| AZD2014 | 95 | 316 | 148 | 59 |
| Embodiment 1 | 155 | 485 | 313 | 61 |
| Embodiment 9 | 262 | ND | ND | ND |
| Embodiment 12 | 251 | ND | ND | ND |
| Embodiment 13 | 255 | ND | ND | ND |
| Embodiment 18 | 258 | ND | ND | ND |
| Embodiment 21 | 190 | ND | ND | ND |
| Embodiment 23 | 163 | 607 | 257 | 94 |
| Embodiment 24 | 206 | ND | ND | ND |

TABLE 2-continued

Screening test results of in vitro cell proliferation inhibitory activity of the compound of the present invention

| Compound | MCF-7 cell $IC_{50}$ (nM) | HT-29 cell $IC_{50}$ (nM) | OE21 cell $IC_{50}$ (nM) | N87 cell $IC_{50}$ (nM) |
|---|---|---|---|---|
| Embodiment 26 | 431 | ND | ND | ND |
| Embodiment 30 | ND | 442 | 158 | ND |
| Embodiment 32-1 | ND | 744 | ND | ND |
| Embodiment 32-2 | ND | 1413 | ND | ND |
| Embodiment 33-1 | ND | 1974 | ND | ND |
| Embodiment 33-2 | ND | 1254 | ND | ND |
| Embodiment 34-1 | ND | 1052 | ND | ND |
| Embodiment 34-2 | ND | 833 | ND | ND |
| Embodiment 35 | 105 | ND | ND | 44 |
| Embodiment 36 | 360 | ND | ND | ND |
| Embodiment 37 | 252 | ND | ND | ND |
| Embodiment 38 | 449 | ND | ND | ND |
| Embodiment 39 | 268 | ND | ND | ND |
| Embodiment 40 | ND | ND | ND | ND |
| Embodiment 41 | ND | ND | ND | ND |
| Embodiment 42 | ND | ND | ND | ND |
| Embodiment 43 | ND | ND | ND | ND |
| Embodiment 44 | 171 | ND | ND | 89 |
| Embodiment 45-1&45-2 | ND | ND | ND | ND |
| Embodiment 46 | ND | ND | ND | ND |
| Embodiment 47-1&47-2 | ND | ND | ND | ND |
| Embodiment 48-1 | ND | ND | ND | ND |
| Embodiment 48-2 | 176 | ND | ND | ND |
| Embodiment 49 | ND | ND | ND | ND |
| Embodiment 50-1 | ND | ND | ND | ND |
| Embodiment 50-2 | 636 | ND | ND | ND |
| Embodiment 51 | 208 | ND | ND | 59 |
| Embodiment 52 | 586 | ND | ND | ND |
| Embodiment 53-1&53-2 | ND | ND | ND | ND |
| Embodiment 54 | ND | ND | ND | 119 |
| Embodiment 55 | ND | ND | ND | 120 |
| Embodiment 56 | ND | ND | ND | 167 |

"ND" refers to undetected.

Conclusion: The compounds of the present invention have significant proliferation inhibitory activity against of MCF-7, N87 and OE-21 cells, and have certain proliferation inhibitory activity against HT-29 cells.

Experimental Embodiment 3: Pharmacokinetic Evaluation

1. Experiment Method

The test compound was mixed with 500 DMSO/95% 1000 polyoxyethylene castor oil (Cremophor EL), vortexed and sonicated to prepare a 1 mg/mL near-clear solution, which was filtered with a microporous filter membrane for future use. Female Balb/c mice of 18 to 20 grams were selected and the solution of the test compound was administered intravenously at a dose of 1 or 2 mg/kg. The test compound was mixed with an aqueous solution of 1% Tween 80, 9% polyethylene glycol 400, and 90% water, vortexed and sonicated to prepare 1 mg/mL near-clear solution, which was filtered with a microporous filter membrane for future use.

Female Balb/c mice of 18 to 20 grams were selected, and the solution of the test compound was orally administered at a dose of 2 or 10 mg/kg. The whole blood was collected at a certain time, and prepared into plasma. The drug concentration was analyzed by LC-MS/MS, and the pharmacokinetic parameters were calculated using Phoenix WinNonlin software (Pharsight Corporation, USA).

Test Results:

The test results are shown in Table 3-Table 8.

TABLE 3

Pharmacokinetic (PK) parameters in plasma of the compounds of the embodiments
PK parameters in plasma of reference compound (AZD2014)

| PK parameters | IV (1 mg/kg) | IV (2 mg/kg) | PO (2 mg/kg) | PO (10 mg/kg) |
|---|---|---|---|---|
| Rsq_adj | 0.996 | 0.999 | 0.972 | 0.966 |
| No. points used for $T_{1/2}$ | 7.00 | 4.00 | 6.00 | 3.00 |
| $C_0$ (nM) | 4786 | 8067 | — | — |
| $C_{max}$ (nM) | — | — | 4370 | 16967 |
| $T_{max}$ (h) | — | — | 0.500 | 0.25 |
| $T_{1/2}$ (h) | 0.967 | 1.05 | 1.14 | 3.46 |
| $V_{dss}$ (L/kg) | 0.677 | 0.599 | — | — |
| Cl (mL/min/kg) | 8.41 | 8.08 | — | — |
| $T_{last}$ (h) | 8.00 | 8.00 | 12.0 | 24.0 |
| $AUC_{0-last}$ (nM · h) | 4270 | 8880 | 8237 | 41443 |
| $AUC_{0-inf}$ (nM · h) | 4281 | 8914 | 7241 | 41508 |
| $MRT_{0-last}$ (h) | 0.268 | 1.20 | 1.95 | 2.45 |
| $MRT_{0-inf}$ (h) | 1.88 | 1.24 | 1.95 | 2.50 |
| $AUC_{Extra}$ (%) | — | 0.384 | 0.0496 | 0.156 |
| $AUMC_{Extra}$ (%) | — | 2.95 | 0.347 | 1.82 |
| Bioavailability (%)a | — | — | 96.2 | 93.1 |

TABLE 4

PK parameters in plasma of the compounds of the embodiments
PK parameters in plasma of the compound of the embodiment 1

| PK parameters | IV (2 mg/kg) | PO (10 mg/kg) |
|---|---|---|
| Rsq_adj | 0.995 | 0.979 |
| No. points used for $T_{1/2}$ | 3.00 | 4.00 |
| $C_0$ (nM) | 7200 | — |
| $C_{max}$ (nM) | — | 15067 |
| $T_{max}$ (h) | — | 0.25 |
| $T_{1/2}$ (h) | 1.65 | 3.33 |
| $V_{dss}$ (L/kg) | 0.793 | — |
| Cl (mL/min/kg) | 9.45 | — |
| $T_{last}$ (h) | 12 | 24.0 |
| $AUC_{0-last}$ (nM · h) | 7412 | 34973 |
| $AUC_{0-inf}$ (nM · h) | 7421 | 35034 |
| $MRT_{0-last}$ (h) | 1.20 | 2.69 |
| $MRT_{0-inf}$ (h) | 1.38 | 2.74 |
| $AUC_{Extra}$ (%) | 0.124 | 0.174 |
| $AUMC_{Extra}$ (%) | 1.27 | 1.83 |
| Bioavailability (%)a | — | 94.4 |

TABLE 5

PK parameters in plasma of the compounds of the embodiments
PK parameters in plasma of the compound of embodiment 23

| PK parameters | IV (2 mg/kg) | PO (10 mg/kg) |
|---|---|---|
| Rsq_adj | 0.995 | 0.782 |
| No. points used for $T_{1/2}$ | 3.00 | 8.00 |
| $C_0$ (nM) | 12185 | — |
| $C_{max}$ (nM) | — | 27850 |
| $T_{max}$ (h) | — | 0.25 |
| $T_{1/2}$ (h) | 1.47 | 2.61 |
| $V_{dss}$ (L/kg) | 0.414 | — |
| Cl (mL/min/kg) | 5.08 | — |
| $T_{last}$ (h) | 12.0 | 24.0 |
| $AUC_{0-last}$ (nM · h) | 13414 | 60052 |
| $AUC_{0-inf}$ (nM · h) | 13422 | 60302 |
| $MRT_{0-last}$ (h) | 1.35 | 2.39 |
| $MRT_{0-inf}$ (h) | 1.36 | 2.49 |

TABLE 5-continued

PK parameters in plasma of the compounds of the embodiments
PK parameters in plasma of the compound of embodiment 23

| PK parameters | IV (2 mg/kg) | PO (10 mg/kg) |
|---|---|---|
| $AUC_{Extra}$ (%) | 0.0592 | 0.414 |
| $AUMC_{Extra}$ (%) | 0.616 | 4.62 |
| Bioavailability (%) | — | 89.9 |

TABLE 6

PK parameters in plasma of the compounds of the embodiments
PK parameters in plasma of the compound of embodiment 51

| PK parameters | IV (2 mg/kg) | PO (10 mg/kg) |
|---|---|---|
| Rsq_adj | 0.993 | 0.903 |
| No. points used for $T_{1/2}$ | 9.00 | 4.00 |
| $C_0$ (nM) | 8237 | — |
| $C_{max}$ (nM) | — | 12850 |
| $T_{max}$ (h) | — | 0.25 |
| $T_{1/2}$ (h) | 1.10 | 1.22 |
| $V_{dss}$ (L/kg) | 0.739 | — |
| Cl (mL/min/kg) | 7.72 | — |
| $T_{last}$ (h) | 12.0 | 12.0 |
| $AUC_{0\text{-}last}$ (nM · h) | 9730 | 41869 |
| $AUC_{0\text{-}inf}$ (nM · h) | 9374 | 41963 |
| $MRT_{0\text{-}last}$ (h) | 1.59 | 3.02 |
| $MRT_{0\text{-}inf}$ (h) | 1.60 | 3.04 |
| $AUC_{Extra}$ (%) | 0.0469 | 0.225 |
| $AUMC_{Extra}$ (%) | 0.400 | 1.02 |
| Bioavailability (%) | — | 89.5 |

TABLE 7

PK parameters in plasma of the compounds of the embodiments
PK parameters in plasma of the compound of embodiment 55

| PK parameters | IV (1 mg/kg) | PO (2 mg/kg) |
|---|---|---|
| Rsq_adj | 0.972 | 0.989 |
| No. points used for T1/2 | 9.00 | 6.00 |
| $C_0$ (nM) | 9696 | — |
| $C_{max}$ (nM) | — | 7725 |
| $T_{max}$ (h) | — | 0.500 |
| $T_{1/2}$ (h) | 1.01 | 1.15 |
| $V_{dss}$ (L/kg) | 0.272 | — |
| Cl (mL/min/kg) | 3.49 | — |
| $T_{last}$ (h) | 12 | 12.0 |
| $AUC_{0\text{-}last}$ (nM · h) | 9461 | 16295 |
| $AUC_{0\text{-}inf}$ (nM · h) | 9466 | 16306 |
| $MRT_{0\text{-}last}$ (h) | 1.29 | 1.86 |
| $MRT_{0\text{-}inf}$ (h) | 1.30 | 1.86 |
| $AUC_{Extra}$ (%) | 0.0522 | 0.0673 |
| $AUMC_{Extra}$ (%) | 0.540 | 0.493 |
| Bioavailability (%) | — | 86.1 |

TABLE 8

PK parameters in plasma of the compounds of the embodiments
PK parameters in plasma of the compound of embodiment 35

| PK parameters | IV (1 mg/kg) | PO (2 mg/kg) |
|---|---|---|
| Rsq_adj | 0.988 | 0.990 |
| No. points used for T1/2 | 8.00 | 5.00 |
| $C_0$ (nM) | 2490 | — |
| $C_{max}$ (nM) | — | 3490 |
| $T_{max}$ (h) | — | 0.250 |
| $T_{1/2}$ (h) | 1.38 | 1.33 |
| $V_{dss}$ (L/kg) | 0.657 | — |
| Cl (mL/min/kg) | 5.07 | — |
| $T_{last}$ (h) | 12.0 | 8.00 |

TABLE 8-continued

PK parameters in plasma of the compounds of the embodiments
PK parameters in plasma of the compound of embodiment 35

| PK parameters | IV (1 mg/kg) | PO (2 mg/kg) |
|---|---|---|
| $AUC_{0\text{-}last}$ (nM · h) | 7382 | 8590 |
| $AUC_{0\text{-}inf}$ (nM · h) | 7400 | 8751 |
| $MRT_{0\text{-}last}$ (h) | 2.13 | 1.98 |
| $MRT_{0\text{-}inf}$ (h) | 2.16 | 2.13 |
| $AUC_{Extra}$ (%) | 0.246 | 1.84 |
| $AUMC_{Extra}$ (%) | 1.59 | 8.59 |
| Bioavailability (%) | — | 56.1 |

"—" refers to undetected or no data obtained.

Experimental conclusion: The test compounds exhibit the same or even better pharmacokinetic properties as the reference compound; the compounds of the present invention have bioavailability of close to 100%, which are excellent developable molecules for oral administration.

Experimental Embodiment 4: In Vivo Pharmacodynamic Study on BALB/c Nude Mouse Model of Human Breast Cancer MCF-7 Cell Subcutaneous Xenograft Tumor Experimental objective: To study the efficacy of the test compounds on human breast cancer MCF-7 cell subcutaneous xenograft tumor in BALB/c nude mouse model.

Experimental animals: Female BALB/c nude mice, 6-8 weeks old, weighing 18-22 grams; supplier: Shanghai Xipuer-Bikai Experimental Animal Co., Ltd.

Experimental Methods and Steps:

4.1 Cell Culture

Human breast cancer MCF-7 cells (ECACC, article number: 86012803) were subjected to in vitro monolayer culture under the conditions of EMEM (EBSS)+2 mM glutamic acid+1% Non Essential Amino Acids (NEAA) medium containing 10% fetal bovine serum, 100 U/mL penicillin and 100 μg/mL streptomycin, and 37° C., 5% $CO_2$incubator. Conventional digestion treatment was carried out with trypsin-EDTA twice a week for cell passage. When the cell saturation was 80%-90%, and the quantity reached the requirement, the cells were collected, counted and inoculated.

4.2 Tumor Cell Inoculation (Tumor Inoculation)

Estrogen tablets (0.18 mg) were inoculated into the left back of each mouse three days before cell inoculation, 0.2 mL ($1\times10^7$) MCF-7 cells (added with matrigel, volume ratio of 1:1) were subcutaneously inoculated into the right back of each mouse. When the average volume of tumor reached 142 $mm^3$, the mice were divided into groups and began to be administrated.

4.3 Preparation of Test Compounds:

The test compounds were prepared into clear solutions of 0.75 mg/mL, 1.5 mg/mL and 3 mg/mL. The vehicles were 5% DMSO+30% polyethylene glycol 300+65% water.

4.4 Tumor Measurement and Experimental Indexes

The experimental indexes were used for investigating whether the growth of the tumors had been inhibited, delayed or cured. The diameters of the tumors were measured with vernier calipers twice a week. The calculation formula of the tumor volume was: $V=0.5a\times b^2$, wherein a and b represent the long and short diameters of the tumor respectively.

The antitumor efficacy of the compound was evaluated by TGI (%) or relative tumor proliferation rate T/C (%). TGI (%) reflects the inhibition rate of the tumor growth. Calculation of TGI (%): TGI (%)=[1−(average tumor volume at the end of administration in the treatment group−average tumor volume at the beginning of administration in the treatment group)/(average tumor volume at the end of treatment in the vehicle control group−average tumor volume at the beginning of treatment in the vehicle control group)]× control group.

Relative tumor proliferation rate T/C (%): The calculation formula was as follows: T/C %=TRTV/CRTV at the beginning of the treatment (TRTV: treatment group RTV; CRTV: negative control group RTV). The relative tumor volume (RTV) was calculated according to the results of tumor measurement. The calculation formula was $RTV=V_t/V_0$, wherein $V_0$ is the average tumor volume measured during administration of the groups (i.e. $d_0$), and $V_t$ is the average tumor volume during a certain measurement, the TRTV and CRTV were taken on the same day.

After the experiment, the weight of the tumor would be detected and the T/weight percentage would be calculated. T weight and C weight represent the tumor weight of the administration group and the vehicle control group, respectively.

4.5 Statistical Analysis

Statistical analysis included the mean and standard error (SEM) of tumor volume at each time point in each group. The treatment group showed the best treatment effect on the 21st day after administration at the end of the trial, so statistical analysis was performed based on this data to evaluate the differences between the groups. The comparison between two groups was analyzed by T-test, and the comparison between three or more groups was analyzed by one-way ANOVA. If there was significant difference in F value, the Games-Howell method was used to testify. If there was no significant difference in F value, Dunnet (2-sided) method was used for analysis. SPSS 17.0 was used for analysis of all data. $p<0.05$ was considered to be a significant difference.

4.6 Experimental Results

In the MCF-7 xenograft tumor model, some compounds have the same efficacy as AZD2014.

TABLE 9

Tumor inhibition effect of compounds on human breast cancer MCF-7 cell subcutaneous xenograft model

| Groups | Tumor volume $(mm^3)^a$ (day 0) | Tumor volume $(mm^3)^a$ ($27^{th}$ day) | RTV ($27^{th}$ day) | T/C[b] (%) | TGI[b] (%) |
|---|---|---|---|---|---|
| Vehicle | 142 ± 7 | 588 ± 75 | 4.17 ± 0.52 | — | — |
| AZD2014 (7.5 mg/kg) | 142 ± 9 | 315 ± 65 | 2.25 ± 0.47 | 53.95 | 61.10 |
| AZD2014 (15 mg/kg) | 141 ± 8 | 121 ± 41 | 0.85 ± 0.26 | 20.36 | 104.37 |
| Embodiment 23 (7.5 mg/kg) | 142 ± 9 | 489 ± 51 | 3.48 ± 0.37 | 83.52 | 22.14 |
| Embodiment 23 (15 mg/kg) | 141 ± 9 | 324 ± 79 | 2.26 ± 0.48 | 54.13 | 59.05 |
| Embodiment 23 (30 mg/kg) | 141 ± 8 | 150 ± 26 | 1.06 ± 0.17 | 25.50 | 98.33 |
| Embodiment 44 (15 mg/kg) | 143 ± 13 | 298 ± 55 | 2.11 ± 0.39 | 50.58 | 65.23 |
| Embodiment 51 (15 mg/kg) | 142 ± 11 | 323 ± 25 | 2.41 ± 0.36 | 57.84 | 59.27 |
| Embodiment 49 (15 mg/kg) | 144 ± 14 | 759 ± 174 | 5.07 ± 0.92 | 121.62 | −37.89 |

Note:
"—" refers to no calculation
[a]Mean ± SEM.
[b]Inhibition of tumor growth was calculated by T/C and TGI (TGI (%) = $[1 - (T_{21} - T_0)/(V_{21} - V_0)] \times 100$).
c. The p-value was based on the tumor volume.

4.7. Experimental Conclusion

Compared with the vehicle group, in the nude mouse model of human breast cancer xenograft tumor, AZD2014 had a significant difference at a dose of 15 mg/kg and embodiment 23 had a significant difference at a dose of 30 mg/kg compared with the vehicle control group. The TGI thereof were 104% and 98%.

What is claimed is:

1. A compound represented by formula (IV), a pharmaceutically acceptable salt thereof or an isomer thereof, (IV)

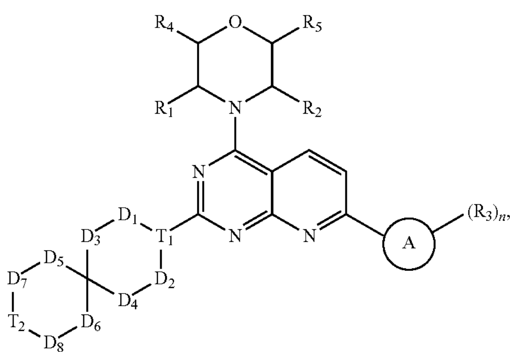

wherein, $R_1$ is H;

$R_2$ is Me;

alternatively, $R_1$, $R_2$ and the N atom on the morpholine ring form a 5-6 membered heterocycloalkyl;

$R_3$ is selected from $NH_2$,

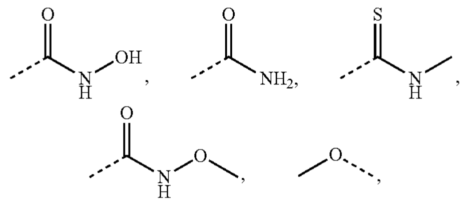

5-6 membered heteroaryl and $C_{3-6}$ cycloalkyl-NH—C(═O)—, wherein the $NH_2$,

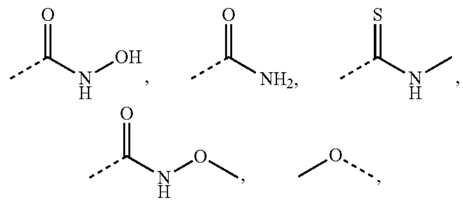

5-6 membered heteroaryl and $C_{3-6}$ cycloalkyl-NH—C(═O)— are optionally substituted by R, and the number of R is 1, 2 or 3; n is selected from 1 and 2;

ring A is selected from phenyl and 6-10 membered heteroaryl;

$R_4$ is H;

$R_5$ is H;

alternatively, $R_4$ and $R_5$ are linked together to form a 5-6 membered heterocycloalkyl;

$D_1$, $D_2$, $D_3$ and $D_4$ are respectively selected from single bond, —$CH_2$—, —$CH_2CH_2$— and —O—, and at least one of $D_1$, $D_2$, $D_3$ and $D_4$ is not a single bond, wherein the —$CH_2$— or —$CH_2CH_2$— is optionally substituted by R, and the number of R is 1 or 2;

$D_5$, $D_6$, $D_7$ and $D_8$ are respectively selected from a single bond, —$CH_2$—, —O— and —NH—, and at least one of $D_5$, $D_6$, $D_7$ and $D_8$ is not a single bond, wherein the —$CH_2$— is optionally substituted by R, and the number of R is 1 or 2, —NH— is optionally substituted by R;

$T_1$ is selected from CH and N;

$T_2$ is selected from —$CH_2$—, —NH—, —O—,

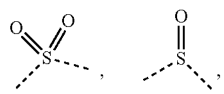

—S— and —C(═O)NH—, wherein the —$CH_2$— is optionally substituted by R, and the number of R is 1 or 2, —NH— is optionally substituted by R;

R is respectively selected from $CF_3$, F, Cl, Br, I, OH, $NH_2$, $C_{1-3}$ alkyl, $C_{1-3}$ alkoxy and $C_{3-6}$ cycloalkyl, wherein the $C_{1-3}$ alkyl, $C_{1-3}$ alkoxy and $C_{3-6}$ cycloalkyl are optionally substituted by R', and the number of R' is 1 or 2;

R' is respectively selected from F, Cl, Br, I, OH and $NH_2$;

the 5-6 membered heteroaryl and 6-10 membered heteroaryl respectively contain 1, 2 or 3 heteroatoms or heteroatom groups independently selected from —O—, —S—, —NH—, N, —C(═O)—, —C(═O)NH— and —C(═S) NH—.

2. The compound, the pharmaceutically acceptable salt thereof or the isomer thereof as defined in claim 1, which is selected from (I)

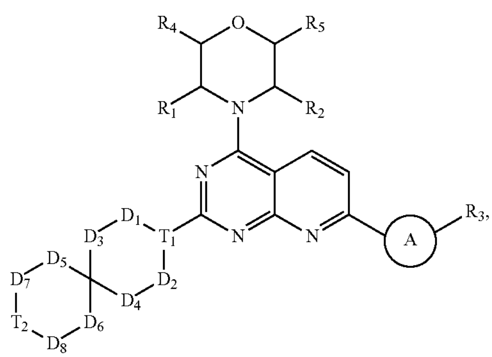

wherein, $R_1$ is H;

$R_2$ is Me;

alternatively, $R_1$, $R_2$ and the N atom on the morpholine ring form a 5-6 membered heterocycloalkyl;

$R_3$ is selected from $NH_2$,

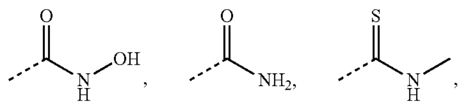

-continued

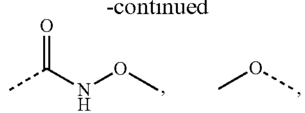

5-6 membered heteroaryl and $C_{3-6}$ cycloalkyl-NH—C(═O)—, wherein the $NH_2$,

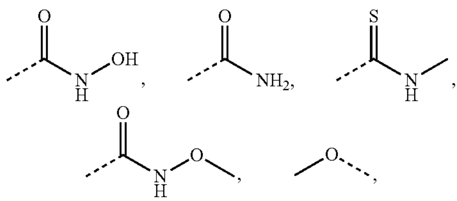

5-6 membered heteroaryl and $C_{3-6}$ cycloalkyl-NH—C(═O)— are optionally substituted by R, and the number of R is 1, 2 or 3;

ring A is selected from phenyl and 6-10 membered heteroaryl;

$R_4$ is selected from H;

$R_5$ is selected from H;

alternatively, $R_4$ and $R_5$ are linked together to form a 5-6 membered heterocycloalkyl;

$D_1$, $D_2$, $D_3$ and $D_4$ are respectively selected from a single bond, —$CH_2$—, —$CH_2CH_2$— and —O—, and at least one of $D_1$, $D_2$, $D_3$ and $D_4$ is not a single bond, wherein the —$CH_2$— or —$CH_2CH_2$— is optionally substituted by R, and the number of R is 1 or 2;

$D_5$, $D_6$, $D_7$ and $D_8$ are respectively selected from a single bond, —$CH_2$—, —O— and —NH—, and at least one of $D_5$, $D_6$, $D_7$ and $D_8$ is not a single bond, wherein the —$CH_2$— is optionally substituted by R, and the number of R is 1 or 2, —NH— is optionally substituted by R;

$T_1$ is selected from CH and N;

$T_2$ is selected from —$CH_2$—, —NH—, —O—,

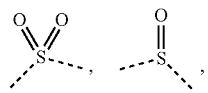

—S— and —C(═O) NH—, wherein —$CH_2$— is optionally substituted by R, and the number of R is 1 or 2, —NH— is optionally substituted by R;

R is respectively selected from $CF_3$, F, Cl, Br, I, OH, $NH_2$, $C_{1-3}$ alkyl, $C_{1-3}$ alkoxy and $C_{3-6}$ cycloalkyl, wherein the $C_{1-3}$ alkyl, $C_{1-3}$ alkoxy and $C_{3-6}$ cycloalkyl are optionally substituted by R', and the number of R' is 1 or 2;

R' is respectively selected from F, Cl, Br, I, OH and $NH_2$;

the $C_{1-3}$ heteroalkyl, 5-6 membered heteroaryl and 6-10 membered heteroaryl respectively contain 1, 2 or 3 heteroatoms or heteroatom groups independently selected from —O—, —S—, —NH—, N, —C(═O)—, —C(═O)NH— and —C(═S)NH—.

3. The compound, the pharmaceutically acceptable salt thereof or the isomer thereof as defined in claim 2, wherein the R is respectively selected from $CF_3$, F, Cl, Br, I, OH, $NH_2$, Me, Et,

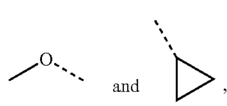

wherein the Me, Et,

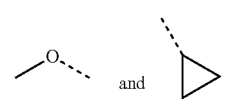

are optionally substituted by R', and the number of R' is 1 or 2.

4. The compound, the pharmaceutically acceptable salt thereof or the isomer thereof as defined in claim 3, wherein the R is respectively selected from F, Cl, Br, I, OH, $NH_2$, Me, $CF_3$, Et,

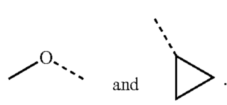

5. The compound, the pharmaceutically acceptable salt thereof or the isomer thereof as defined in claim 1, wherein the moiety

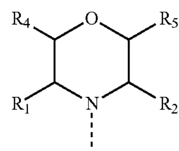

is selected from

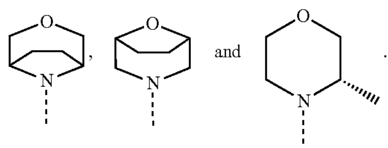

6. The compound, the pharmaceutically acceptable salt thereof or the isomer thereof as defined in claim 1, wherein the $R_3$ is selected from $NH_2$,

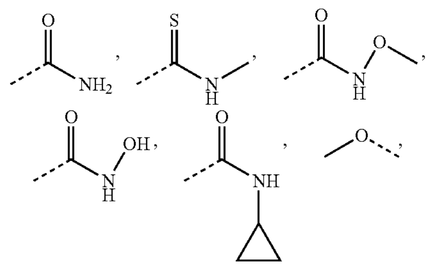

1H-pyrazolyl and 1H-1,2,4-triazolyl, wherein the $NH_2$,

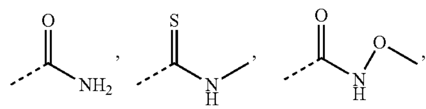

-continued

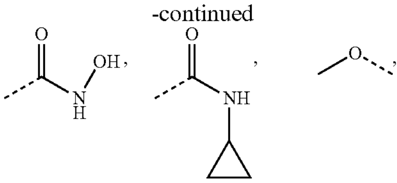

1H-pyrazolyl and 1H-1,2,4-triazolyl are optionally substituted by R, and the number of R is 1, 2 or 3.

7. The compound, the pharmaceutically acceptable salt thereof or the isomer thereof as defined in claim 6, wherein the $R_3$ is selected from $NH_2$,

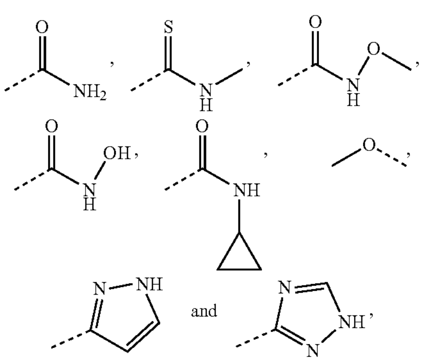

wherein the $NH_2$,

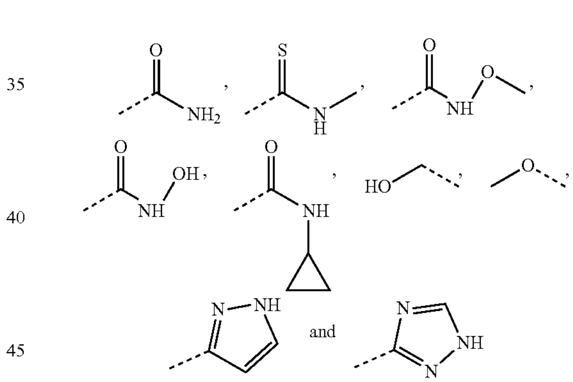

are optionally substituted by R, and the number of R is 1, 2 or 3.

8. The compound, the pharmaceutically acceptable salt thereof or the isomer thereof as defined in claim 7, wherein the $R_3$ is selected from $NH_2$,

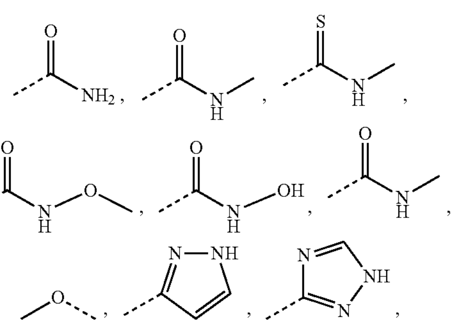

-continued

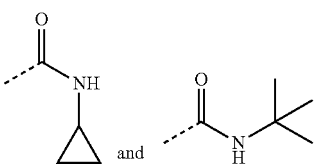

9. The compound, the pharmaceutically acceptable salt thereof or the isomer thereof as defined in claim 1, wherein ring A is selected from phenyl, benzo[d]oxazole, quinolinyl and quinazolinyl.

10. The compound, the pharmaceutically acceptable salt thereof or the isomer thereof as defined in claim 9, wherein ring A is selected from

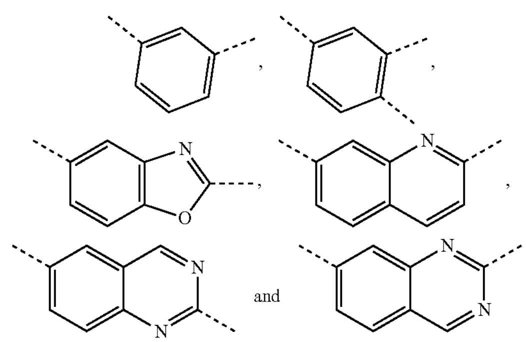

11. The compound, the pharmaceutically acceptable salt thereof or the isomer thereof as defined in claim 1, wherein the moiety

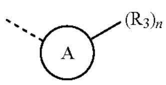

is selected from

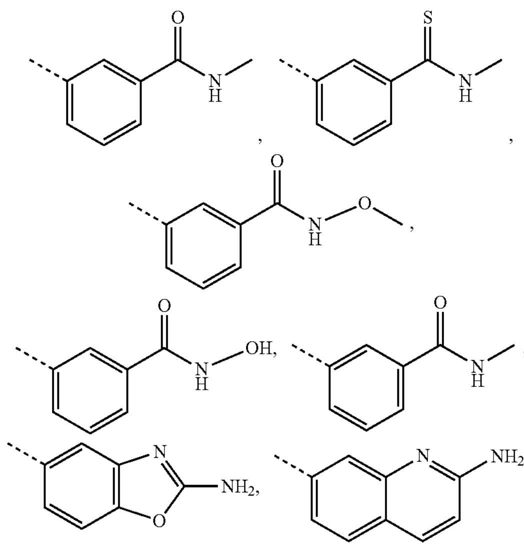

-continued

12. The compound, the pharmaceutically acceptable salt thereof or the isomer thereof as defined in claim 2, wherein the moiety is selected from

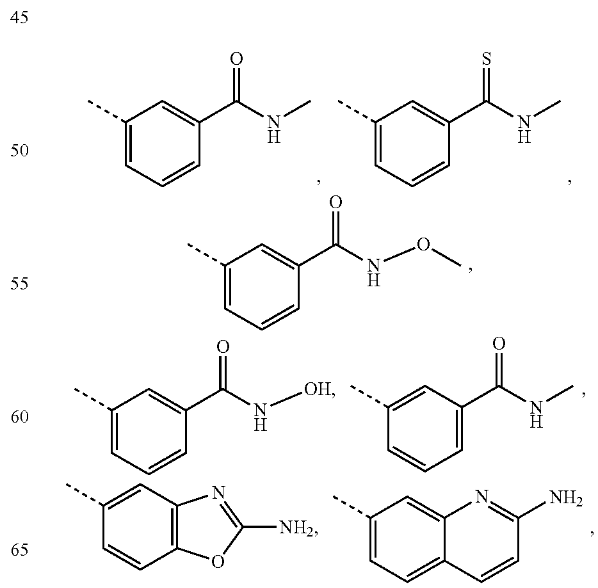

-continued

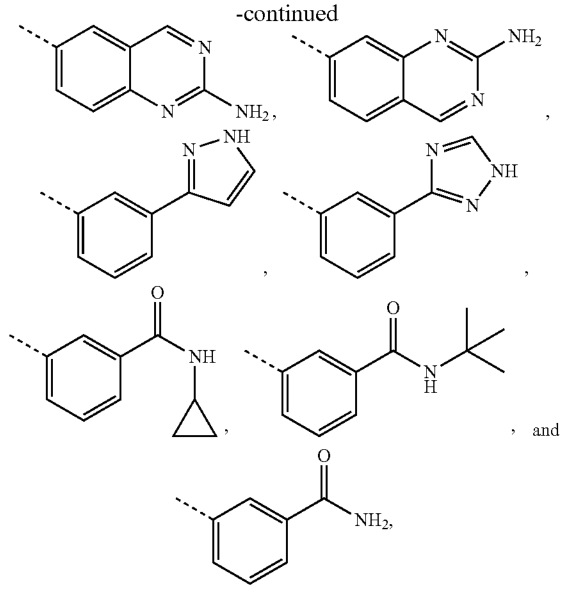

13. The compound, the pharmaceutically acceptable salt thereof or the isomer thereof as defined in claim 1, wherein $D_1$, $D_2$, $D_3$ and $D_4$ are respectively selected from a single bond, —$CH_2$—, —$CH_2CH_2$—, —O— and

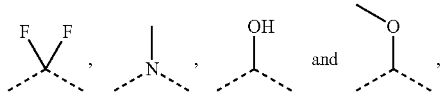

and at least one of $D_1$, $D_2$, $D_3$ and $D_4$ is not a single bond; or, $D_5$, $D_6$, $D_7$ and $D_8$ are respectively selected from a single bond, —$CH_2$—, —O—, —NH—, and at least one of $D_5$, $D_6$, $D_7$ and $D_8$ is not a single bond.

14. The compound, the pharmaceutically acceptable salt thereof or the isomer thereof as defined in claim 1, wherein the moiety

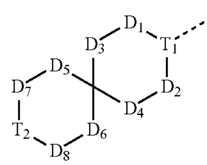

is selected from

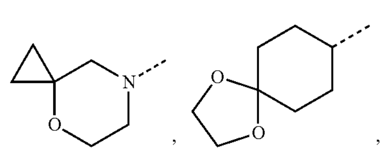

-continued

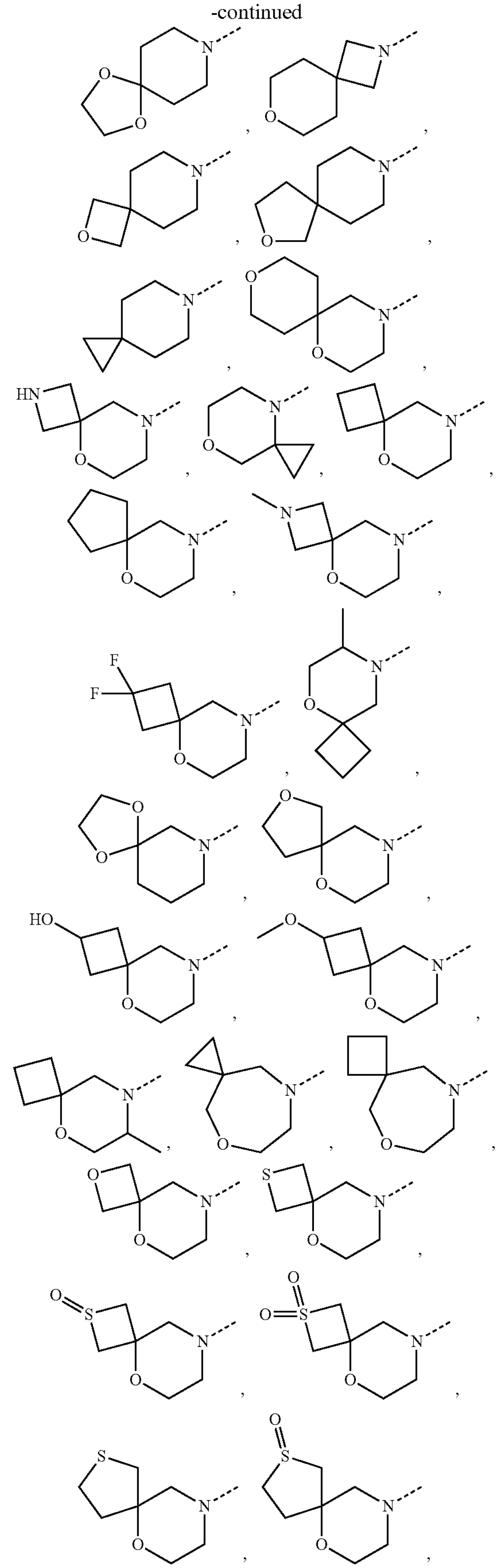

-continued
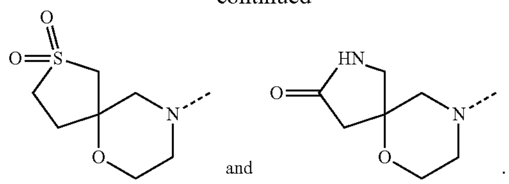
15. The compound, the pharmaceutically acceptable salt thereof or the isomer thereof as defined in claim 1, which is selected from:
(I-1)
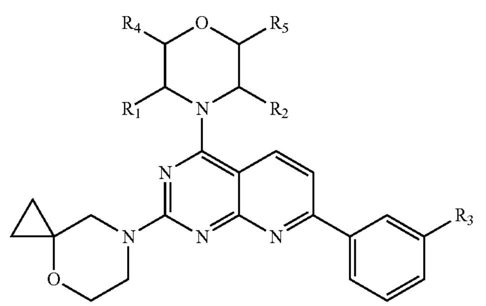
(I-2)
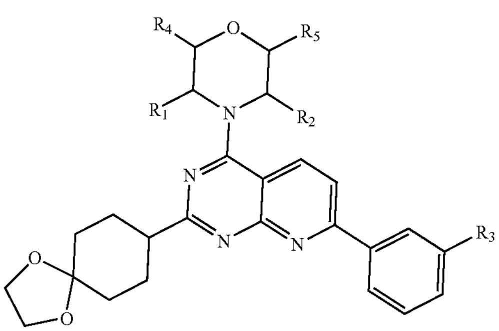
(I-3)
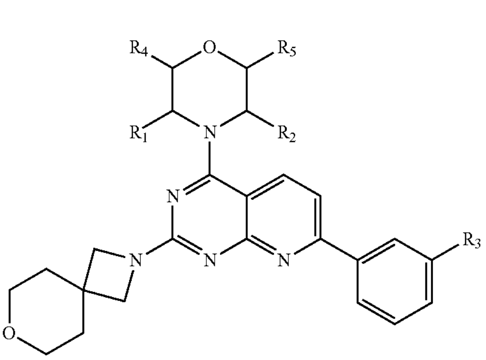
(I-4)
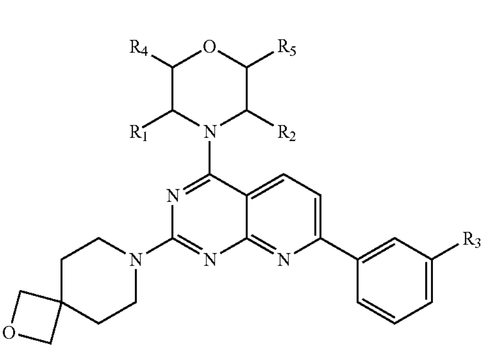
-continued
(I-5)
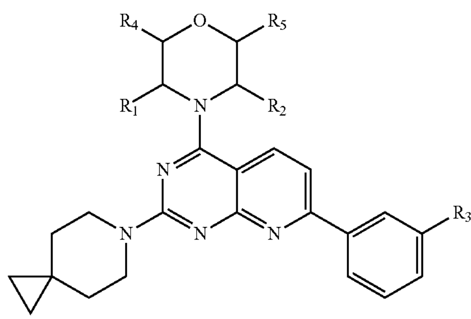
(I-6)
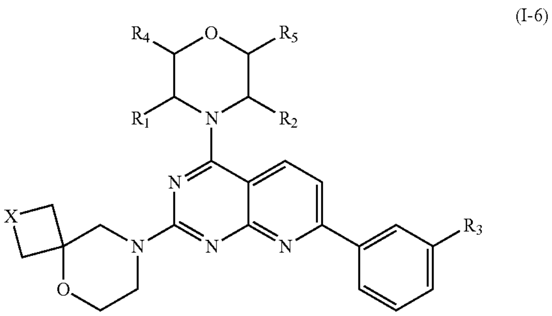
(I-7)
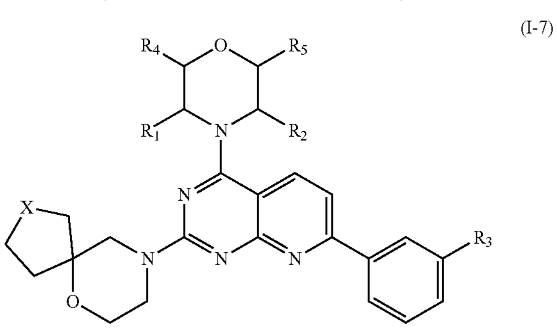
(I-8)
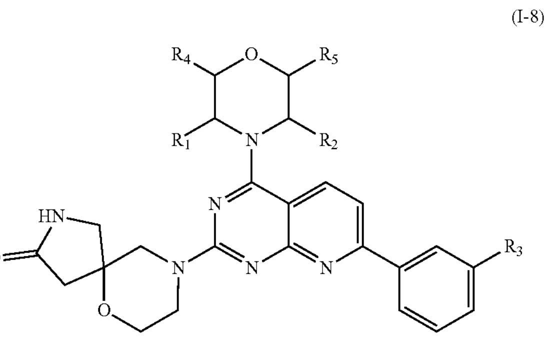
(I-9)
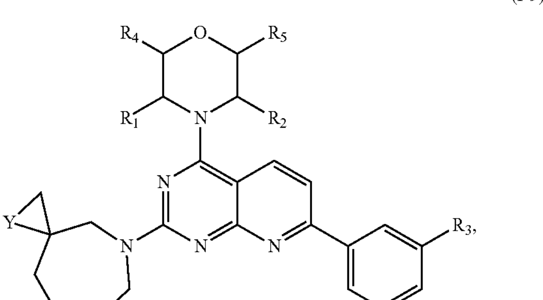

wherein, $R_1$, $R_2$, $R_3$, $R_4$ and $R_5$ are as defined in claim 1;

X is selected from —$CH_2$—, —$CF_2$—,

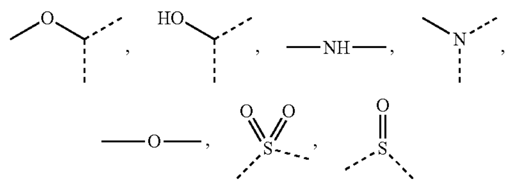

and —S—;

Y is selected from —$CH_2$— and —$CH_2CH_2$—.

16. The compound, the pharmaceutically acceptable salt thereof or the isomer thereof as defined in claim 1, which is selected from:

(IV-1)

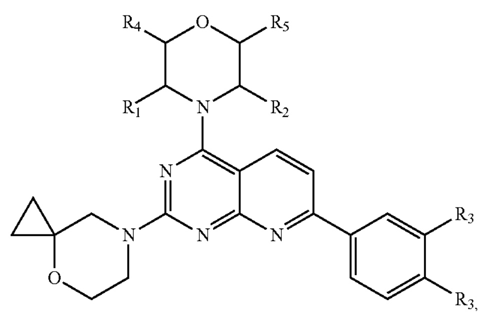

wherein, $R_1$, $R_2$, $R_3$, $R_4$ and $R_5$ are as defined in claim 1.

17. A compound as shown below, a pharmaceutically acceptable salt thereof or an isomer thereof,

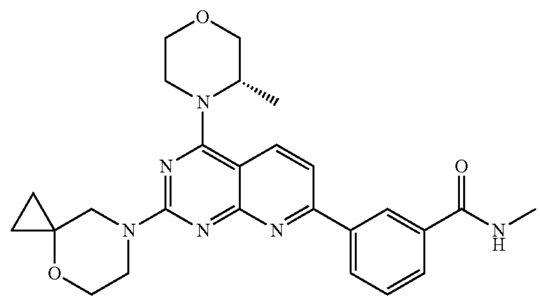

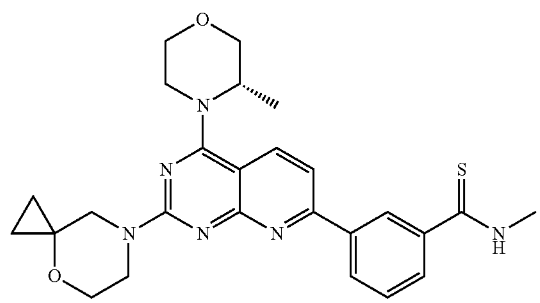

-continued

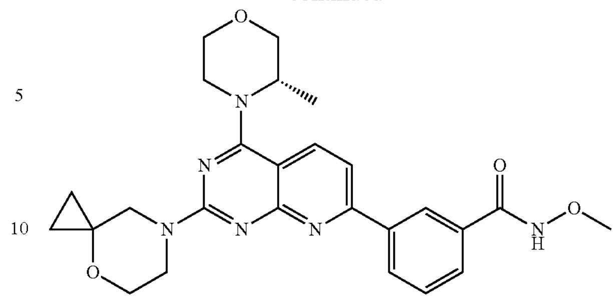

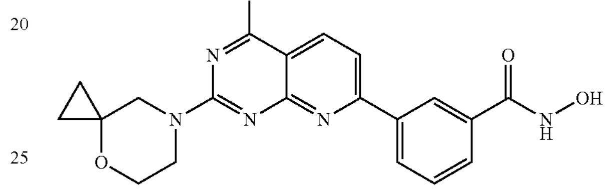

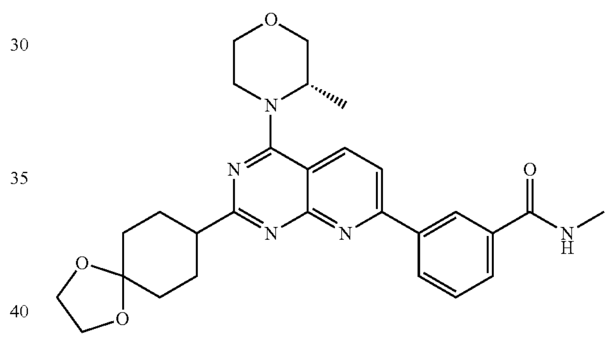

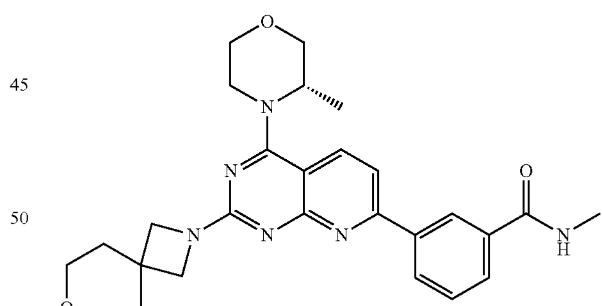

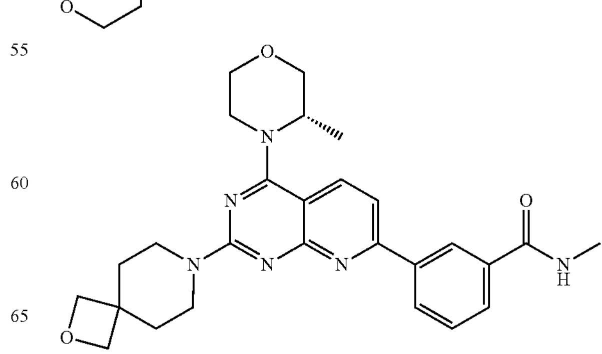

-continued
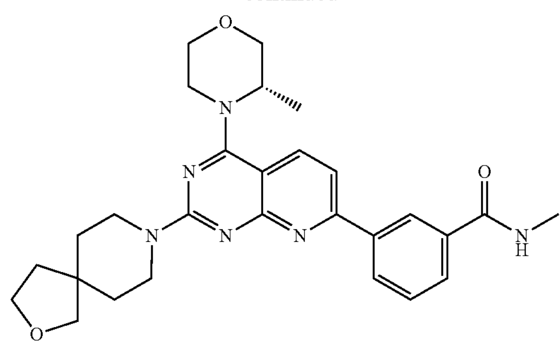
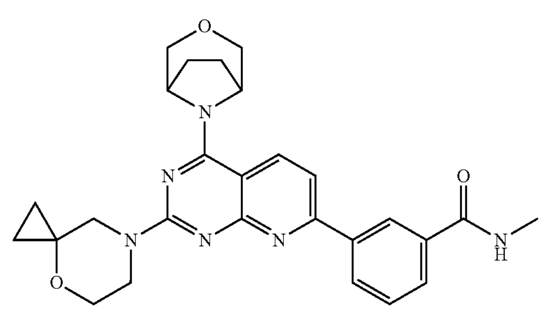
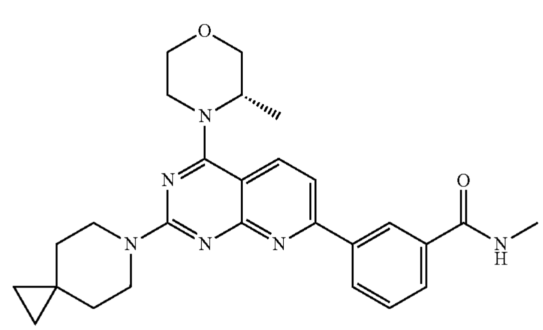
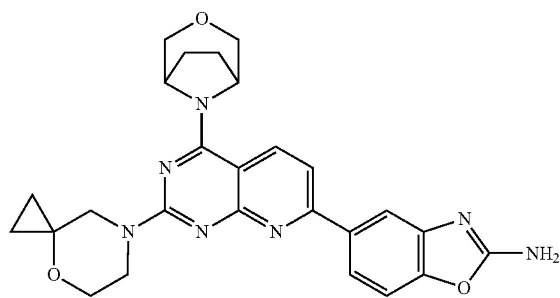
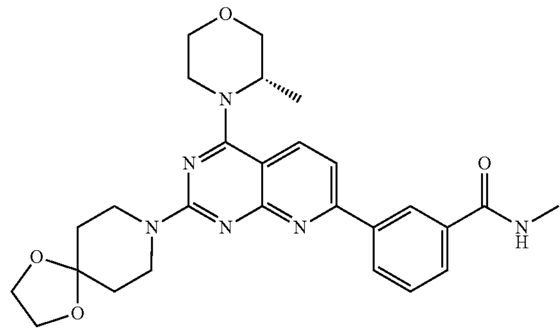
-continued
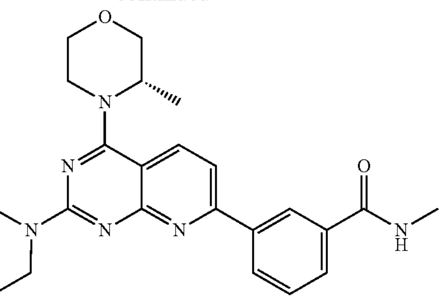
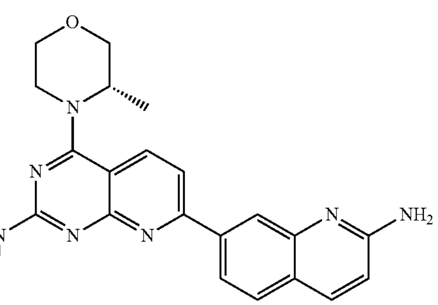
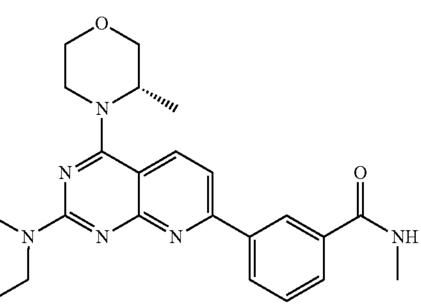
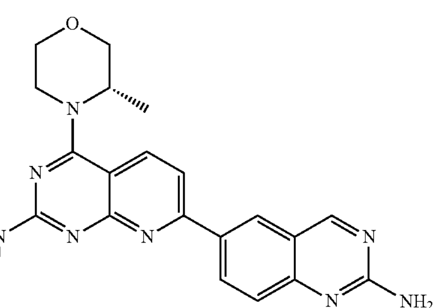
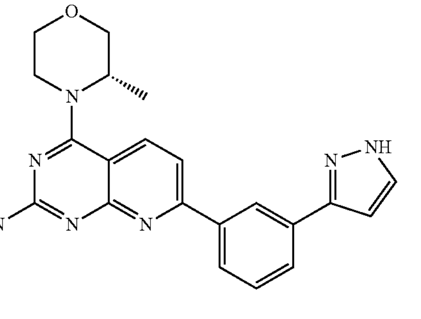

-continued
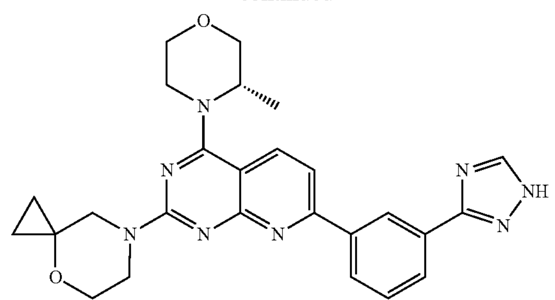
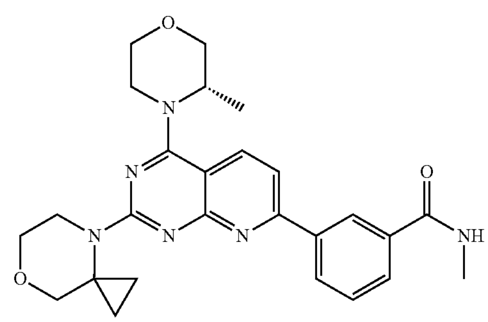
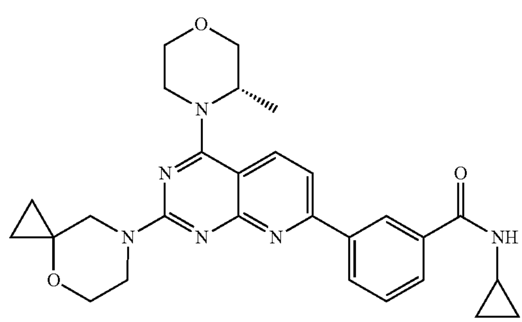
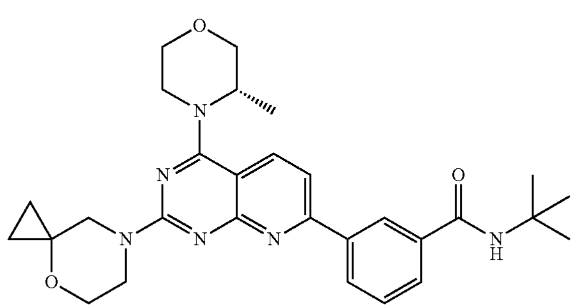
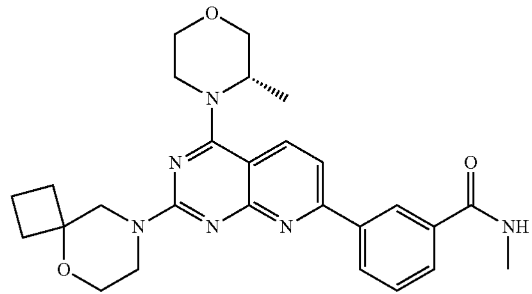
-continued
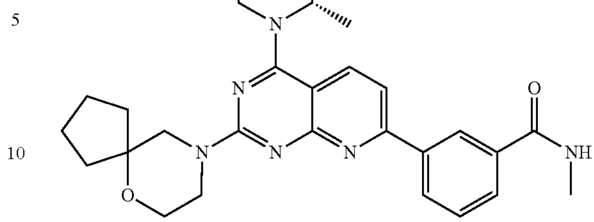
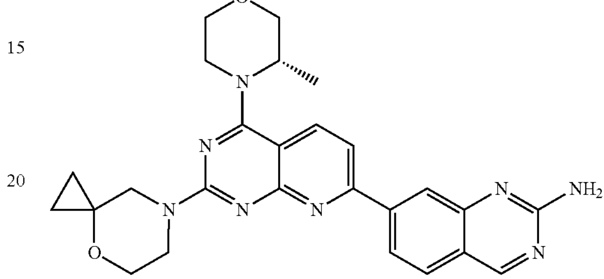
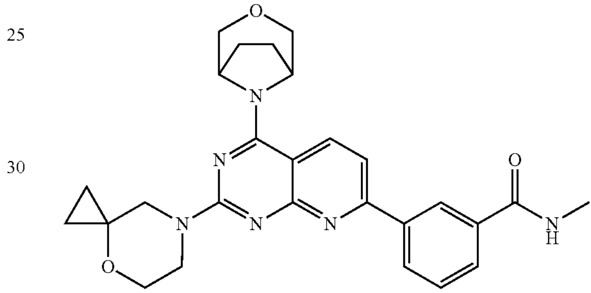
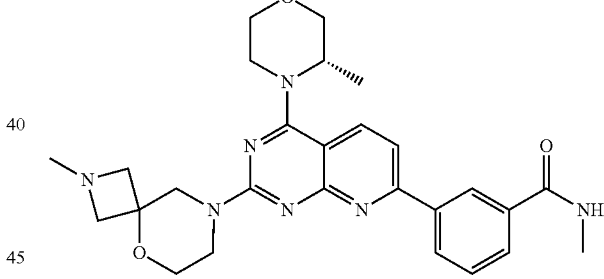
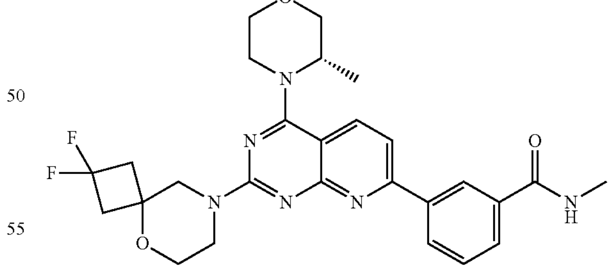
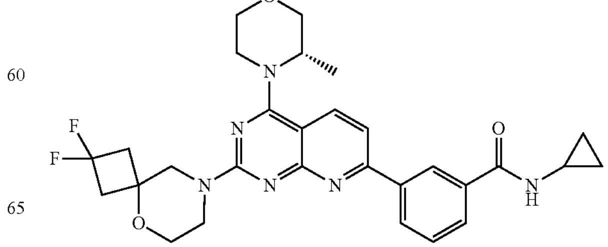

-continued
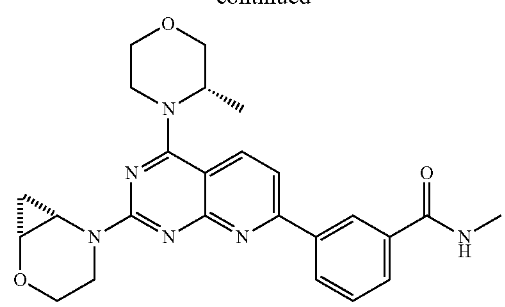
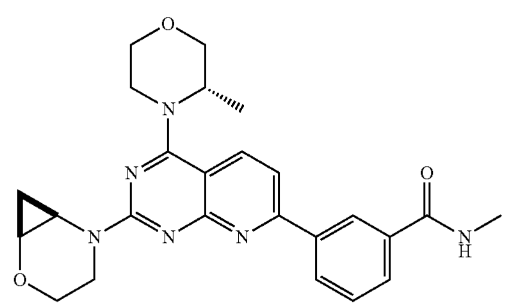
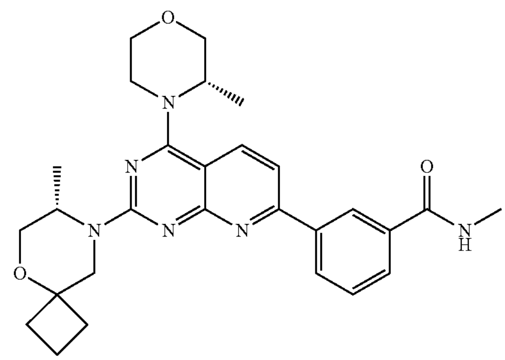
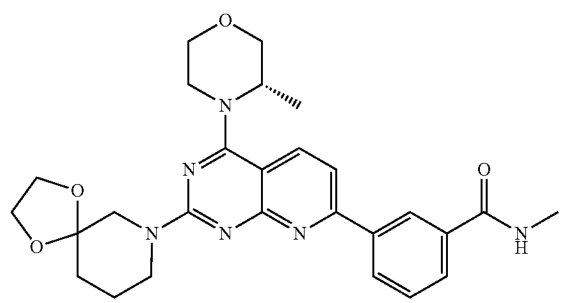
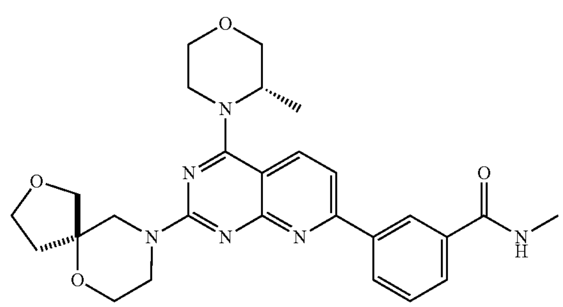
-continued
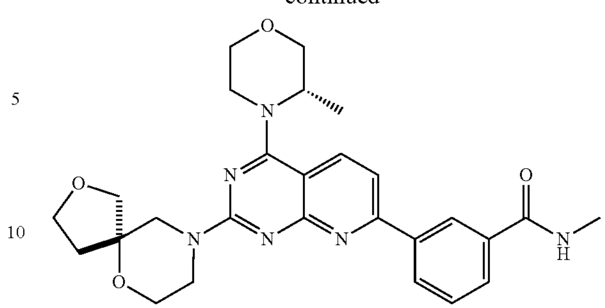
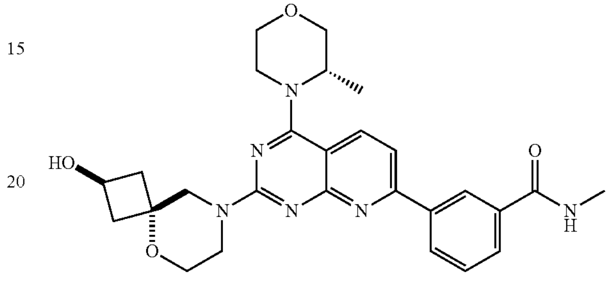
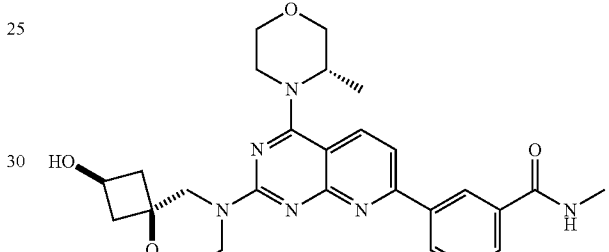
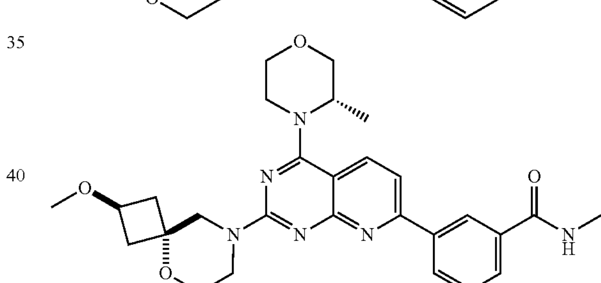
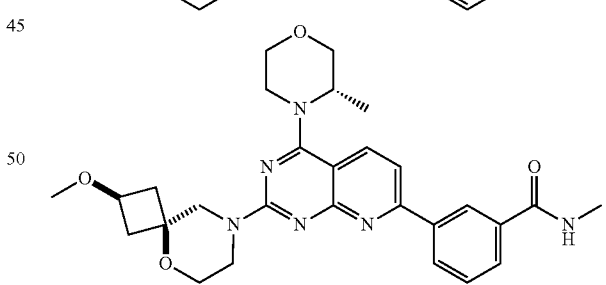
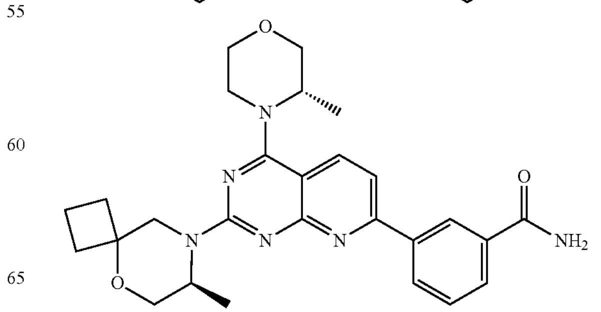

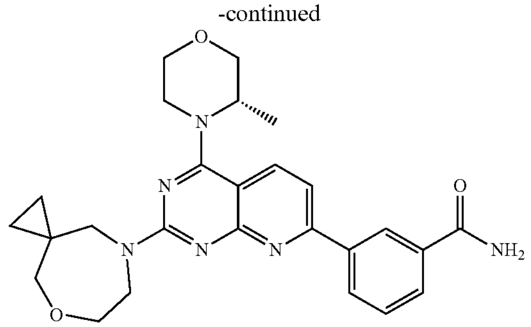
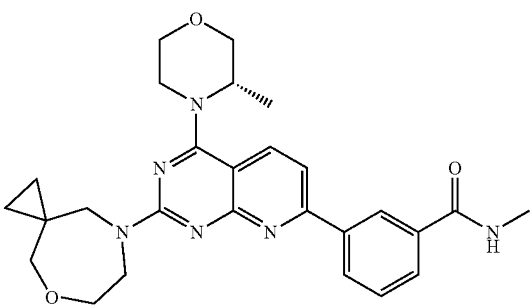
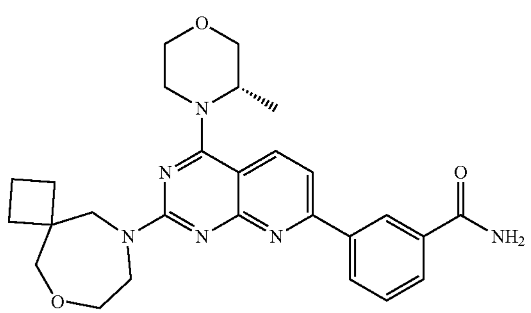
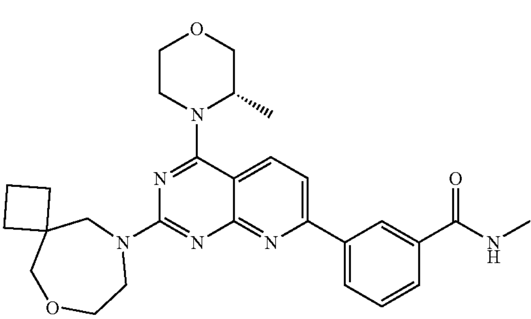
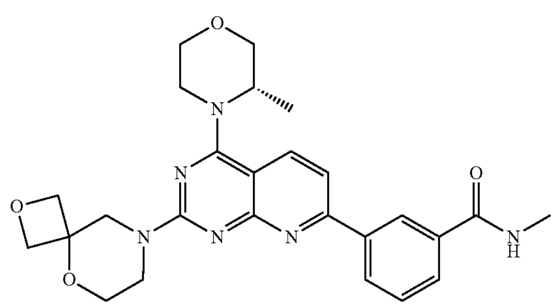
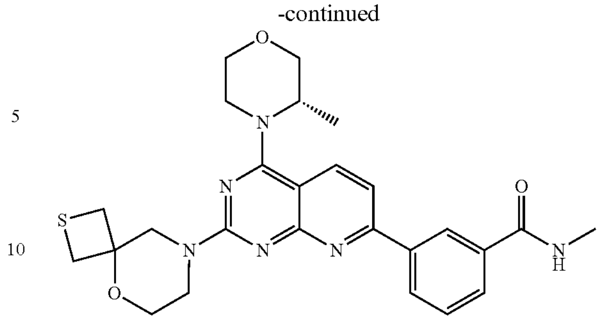
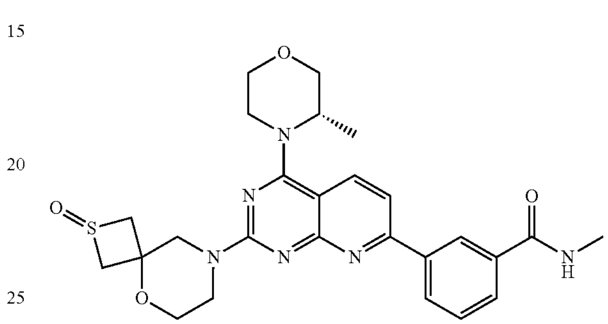
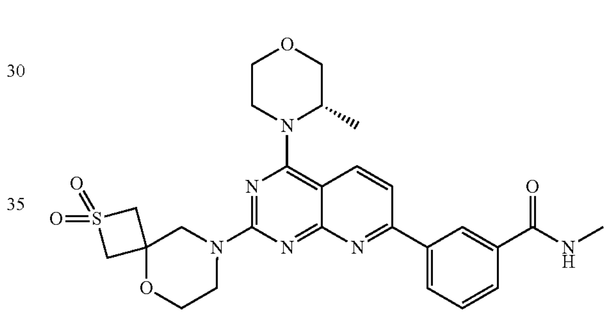
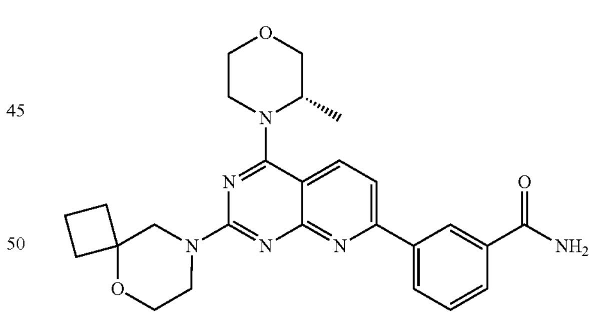
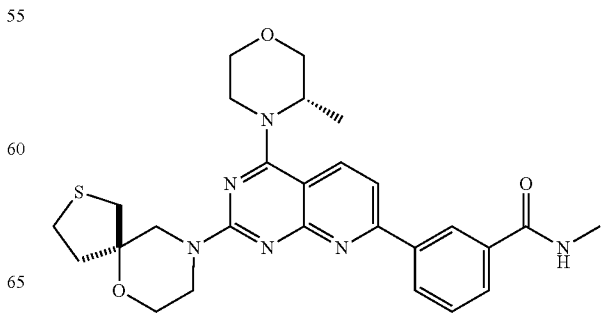

-continued
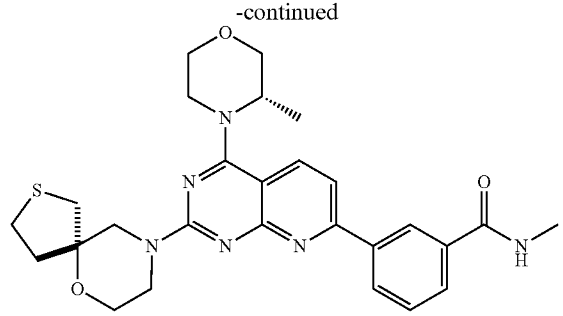
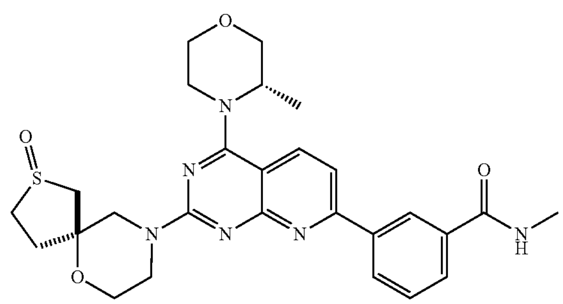
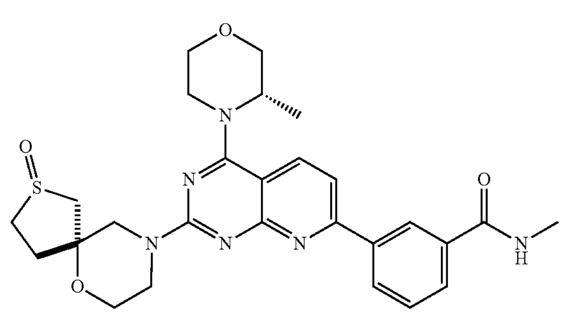
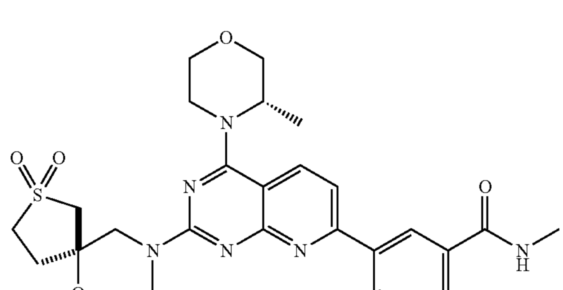
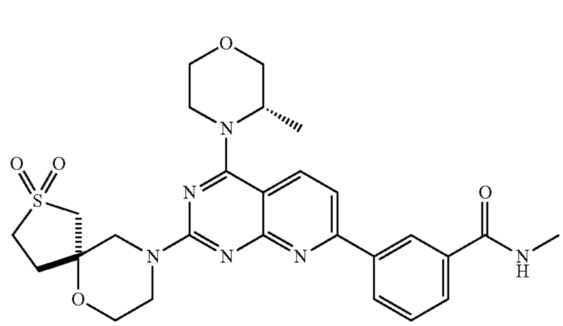
-continued
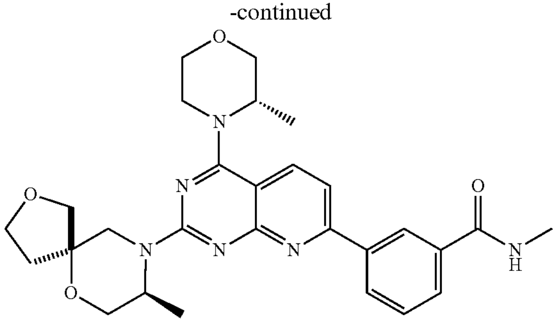
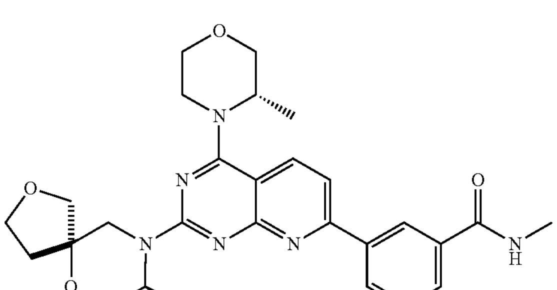
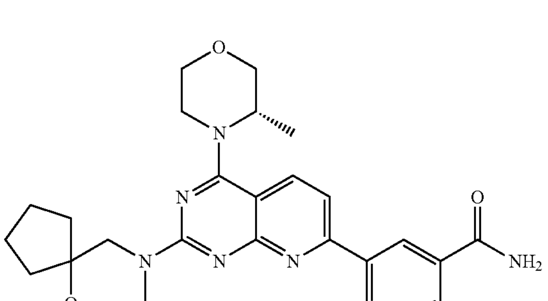
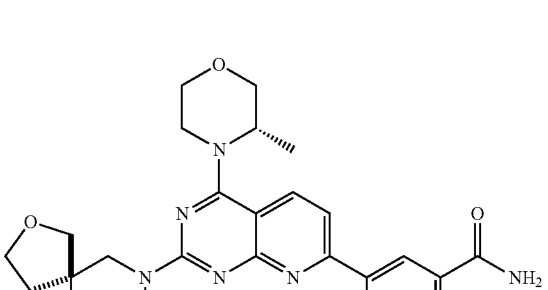
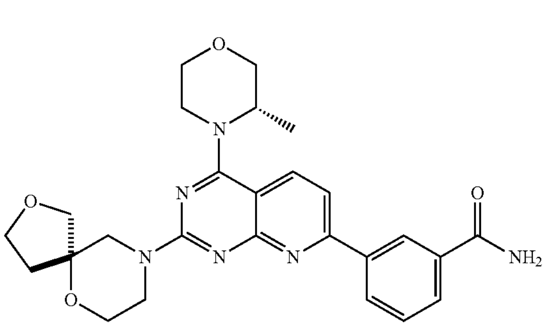

-continued

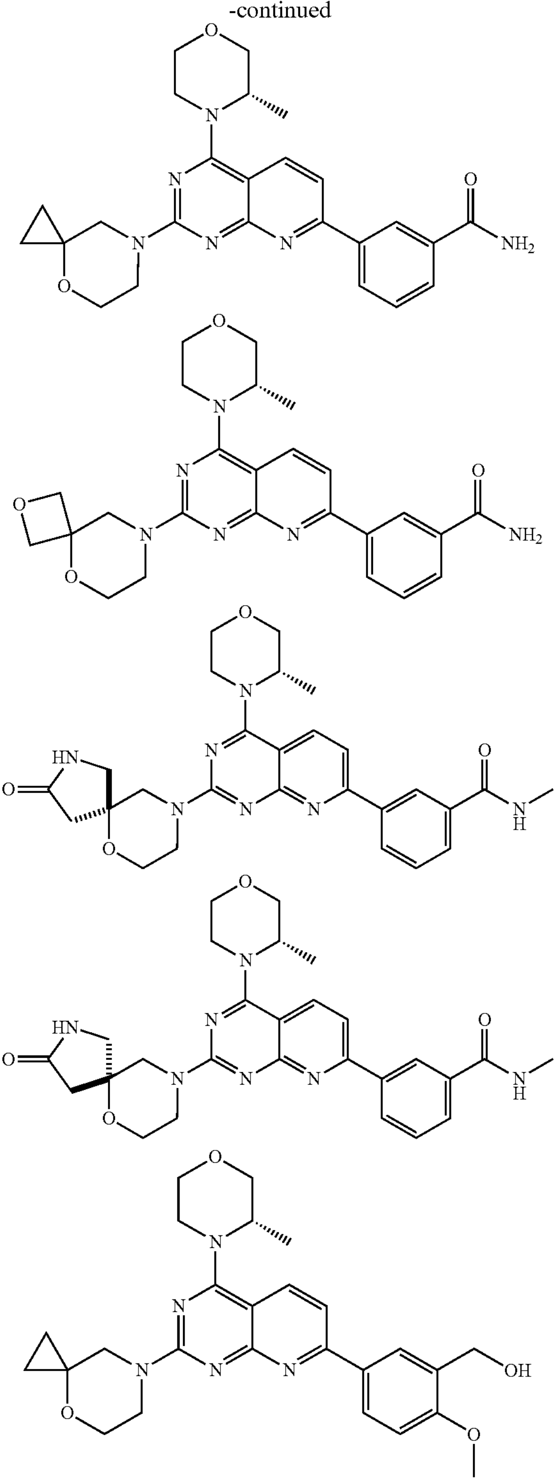

-continued

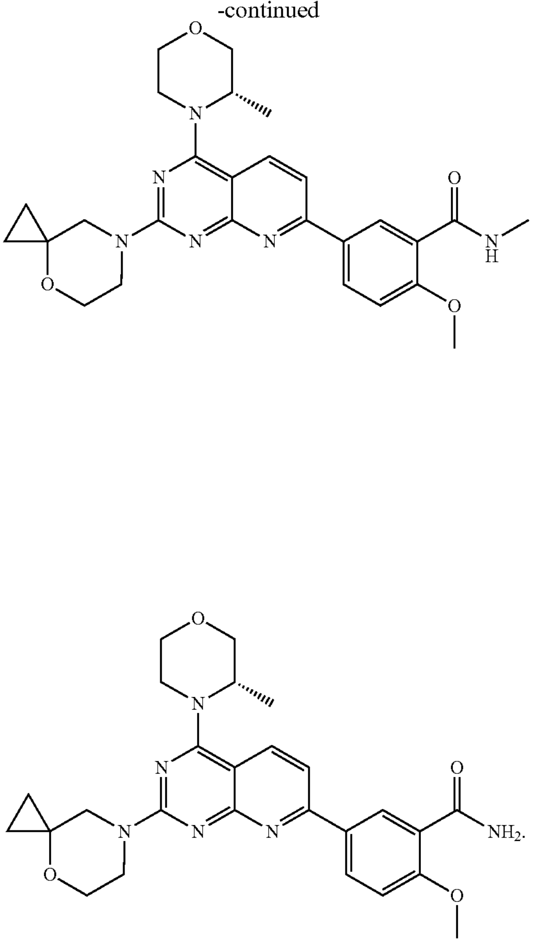

18. A pharmaceutical composition comprising a therapeutically effective amount of the compound, the pharmaceutically acceptable salt thereof or the isomer thereof as defined in claim 1 as an active ingredient, and a pharmaceutically acceptable carrier.

19. A method for treating breast cancer, head and neck cancer, or colorectal cancer in a subject in need thereof, comprising: administering an effective amount of the compound, the pharmaceutically acceptable salt thereof or the isomer thereof as defined in claim 1 to the subject.

20. A method for treating breast cancer, head and neck cancer, or colorectal cancer in a subject in need thereof, comprising: administering an effective amount of the pharmaceutical composition as defined in claim 18 to the subject.

* * * * *